(12) United States Patent
Friedman et al.

(10) Patent No.: US 10,280,184 B2
(45) Date of Patent: May 7, 2019

(54) HETEROCYCLIC KINASE INHIBITORS

(71) Applicant: AbbVie Inc., North Chicago, IL (US)

(72) Inventors: Michael M. Friedman, Kennebunkport, ME (US); Philip Cox, Grayslake, IL (US); Kristine E. Frank, Grayslake, IL (US); Michael Z. Hoemann, Shrewsbury, MA (US); Augustine Osuma, Lindenhurst, IL (US); Noel S. Wilson, Kenosha, WI (US); Xiangdong Xu, Vernon Hills, IL (US); Kevin Cusack, Holden, MA (US); Raymond Huntley, Millbury, MA (US); J. Martin Herold, Cambridge, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/304,131

(22) PCT Filed: Apr. 16, 2015

(86) PCT No.: PCT/CN2015/076766
§ 371 (c)(1),
(2) Date: Oct. 14, 2016

(87) PCT Pub. No.: WO2015/158283
PCT Pub. Date: Oct. 22, 2015

(65) Prior Publication Data
US 2017/0114077 A1  Apr. 27, 2017

(30) Foreign Application Priority Data
Apr. 17, 2014 (WO) ................. PCT/CN2014/075560

(51) Int. Cl.
| C07D 471/04 | (2006.01) |
| C07D 519/00 | (2006.01) |
| A61K 31/437 | (2006.01) |
| C07D 487/04 | (2006.01) |
| C07D 498/04 | (2006.01) |

(52) U.S. Cl.
CPC .......... *C07D 519/00* (2013.01); *A61K 31/437* (2013.01); *C07D 471/04* (2013.01); *C07D 487/04* (2013.01); *C07D 498/04* (2013.01); *Y02A 50/401* (2018.01); *Y02A 50/463* (2018.01)

(58) Field of Classification Search
CPC .................................................. C07D 471/04
See application file for complete search history.

(56) References Cited

U.S. PATENT DOCUMENTS

| 2009/0258877 A1 | 10/2009 | Siegel et al. |
| 2011/0053929 A1 | 3/2011 | Siegel et al. |
| 2012/0309746 A1 * | 12/2012 | Hermann ............. C07D 471/04 514/218 |

FOREIGN PATENT DOCUMENTS

| JP | 2008516973 A | 5/2008 |
| JP | 2011506378 A | 3/2011 |
| JP | 2011528006 A | 11/2011 |
| JP | 2012510998 A | 5/2012 |
| JP | 2013522238 A | 6/2013 |
| JP | 2013537174 A | 9/2013 |
| JP | 2013545776 A | 12/2013 |
| WO | 20020060492 A1 | 8/2002 |
| WO | 02072579 A1 | 9/2002 |
| WO | 2005014599 A1 | 2/2005 |
| WO | 2005085252 A1 | 9/2005 |
| WO | 2006/044687 A2 | 4/2006 |
| WO | 2007032936 A2 | 3/2007 |
| WO | 2009077334 A1 | 6/2009 |
| WO | 2010027500 A1 | 3/2010 |
| WO | WO-2010/068806 A1 | 6/2010 |
| WO | WO-2010068810 A2 | 6/2010 |
| WO | 2011063907 A1 | 6/2011 |
| WO | 2012080230 A1 | 6/2012 |
| WO | WO-2012/136531 A1 | 10/2012 |
| WO | 2013064445 A1 | 5/2013 |
| WO | WO-2013/067260 | 5/2013 |
| WO | WO-2013/083666 | 6/2013 |

OTHER PUBLICATIONS

ISR of PCT/CN2014/075560, dated Jan. 23, 2015.
ISR of PCT/CN2015/076766, dated Jul. 8, 2015.
Lucas, Matthew C., et al., "Rational Design of Highly Selective Spleen Tyrosine Kinase Inhibitors", Journal of Medicinal Chemistry, Nov. 14, 2012, 55 pp. 10414-10423.

* cited by examiner

*Primary Examiner* — Brian E McDowell
(74) *Attorney, Agent, or Firm* — Foley Hoag LLP

(57) ABSTRACT

The invention provides compounds of Formula (I) pharmaceutically acceptable salts, pro-drugs, biologically active metabolites, stereoisomers and isomers thereof wherein the variable are defined herein. The compounds of the invention are useful for treating immunological and oncological conditions.

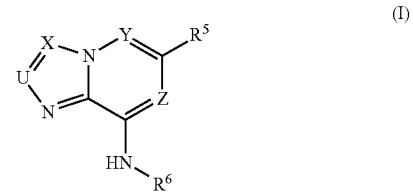

(I)

12 Claims, No Drawings

HETEROCYCLIC KINASE INHIBITORS

REFERENCE TO RELATED APPLICATION APPLICATIONS

This application is a U.S. national stage application filed under 35 U.S.C. § 371(c), based on International Application No. PCT/CN2015/076766, filed on Apr. 16, 2015, which claims priority to and the benefit of the filing date, under 35 U.S.C. § 365(b), of International Application No. PCT/CN2014/075560, filed on Apr. 17, 2014. The entire contents of each of the aforementioned applications are incorporated herein by reference.

BACKGROUND OF THE INVENTION

The protein kinases represent a large family of proteins that play a central role in the regulation of a wide variety of cellular processes and maintenance of cellular function. A partial, non-limiting, list of these kinases include: non-receptor tyrosine kinases such as the Tec family (BTK, ITK, Tec, ETK/BMX & RLK/TXK), Janus kinase family (Jak1, Jak2, Jak3 and Tyk2); the fusion kinases, such as BCR-Abl, focal adhesion kinase (FAK), Fes, Lck and Syk; receptor tyrosine kinases such as colony stimulating factor 1 receptor (CSF-1R), epidermal growth factor receptor (EGFR), the platelet-derived growth factor receptor kinase (PDGF-R), the receptor kinase for stem cell factor, c-kit, the hepatocyte growth factor receptor, c-Met, and the fibroblast growth factor receptor, FGFR3; and serine/threonine kinases such as b-RAF, mitogen-activated protein kinases (e.g., MKK6) and SAPK2β. Aberrant kinase activity has been observed in many disease states including benign and malignant proliferative disorders as well as diseases resulting from inappropriate activation of the immune and nervous systems. The novel compounds of this invention inhibit the activity of one or more protein kinases and are, therefore, expected to be useful in the treatment of kinase-mediated diseases.

Bruton's tyrosine kinase (BTK) is a non-receptor tyrosine kinase with a key role in immunoreceptor signaling (BCR, FcεR, FcγR, DAP12, Dectin-1, GPVI etc) in a host of hematopoietic cells including B cells, platelets, mast cells, basophils, eosinophils, macrophages and neutrophils as well as osteoclasts involved in bone destruction (for reviews, see Brunner et al., 2005 *Histol. Histopathol.*, 20:945, Mohamed et al., 2009 *Immunol. Rev.*, 228:58). Mutations in BTK are known to lead to X-linked agammaglobulinemia (XLA) in humans and X-linked immunodeficiency (Xid) in mice, which are characterized by limited B-cell production & reduced antibody titers (Lindvall et al., 2005 *Immunol. Rev.*, 203:200). The combined action of BTK in multiple cell types makes it an attractive target for autoimmune disease. BTK is related with sequence homology to other Tec family kinases (ITK, Tec, ETK/BMX & RLK/TXK).

In B-lymphocytes, BTK is required for B-cell development and for $Ca^{2+}$ mobilization following of B-cell receptor (BCR) engagement (Khan et al., 1995 *Immunity* 3:283; Genevier et al., 1997 *Clin. Exp. Immun.*, 110:286) where it is believed to downstream of Src family kinases (such as Lyn), Syk & PI3K. BTK has been shown to be important for both thymus-dependent and thymus-independent type 2 responses to antigens (Khan et al., *Immunity* 1995; 3; 283). In mast cells, studies using BTK mouse knock-outs (Hata et al., 1998 *J. Exp. Med.*, 187:1235; Schmidt et al., 2009 *Eur. J. Immun.*, 39:3228) indicate a role for BTK in FcεRI induced signaling, histamine release & production of cytokines such as TNF, IL-2, & IL-4. In platelets, BTK is important for signaling through the glycoprotein VI (GPVI) receptor that responds to collagen and has been shown to promote platelet aggregation and contribute to cytokine production from fibroblast-like synoviocytes (Hsu et al., 2013 *Immun. Letters*, 150:97). In monocytes and macrophages, the action of BTK in invoked in FcγRI induced signaling and may also have role in Toll-Like Receptor-induced cytokine responses including TLR2, TLR4, TLR8 & TLR9 (Horwood et al., 2003 *J. Exp. Med.*, 197:1603; Horwood et al., 2006 *J. Immunol.*, 176:3635; Perez de Diego et al., 2006 *Allerg. Clin. Imm.*, 117:1462; Doyle et al., 2007 *J. Biol. Chem.*, 282:36959, Hasan et al., 2007 *Immunology*, 123:239; Sochorava et al., 2007 *Blood*, 109:2553; Lee et al., 2008, *J. Biol. Chem.*, 283:11189).

Therefore, inhibition of BTK is expected to intervene at several critical junctions of the inflammatory reactions resulting in an effective suppression of autoimmune response. As such diseases involving B-cell receptor activation, antibody-Fc receptor interactions & GPVI receptor signaling may be modulated by treatment with BTK inhibitors. BTK inhibition is likely to act on both the initiation of autoimmune disease by blocking BCR signaling and the effector phase by abrogation of FcR signaling on macrophages, neutrophils, basophils, and mast cells. Furthermore, blocking BTK would provide additional benefit via inhibition of osteoclast maturation and therefore attenuate the bone erosions & overall joint destruction associated with rheumatoid arthritis. Inhibiting BTK may be useful in treating a host of inflammatory and allergic diseases—for example (but not limited to), rheumatoid arthritis (RA), systemic lupus erythematosus (SLE), multiple sclerosis (MS) and type I hypersensitivity reactions such as allergic rhinitis, allergic conjunctivitis, atopic dermatitis, allergic asthma and systemic anaphylaxis. For a review on targeting BTK as a treatment for inflammatory disorders and autoimmunity as well as leukemias and lymphomas, see Uckun & Qazi, 2010 *Expert Opin. Ther. Pat.*, 20:1457. Because BTK is highly expressed in cancers of the hematopoietic system & BTK-dependent signaling in believed to be disregulated there, BTK inhibitors are expected to be useful treatments for B-cell lymphomas/leukemias & other oncologic disease—for example (but not limited to) acute lymphoblastic leukemia (ALL), chronic lymphocytic leukemia (CLL), non-Hodgkin's lymphoma (NHL), small lymphocytic lymphoma (SLL), and acute myeloid leukemia (for review, see Buggy & Elias 2012 *Int Rev Immunol.* 31:119). Taken together, BTK inhibitors provide a strong method to treat a host of inflammatory diseases and immunological disorders as well as hematologic cancers.

Colony stimulating factor 1 receptor (CSF-1R) is a homodimeric, class III receptor tyrosine kinase that is encoded by the FMS proto-oncogene. It is a 972 amino acid transmembrane protein characterized by an extracellular ligand-binding domain, a single transmembrane domain (TM) a juxtamembrane domain (JM), two intracellular kinase domains (TK1 and TK2), divided by a kinase insert domain (KI), and a c-Terminal domain, UniProt Entry P07333 (Patel et al 2009 *Current Topics in Medicinal Chemistry* 9:599). Binding of CSF-1 to the extracellular domain of CSF-1R stabilizes receptor dimerization, induces trans-autophosphorylation of the intracellular domain, and activates downstream cytoplasmic signaling. Small molecule inhibitors of CSF-1R active site block receptor autophosphorylation and subsequently block the signals that control the survival, expression, proliferation and differentiation of macrophages.

CSF-1R regulates monocyte survival, proliferation and differentiation as well as macrophage migration (Pixley et al 2004 *TRENDS in Cell Biology*, 14:628). The natural ligands for CSF-1R have been identified as CSF-1 and IL-34. CSF-1R is expressed in myelomonocytic lineage cell, including hemopoietic progenitors, tissue macrophages, immature B cells, which are implicated in RA pathogenesis (Hamilton 2008 *Nature Reviews Immunology* 8:533). Activation of CSF-1R is known to play a role in a number of diseases including, but not limited to, RA, Chrohn's disease, ulcerative colitis, ankylosing spondylitis and cancer (Toh et al 2014 *Arthritis & Rheumatology* 66:2989: Hume et al 2012 *Blood* 119:1810 and Campbell et al 2000 *Journal of Leukocyte Biology* 68:144). The natural ligands, CSF-1 and IL-34, are highly expressed in the synovial membrane of RA patients, and CSF-1 levels are increased in the serum and synovial fluid of RA patients and associated with disease activity (Firestein et al 1988 *Journal of Experimental Medicine* 168:1573; Kawaji et al 1995 *Nippon Ika Daigaku Zasshi* 62:260; Ritchlin et al 1994 *Scand. J. Immunol.* 40:292; Takei et al 2000 *J. Rheumatol.* 27:894; Hwang et al 2012 *Arthritis Research & Therapy* 14:R14 and Chemel et al 2012 *Ann. Rheum. Dis.* 71:150).

Monocytes derived from RA patients express elevated levels of FcγR I, IIa and IIIa, increased CD14 and oxygen radicals, and reduced HLA-DR (Shinohara et al 1992 *J. Rheumatol.* 19:211). This monocyte phenotype can be produced in vitro and in vivo with recombinant CSF-1 (Weiner et al 1994 *Cancer Res.* 54:4084). Therefore, CSF-1 may drive the recruitment, differentiation and survival of RA synovial macrophages, and in the local proliferation of myeloid progenitors. Further, CSF-1 primes macrophages for greater expression of TNF and other cytokines (Hanamura 1997 *Immunopharmacology* 37:15). It has been proposed that CSF-1R is involved in a positive feedback loop for chronic inflammation where macrophages secrete TNF and IL-1 that induce stromal cell expression of CSF-1, leading to further expansion of macrophages and additional expression of TNF and IL-1 (Hamilton 1993 *Lancet* 342: 536).

CSF-1 deficient mice have been reported to be resistant to collagen induced arthritis and in a murine model of CIA, CSF-1 was shown to exacerbate disease while the neutralizing anti-CSF-1 antibody ameliorated disease (Campbell et al 2000 *Journal of Leukocyte Biology* 68:144). An anti-CSF-1R monoclonal antibody was also shown to be efficacious in 2 different animal models for RA (Toh et al 2014 *Arthritis & Rheumatology* 66:2989). Small molecule inhibitor, GW2580, has been shown to inhibit LPS-induced TNF production in mice (Conway et al 2005 *PNAS* 102:16078). Additionally, there are several reports of non-selective small molecule CSF-1R inhibitors that have shown efficacy in preclinical disease models for arthritis (Paniagua et al 2006 *J. Clin. Invest.* 116:2633; Conway et al 2008 *J. Pharmacol. Exp. Ther.* 326:41; Ohno et al 2008 *Eur. J. Immunol.* 38:283; Paniagua et al 2010 *Arthritis Res. Ther.* 12:R32 and Madan et al 2012 *J. Imuunol.* 189:4123).

Tumor associated macrophages have been associated with poor prognosis in various cancers and are involved in the promotion of angiogenesis, invasion and metastasis (Bingle et al 2002 *J. Pathol.* 196:254; Pollard 2004 *Nat. Rev. Cancer* 4:71 and Lewis et al 2006 *Cancer Res.* 66:605). CSF-1 deficient mice with MMTV-PyMT transgenic tumors exhibited decreased macrophage recruitment and a decreased rate of tumor progression to metastasis (Lewis et al 2006 *Cancer Res.* 66:605). Mammary epithelial expression of CSF-1 was shown to restore macrophage infiltration and metastatic tumor vasculature was characterized, and the induction of vasculature, was shown to be regulated by Tumor-associated macrophages (TAMs) (Lin et al 2001 *J. Exp. Med.* 193:727). Human mammary tumor xenografts in mice with CSF-1 antisense oligonucleotide (ODN-196) or small interfering RNAs CSF-1 siRNA and FMS siRNA) down-regulated target proteins and suppressed mammary tumor growth (Biswas et al 2008 *J. Immunol.* 180:2011). Expression of FMS in breast cancer has been linked to poor survivability and increased tumor size (Kluger et al 2004 *Clin. Cancer Res.* 10:173; Lin et al 2001 *J. Exp. Med.* 193:727; Yee et al 2000 *Anticancer Res.* 20:4379).

CSF-1 antibodies have shown therapeutic potential in treating solid tumors. Treatment with Anti-CSF01 Fab antibody in an MCF-7 mammary xenograft mouse model suppressed tumor growth (Paulus et al 2006 *Cancer Res.* 66:4349). A small molecule inhibitor, Ki20227, of CSF-1R suppressed osteolytic bone destruction in a metastasis model (Ohno 2006 *Mol. Cancer Ther.* 5:2634). In a separate study, CSF-1 production was also shown to contribute to osteoclastogenesis from TAMs and to tumor-associated osteolysis (Yang 2002 *J. Bone Joint Surg. Br.* 84:452).

Therefore inhibition of CSF-1 might be of therapeutic value in treatment of autoimmune diseases and cancer.

SUMMARY OF THE INVENTION

In a first embodiment the invention provides a compound of Formula (I)

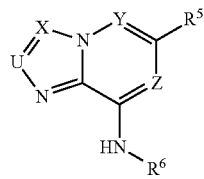

Formula (I)

wherein
U is $CR^1$ or N;
X is $CR^2$ or N;
Y is $CR^3$ or N;
Z is $CR^4$ or N;
$R^1$ is independently H or deuterium;
$R^2$ is H, deuterium, optionally substituted $(C_1-C_3)$alkyl, or $CF_3$;
$R^3$ is H, deuterium or optionally substituted $(C_1-C_3)$alkyl;
$R^4$ is H or deuterium;
$R^5$ is —$R^{501}$-L-$R^{502}$ wherein
  $R^{501}$ is a bond, —O—, —$OCH_2$—, or optionally substituted $(C_1-C_3)$alkylene,
  L is —C(=O)—, —$CH_2$N(H)C(=O)—, —N(H)C(=O)—, or —N(H)S(O)$_2$; or
  L is a bond and $R^{502}$ is —CN; or
  L is -$L^1$-$L^2$ wherein $L^1$ is attached to $R^{501}$ wherein
    $L^1$ is optionally substituted phenyl, optionally substituted heteroaryl, optionally substituted saturated or partially saturated heterocyclyl, or optionally substituted saturated or partially saturated $(C_3-C_7)$cycloalkyl and $L^2$ is a bond, —$CH_2$N($R^a$)—, —$CH_2$N($R^a$)C(O)—, —N($R^a$)C(O)—, —N($R^a$)S(O)$_2$— or —N($R^a$)—; or
    $L^1$ is a saturated or partially saturated heterocyclyl containing one or more heteroatoms wherein at least one heteroatom is nitrogen and $L^2$ is a bond, C(O) or —S(O)$_2$—;

$R^{502}$ is H, $CF_3$, OH, optionally substituted $(C_1-C_6)$alkyl, optionally substituted alkenyl, optionally substituted alkynyl, CN, or optionally substituted $(C_3-C_6)$cycloalkenyl;

$R^6$ is optionally substituted $(C_1-C_6)$alkyl, optionally substituted $(C_3-C_{12})$cycloalkyl, optionally substituted phenyl, optionally substituted heteroaryl, or optionally substituted heterocyclyl; or $R^6$ is —$R^{601}$-$R^{602}$ wherein $R^{601}$ is attached to the —N(H)— and $R^{601}$ is optionally substituted heteroaryl;

$R^{602}$ is $N(R^a)_2$, optionally substituted $(C_1-C_6)$alkyl, optionally substituted $(C_3-C_6)$cycloalkyl, or optionally substituted heterocyclyl; and $R^a$ is independently H or optionally substituted $(C_1-C_6)$alkyl;

provided the compound is not 2-(3-{8-[5-(morpholine-4-carbonyl)-pyridin-2-ylamino]-imidazo[1,2-a]pyridine-6-yl}-phenyl)-N-(5,5,5-trifluoro-4-hydroxy-4-methyl-pent-2-ynyl)-acetamide.

In a second embodiment the invention provides a compound according to the first embodiment wherein U is $CR^1$ or N;
X is $CR^2$ or N;
Y is $CR^3$ or N;
Z is $CR^4$ or N;
$R^1$ is independently H or deuterium;
$R^2$ is H, deuterium, optionally substituted $(C_1-C_3)$alkyl, or $CF_3$;
$R^3$ is H, deuterium or optionally substituted $(C_1-C_3)$alkyl;
$R^4$ is H or deuterium;
$R^5$ is —$R^{501}$-L-$R^{502}$ wherein
$R^{501}$ is a bond, —O—, —$OCH_2$—, or optionally substituted $(C_1-C_3)$alkylene,
L is —C(=O)—, —$CH_2$N(H)C(=O)—, —N(H)C(=O)—, or —N(H)S(O)$_2$; or
L is a bond and $R^{502}$ is —CN; or
L is -$L^1$-$L^2$ wherein $L^1$ is attached to $R^{501}$ wherein
  $L^1$ is optionally substituted phenyl, optionally substituted heteroaryl, optionally substituted saturated or partially saturated heterocyclyl, or optionally substituted saturated or partially saturated $(C_3-C_6)$cycloalkyl and $L^2$ is a bond, —$CH_2$N($R^a$)—, —$CH_2$N($R^a$)C(O)—, —N($R^a$)C(O)—, —N($R^a$)S(O)$_2$— or —N($R^a$)—; or
  $L^1$ is a saturated or partially saturated heterocyclyl containing one or more heteroatoms wherein at least one heteroatom is nitrogen and $L^2$ is a bond, C(O) or —S(O)$_2$—;
$R^{502}$ is H, optionally substituted alkenyl, optionally substituted alkynyl, CN, or optionally substituted $(C_3-C_6)$cycloalkenyl;
$R^6$ is optionally substituted $(C_1-C_6)$alkyl, optionally substituted $(C_3-C_{12})$cycloalkyl, optionally substituted phenyl, optionally substituted heteroaryl, or optionally substituted heterocyclyl; and
$R^a$ is independently H or optionally substituted $(C_1-C_6)$alkyl.

In a third embodiment the invention provides a compound according to any of the foregoing embodiments wherein
L is —C(=O)—, —$CH_2$N(H)C(=O)—, —N(H)C(=O)—, or —S(O)$_2$; and $R^{502}$ is H, —CH=$CH_2$ or —C≡CH; or
L is a bond and $R^{502}$ is —CN; or
L is -$L^1$-$L^2$ wherein $L^1$ is attached to $R^{501}$ wherein
  $L^1$ is optionally substituted phenyl, optionally substituted heteroaryl or optionally substituted saturated or partially saturated $(C_3-C_6)$cycloalkyl and $L^2$ is —$CH_2$N($R^a$)—, —$CH_2$N($R^a$)C(O)—, —N($R^a$)C(O)—, —N($R^a$)S(O)$_2$— or —N($R^a$)—; or
$L^1$ is optionally substituted heteroaryl, optionally substituted azepanyl, optionally substituted azetidinyl, optionally substituted morpholinyl, optionally substituted oxazepanyl, optionally substituted piperidinyl, optionally substituted pyrrolidinyl, optionally substituted tetrahydrofuranyl, or optionally substituted tetrahydropyranyl, and $L^2$ is a bond, C(O) or —S(O)$_2$—.

In a fourth embodiment the invention provides a compound according to any of the foregoing embodiments wherein $R^6$ is optionally substituted $(C_1-C_6)$alkyl, optionally substituted phenyl, optionally substituted bicycle[1.1.1]pentanyl, optionally substituted 1,2,4 oxadiazolyl, optionally substituted pyrazolyl, optionally substituted pyridazinyl, optionally substituted pyridinyl, 4,5-dihydro-1H-benzo[b]azepin-2(3H)-one, 3,4-dihydroquinolin-2(1H)-one, 2H-benzo[b][1,4]oxazin-3(4H)-one, or 6,7-dihydro-4H-pyrazolo[5,1-c][1,4]oxazinyl.

In a fifth embodiment the invention provides a compound according to any of the foregoing embodiments wherein $R^6$ is optionally substituted with one or more substituents independently selected from $(C_1-C_3)$alkyl, $(C_1-C_3)$alkoxy, optionally substituted imidazolidinone, or morpholinyl.

In a sixth embodiment the invention provides a compound according to any of the foregoing embodiments wherein -L-$R^{502}$ forms —CN, —$CH_2$N(H)C(=O)CH=$CH_2$, —C(=O)CH=$CH_2$, —N(H)C(=O)CH=$CH_2$, —N(H)CN, or —S(O)$_2$CH=$CH_2$.

In a seventh embodiment the invention provides a compound according to compound according to any of the foregoing embodiments wherein the compound is N-(3-(8-((4-morpholinophenyl)amino)-1,8a-dihydro-[1,2,4]triazolo[1,5-a]pyrazin-5-yl)benzyl)acrylamide;

N-(3-(8-(bicyclo[1.1.1]pentan-1-ylamino)-1,8a-dihydro-[1,2,4]triazolo[1,5-a]pyrazin-5-yl)benzyl)acrylamide;

N-(3-(8-(bicyclo[0.1.1.1]pentan-1-ylamino)-1,8a-dihydro-[1,2,4]triazolo[1,5-a]pyrazin-5-yl)phenyl)acrylamide;

1-(3-(8-((3,4-dimethoxyphenyl)amino)-1,8a-dihydro-[1,2,4]triazolo[1,5-a]pyrazin-5-yl)pyrrolidin-1-yl)prop-2-en-1-one;

8-((5-(1-acryloylpyrrolidin-3-yl)-1,8a-dihydro-[1,2,4]triazolo[1,5-a]pyrazin-8-yl)amino)-4,5-dihydro-1H-benzo[b]azepin-2(3H)-one;

1-(3-(8-((4-morpholinopyridin-2-yl)amino)-1,8a-dihydro-[1,2,4]triazolo[1,5-a]pyrazin-5-yl)pyrrolidin-1-yl)prop-2-en-1-one;

1-(3-(8-((5-methoxypyridazin-3-yl)amino)-1,8a-dihydro-[1,2,4]triazolo[1,5-a]pyridin-5-yl)pyrrolidin-1-yl)prop-2-en-1-one;

N-(2-(8-(bicyclo[1.1.1]pentan-1-ylamino)-1,8a-dihydro-[1,2,4]triazolo[1,5-a]pyrazin-5-yl)phenyl)acrylamide;

1-((3R)-3-(8-((3,4-dimethoxyphenyl)amino)-1,8a-dihydro-[1,2,4]triazolo[1,5-a]pyrazin-6-yl)pyrrolidin-1-yl)prop-2-en-1-one;

1-((3S)-3-(8-((3,4-dimethoxyphenyl)amino)-1,8a-dihydro-[1,2,4]triazolo[1,5-a]pyrazin-6-yl)pyrrolidin-1-yl)prop-2-en-1-one;

8-((6-(1-acryloylpiperidin-3-yl)-[1,2,4]triazolo[1,5-a]pyrazin-8-yl)amino)-4,5-dihydro-1H-benzo[b]azepin-2(3H)-one;

N-(3-(8-((2-oxo-2,3,4,5-tetrahydro-1H-benzo[b]azepin-8-yl)amino)-[1,2,4]triazolo[1,5-a]pyrazin-6-yl)phenyl)acrylamide;

N-(3-(8-((2-oxo-2,3,4,5-tetrahydro-1H-benzo[b]azepin-8-yl)amino)-[1,2,4]triazolo[1,5-a]pyrazin-6-yl)benzyl)acrylamide;

1-(3-(8-((1-methyl-1H-pyrazol-3-yl)amino)-[1,2,4]triazolo[1,5-a]pyridin-6-yl)pyrrolidin-1-yl)prop-2-en-1-one;

7-((6-(1-acryloylpyrrolidin-3-yl)-[1,2,4]triazolo[1,5-a]pyrazin-8-yl)amino)-3,4-dihydroquinolin-2(1H)-one;

6-((6-(1-acryloylpyrrolidin-3-yl)-[1,2,4]triazolo[1,5-a]pyrazin-8-yl)amino)-2H-benzo[b][1,4]oxazin-3(4H)-one;

8-((6-(1-acryloylpyrrolidin-3-yl)-[1,2,4]triazolo[1,5-a]pyridin-8-yl)amino)-4,5-dihydro-1H-benzo[b]azepin-2(3H)-one;

(S)-8-((6-(1-acryloylpyrrolidin-3-yl)imidazo[1,2-a]pyrazin-8-yl)amino)-4,5-dihydro-1H-benzo[b]azepin-2(3H)-one;

(R)-8-((6-(1-acryloylpyrrolidin-3-yl)imidazo[1,2-a]pyrazin-8-yl)amino)-4,5-dihydro-1H-benzo[b]azepin-2(3H)-one;

(S)—N-(3,4-dimethoxyphenyl)-6-(1-(vinylsulfonyl)pyrrolidin-3-yl)-[1,2,4]triazolo[1,5-a]pyrazin-8-amine;

1-(3-(8-((6,7-dihydro-4H-pyrazolo[5,1-c][1,4]oxazin-2-yl)amino)-[1,2,4]triazolo[1,5-a]pyridin-6-yl)pyrrolidin-1-yl)prop-2-en-1-one;

1-(3-(8-((1-methyl-1H-pyrazol-3-yl)amino)-[1,2,4]triazolo[1,5-a]pyridin-6-yl)piperidin-1-yl)prop-2-en-1-one;

1-(3-(8-((6-morpholinopyridazin-3-yl)amino)-[1,2,4]triazolo[1,5-a]pyridin-6-yl)piperidin-1-yl)prop-2-en-1-one;

1-(3-(8-(methylamino)-[1,2,4]triazolo[1,5-a]pyrazin-6-yl)pyrrolidin-1-yl)prop-2-en-1-one;

1-(3-(8-((2-methoxyethyl)amino)-[1,2,4]triazolo[1,5-a]pyrazin-6-yl)pyrrolidin-1-yl)prop-2-en-1-one;

1-(3-(8-((5-morpholinopyridin-2-yl)amino)-[1,2,4]triazolo[1,5-a]pyridin-6-yl)piperidin-1-yl)prop-2-en-1-one;

1-(3-(8-((1-methyl-1H-pyrazol-4-yl)amino)-[1,2,4]triazolo[1,5-a]pyrazin-6-yl)pyrrolidin-1-yl)prop-2-en-1-one;

1-(3-(8-((6-morpholinopyridin-2-yl)amino)-[1,2,4]triazolo[1,5-a]pyridin-6-yl)piperidin-1-yl)prop-2-en-1-one;

1-(3-(8-((6,7-dihydro-4H-pyrazolo[5,1-c][1,4]oxazin-2-yl)amino)-[1,2,4]triazolo[1,5-a]pyridin-6-yl)piperidin-1-yl)prop-2-en-1-one;

(S)-1-(3-(8-((1-methyl-1H-pyrazol-3-yl)amino)-[1,2,4]triazolo[1,5-a]pyridin-6-yl)pyrrolidin-1-yl)prop-2-en-1-one;

(R)-1-(3-(8-((1-methyl-1H-pyrazol-3-yl)amino)-[1,2,4]triazolo[1,5-a]pyridin-6-yl)pyrrolidin-1-yl)prop-2-en-1-one;

1-(3-(8-((6-morpholinopyridin-3-yl)amino)-[1,2,4]triazolo[1,5-a]pyridin-6-yl)piperidin-1-yl)prop-2-en-1-one;

1-(3-(8-((6-morpholinopyridin-3-yl)amino)-[1,2,4]triazolo[1,5-a]pyridin-6-yl)pyrrolidin-1-yl)prop-2-en-1-one;

1-(3-(8-((3-isopropyl-1,2,4-oxadiazol-5-yl)amino)-[1,2,4]triazolo[1,5-a]pyridin-6-yl)piperidin-1-yl)prop-2-en-1-one;

N-((1R,3S)-3-(8-((1-methyl-1H-pyrazol-3-yl)amino)-[1,2,4]triazolo[1,5-a]pyridin-6-yl)cyclohexyl)acrylamide;

N—((1S,3S)-3-(8-((1-methyl-1H-pyrazol-3-yl)methyl)-[1,2,4]triazolo[1,5-a]pyridin-6-yl)cyclohexyl)acrylamide;

1-(3-(8-((3-methyl-1,2,4-oxadiazol-5-yl)amino)-[1,2,4]triazolo[1,5-a]pyridin-6-yl)piperidin-1-yl)prop-2-en-1-one;

N—((1S,3S)-3-(8-((1-methyl-1H-pyrazol-3-yl)amino)-[1,2,4]triazolo[1,5-a]pyridin-6-yl)cyclohexyl)cyanamide;

3-(8-((1-methyl-1H-pyrazol-3-yl)amino)-[1,2,4]triazolo[1,5-a]pyridin-6-yl)piperidine-1-carbonitrile;

3-(8-((1-methyl-1H-pyrazol-3-yl)amino)-[1,2,4]triazolo[1,5-a]pyridin-6-yl)pyrrolidine-1-carbonitrile;

1-(4-((6-(1-acryloylpyrrolidin-3-yl)-[1,2,4]triazolo[1,5-a]pyrazin-8-yl)amino)phenyl)-3-methylimidazolidin-2-one;

3-(8-((1-methyl-1H-pyrazol-3-yl)amino)-[1,2,4]triazolo[1,5-a]pyrazin-6-yl)pyrrolidine-1-carbonitrile;

N-((1R,3S)-3-(8-((1-methyl-1H-pyrazol-3-yl)amino)-[1,2,4]triazolo[1,5-a]pyridin-6-yl)cyclopentyl)acrylamide;

N-((1S)-3-(8-((1-methyl-1H-pyrazol-3-yl)amino)-[1,2,4]triazolo[1,5-a]pyridin-6-yl)cyclopentyl)acrylamide;

3-(8-((6,7-dihydro-4H-pyrazolo[5,1-c][1,4]oxazin-2-yl)amino)-[1,2,4]triazolo[1,5-a]pyridin-6-yl)piperidine-1-carbonitrile;

(S)-1-(3-(8-((6,7-dihydro-4H-pyrazolo[5,1-c][1,4]oxazin-2-yl)amino)-[1,2,4]triazolo[1,5-a]pyridin-6-yl)pyrrolidin-1-yl)prop-2-en-1-one;

(R)-1-(3-(8-((6,7-dihydro-4H-pyrazolo[5,1-c][1,4]oxazin-2-yl)amino)-[1,2,4]triazolo[1,5-a]pyridin-6-yl)pyrrolidin-1-yl)prop-2-en-1-one;

1-(3-(8-((1-methyl-1H-pyrazol-3-yl)amino)-[1,2,4]triazolo[1,5-a]pyrazin-6-yl)pyrrolidin-1-yl)prop-2-en-1-one;

(S)-1-(3-(8-((1-methyl-1H-pyrazol-4-yl)amino)-[1,2,4]triazolo[1,5-a]pyridin-6-yl)pyrrolidin-1-yl)prop-2-en-1-one;

(R)-1-(3-(8-((1-methyl-1H-pyrazol-4-yl)amino)-[1,2,4]triazolo[1,5-a]pyridin-6-yl)pyrrolidin-1-yl)prop-2-en-1-one;

(S)-1-(3-(8-((6,7-dihydro-4H-pyrazolo[5,1-c][1,4]oxazin-2-yl)amino)-[1,2,4]triazolo[1,5-a]pyridin-6-yl)piperidin-1-yl)prop-2-en-1-one;

1-(3-(8-((6,7-dihydro-4H-pyrazolo[5,1-c][1,4]oxazin-2-yl)amino)imidazo[1,2-b]pyridazin-6-yl)pyrrolidin-1-yl)prop-2-en-1-one; or (R)-1-(3-(8-((6,7-dihydro-4H-pyrazolo[5,1-c][1,4]oxazin-2-yl)amino)-[1,2,4]triazolo[1,5-a]pyridin-6-yl)piperidin-1-yl)prop-2-en-1-one.

In an eighth embodiment the invention provides a compound according to compound according to any of the foregoing embodiments wherein $R^5$ is —$R^{501}$-L-$R^{502}$ wherein
$R^{501}$ is a bond;
L is -$L^1$-$L^2$ wherein $L^1$ is attached to $R^{501}$ wherein
$L^1$ is optionally substituted saturated or partially saturated ($C_3$-$C_7$)cycloalkyl and $L^2$ is a bond-$CH_2N(R^a)C(O)$—, or —$N(R^a)C(O)$—; and
$R^{502}$ is H, $CF_3$, OH, optionally substituted ($C_1$-$C_6$)alkyl, optionally substituted alkenyl, optionally substituted alkynyl, CN, or optionally substituted ($C_3$-$C_6$)cycloalkenyl.

In a ninth embodiment the invention provides a compound according to compound according to any of the foregoing embodiments wherein $R^6$ is optionally substituted ($C_1$-$C_6$)alkyl, optionally substituted ($C_3$-$C_{12}$)cycloalkyl, optionally substituted phenyl, optionally substituted pyrazolyl, optionally substituted 6,7-dihydro-4H-pyrazolo[5,1-c][1,4]oxazinyl, optionally substituted 4,5,6,7-tetrahydropyrazolo[1,5-a]pyrazinyl; or $R^6$ is —$R^{601}$-$R^{602}$ wherein $R^{601}$ is attached to the —N(H)— and
$R^{601}$ is optionally substituted pyrazolyl, or optionally substituted pyridinyl;
$R^{602}$ is N($R^a$)$_2$, optionally substituted ($C_1$-$C_6$)alkyl, optionally substituted ($C_3$-$C_6$)cycloalkyl, optionally substituted azetidinyl, optionally substituted morpholinyl, optionally substituted piperidinyl, or optionally substituted tetrahydropyranyl.

In a tenth embodiment the invention provides a compound according to claim 9 wherein $R^1$ is H.

In an eleventh embodiment the invention provides a compound according to compound according to any of the foregoing embodiments wherein X is N or CR² wherein R² is H, optionally substituted (C₁-C₃)alkyl, or CF₃.

In a twelfth embodiment the invention provides a compound according to compound according to any of the foregoing embodiments wherein R³ is H, deuterium or optionally substituted (C₁-C₃)alkyl.

In a thirteenth embodiment the invention provides a according to compound according to any of the foregoing embodiments wherein U is CH.

In a fourteenth embodiment the invention provides a compound according to compound according to any of the foregoing embodiments wherein X is N.

In a fifteenth embodiment the invention provides a compound according to compound according to any of the foregoing embodiments wherein the compound is
4-(4-((6-cyclohexyl-[1,2,4]triazolo[1,5-a]pyrazin-8-yl)amino)-1H-pyrazol-1-yl)-2-methylbutan-2-ol;
6-cyclohexyl-N-(1-(tetrahydro-2H-pyran-4-yl)-1H-pyrazol-4-yl)-[1,2,4]triazolo[1,5-a]pyrazin-8-amine;
6-cyclohexyl-N-(1-(2,2,6,6-tetramethyltetrahydro-2H-pyran-4-yl)-1H-pyrazol-4-yl)-[1,2,4]triazolo[1,5-a]pyrazin-8-amine;
6-cyclohexyl-N-(1-(oxetan-3-yl)-1H-pyrazol-4-yl)-[1,2,4]triazolo[1,5-a]pyrazin-8-amine;
(1R,4R)-4-(4-((6-cyclohexyl-[1,2,4]triazolo[1,5-a]pyrazin-8-yl)amino)-1H-pyrazol-1-yl)cyclohexanol;
(1s,4s)-4-(4-((6-cyclohexyl-[1,2,4]triazolo[1,5-a]pyrazin-8-yl)amino)-1H-pyrazol-1-yl)cyclohexanol;
6-cyclohexyl-N-(1H-pyrazol-4-yl)-[1,2,4]triazolo[1,5-a]pyrazin-8-amine;
(6-cyclohexyl-N-(1-(piperidin-4-yl)-1H-pyrazol-4-yl)-[1,2,4]triazolo[1,5-a]pyrazin-8-amine;
6-cyclopentyl-N-(1-(piperidin-4-yl)-1H-pyrazol-4-yl)-[1,2,4]triazolo[1,5-a]pyrazin-8-amine;
6-cyclohexyl-N-(1-isopropyl-1H-pyrazol-4-yl)-[1,2,4]triazolo[1,5-a]pyrazin-8-amine;
6-(4,4-dimethylcyclohexyl)-N-(1-methyl-1H-pyrazol-4-yl)-[1,2,4]triazolo[1,5-a]pyrazin-8-amine;
N-(1-methyl-1H-pyrazol-4-yl)-6-((1R,4R)-4-methylcyclohexyl)-[1,2,4]triazolo[1,5-a]pyrazin-8-amine;
N-(1-methyl-1H-pyrazol-4-yl)-6-((1S,4S)-4-methylcyclohexyl)-[1,2,4]triazolo[1,5-a]pyrazin-8-amine;
N-(1-methyl-1H-pyrazol-4-yl)-6-((1R,4R)-4-(trifluoromethyl)cyclohexyl)-[1,2,4]triazolo[1,5-a]pyrazin-8-amine;
N-(6-cyclohexyl-[1,2,4]triazolo[1,5-a]pyridin-8-yl)-6,7-dihydro-4H-pyrazolo[5,1-c][1,4]oxazin-2-amine;
6-cyclohexyl-N-(5-methyl-4,5,6,7-tetrahydropyrazolo[1,5-a]pyrazin-2-yl)-[1,2,4]triazolo[1,5-a]pyridin-8-amine;
6-cyclopentyl-N-(1-methyl-1H-pyrazol-4-yl)-[1,2,4]triazolo[1,5-a]pyrazin-8-amine;
6-cyclopentyl-N-(5-methyl-4,5,6,7-tetrahydropyrazolo[1,5-a]pyrazin-2-yl)-[1,2,4]triazolo[1,5-a]pyridin-8-amine;
1-(4-(4-((6-cyclohexyl-[1,2,4]triazolo[1,5-a]pyrazin-8-yl)amino)-1H-pyrazol-1-yl)piperidin-1-yl)ethanone;
4-(4-((6-cyclohexyl-[1,2,4]triazolo[1,5-a]pyrazin-8-yl)amino)-1H-pyrazol-1-yl)-N-methylpiperidine-1-carboxamide;
(1S,3S)-3-(4-((6-cyclohexyl-[1,2,4]triazolo[1,5-a]pyrazin-8-yl)amino)-1H-pyrazol-1-yl)cyclohexanol;
(1R,3R)-3-(4-((6-cyclohexyl-[1,2,4]triazolo[1,5-a]pyrazin-8-yl)amino)-1H-pyrazol-1-yl)cyclohexanol;
(1R,3S)-3-(4-((6-cyclohexyl-[1,2,4]triazolo[1,5-a]pyrazin-8-yl)amino)-1H-pyrazol-1-yl)cyclohexanol;
(1S,3R)-3-(4-((6-cyclohexyl-[1,2,4]triazolo[1,5-a]pyrazin-8-yl)amino)-1H-pyrazol-1-yl)cyclohexanol;
(1R,3R)-3-(8-((1-methyl-1H-pyrazol-4-yl)amino)-[1,2,4]triazolo[1,5-a]pyrazin-6-yl)cyclohexanol;
1-(4-((6-cyclohexyl-[1,2,4]triazolo[1,5-a]pyrazin-8-yl)amino)-1H-pyrazol-1-yl)-2-methylpropan-2-ol;
N-(6-cyclopentyl-[1,2,4]triazolo[1,5-a]pyridin-8-yl)-6,7-dihydro-4H-pyrazolo[5,1-c][1,4]oxazin-2-amine;
1-(6-((6-cyclohexyl-[1,2,4]triazolo[1,5-a]pyridin-8-yl)amino)pyridin-3-yl)piperidin-4-ol;
6-cyclohexyl-N-(1-(1-methylpiperidin-4-yl)-1H-pyrazol-4-yl)-[1,2,4]triazolo[1,5-a]pyrazin-8-amine;
(1S,4S)-ethyl 4-(4-((6-cyclohexyl-[1,2,4]triazolo[1,5-a]pyrazin-8-yl)amino)-1H-pyrazol-1-yl)cyclohexanecarboxylate;
6-cyclopentyl-N-(1-(piperidin-4-yl)-1H-pyrazol-4-yl)-[1,2,4]triazolo[1,5-a]pyrazin-8-amine; or
6-cyclohexyl-N-(1-methyl-1H-pyrazol-4-yl)-[1,2,4]triazolo[1,5-a]pyrazin-8-amine.

In a sixteenth embodiment, the invention provides a method of treating a disease comprising administering a therapeutically effective amount of a compound according to any of the foregoing embodiments to a patient in need thereof.

In a seventeenth embodiment the invention provides a method according to the sixteenth embodiment, wherein the disease is rheumatoid arthritis, juvenile rheumatoid arthritis, osteoarthritis, Crohn's disease, inflammatory bowel disease, irritable bowel syndrome, ulcerative colitis, psoriatic arthritis, psoriasis, ankylosing spondylitis, interstitial cystitis, asthma, systemic lupus erythematosus, lupus nephritis, B cell chronic lymphocytic lymphoma, multiple sclerosis, chronic lymphocytic leukemia, small lymphocytic lymphoma, mantle cell lymphoma, B-cell non-Hodgkin's lymphoma, activated B-cell like diffuse large B-cell lymphoma, multiple myeloma, diffuse large B-cell lymphoma, follicular lymphoma, hairy cell leukemia or Lymphoblastic lymphoma.

In an eighteenth embodiment the invention provides a kit comprising a packaged product comprising components with which to administer a compound according to any of the first through fifteenth embodiments for treatment of an autoimmune disorder.

In a nineteenth embodiment the invention provides a kit according to the eighteenth embodiment, wherein the packaged product comprises a compound first through fifteenth embodiments and instructions for use.

In a twentieth embodiment the invention provides a pharmaceutical composition comprising a compound according to any one of the first to the fifteenth embodiment, and one or more pharmaceutically acceptable excipients.

DETAILED DESCRIPTION OF THE INVENTION

Protein kinases are a broad and diverse class, of over 500 enzymes, that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and serine/threonine kinases as a result of their substrate specificity.

The protein kinases represent a large family of proteins that play a central role in the regulation of a wide variety of cellular processes and maintenance of cellular function. A partial, non-limiting, list of these kinases include: non-receptor tyrosine kinases such as the Tec family (BTK, ITK, Tec, ETK/BMX & RLK/TXK), Janus kinase family (Jak1, Jak2, Jak3 and Tyk2); the fusion kinases, such as BCR-Abl, focal adhesion kinase (FAK), Fes, Lck and Syk; receptor tyrosine kinases such as epidermal growth factor receptor (EGFR), the platelet-derived growth factor receptor kinase (PDGF-R), the receptor kinase for stem cell factor, c-kit, the hepatocyte growth factor receptor, c-Met, and the fibroblast growth factor receptor, FGFR3; and serine/threonine kinases such as b-RAF, mitogen-activated protein kinases (e.g., MKK6) and SAPK2β. Aberrant kinase activity has been observed in many disease states including benign and malignant proliferative disorders as well as diseases resulting from inappropriate activation of the immune and nervous systems. The novel compounds of this invention inhibit the activity of one or more protein kinases and are, therefore, expected to be useful in the treatment of kinase-mediated diseases.

Bruton's tyrosine kinase (BTK) is a non-receptor tyrosine kinase with a key role in immunoreceptor signaling (BCR, FcεR, FcγR, DAP12, Dectin-1, GPVI, etc.) in a host of hematopoietic cells including B cells, platelets, mast cells, basophils, eosinophils, macrophages and neutrophils as well as osteoclasts involved in bone destruction (for reviews, see Brunner et al., 2005 *Histol. Histopathol.*, 20:945, Mohamed et al., 2009 *Immunol. Rev.*, 228:58). Mutations in BTK are known to lead to X-linked agammaglobulinemia (XLA) in humans and X-linked immunodeficiency (Xid) in mice, which are characterized by limited B-cell production & reduced antibody titers (Lindvall et al., 2005 *Immunol. Rev.*, 203:200). The combined action of BTK in multiple cell types makes it an attractive target for autoimmune disease. BTK is related with sequence homology to other Tec family kinases (ITK, Tec, ETK/BMX & RLK/TXK).

In B-lymphocytes, BTK is required for B-cell development and for Ca2+ mobilization following of B-cell receptor (BCR) engagement (Khan et al., 1995 *Immunity* 3:283; Genevier et al., 1997 *Clin. Exp. Immun.*, 110:286) where it is believed to downstream of Src family kinases (such as Lyn), Syk & PI3K. BTK has been shown to be important for both thymus-dependent and thymus-independent type 2 responses to antigens (Khan et al., *Immunity* 1995; 3; 283). In mast cells, studies using BTK mouse knock-outs (Hata et al., 1998 *J. Exp. Med.*, 187:1235; Schmidt et al., 2009 *Eur. J. Immun.*, 39:3228) indicate a role for BTK in FcεRI induced signaling, histamine release & production of cytokines such as TNF, IL-2, & IL-4. In platelets, BTK is important for signaling through the glycoprotein VI (GPVI) receptor that responds to collagen and has been shown to promote platelet aggregation and contribute to cytokine production from fibroblast-like synoviocytes (Hsu et al., 2013 *Immun. Letters* 150:97). In monocytes and macrophages, the action of BTK in invoked in FcγRI induced signaling and may also have role in Toll-Like Receptor-induced cytokine responses including TLR2, TLR4, TLR8 & TLR9 (Horwood et al., 2003 *J. Exp. Med.*, 197:1603; Horwood et al., 2006 *J. Immunol.*, 176:3635; Perez de Diego et al., 2006 *Allerg. Clin. Imm.*, 117:1462; Doyle et al., 2007 *J. Biol. Chem.*, 282:36959, Hasan et al., 2007 *Immunology*, 123:239; Sochorava et al., 2007 *Blood*, 109:2553; Lee et al., 2008, *J. Biol. Chem.*, 283:11189).

Therefore, inhibition of BTK is expected to intervene at several critical junctions of the inflammatory reactions resulting in an effective suppression of autoimmune response. As such diseases involving B-cell receptor activation, antibody-Fc receptor interactions & GPVI receptor signaling may be modulated by treatment with BTK inhibitors. BTK inhibition is likely to act on both the initiation of autoimmune disease by blocking BCR signaling and the effector phase by abrogation of FcR signaling on macrophages, neutrophils, basophils, and mast cells. Furthermore, blocking BTK would provide additional benefit via inhibition of osteoclast maturation and therefore attenuate the bone erosions & overall joint destruction associated with rheumatoid arthritis. Inhibiting BTK may be useful in treating a host of inflammatory and allergic diseases—for example (but not limited to), rheumatoid arthritis (RA), systemic lupus erythematosus (SLE), multiple sclerosis (MS) and type I hypersensitivity reactions such as allergic rhinitis, allergic conjunctivitis, atopic dermatitis, allergic asthma and systemic anaphylaxis. For a review on targeting BTK as a treatment for inflammatory disorders and autoimmunity as well as leukemias and lymphomas, see Uckun & Qazi 2010 *Expert Opin Ther Pat* 20:1457. Because BTK is highly expressed in cancers of the hematopoietic system & BTK-dependent signaling in believed to be disregulated there, BTK inhibitors are expected to be useful treatments for B-cell lymphomas/leukemias & other oncologic disease—for example (but not limited to) acute lymphoblastic leukemia (ALL), chronic lymphocytic leukemia (CLL), non-Hodgkin's lymphoma (NHL), small lymphocytic lymphoma (SLL), and acute myeloid leukemia (for review, see Buggy & Elias 2012 *Int Rev Immunol*. 31:119). Taken together, BTK inhibitors provide a strong method to treat a host of inflammatory diseases and immunological disorders as well as hematologic cancers.

All kinases bind a common molecule, ATP, and therefore have structurally similar binding pockets. Therefore, one of the challenges for any kinase inhibitor is that they are prone to inhibit more than one kinase due to the homology of the binding pocket. For example, staurosporine, a well characterized promiscuous kinase inhibitor, has been shown to inhibit at least 253 with a $k_d$ of <3 μM kinases from the human kinome (see Nature Biotechnology, 208, 26, p. 127). Additionally, several marketed kinase inhibitors are known to inhibit more than one intended kinase, for example Imatinib (Gleevec®) targets ABL, ARG, PDGFR-α/β and c-KIT kinases, sorafenib (Nexavar®) targets B-RAF, VEGFRs, PDGFR-α/β, FLT3 and c-KIT and sunitinib (Sutent®) targets VEGFR, PDGFR, CSF-1R, FLT3 and c-KIT (Nature Reviews Drug Discovery 2011, 10, 111).

Inhibition of certain kinases in the human kinome are known to have undesired effects when used as pharmaceutical treatment. For instance, a number of kinase targets have been implicated in playing a role in the cardiotoxicity profiles for kinase inhibitors that are currently on the market. These kinases can include, but not limited to, VEGFR2, PI3K, AKT, PDGFR-α/β, AMPK, GSK3, ERKs, CDK2, Aurora, PLK, JNK, CAMKII<, PDK1, mTOR, LKB1, CAMKKβ, MEK1/2, PKA, PKCα, RAF1, B-RAF, EGFR, ERBB2, c-Kit, ABL, ARG, JAK2, FAK, DMPK, LTK, ROCK, LKB1, LDB3, PIM, GRK2, GRK5, ASK1, and PTEN (see *Nature Reviews Drug Discovery* 2011, 10:111). One example from a marketed kinase inhibitor is that in clinical trials with sunitinib, patients were found to be at increased risk for hypertension (see *The Lancet* 2006, 368: 1329; and *J. Clin. Oncol.* 2009, 27:3584). Subsequent research on the mechanism for the increased hypertension suggest that while PDGFR and VEGFR may be playing a role, off-target kinase inhibition, such as AMPK, may also be contributing to sunitinib's increased risk for hypertension (*Curr. Hypertens. Rep.* 2011, 13:436). Additionally, there is a patent application, US 2011/0212461, that has been filed that is a method for the prediction of cardiotoxicity based on the activity versus a list of kinases including KIT, FYN, PDGFR beta, FGR, LCK, Ephrin Receptor B2, FRK, ABL1, PDGFR1 alpha, HCK, ABL2, LYN, ZAK, YES1, MAP4K4, PKN1, BRAF, DDR2, MAP4K5 and STK24. Therefore, identification of kinase inhibitors with a selective profile Btk or CSF-1R kinase are desirable. The compounds of this invention are selective for the inhibition of Btk or CSF-1R over other kinases.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

Many autoimmune diseases and disease associated with chronic inflammation, as well as acute responses, have been linked to excessive or unregulated production or activity of one or more cytokines.

The compounds of the invention are also useful in the treatment of rheumatoid arthritis, asthma, allergic asthma, osteoarthritis, juvenile arthritis, ankylosing spondylitis, an ocular condition, interstitial cystitis, a cancer, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, irritable bowel syndrome, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, pneumocystis carinii pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

In yet other embodiments, the compounds described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplamacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt's lymphoma/leukemia, lymphomatoid granulomatosis, pancreatic cancer, solid or hematological tumors, a benign or malignant tumor, carcinoma of the brain, kidney (e.g., renal cell carcinoma (RCC)), squamous cell carcinoma, salivary gland carcinoma, liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia.

In yet other embodiments, the compounds described herein can be used to treat Behcet's disease, osteoporosis, bone cancer, and bone metastasis, systemic sclerosis, contact dermatitis and other eczematous dermatitis, seborrhoetic dermatitis, lichen planus, epidermolysis bullosa, angiodermas, vasculitides, cutaneous eosinophilias, or vernal conjunctivitis.

In yet other embodiments, the compounds described herein can be used to treat those conditions characterized by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung, and idiopathic interstitial pneumonia.

Compounds of Formula (I) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, MMP-13 and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (U.S. Pat. No. 6,090,382, HUMIRA™), CA2

(REMICADE™), SIMPONI™ (golimumab), CIMZIA™, ACTEMRA™, CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, JAK1, JAK2, JAK3, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, tofacitinib, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. Preferred combinations include methotrexate and leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, p38 or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (U.S. Pat. No. 6,090,382, HUMIRA™), CA2 (REMICADE™), CDP 571, TNFR-Ig constructs, (p75TNFRIgG (ENBREL™) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

Non-limiting examples of therapeutic agents for asthma with which a compound of Formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (I) (can be combined include the following: Interferon-alpha-2α, Interferon-alpha-2β, Interferon-alpha con1, Interferon-alpha-n1, pegylated interferon-alpha-2α, pegylated interferon-alpha-2β, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) (can be combined include the following: prednisone, azathioprine, albuterol, colchicine, albuterol sulfate, digoxin, gamma interferon, methylprednisolone sodium succinate, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hydrochloride/magnesium carbonate, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (U.S. Pat. No. 6,090,382, HUMIRA™), and efalizumab.

Non-limiting examples of therapeutic agents for restenosis with which a compound of Formula (I) can be combined include the following: sirolimus, paclitaxel, everolimus, tacrolimus, ABT-578, and acetaminophen.

Non-limiting examples of therapeutic agents for sciatica with which a compound of Formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene n-pap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) (can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with IJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I) (and mixtures thereof.

Certain compounds of Formula (I) may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) (and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by $(C_1-C_4)$alkyl, $(C_1-C_{12})$alkanoyloxymethyl, $(C_4-C_9)$ 1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

Other exemplary pro-drugs release an alcohol of Formula (I) wherein the free hydrogen of the hydroxyl substituent (e.g., $R^1$ contains hydroxyl) is replaced by $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_{12})$alkoxycarbonyloxymethyl, N—$(C_1-C_6)$alkoxycarbonylamino-methyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, P(O)(OH)$_2$, —P(O)(O($C_1-C_6$)alkyl)$_2$ or glycosyl (the radical resulting from detachment of the hydroxyl of the hemiacetal of a carbohydrate).

The term "heterocyclic," "heterocyclyl" or "heterocyclylene," as used herein, include non-aromatic, ring systems, including, but not limited to, monocyclic, bicyclic, tricyclic and spirocyclic rings, which can be completely saturated or which can contain one or more units of unsaturation, for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo [3,4-d]pyrimidinyl, quinolinyl, quinazolinyl, triazolyl, thiazolyl, thiophenyl, tetrazolyl, thiadiazolyl, thienyl, 6H-pyrrolo[2,3-e][1,2,4]triazolo[4,3-a]pyrazinyl, 6H-imidazo[1,5-a]pyrrolo[2,3-e]pyrazinyl, 1,6-dihydropyrazolo[3,4-d] pyrrolo[2,3-b]pyridine, 3H-3,4,6,8a-tetraaza-asindacenyl, 3H-imidazo[1,2-a]pyrrolo[2,3-e]pyrazinyl, pyrazolo[3,4-d]pyrrolo[2,3-b]pyridinyl, 1,6-dihydro-1,2,5,6-tetraza-as-indacenyl, 3H-3,4,8a-triaza-as-indacenyl, 6H-3-oxa-2,5,6-triaza-as-indacenyl, 3,6-dihydro-2,3,6-tetraaza-as-indacenyl, 1,6-dihydro-dipyrrolo[2,3-b; 2'3'-d]pyridinyl, 6H-3-thia-2,5,6-triaza-as-indacenyl, 4,5-dihydro-1H-benzo[b]azepin-2(3H)-one, 3,4-dihydroquinolin-2(1H)-one, 2H-benzo[b][1,4]oxazin-3(4H)-one, or 6,7-dihydro-4H-pyrazolo[5,1-c][1,4]oxazinyl or 1,6-dihydroimidazo[4,5-d]pyrrolo[2,3-b]pyridine.

As used herein, "alkyl," "alkylene" or notations such as "($C_1$-$C_8$)" include straight chained or branched hydrocarbons which are completely saturated. Examples of alkyls are methyl, ethyl, propyl, isopropyl, butyl, pentyl, hexyl and isomers thereof. As used herein, "alkenyl," "alkenylene," "alkynylene" and "alkynyl" means $C_2$-$C_8$ and includes straight chained or branched hydrocarbons which contain one or more units of unsaturation, one or more double bonds for alkenyl and one or more triple bonds for alkynyl.

As used herein, "aromatic" groups (or "aryl" or "arylene" groups) include aromatic carbocyclic ring systems (e.g. phenyl) and fused polycyclic aromatic ring systems (e.g. naphthyl, biphenyl and 1,2,3,4-tetrahydronaphthyl).

As used herein, "cycloalkyl" or "cycloalkylene" means $C_3$-$C_{12}$ monocyclic or multicyclic (e.g., bicyclic, tricyclic, spirocyclic, etc.) hydrocarbons that are completely saturated. Examples of a cycloalkyl group are cyclopropyl, cyclobutyl, cyclopentyl, bicyclo[1.1.1]pentyl, and cyclohexyl.

As used herein, "cycloalkenyl" means $C_3$-$C_{12}$ monocyclic or multicyclic (e.g., bicyclic, tricyclic, spirocyclic, etc.) hydrocarbons that has one or more unsaturated bonds but does not amount to an aromatic group. Examples of a cycloalklenyl group are cyclopentenyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: ($C_1$-$C_8$)alkyl groups, ($C_2$-$C_8$)alkenyl groups, ($C_2$-$C_8$)alkynyl groups, ($C_3$-$C_{10}$)cycloalkyl groups, halogen (F, Cl, Br or I), halogenated ($C_1$-$C_8$)alkyl groups (for example but not limited to —$CF_3$), —O—($C_1$-$C_8$)alkyl groups, =O, =$CH_2$, —OH, —$CH_2$OH, —$CH_2NH_2$, ($C_1$-$C_4$)alkyl-OH, —$CH_2CH_2OCH_2CH_3$, —S—($C_1$-$C_8$)alkyl groups, —SH, —NH($C_1$-$C_8$)alkyl groups, —N(($C_1$-$C_8$)alkyl)$_2$ groups, —$NH_2$, —C(O)$NH_2$, —$CH_2$NHC(O)($C_1$-$C_4$)alkyl, —$CH_2$NHC(O)$CH_2$Cl, —$CH_2$NHC(O)$CH_2$CN, —$CH_2$NHC(O)$CH_2CH_2$N($CH_3$)$_2$, —$CH_2$NHC(O)C(=$CH_2$)$CH_3$, —$CH_2$NHC(O)$C_2$-$C_4$)alkynyl, —$CH_2$NHC(O)$CH_2CH_2$-piperidinyl, —($C_1$-$C_4$)alkyl-morpholinyl, —$CH_2$NHC(O)$CH_2$O-phenyl wherein the phenyl is optionally substituted with halogen, ($C_1$-$C_4$)alkoxy, —C(O)($C_1$-$C_4$)alkyl, —C(O)($C_1$-$C_4$)alkoxy, —C(O)N(H)$_2$, —C(O)N($CH_3$)$_2$, —C(O)$C_1$-$C_6$)heteroaryl, —N($CH_3$)$_2$, —NHC(O)$C_1$-$C_4$)alkyl, —NHC(O)($C_2$-$C_4$)alkenyl, —NHC(O)$CH_2$CN, —S(O)$_2$($C_1$-$C_4$)alkyl, —S(O)$_2$($C_1$-$C_6$)heteroaryl, —S(O)$_2$($C_1$-$C_6$) ($C_1$-$C_6$)heterocyclyl, 4-methylpiperazinecarbonyl, —($C_1$-$C_4$)alkylC(O)$NH_2$, —C(O)NH($C_1$-$C_8$)alkyl groups, —C(O)N(($C_1$-$C_8$)alkyl)$_2$, —C(O)N(H)($C_3$-$C_8$)cycloalkyl groups, —C(O)($C_1$-$C_4$)alkoxy, —NHC(O)H, —NHC(O)$C_1$-$C_8$)alkyl groups, —NHC(O)($C_3$-$C_8$)cycloalkyl groups, —N(($C_1$-$C_8$)alkyl)C(O)H, —N(($C_1$-$C_8$)alkyl)C(O)$C_1$-$C_8$)alkyl groups, —NHC(O)$NH_2$, —NHC(O)NH($C_1$-$C_8$)alkyl groups, —N(($C_1$-$C_8$)alkyl)C(O)$NH_2$ groups, —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —$NHCH_2$— heteroaryl, benzyl, —$OCH_2$-heteroaryl, —C(O)H, —C(O)$C_1$-$C_8$)alkyl groups, —CN, —$NO_2$, —S(O)($C_1$-$C_8$)alkyl groups, —S(O)$_2$($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2NH_2$ groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$)alkyl-O—($C_1$-$C_8$)alkyl groups, —C(O)OH, —C(O)O($C_1$-$C_8$)alkyl groups, NHOH, NHO($C_1$-$C_8$)alkyl groups, —O-halogenated ($C_1$-$C_8$)alkyl groups (for example but not limited to —$OCF_3$), —S(O)$_2$-halogenated ($C_1$-$C_8$)alkyl groups (for example but not limited to —S(O)$_2CF_3$), —S-halogenated ($C_1$-$C_8$)alkyl groups (for example but not limited to —$SCF_3$), —($C_1$-$C_6$)heterocyclyl (for example but not limited to pyrrolidine, tetrahydrofuran, pyran or morpholine), —($C_1$-$C_6$)heteroaryl (for example but not limited to tetrazole, imidazole, furan, pyrazine or pyrazole), -phenyl, optionally substituted benzyl, —NHC(O)O—($C_1$-$C_6$)alkyl groups, —N(($C_1$-$C_6$)alkyl)C(O)O—($C_1$-$C_6$)alkyl groups, —C(=NH)—($C_1$-$C_6$)alkyl groups, —C(=NOH)—($C_1$-$C_6$) alkyl groups, or —C(=N—O—($C_1$-$C_6$)alkyl)-($C_1$-$C_6$)alkyl groups.

The term "kit" as used herein refers to a packaged product comprising components with which to administer a compound of Formula (I) of the invention for treatment of an autoimmune disorder. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering a compound of Formula (I).

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counter ions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (e.g., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, in *The Pharmacological Basis of Therapeutics*, Ch. 1, p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

A further aspect of the present invention provides the use of a compound of Formula (I) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (I) to a mammal, particularly a human being, in need thereof.

ABBREVIATIONS

| | | | |
| --- | --- | --- | --- |
| AcOH | Glacial acetic acid | Me | Methyl |
| $Boc_2O$ | di-tert-Butyl-dicarbonate | MeCN | Acetonitrile |
| hr | broad | MeOH | Methyl alcohol |
| BuOH | Butanol | 2-MeTHF | 2-Methyltetrahydrofuran |
| n-BuOH | 1-Butanol | min | Minute(s) |
| t-BuOH | 2-Methyl-2-propanol | mL | Milliliter(s) |
| tert-butyl XPhos | 2-Di-tert-butylphosphino-2',4',6'-triisopropylbiphenyl | mmol | Millimole |
| d | Doublet | MS | Mass spectrometry |
| dd | Doublet of doublets | N | Normal |
| dba | Dibenzylideneacetone | MTBE | Methyl tert-butyl ether |
| DCE | 1,2-Dichlorethane | NaOt-Bu | Sodium tert-butoxide |
| DCM | Dichloromethane (methylene chloride) | $NH_4OAc$ | Ammonium acetate |
| DEA | Diethylamine | NMP | 1-Methyl-2-pyrrolidinone |
| DIAD | Diisoporpyl azodicarboxylate | NMR | Nuclear magnetic resonance |
| DIEA | N,N-Diisopropylethylamine | or | Optical rotation |
| DMA | Dimethylacetamide | $Pd(OAc)_2$ | Palladium(II) acetate |
| DMAP | 4-(Demethylamino)pyridine | PE | Petroleum ether |
| DME | 1,2-Dimethoxyethane | pH | $-\log[H^+]$ |
| DMF | N,N-Dimethylformamide | $PPh_3$ | Triphenylphosphine |
| DMSO | Dimethyl sulfoxide | ppm | Parts per million |
| dppf | 1,1'-Bis(diphenylphosphino)ferrocene | prep | Preparatory |
| equiv | Equivalent(s) | psi | Pounds per square inch |
| Et | Ethyl | $R_t$ | Rentention time |
| EtOAc | Ethyl acetate | rt | Room temperature |
| $Et_2O$ | Diethyl ether | q | Quartet |
| EtOH | Ethanol | S | Singlet |
| g | Gram(s) | SFC | Supercritical fluid chromatography |

-continued

| | | | |
|---|---|---|---|
| h | Hour(s) | t | Triplet |
| HPLC | High-pressure liquid chromatography | tq | triplet of quartets |
| Hz | Hertz | t- | Tertiary |
| i-PrOH | Isopropyl alcohol | TEA | Triethylamine |
| n-PrOH | 1-Propanol | TFA | Trifluoroacetic acid |
| KOAc | Potassium acetate | THF | Tetrahydrofuran |
| KOt-Bu | Potassium tert-butoxide | TLC | Thin layer chromatography |
| LC | Liquid chromatography | USP | United States Pharmacopeia |
| LDA | lithiumdiisopropylamide | UV | Ultraviolet |
| m | Multiplet | wt % | Weight percent |
| M | Molar | Xantphos | 4,5-Bis(diphenylphosphino)-9,9-dimethylxanthene |
| | | XPhos | 2-Dicyclohexylphosphino-2',4',6'-triisopropylbiphenyl |

In Vitro BTK Kinase Activity Measured by Time-Resolved Fluorescence Resonance Energy Transfer (trFRET)

The in-house BTK corresponds to recombinant human catalytic domain (aa 393-659), which was expressed in SF9 cells with an N-terminal his tag and purified by immobilized metal affinity chromatography. BTK was mixed with peptide substrate (biotin-TYR1, Sequence: Biotin-(Ahx)-GAEEEI-YAAFFA-COOH, 0.4 µM final) at varying inhibitor concentrations in reaction buffer: 50 mM MOPSO pH 6.5, 10 mM $MgCl_2$, 2 mM $MnCl_2$, 2.5 mM DTT, 0.01% BSA, 0.1 mM $Na_3VO_4$ and 0.01 mM ATP. After about 60 min incubation at rt, the reaction was quenched by addition of EDTA (final concentration: 100 mM) and developed by addition of detection reagents (final approximate concentrations: 30 mM HEPES pH 7.0, 0.06% BSA, 0.006% Tween-20, 0.24 M KF, 80 ng/mL PT66K (europium labeled anti-phosphotyrosine antibody cat #61T66KLB Cisbio, Bedford, Mass.) and 0.6 µg/mL SAXL (Phycolink streptavidin-allophycocyanin acceptor, cat #PJ25S, Prozyme, San Leandro, Calif.). The developed reaction was incubated in the dark for about 60 min at rt, then read via a time-resolved fluorescence detector (Rubystar, BMG) using a 337 nm laser for excitation and monitoring emission wavelength at 665 nm. Within the linear range of the assay, the observed signal at 665 nm was directly related to phosphorylated product and can be used to calculate the $IC_{50}$ values.

In Vitro CSF-1R Kinase Activity Measured by Time-Resolved Fluorescence Resonance Energy Transfer (trFRET)

The CSF-1R construct corresponds to recombinant human catalytic domain (aa 538-910), which was purchased from Invitrogen (cat #PV4092). CSF-1R was mixed with peptide substrate (biotin-TYR1, Sequence: Biotin-(Ahx)-GAEEEIYAAFFA-COOH, 4 µM final) at varying inhibitor concentrations in reaction buffer: 50 mM MOPSO pH 6.5, 10 mM $MgCl_2$, 2 mM $MnCl_2$, 2.5 mM DTI, 0.01% BSA, 0.1 mM $Na_3VO_4$ and 0.1 mM ATP. After about 60 min incubation at rt, the reaction was quenched by addition of EDTA (final concentration: 100 mM) and developed by addition of detection reagents (final approximate concentrations: 30 mM HEPES pH 7.0, 0.06% BSA, 0.006% Tween-20, 0.24 M KF, 80 ng/mL PT66K (europium labeled anti-phosphotyrosine antibody cat #61T66KLB Cisbio, Bedford, Mass.) and 0.6 µg/mL SAXL (Phycolink streptavidin-allophycocyanin acceptor, cat #PJ25S, Prozyme, San Leandro, Calif.). The developed reaction was incubated in the dark for about 60 min at rt, then read via a time-resolved fluorescence detector (Rubystar, BMG) using a 337 nm laser for excitation and monitoring emission wavelength at 665 nm. Within the linear range of the assay, the observed signal at 665 nm was directly related to phosphorylated product and can be used to calculate the $IC_{50}$ values.

For the purpose of the Tables and Examples below, the Btk or CSF-1R $IC_{50}$ values of each compound is expressed as follows: A=a compound with $IC_{50}$ less than 0.1 µM, B=a compound with $IC_{50}$ within the range of 0.1 µM to 1 µM, and C=a compound with a Btk $IC_{50}$ within the range of 1 µM to 50 µM. NT=not tested The teachings of all references, including journal articles, patents and published patent applications, are incorporated herein by reference in their entirety.

The following examples are for illustrative purposes and are not to be construed as limiting the scope of the present invention.

General Synthetic Schemes

Compounds of the invention may be prepared using synthetic transformations such as those illustrated in Schemes I-IV. Starting materials are commercially available, may be prepared by the procedures described herein, by literature procedures, or by procedures that would be well known to one skilled in the art of organic chemistry (see, for example, Larock, R. C. "Comprehensive Organic Transformations: A Guide to Functional Group Preparations, $2^{nd}$ edition", 1999, Wiley-VCH or Greene, T. W. and Wuts, P. G. M. "Protective Groups in Organic Synthesis, $3^{rd}$ Edition", 1999, Wiley-Interscience). Methods for preparing [1,2,4]triazolo[1,5-a]pyrazin-8-amine compounds of the invention are illustrated in Scheme I. 6,8-Dibromo-[1,2,4]triazolo[1,5-a]pyrazine 1 is commercially available (e.g. Ark Pharm) and can be reacted with amines via displacement chemistry using conditions known to one skilled in the art such as those described in General Procedure A or via palladium-mediated chemistry as described in General Procedure B to give compounds 2. Compounds 3 may be obtained from Suzuki coupling reaction (for example General Procedure C) of compounds 2 with commercially available boronic acids or boronates or with boronates prepared from halides as described in Larock, R. C. (referenced above). Further functionalization of [1,2,4]triazolo[1,5-a]pyrazin-8-amines 3 can be performed, if desired, using reactions known to one skilled in the art (for example Larock, R. C. referenced above). For example, triazolopyrazines 3 containing a double bond may be reduced to saturated systems using hydrogenation conditions such as those described in General Procedure E. In addition, amides can be prepared from triazolopyrazines 3 containing a primary or secondary amine (for example General Procedures F). Also, deprotection of triazolopyrazines 3 containing a protected primary or secondary amine can be performed using conditions such as those described in Greene, T. W. and Wuts, P. G. M. referenced above or in General Procedures D. For example, for R' containing a protecting group (for example a Boc group), the protecting group can be removed to yield the unprotected amine (for example General Procedure D) and the deprotected compounds 3 may then be reacted further as described above.

containing a primary or secondary amine (for example General Procedures F). Also, deprotection of triazolopyridines 8 containing a protected primary or secondary amine can be performed using conditions such as those described in Greene, T. W. and Wuts, P. G. M. referenced above or in General Procedures D. For example, for R' containing a protecting group (for example a Boc group), the protecting group can be removed to yield the unprotected amine (for example General Procedure D) and the deprotected compounds 8 may then be reacted further as described above.

Scheme I

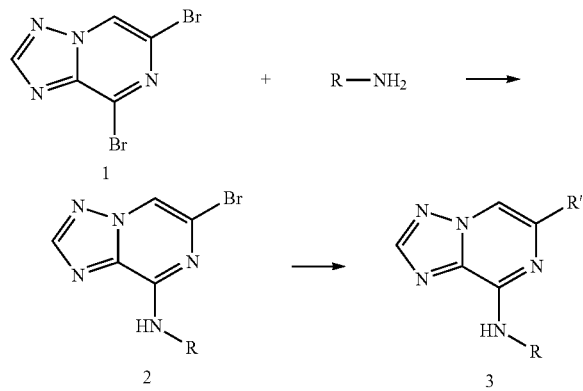

Scheme II

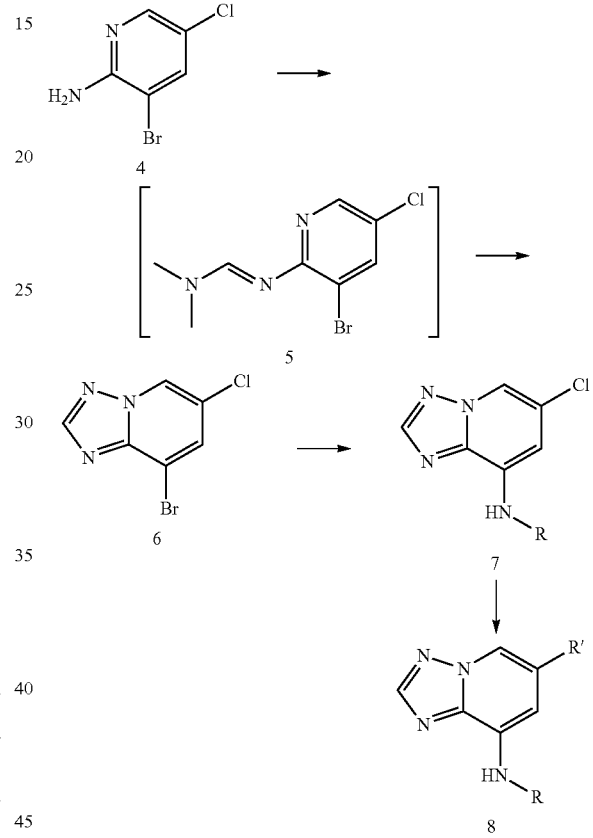

Methods for preparing [1,2,4]triazolo[1,5-a]pyridin-8-amine compounds of the invention are illustrated in Scheme II. Using conditions such as those described in Example #1, Step A, commercially available 2-amino-3-bromo-5-chloropyridine 4 (e.g. Ark Pharm) can be reacted with DMF-DMA to give intermediate 5 which may then be cyclized to give 8-bromo-6-chloro-[1,2,4]triazolo[1,5-a]pyridine 6. 8-Bromo-6-chloro-[1,2,4]triazolo[1,5-a]pyridine 6 can be reacted with amines via palladium-mediated conditions known to one skilled in the art such as those described in General Procedure B to give compounds 7. Compounds 8 may be obtained from Suzuki coupling reaction (for example General Procedure C) of compounds 7 with commercially available boronic acids or boronates or with boronates prepared from halides as described in Larock, R. C. (referenced above) or General Procedure H. Alternatively, compounds 8 can be synthesized by using a different route illustrated in Scheme IIa. Using conditions such as those described in Example #4, Step A, commercially available 5-bromo-3-chloropyridin-2-amine 12 (e.g. Ark Pharm) can be converted to 6-bromo-8-chloro-[1,2,4]triazolo[1,5-a]pyridine 13 in a similar manner as Step A in Example #1. Synthesis of compounds 14 may be achieved by Suzuki coupling reaction of compound 13 with commercially available boronic acids or boronates or with boronates prepared from halides as described in Larock, R. C. (referenced above) or General Procedure H. Compounds 14 can react with amines via palladium-mediated conditions known to one skilled in the art such as those described in General Procedure B to give compounds 8. Further functionalization of [1,2,4]triazolo[1,5-a]pyridin-8-amine 8 can be performed, if desired, using reactions known to one skilled in the art (for example Larock, R. C. referenced above). For example, triazolopyridines 8 containing a double bond may be reduced to saturated systems using hydrogenation conditions such as those described in General Procedure E. In addition, amides can be prepared from triazolopyridines 8

Scheme IIa

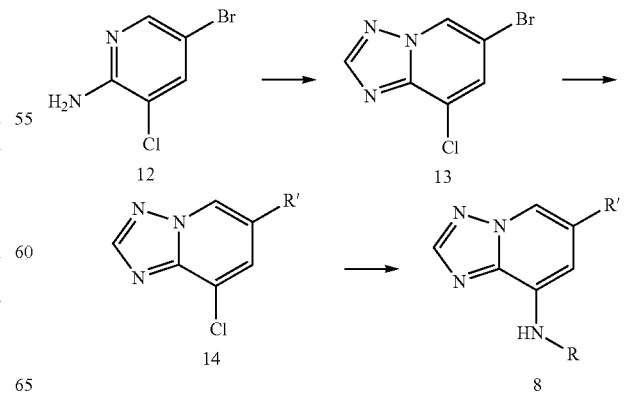

Methods for preparing [1,2,4]triazolo[1,5-a]pyrazin-8-amine compounds of the invention are illustrated in Scheme III. 6,8-Dibromoimidazo[1,2-a]pyrazine 9 is commercially available (e.g. Ark Pharm) and can be reacted with amines via displacement chemistry using conditions known to one skilled in the art such as those described in General Procedure A or via palladium-mediated chemistry as described in General Procedure B to give compounds 10. Compounds 11 may be obtained from Suzuki coupling reaction (for example General Procedure C) of compounds 10 with commercially available boronic acids or boronates or with boronates prepared from halides as described in Larock, R. C. (referenced above). Further functionalization of imidazo[1,2-a]pyrazin-8-amines 11 can be performed, if desired, using reactions known to one skilled in the art (for example Larock, R. C. referenced above). For example, imidazopyrazines 11 containing a double bond may be reduced to saturated systems using hydrogenation conditions such as those described in General Procedure E. In addition, amides can be prepared from imidazopyrazines 11 containing a primary or secondary amine (for example General Procedures F). Also, deprotection of imidazopyrazines 11 containing a protected primary or secondary amine can be performed using conditions such as those described in Greene, T. W. and Wuts, P. G. M. referenced above or in General Procedures D. For example, for R' containing a protecting group (for example a Boc group), the protecting group can be removed to yield the unprotected amine (for example General Procedure D) and the deprotected compounds 11 may then be reacted further as described above.

Scheme III

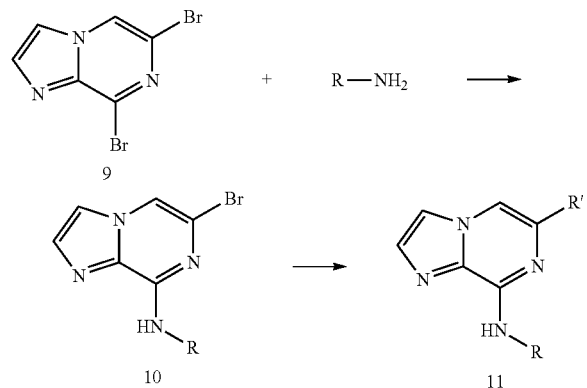

Methods for preparing imidazo[1,2-b]pyridazine compounds of the invention are illustrated in Scheme III. 8-Bromo-6-chloroimidazo[1,2-b]pyridazine 12 is commercially available (e.g. Astatech) and can be reacted with amines via displacement chemistry using conditions known to one skilled in the art such as those described in General Procedure A or via palladium-mediated chemistry as described in General Procedure B to give compounds 13. Compounds 14 may be obtained from Suzuki coupling reaction (for example General Procedure C) of compounds 13 with commercially available boronic acids or boronates or with boronates prepared from halides as described in Larock, R. C. (referenced above). Further functionalization of imidazo[1,2-b]pyridazin-8-amines 14 can be performed, if desired, using reactions known to one skilled in the art (for example Larock, R. C. referenced above). For example, imidazopyridazines 14 containing a double bond may be reduced to saturated systems using hydrogenation conditions such as those described in General Procedure E. In addition, amides can be prepared from imidazopyridazines 14 containing a primary or secondary amine (for example General Procedures F). Also, deprotection of imidazopyridazines 14 containing a protected primary or secondary amine can be performed using conditions such as those described in Greene, T. W. and Wuts, P. G. M. referenced above or in General Procedures D. For example, for R' containing a protecting group (for example a Boc group), the protecting group can be removed to yield the unprotected amine (for example General Procedure D) and the deprotected compounds 14 may then be reacted further as described above.

Scheme IV

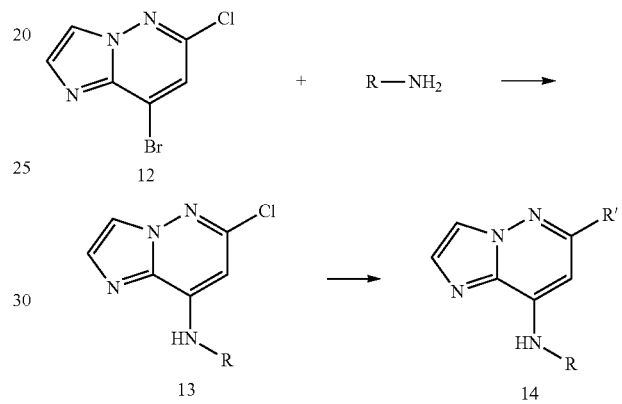

General Procedures and Examples

The general synthetic schemes that were utilized to construct the majority of compounds disclosed in this application are described below in Schemes 1-9. These schemes are provided for illustrative purposes only and are not to be construed as limiting the scope of the invention.

Scheme 1: Nucleophilic displacement of an aryl or heteroaryl halide with an amine (General Procedure A)

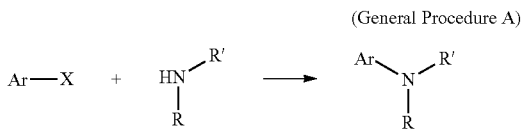

Scheme 2: Buchwald-Hartwig reaction of an aryl or heteroaryl halide with an amine (General Procedure B)

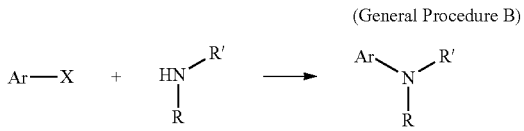

Scheme 3: Reaction of an aryl or heteroaryl halide with a boronic acid or boronate ester (General Procedure C)

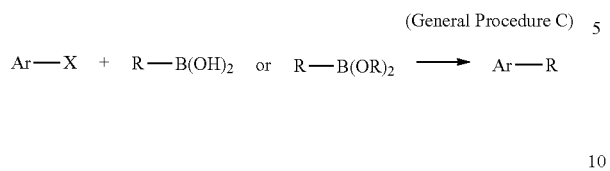

Scheme 4: Acidic cleavage of a Boc-protected amine (General Procedure D)

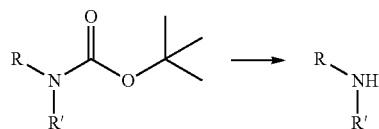

Scheme 5: Hydrogenation of a double bond (General Procedure E)

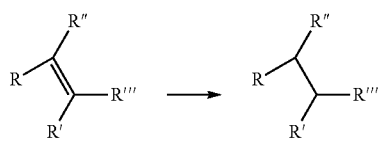

Scheme 6: Formation of an amide from an acid chloride and an amine or of a carbamate from a carbonochloridate and an amine (General Procedure F)

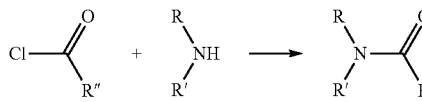

Scheme 7: Chiral preparative HPLC separation of stereoisomers (General Procedure G)

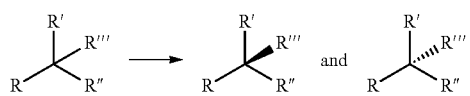

Scheme 8: Formation of a sulfonamide from a sulfonyl chloride and an amine (General Procedure H)

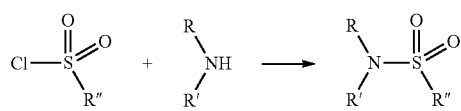

Scheme 9: Formation of a cyanamide from an amine with cyanogen bromide (General Procedure I)

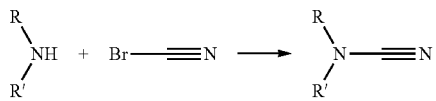

LIST OF GENERAL PROCEDURES

| | |
|---|---|
| General Procedure A | Nucleophilic displacement of an aryl or heteroaryl halide with an amine |
| General Procedure B | Buchwald-Hartwig reaction of an aryl or heteroaryl halide with an amine |
| General Procedure C | Reaction of an aryl or heteroaryl halide with a boronic acid or boronate ester |
| General Procedure D | Acidic cleavage of a Boc-protected amine |
| General Procedure E | Hydrogenation of a double bond |
| General Procedure F | Formation of an amide from an acid chloride and an amine or of a carbamate from a carbonochloridate and an amine |
| General Procedure G | Chiral preparative HPLC separation of stereoisomers |
| General Procedure H | Formation of a sulfonamide from a sulfonyl chloride and an amine |
| General Procedure I | Formation of a cyanamide from an amine with cyanogen bromide |

The following examples are ordered according to the final general procedure used in their preparation. The synthetic routes to any novel intermediates are detailed by sequentially listing the general procedure (letter codes) in parentheses after their name with additional reactants or reagents as appropriate. A worked example of this protocol is given below using Example #F.1.4 as a non-limiting illustration. Example # F.1.4 is 8-((6-(1-acryloylpiperidin-3-yl)-[1,2,4]triazolo[1,5-a]pyrazin-8-yl)amino)-4,5-dihydro-1H-benzo[b]azepin-2(3H)-one, which was prepared from 8-((6-(piperidin-3-yl)-[1,2,4]triazolo[1,5-a]pyrazin-8-yl)amino)-4,5-dihydro-1H-benzo[b]azepin-2(3H)-one using General Procedure F as represented in Scheme A.

Scheme A

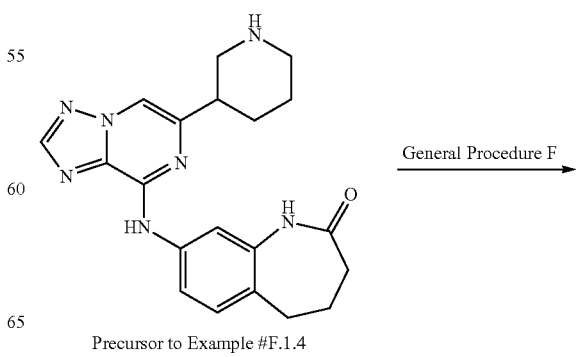

Precursor to Example #F.1.4

General Procedure F →

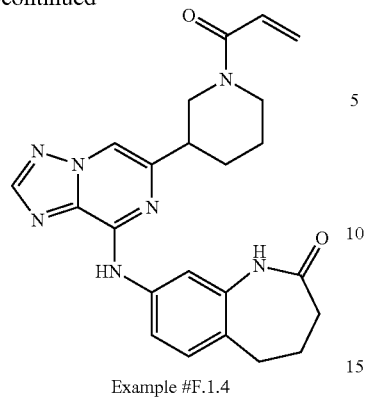

Example #F.1.4

Scheme B

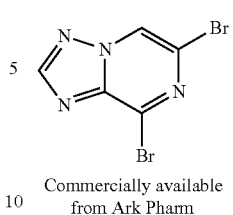

Commercially available from Ark Pharm

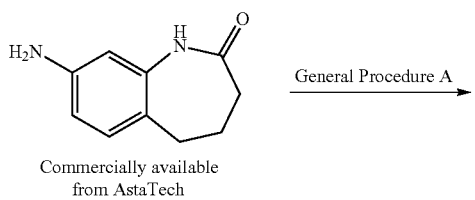

Commercially available from AstaTech

General Procedure A →

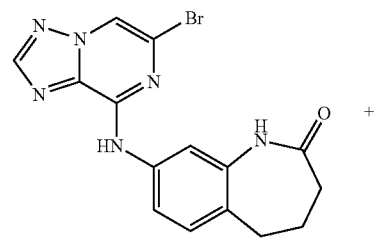

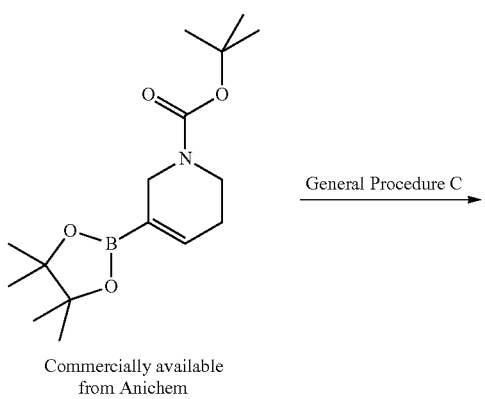

Commercially available from Anichem

General Procedure C →

The precursor to Example #F.1.4, 8-((6-(piperidin-3-yl)-[1,2,4]triazolo[1,5-a]pyrazin-8-yl)amino)-4,5-dihydro-1H-benzo[b]azepin-2(3H)-one, was prepared (as shown in Scheme B) by initially reacting 6,8-dibromo-[1,2,4]triazolo[1,5-a]pyrazine, commercially available from Ark Pharm, and 8-amino-4,5-dihydro-1H-benzo[b]azepin-2(3H)-one, commercially available from AstaTech, following the conditions given in General Procedure A, to give 8-((6-bromo-[1,2,4]triazolo[1,5-a]pyrazin-8-yl)amino)-4,5-dihydro-1H-benzo[b]azepin-2(3H)-one, which is subsequently reacted with tert-butyl 3-(4,4,5,5-tetramethyl-1,3,2-dioxaborolan-2-yl)-5,6-dihydropyridine-1(2H)-carboxylate, commercially available from Anichem, using the conditions given in General Procedure C to give tert-butyl 3-(8-((2-oxo-2,3,4,5-tetrahydro-1H-benzo[b]azepin-8-yl)amino)-[1,2,4]triazolo[1,5-a]pyrazin-6-yl)-5,6-dihydropyridine-1(2H)-carboxylate, which is subsequently reacted with Pd/C using the conditions provided in General Procedure E to give tert-butyl 3-(8-((2-oxo-2,3,4,5-tetrahydro-1H-benzo[b]azepin-8-yl)amino)-[1,2,4]triazolo[1,5-a]pyrazin-6-yl)piperidine-1-carboxylate, which is subsequently reacted with TFA using the conditions given in General Procedure D to give 8-((6-(piperidin-3-yl)-[1,2,4]triazolo[1,5-a]pyrazin-8-yl)amino)-4,5-dihydro-1H-benzo[b]azepin-2(3H)-one. The reaction sequence to synthesize the precursor to Example #F.1.4, 8-((6-(piperidin-3-yl)-[1,2,4]triazolo[1,5-a]pyrazin-8-yl) amino)-4,5-dihydro-1H-benzo[b]azepin-2(3H)-one, (detailed above) is consequently translated in the preparations and examples section to: 8-((6-(piperidin-3-yl)-[1,2,4]triazolo[1,5-a]pyrazin-8-yl)amino)-4,5-dihydro-1H-benzo[b]azepin-2(3H)-one (prepared using A from 6,8-dibromo-[1,2,4]triazolo[1,5-a]pyrazine [Ark Pharm] and 8-amino-4,5-dihydro-1H-benzo[b]azepin-2(3H)-one [AstaTech], C from tert-butyl 3-(4,4,5,5-tetramethyl-1,3,2-dioxaborolan-2-yl)-5,6-dihydropyridine-1(2H)-carboxylate [Anichem], E with Pd/C, D with TFA).

Hence the Example #F.1.4 would be written as: Example #F.1.4 was prepared from acryloyl chloride and 8-((6-(piperidin-3-yl)-[1,2,4]triazolo[1,5-a]pyrazin-8-yl)amino)-4,5-dihydro-1H-benzo[b]azepin-2(3H)-one (prepared using A from 6,8-dibromo-[1,2,4]triazolo[1,5-a]pyrazine [Ark Pharm] and 8-amino-4,5-dihydro-1H-benzo[b]azepin-2 (3H)-one [AstaTech], C from tert-butyl 3-(4,4,5,5-tetramethyl-1,3,2-dioxaborolan-2-yl)-5,6-dihydropyridine-1(2H)-carboxylate [Anichem], E with Pd/C, D with TFA). In the tables after a General Procedure, this is represented by having one reactant in the title of the table and one in a separate column in the same row as the product.

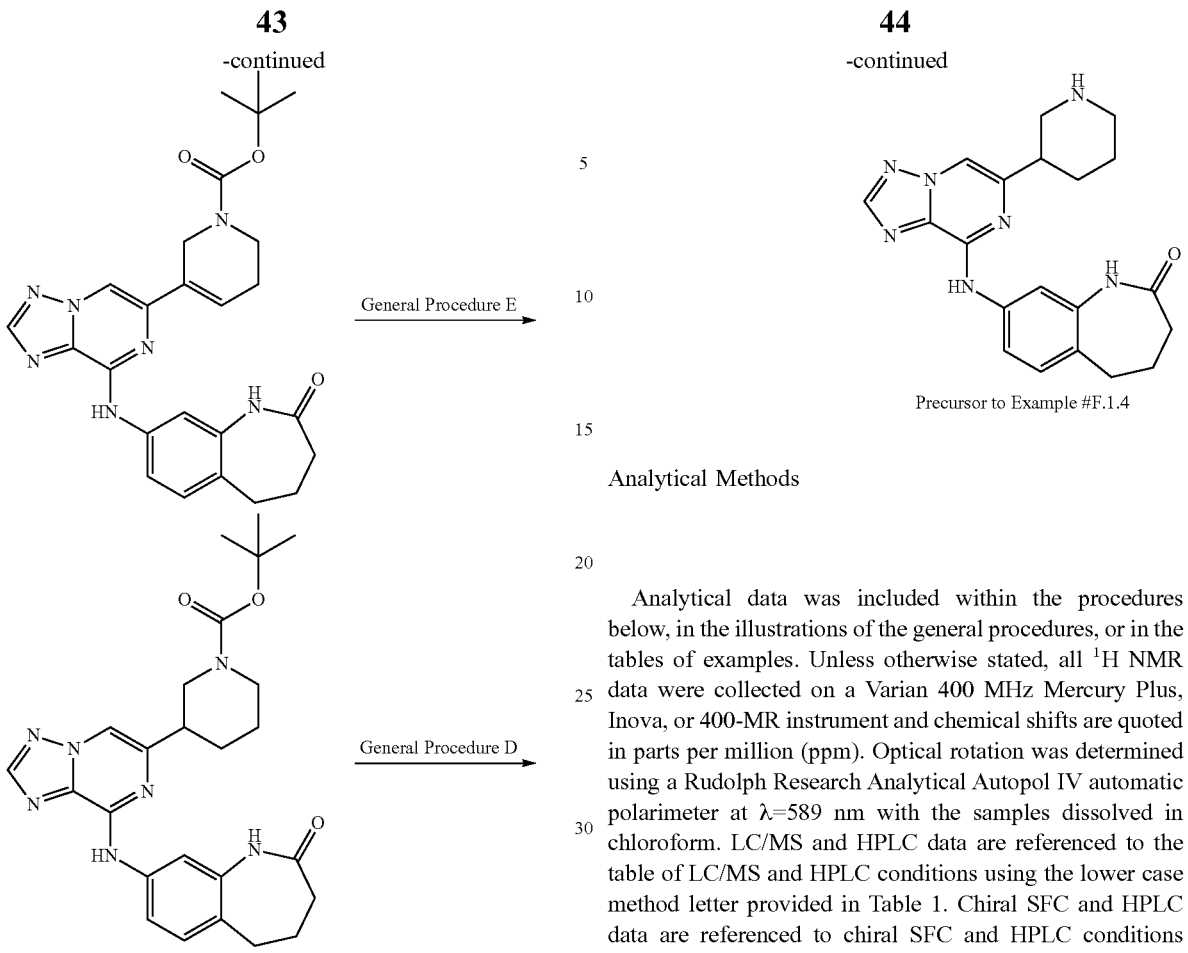

Precursor to Example #F.1.4

Analytical Methods

Analytical data was included within the procedures below, in the illustrations of the general procedures, or in the tables of examples. Unless otherwise stated, all $^1$H NMR data were collected on a Varian 400 MHz Mercury Plus, Inova, or 400-MR instrument and chemical shifts are quoted in parts per million (ppm). Optical rotation was determined using a Rudolph Research Analytical Autopol IV automatic polarimeter at λ=589 nm with the samples dissolved in chloroform. LC/MS and HPLC data are referenced to the table of LC/MS and HPLC conditions using the lower case method letter provided in Table 1. Chiral SFC and HPLC data are referenced to chiral SFC and HPLC conditions using the numeric method letter provided in Table 2.

TABLE 1

| Method | Conditions |
|---|---|
| | LC/MS and HPLC methods |
| a | LC/MS: The gradient was 5% B for 0.1 min, 5-100% B in 5.1 min with a hold at 100% B for 0.5 min then 100-5% B in 0.3 min (2.0 mL/min flow rate). Mobile phase A was 0.1% TFA in water, mobile phase B was HPLC grade MeCN. The column used for the chromatography was a 2.1 × 50 mm Phenomenex Luna Combi-HTS C8(2) column (5 μm particles) at a temperature of 65° C. Detection methods are diode array (DAD) and evaporative light scattering (ELSD) detection under positive APCI ionization conditions. |
| b | LC/MS: The gradient was 5% B for 0.1 min, 5-100% B in 2.5 min with a hold at 100% B for 0.3 min then 100-5% B in 0.1 min (2.0 mL/min flow rate). Mobile phase A was 0.1% TFA in water, mobile phase B was HPLC grade MeCN. The column used for the chromatography was a 2.1 × 50 mm Phenomenex Luna Combi-HTS C8(2) column (5 μm particles) at a temperature of 55° C. Detection methods are diode array (DAD) and evaporative light scattering (ELSD) detection under positive APCI ionization conditions. |
| c | LC/MS: The gradient was 10-90% B in 1.15 with a hold at 90% B for 0.40 min, 90-10% B in 0.01 min, and then hold at 10% B for 0.54 min (1.0 mL/min flow rate). Mobile phase A was 0.0375% TFA in water, mobile phase B was 0.018% TFA in MeCN. The column used for the chromatography was a 2.1 × 30 mm Halo C18 column (2.7 μm particles). Detection methods are diode array (DAD) and positive/negative electrospray ionization. |
| d | LC/MS: The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% TFA in water, mobile phase B was 0.018% TFA in MeCN. The column used for the chromatography was a 2.1 × 50 mm Venusil XBP-C18 column (5 μm particles). Detection methods are diode array (DAD) and evaporative light scattering (ELSD) detection as well as positive/negative electrospray ionization. |
| e | LC/MS: The gradient was 5% B for 0.1 min, 5-100% B in 5.1 min with a hold at 100% B for 0.5 min then 100-5% B in 0.3 min (2.0 mL/min flow rate). Mobile phase A was 0.1% trifluoroacetic acid in water, mobile phase B was HPLC grade MeCN. The column used for the chromatography was a 2.1 mm × 50 mm |

TABLE 1-continued

LC/MS and HPLC methods

| Method | Conditions |
|---|---|
| | Phenomenex Luna Combi-HTS C8(2) column (5 μm particles) at a temperature of 55° C. Detection methods are diode array (DAD) and evaporative light scattering (ELSD) detection under positive APCI ionization conditions. |
| f | LC/MS: The gradient was 5-100% B in 3.4 min with a hold at 100% B for 0.45 min, 100-5% B in 0.01 min, and then held at 5% B for 0.65 min (0.8 mL/min flow rate). Mobile phase A was 10 mM $NH_4HCO_3$, mobile phase B was HPLC grade MeCN. The column used for the chromatography is a 2.1 × 50 mm Xbridge Shield RPC18 column (5 μm particles). Detection methods are diode array (DAD) and evaporative light scattering (ELSD) detection as well as positive/negative electrospray ionization. |
| g | LC/MS: The gradient was 5% B for 0.1 min, 5-100% B in 2.5 min with a hold at 100% B for 0.3 min then 100-5% B in 0.1 min (2.0 mL/min flow rate). Mobile phase A was 0.1% TFA in water, mobile phase B was HPLC grade MeCN. The column used for the chromatography was a 2.1 × 50 mm Phenomenex Luna Combi-HTS C8(2) column (5 μm particles) at a temperature of 65° C. Detection methods are diode array (DAD) and evaporative light scattering (ELSD) detection under positive APCI ionization conditions. |
| h | LC/MS: The gradient was 5-60% B in 1.5 min then 60-95% B to 2.5 min with a hold at 95% B for 1.2 min (1.3 mL/min flow rate). Mobile phase A was 0.1% formic acid in water, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| i | HPLC: The gradient was 20-50% B in 12 min with a hold at 50% B for 2 min, then 50-100% B in 0.2 min with a hold at 100% B for 2 min then 100-20% B in 0.2 min with a hold at 20% B for 1.6 min (1.0 mL/min flow rate). (25.0 mL/min flow rate). Mobile phase A was 0.75% TFA in water, mobile phase B was MeCN. The column used for the chromatography was a 25 × 200 mm Phenomenex Luna C18 column (5 gm particles). Detection method is UV at wavelengths of 220 nm and 254 nm. |
| j | Prep HPLC: The column is a Phenomenex Luna C18(2) 10 μm 100Å AXIA column (250 mm × 21.2 mm). A gradient of MeCN (A) and 0.1% TFA in water (B) is used, at a flow rate of 25 mL/min. A linear gradient is used from about 5% of A to about 95% of A over about 10 minutes. Detection method is UV at wave length of 220 nM and 254 nM. |
| k | HPLC: The gradient was 2-60% B in 11.5 min then 60-95% B in 1 min with a hold at 95% B for 2 min then 95-2% B in 0.5 min (25.0 mL/min flow rate). (25.0 mL/min flow rate). Mobile phase A was 0.1% formic acid in water, mobile phase B was MeCN. The column used for the chromatography was a 50 × 100 mm Waters Atlantis T3 OBD column (5 μm particles). Detection method is UV at wavelength range from 210 nm and 400 nm. |
| l | LC/MS (The gradient was 5-60% B in 1.5 min then 60-95% B to 2.5 min with a hold at 95% B for 1.2 min (1.3 mL/min flow rate). Mobile phase A was 10 mM $NH_4OAc$, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization.) |
| m | LC/MS: The gradient was 5-95% B in 1.3 min then hold at 95% B for 1.5 min, back to 5% B within 0.01 min (1.8 mL/min flow rate). Mobile phase A was 0.1% $NH_4OAc$ in water, mobile phase B was HPLC grade MeCN. The column used for the chromatography is a 4.6 × 50 mm XBridge C18 (3.5 μm particles). Detection methods are diode array (DAD) and evaporative light scattering (ELSD) detection as well as positive/negative electrospray ionization. |
| n | LC/MS: The gradient was 5-95% B in 1.4 min then hold at 95% B for 1.4 min, back to 5% B within 0.01 min (1.8 mL/min flow rate). Mobile phase A was 0.1% $NH_4OAc$ in water, mobile phase B was HPLC grade MeCN. The column used for the chromatography is a 4.6 × 50 mm XBridge C18 (3.5 μm particles). Detection methods are diode array (DAD) and evaporative light scattering (ELSD) detection as well as positive/negative electrospray ionization. |
| o | LC/MS: The gradient was 5-100% B in 1.3 min (2.0 mL/min flow rate). Mobile phase A was 0.1% TFA in water, mobile phase B was HPLC grade MeCN containing 0.1% TFA. The column used for the chromatography is a 4.6 × 50 mm Sunfire C18 (3.5 μm particles). Detection methods are diode array (DAD) and evaporative light scattering (ELSD) detection as well as positive/negative electrospray ionization. |
| p | LC/MS: The gradient was 5-95% B in 1.3 min (1.8 mL/min flow rate). Mobile phase A was 0.1% $NH_4OAc$ in water, mobile phase B was HPLC grade MeCN. The column used for the chromatography is a 4.6 × 50 mm XBridge C18 (3.5 μm particles). Detection methods are diode array (DAD) and evaporative light scattering (ELSD) detection as well as positive/negative electrospray ionization. |
| q | LC/MS: The gradient was 5-95% B in 2.5 min (1.8 mL/min flow rate). Mobile phase A was 0.1% $NH_4OAc$ in water, mobile phase B was HPLC grade MeCN. The column used for the chromatography is a 4.6 × 50 mm Gemini-NX C18 (3.0 μm particles). Detection methods are diode array (DAD) and evaporative light scattering (ELSD) detection as well as positive/negative electrospray ionization. |

TABLE 1-continued

LC/MS and HPLC methods

| Method | Conditions |
|---|---|
| r | LC/MS: The gradient was 5-95% B in 1.4 min then hold at 95% B for 1.6 min, back to 5% B within 0.01 min (1.8 mL/min flow rate). Mobile phase A was 0.1% $NH_4OAc$ in water, mobile phase B was HPLC grade MeCN. The column used for the chromatography is a 4.6 × 50 mm XBridge C18 (3.5 μm particles). Detection methods are diode array (DAD) and evaporative light scattering (ELSD) detection as well as positive/negative electrospray ionization. |
| s | LC/MS: The gradient was 5-95% B in 1.2 min then hold at 95% B for 1.3 min, back to 5% B within 0.01 min (1.8 mL/min flow rate). Mobile phase A was 0.1% TFA in water, mobile phase B was HPLC grade MeCN (with 0.1% TFA). The column used for the chromatography is a 4.6 × 50 mm Sunfire C18 (3.5 μm particles). Detection methods are diode array (DAD) and evaporative light scattering (ELSD) detection as well as positive/negative electrospray ionization. |
| t | LC/MS: The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0 × 50 mm phenomenex Luna-C18 column (5 μm particles). Detection methods are diode array (DAD) and evaporative light scattering (ELSD) detection as well as positive electrospray ionization(MS). |
| u | Prep HPLC: The column is a Luna C18 100*30 5u column. A gradient of 0.1% formic acid in water (A) and ACN (B) is used, at a flow rate of 25 mL/min. A linear gradient is used from about 35% of B to 100% of B over about 12 minutes. Detection method is UV at wave length of 220 nM and 254 nM. |
| v | LC/MS: The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0 × 50 mm phenomenex Luna-C18 column (5 μm particles). Detection methods are diode array (DAD) and evaporative light scattering (ELSD) detection as well as positive electrospray ionization(MS).) |
| w | LC/MS: The gradient was 10-90% B in 1.15 with a hold at 90% B for 0.4 min, 90-10% B in 0.01 min, and then hold at 10% B for 0.54 min (1.0 mL/min flow rate). Mobile phase A was 0.0375% trifluoroacetic acid in water, mobile phase B was 0.018% trifluoroacetic acid in $CH_3CN$. The column used for the chromatography was a 2.1 × 30 mm Halo C18 column (2.7 μm particles). Detection methods are diode array (DAD) and positive electrospray ionization(MS). |
| x | LC/MS: The gradient was 15-90% B in 3.4 min, 90-100% B in 0.45 min, 100-15% B in 0.01 min, and then held at 15% B for 0.65 min (0.8 mL/min flow rate). Mobile phase A was 10 mM $NH_4HCO_3$, mobile phase B was HPLC grade ACN. The column used for the chromatography is a 2.1 × 50 mm Xbridge Shield RPC18 column (5 μm particles). Detection methods are diode array (DAD) and evaporative light scattering (ELSD) detection as well as positive electrospray ionization(MS). |
| y | Prep HPLC: The column used for the chromatography is a 19 × 50 mm Waters Atlantis T3 OBD (5 μm particles). Mobile phase A was 50 mM ammonium acetate, mobile phase B was HPLC grade acetonitrile. The gradient was a held at 16% B for 3 min, 16%-73% to 12.5 min and then 73%-95.5% B to 13.5 min. Detection methods are diode array (DAD) and positive/negative ESI ionization. |
| z | Prep HPLC: The column is a MAC-MOD: ACE C18 Prep, 5 um particle size 21.2 × 150 mm A gradient of 0.1% formic acid in water (A) and ACN (B) is used, at a flow rate of 25 mL/min. A linear gradient is used from about 10% of B to 95% of B over about 14 minutes. Detection method is UV at wave length of 254 nM. |
| aa | Prep HPLC: The column is a MAC-MOD: ACE C18 Prep, 5 um particle size 21.2 × 150 mm A gradient of 0.1% formic acid in water (A) and ACN (B) is used, at a flow rate of 25 mL/min. The gradient used was 10% of B for 1.5 min, to 85% of B over 12.5 minutes, then 85-95% B to 13 minutes. Detection method is UV at wave length of 254 nM. |
| ab | Prep HPLC: The column is a MAC-MOD: ACE C18 Prep, 5 um particle size 21.2 × 150 mm A gradient of 0.1% formic acid in water (A) and ACN (B) is used, at a flow rate of 25 mL/min. The gradient used was 5% of B for 1.5 min, to 5-80% of B over 12.5 minutes, then 80-95% B to 13 minutes. Detection method is UV at wave length of 254 nM. |

TABLE 2

Chiral SFC and HPLC methods

| Method | Conditions |
|---|---|
| 1 | Preparative SFC was performed on a THAR/Waters SFC 80 system running under SuperChrom software control. The preparative SFC system was equipped with a $CO_2$ pump, modifier pump, automated back pressure regulator (ABPR), UV |

TABLE 2-continued

Chiral SFC and HPLC methods

| Method | Conditions |
|---|---|
|  | detector, injector, and 6-position fraction collector. The mobile phase comprised of supercritical $CO_2$ supplied by a dewar of bone-dry non-certified $CO_2$ pressurized to 800 psi with a modifier of MeOH buffered with 0.05% $NH_4OH$ at a flow rate of 65 g/min. UV detection was set to collect at a wavelength of 254 nm, the column was at 40 C., and the backpressure regulator was set to maintain 100 bar. The sample was dissolved in MeOH. The mobile phase was held isocratically at 25% MeOH (0.05% $NH_4OH$):$CO_2$. The instrument was fitted with a ChiralCel OJ-H column with dimensions 30 mm i.d. × 250 mm length with 5 μm particles. |
| 2 | Preparative SFC was performed on a THAR/Waters SFC 80 system running under SuperChrom software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by a dewar of bone-dry non-certified $CO_2$ pressurized to 350 psi with a modifier of MeOH buffered with 0.1% DEA at a flow rate of 70 g/min. UV detection was set to collect at a wavelength of 220 nm, the column was at ambient temperature, and the backpressure regulator was set to maintain 100 bar. The sample was dissolved in MeOH at a concentration of 75 mg/mL. The sample was loaded into the modifier stream in 0.2 mL (15 mg) injections. The mobile phase was held isocratically at 20% MeOH (0.1% DEA):$CO_2$. Fraction collection was time triggered. The instrument was fitted with a Regis Whelk-O (S,S) column with dimensions 21 mm i.d. × 250 mm length with 5 μm particles. |
| 3 | HPLC: The gradient was 25-37% B in 22.0 min then 37-50% A in the next 7 min then held at 50% A for an extra 1 min. After the 1 min it is equilibrated back down to 25% for 3 min. (20 mL/min flow rate). Mobile phase B was EtOH (200 proof), mobile phase A was HPLC grade heptane with 0.20% DEA added. The column used for the chromatography was a Daicel IF, 20 × 250 mm column (5 μm particles). Detection methods were UV ($\lambda$ = 298 nm) and optical rotation. |
| 4 | HPLC: The gradient was 17% B held for 19 min then bumped up to 40% B for 5 min. After 5 min it is equilibrated back down to 17% for 3 min (20 mL/min flow rate). Mobile phase B was HPLC grade isopropanol, mobile phase A was HPLC grade heptane with 0.20% DEA added. The column used for the chromatography was a Daicel IA, 20 × 250 mm column (5 μm particles). Detection methods were UV ($\lambda$ = 322 nm) and optical rotation. |
| 5 | HPLC: The gradient was 15-29% A in 26 min then step to 60% A for 4 min (20 mL/min flow rate). Mobile phase A was EtOH (200 proof), mobile phase B was HPLC grade heptane no modifier. The chromatography used a Daicel IB, 20 × 250 mm column (5 μm particles). |
| 6 | HPLC: Isocratic 17% A for 19 min then step to 40% A for 6 min (20 mL/min flow rate). Mobile phase A was EtOH (200 proof), mobile phase B was HPLC grade heptane with 0.1% DEA added. The chromatography used a Daicel IA, 21 × 250 mm column (5 μm particles). |
| 7 | HPLC: The gradient was 25-37% A in 22 min then 37-50% in 7 min (20 mL/min flow rate). Mobile phase A was EtOH (200 proof), mobile phase B was HPLC grade heptane with 0.1% DEA added. The chromatography used a Daicel IF, 20 × 250 mm column (5 μm particles). |
| 8 | HPLC was performed using the following step gradient: the gradient was 25 to 35% B in 16 min then stepped to 65% B in .05 min, then 65-80% B in the next 6.95 min. It is equilibrated back to 25% for 4 min. (20 mL/min flow rate). Mobile phase B was EtOH (200 proof), mobile phase A was HPLC grade heptane with 0.20% DEA added. The chromatography used a Daicel IC, 20 × 2 50 mm column (5 μm particles). |
| 9 | HPLC: The gradient was 36-45% A in 19.5 min then 65-80% A in 5.4 min (20 mL/min flow rate). Mobile phase A was HPLC grade EtOAc, mobile phase B was HPLC grade heptane with 0.2% DEA added. The chromatography used a Daicel ID, 21 × 250 mm column (5 μm particles). |
| 10 | HPLC: Isocratic 31% A for 32 min (20 mL/min flow rate). Mobile phase A was HPLC grade isopropanol, mobile phase B was HPLC grade heptane with no modifier. The chromatography used a Daicel IB, 20 × 250 mm column (5 μm particles) |
| 11 | HPLC: Isocratic 30% A. (1 mL/min flow rate). Mobile phase A was HPLC grade EtOH with 1% DEA added, mobile phase B was HPLC grade n-hexane with 0.1% DEA added. The column used for the chromatography was a AD-H, 4.6 × 250 mm column (5 μm particles). Detection methods were UV ($\lambda$ = 214, 254 nm). |
| 12 | HPLC: Isocratic 30% A. (3 mL/min flow rate). Mobile phase A was HPLC grade EtOH with 0.1% DEA added, mobile phase B was HPLC grade n-hexane with 0.1% DEA added. The column used for the chromatography was a OZ-H, 4.6 × 250 mm column (5 μm particles). |
| 13 | HPLC: Isocratic 20% A. (3 mL/min flow rate). Mobile phase A was HPLC grade MeOH with 0.1% DEA added, mobile phase B was HPLC grade n-hexane with 0.1% DEA added. The column used for the chromatography was a AS-H, 4.6 × 250 mm column (5 μm particles). |
| 14 | HPLC: Isocratic 50% A. (1 mL/min flow rate). Mobile phase A was HPLC grade EtOH with 0.1% DEA added, mobile phase B was HPLC grade n-hexane with 0.1% DEA added. The column used for the chromatography was a IA, 4.6 × 250 mm column (5 μm particles). Detection methods were UV ($\lambda$ = 214, 254 nm). |

TABLE 2-continued

Chiral SFC and HPLC methods

| Method | Conditions |
|---|---|
| 15 | HPLC: Isocratic 15% A. (3 mL/min flow rate). Mobile phase A was HPLC grade MeOH with 0.1% DEA added, mobile phase B was HPLC grade n-hexane with 0.1% DEA added. The column used for the chromatography was a OJ-H, 4.6 × 250 mm column (5 µm particles). |
| 16 | HPLC 2-Dimensional purification: Dim 1: 35% A for 20 min (20 mL/min flow rate). Mobile phase A was EtOH (200 proof), mobile phase B was HPLC grade heptane with 0.2% diethylamine added. The chromatography used a Daicel IC 20 × 250 mm column (5 µm particles). Dim 2: 30% A for 14 min (20 mL/min flow rate). Mobile phase A was EtOH (200 proof), mobile phase B was HPLC grade heptane with 0.2% diethylamine added. The chromatography used a Cel-4, 21 × 250 mm column (5 µm particles) from Phenomenex. |
| 17 | Preparative SFC was performed on a THAR/Waters SFC 80 system running under SuperChrom software control. The preparative SFC system was equipped with a $CO_2$ pump, modifier pump, automated back pressure regulator (ABPR), UV detector, injector, and 6-position fraction collector. The mobile phase comprised of supercritical $CO_2$ supplied by a dewar of bone-dry non-certified $CO_2$ pressurized to 800 psi with a modifier of MeOH buffered with 0.1 % $NH_3$ in water at a flow rate of 60 g/min. UV detection was set to collect at a wavelength of 254 nm, the backpressure regulator was set to maintain 100 bar. The sample was dissolved in MeOH. The mobile phase was held isocratically at 20% MeOH (0.1 % $NH_3$ in water):$CO_2$. The instrument was fitted with a ChiralCel OJ 10 mm column with dimensions 3.0 cm i.d. × 50 cm length |
| 18 | Preparative SFC was performed on a THAR/Waters SFC 80 system running under SuperChrom software control. The preparative SFC system was equipped with a $CO_2$ pump, modifier pump, automated back pressure regulator (ABPR), UV detector, injector, and 6-position fraction collector. The mobile phase comprised of supercritical $CO_2$ supplied by a dewar of bone-dry non-certified $CO_2$ pressurized to 800 psi with a modifier of IPA buffered with 0.1 % $NH_3$ in $H_2O$ at a flow rate of 60 g/min. UV detection was set to collect at a wavelength of 254 nm, the backpressure regulator was set to maintain 100 bar. The sample was dissolved in IPA. The mobile phase was held isocratically at 20% IPA (0.1 % $NH_3$ in water):$CO_2$. The instrument was fitted with a ChiralCel OJ 10 mm column with dimensions 3.0 cm i.d. × 50 cm length |
| 19 | Preparative SFC was performed on a THAR/Waters SFC 80 system running under SuperChrom software control. The preparative SFC system was equipped with a $CO_2$ pump, modifier pump, automated back pressure regulator (ABPR), UV detector, injector, and 6-position fraction collector. The mobile phase comprised of supercritical $CO_2$ supplied by a dewar of bone-dry non-certified $CO_2$ pressurized to 800 psi with a modifier of IPA buffered with 0.1 % $NH_4OH$ at a flow rate of 55 g/min. UV detection was set to collect at a wavelength of 220 nm, the backpressure regulator was set to maintain 100 bar. The sample was dissolved in IPA. The mobile phase was held isocratically at 70% IPA (0.1 % $NH_3$ in water):$CO_2$. The instrument was fitted with a Chiralpak AD-H 5 µm, 3.0 cm id × 25 cm length |

Purification Methods

For examples without detailed procedures, the compounds may be purified by any technique or combination of techniques known to one skilled in the art. Some examples that are not limiting include flash chromatography with a solid phase (e.g. silica gel, alumina, etc.) and a solvent (or combination of solvents) that elutes the desired compounds (e.g. heptane, EtOAc, DCM, MeOH, MeCN, water, etc.); preparatory TLC with a solid phase (e.g. silica gel, alumina etc.) and a solvent (or combination of solvents) that elutes the desired compounds (e.g. heptane, EtOAc, DCM, MeOH, MeCN, water, etc.); reverse phase HPLC (see Table 1 for some non-limiting conditions); recrystallization from an appropriate solvent or combination of solvents (e.g. MeOH, EtOH, i-PrOH, EtOAc, toluene, etc.) or combination of solvents (e.g. EtOAc/heptane, EtOAc/MeOH, etc.); chiral HPLC with a solid phase and an appropriate solvent (see Table 2 for some non-limiting conditions) to elute the desired compound; chiral SFC with a solid phase and $CO_2$ with an appropriate modifier (e.g. MeOH, EtOH, i-PrOH with or without additional modifier such as DEA, TFA, etc.); precipitation from a combination of solvents (e.g. DMF/water, DMSO/DCM, EtOAc/heptane, etc.); trituration with an appropriate solvent (e.g. EtOAc, DCM, MeCN, MeOH, EtOH, i-PrOH, etc.); extractions by dissolving a compound in a liquid and washing with an appropriately immiscible liquid (e.g. DCM/water, EtOAc/water, DCM/saturated aqueous $NaHCO_3$, EtOAc/saturated aqueous $NaHCO_3$, DCM/10% aqueous HCl, EtOAc/10% aqueous HCl, etc.); distillation (e.g. simple, fractional, Kugelrohr, etc.); gas chromatography using an appropriate temperature, carrier gas and flow rate; sublimation at an appropriate temperature and pressure; filtration through a media (e.g. Florosil®, alumina, Celite®, silica gel, etc.) with a solvent (e.g. heptane, hexanes, EtOAc, DCM, MeOH, etc.) or combination of solvents; salt formation with solid support (resin based, e.g. ion exchange) or without. Compounds of interest may be isolated as a salt without the use of a specific salt formation purification method. For example, on occasions where purification is accomplished with reverse phase HPLC with an aqueous TFA buffer, the TFA salt may be isolated. Some descriptions of these techniques can be found in the following references: Gordon, A. J. and Ford, R. A. "The Chemist's Companion", 1972; Palleros, D. R. "Experimental Organic Chemistry", 2000; Still, W. C., Kahn and M. Mitra, A. *J. Org. Chem.* 1978, 43, 2923; Yan, B. "Analysis and Purification Methods in Combinatorial Chemistry", 2003; Harwood, L. M., Moody, C. J. and Percy, J. M. "Experimental Organic Chemistry: Standard and Microscale, 2nd Edition", 1999; Stichlmair, J. G. and Fair, J. R. "Distillation; Principles and Practices", 1998; Beesley, T. E. and Scott, R. P. W. "Chiral Chromatography", 1999; Landgrebe, J. A. "Theory and Practice in the Organic Laboratory, 4th Ed.", 1993; Skoog, D. A. and Leary, J. J. "Principles of Instrumental Analysis, 4th Ed.", 1992; G. Subramanian, "Chiral Separation Techniques, 3rd Edition", 2007; Y. Kazakevich, R. Lobrutto, "HPLC for Pharmaceutical Scientists", 2007. Intermediates and final compounds prepared via the General Procedures listed below can be optionally purified using one or more of the Purification Methods described above.

PREPARATIONS AND EXAMPLES

All starting materials are commercially available from Sigma-Aldrich (including Fluka, Aldrich Market Select, and Discovery CPR) unless otherwise noted after the chemical name. Reagent/reactant names given are as named on the commercial bottle or as generated by IUPAC conventions, CambridgeSoft® ChemDraw Ultra 12.0, CambridgeSoft® Chemistry E-Notebook 11, or AutoNom 2000. The general synthetic methods used in each General Procedure follow and include an illustration of a compound that was synthesized using the designated General Procedure. None of the specific conditions and reagents noted herein are to be construed as limiting the scope of the invention and are provided for illustrative purposes only. Compounds designated as salts (e.g. hydrochloride, trifluoroacetate) may contain more than one molar equivalent of the salt or may contain the acid as an excipient. Compounds of the invention where the absolute stereochemistry has been determined by the use of a commercially available enantiomerically pure starting material or a stereochemically defined intermediate or by X-ray diffraction are denoted by an asterisk after the example number. Otherwise the absolute stereochemistry is unknown and assigned randomly as drawn.

Preparation #1: 6,7-dihydro-4H-pyrazolo[5,1-c][1,4]oxazin-2-amine

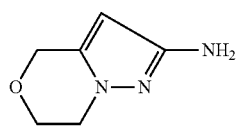

Step A. methyl 3-nitro-1H-pyrazole-5-carboxylate

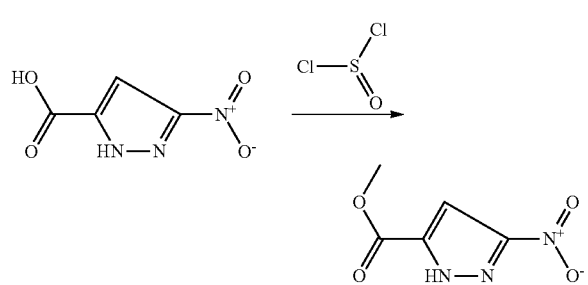

To a solution of 3-nitro-1H-pyrazole-5-carboxylic acid (69.75 g, 444 mmol) (ArkPharm) in MeOH (1 L) was added thionyl chloride (84 mL, 1154 mmol) at 0° C. The mixture was stirred for about 20 min at about 0° C. then heated to reflux for about 2 h. The resulting solution was concentrated under reduced pressure to give methyl 3-nitro-1H-pyrazole-5-carboxylate (61.25 g, 81%): LC/MS (Table 1, Method 1) $R_t$=1.42 min.; MS m/z: 169 (M+H)$^+$.

Step B. methyl 1-(2-bromoethyl)-3-nitro-1H-pyrazole-5-carboxylate

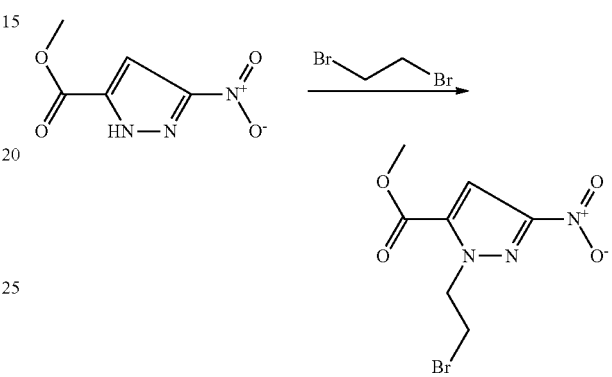

A 3 L 3-necked flask fitted with reflux condenser and thermocoupler was charged with methyl 3-nitro-1H-pyrazole-5-carboxylate (75.5 g, 441 mmol) and DMF (735 mL). Cesium carbonate (173 g, 529 mmol) was added portionwise and the reaction was heated to about 98° C. for 5 min, then cooled to ambient temperature for about 30 min. The reaction was cooled in an ice bath to about 0° C. before the addition of 1,2-dibromoethane (380 mL, 4412 mmol). The reaction was stirred, warming to ambient temperature, for about 5 h. The reaction mixture was quenched with the addition of an aqueous solution of potassium phosphate monobasic (120 g in 1 L). The resulting solution was extracted with EtOAc (3×300 mL). The combined organic portion was dried over MgSO4, filtered and concentrated under reduced pressure to afford methyl 1-(2-bromoethyl)-3-nitro-1H-pyrazole-5-carboxylate (120 g, 92%): LC/MS (Table 1, Method 1) $R_t$=2.10 min.; MS m/z: 278, 280 (M+H)$^+$.

Step C. (1-(2-bromoethyl)-3-nitro-1H-pyrazol-5-yl)methanol

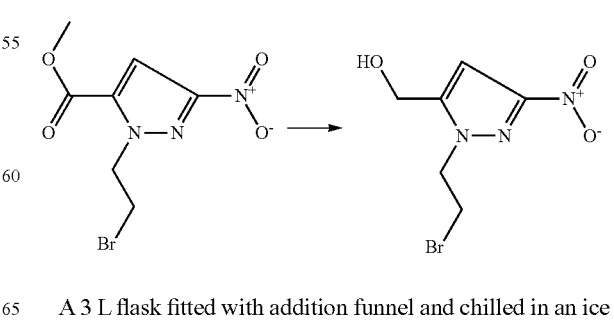

A 3 L flask fitted with addition funnel and chilled in an ice bath was charged with lithium tetrahydroborate (259 mL, 518 mmol) (2N in THF) and THF (252 mL). The reaction mixture was cooled to about 0° C. before the dropwise addition of a solution of methyl 1-(2-bromoethyl)-3-nitro-1H-pyrazole-5-carboxylate (72 g, 259 mmol) in THF (126 mL). The reaction stirred for about 2 h at ambient temperature. The reaction mixture was quenched with the addition of aqueous saturated NaCl (400 mL). The resulting mixture was extracted with EtOAc (3×400 mL). The combined organic portion was dried over MgSO4, filtered, and concentrated under reduced pressure to afford (1-(2-bromoethyl)-3-nitro-1H-pyrazol-5-yl)methanol (56.1 g, 87%): LC/MS (Table 1, Method 1) $R_t$=1.52 min.; MS m/z: 250, 252 (M+H)$^+$.

Step D. 2-nitro-6,7-dihydro-4H-pyrazolo[5,1-c][1,4]oxazine

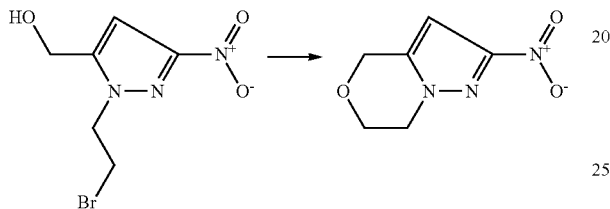

A 2 L flask was charged with (1-(2-bromoethyl)-3-nitro-1H-pyrazol-5-yl)methanol (56 g, 190 mmol) and dissolved in DMA (747 mL). The reaction was heated to about 140° C. for about 5 h. The reaction cooled to ambient temperature and the solvent was concentrated under reduced pressure. The resulting residue was partitioned between EtOAc (500 mL) and aqueous saturated NaHCO$_3$ (150 mL). The aqueous portion was extracted with EtOAc (3×400 mL). The combined organic portion was dried over MgSO$_4$, filtered, and concentrated under reduced pressure. 200 mL of Et$_2$O was added to the resulting residue and the solid was collected via filtration to afford 2-nitro-6,7-dihydro-4H-pyrazolo[5-c][1,4]oxazine (14 g, 43.5%). The remaining filtrate was concentrated under reduced pressure and purified using silica gel chromatography to afford 2-nitro-6,7-dihydro-4H-pyrazolo[5-c][1,4]oxazine (6.5 g, 38.4 mmol, 20.19% yield):): LC/MS (Table 1, Method 1) $R_t$=1.31 min.; MS m/z: 170 (M+H)$^+$.

Step E. 6,7-dihydro-4H-pyrazolo[5,1-c][1,4]oxazin-2-amine

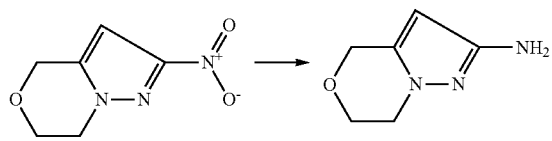 [SMILES: O=[N+]([O-])c1cc2n(n1)CCOC2 ; Nc1cc2n(n1)CCOC2]

A flask was charged with 10% palladium on carbon (2.64 g, 2.483 mmol). The flask was evacuated and put under nitrogen atmosphere before the addition of MeOH (100 mL) and 2-nitro-6,7-dihydro-4H-pyrazolo[5,1-c][1,4]oxazine (14 g, 83 mmol) in EtOAc (300 mL). The reaction was evacuated and purged with hydrogen three times. The reaction stirred at ambient temperature for about 16 h. The catalyst was filtered off through a pad of Celite® and the compound was washed with about 300 mL of EtOAc. The solvent was concentrated under reduced pressure to give, 6,7-dihydro-4H-pyrazolo[5,1-c][1,4]oxazin-2-amine (10.9 g, 95%): LC/MS (Table 1, Method 1) $R_t$=0.61 min.; MS m/z: 140 (M+H)$^+$.

Preparation #2: tert-butyl 3-(8-((tert-butoxycarbonyl)(6,7-dihydro-4H-pyrazolo[5,1-c][1,4]oxazin-2-yl)amino)-[1,2,4]triazolo[1,5-a]pyridin-6-yl)azetidine-1-carboxylate

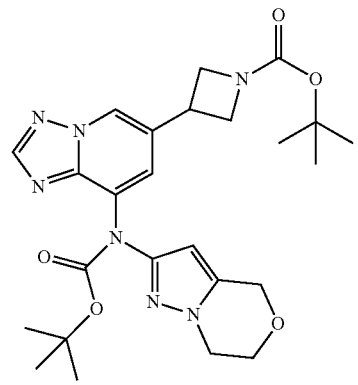 [SMILES: CC(C)(C)OC(=O)N1CC(c2cc(N(C(=O)OC(C)(C)C)c3cc4n(n3)CCOC4)c3ncnn3c2)C1]

Step A: N-(6-bromo-[1,2,4]triazolo[1,5-a]pyridin-8-yl)-6,7-dihydro-4H-pyrazolo[5,1-c][1,4]oxazin-2-amine

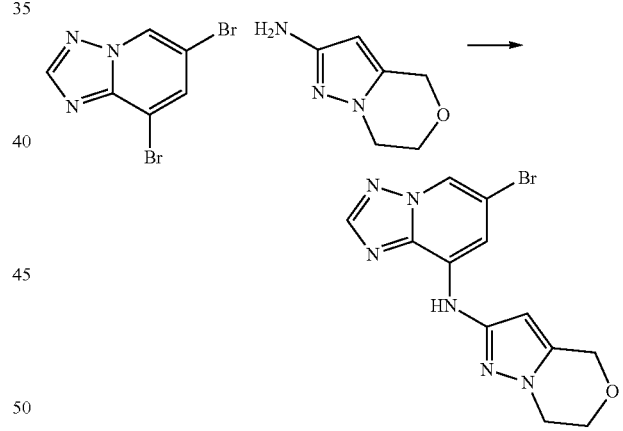

To a microwave reaction vial were added tert-butyl 6,8-dibromo-[1,2,4]triazolo[1,5-a]pyridine (1.0 g, 3.6 mmol, ArkPharm), 6,7-dihydro-4H-pyrazolo[5,1-c][1,4]oxazin-2-amine (0.503 g, 3.61 mmol, Preparation #1), 1,4-dioxane (12 mL), Cs$_2$CO$_3$ (2.353 g, 7.22 mmol), Xantphos (0.104 g, 0.181 mmol) and Pd$_2$(dba)$_3$ (0.165 g, 0.181 mmol), The reaction vial was flushed with nitrogen, capped, stirred and heated to about 120° C. in a Biotage microwave reactor for about 3 h. The reaction was diluted with DCM (80 mL) and water (50 mL). The organic layer was separated, washed with water (50 mL), brine (50 mL), and dried over Na$_2$SO$_4$. The organic layer was filtered and concentrated under reduced pressure The crude product was purified via silica chromatography eluting with 5% MeOH in DCM to afford N-(6-bromo-[1,2,4]triazolo[1,5-a]pyridin-8-yl)-6,7-dihydro-4H-pyrazolo[5,1-c][1,4]oxazin-2-amine (0.80 g, 43%) as a yellow solid: LC/MS (Table 1, Method p) R$_t$=1.59 min.; MS m/z: 335/337 (M+H)$^+$.

Step B: tert-butyl (6-bromo-[1,2,4]triazolo[1,5-a]pyridin-8-yl)(6,7-dihydro-4H-pyrazolo[5,1-c][1,4]oxazin-2-yl)carbamate

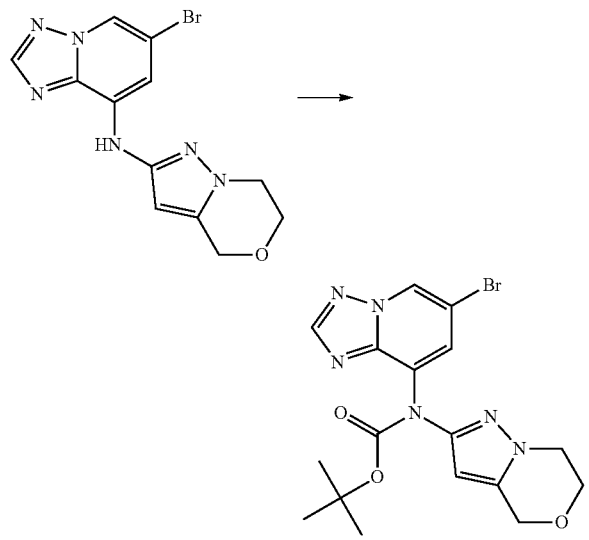 [SMILES: Brc1cc(Nc2cc3n(n2)CCOC3)c2ncnn2c1 ; CC(C)(C)OC(=O)N(c1cc2n(n1)CCOC2)c1cc(Br)cn2ncnc12]

A mixture of N-(6-bromo-[1,2,4]triazolo[1,5-a]pyridin-8-yl)-6,7-dihydro-4H-pyrazolo[5,1-c][1,4]oxazin-2-amine (0.80 g, 1.5 mmol), BOC$_2$O (1.08 mL, 4.65 mmol), TEA (0.649 mL, 4.65 mmol) and DMAP (0.190 g, 1.55 mmol) in DCM, (60 mL) was stirred at rt overnight. The organic layer was washed with saturated NH$_4$Cl (3×50 mL). The organic layer was dried with Na$_2$SO$_4$, filtered and concentrated. The product was purified via silica chromatography eluting with EtOAc:petroleum ether (2:1) to afford tert-butyl (6-bromo-[1,2,4]triazolo[1,5-a]pyridin-8-yl)(6,7-dihydro-4H-pyrazolo[5,1-c][1,4]oxazin-2-yl)carbamate (0.53 g, 77%) as white solid: LC/MS (Table 1, Method n) R$_t$=1.73 min.; MS m/z: 435/437 (M+H)$^+$.

Step C: tert-butyl 3-(8-((tert-butoxycarbonyl)(6,7-dihydro-4H-pyrazolo[5,1-c][1,4]oxazin-2-yl)amino)-[1,2,4]triazolo[1,5-a]pyridin-6-yl)azetidine-1-carboxylate

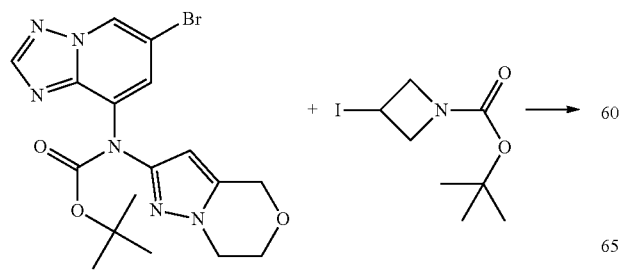

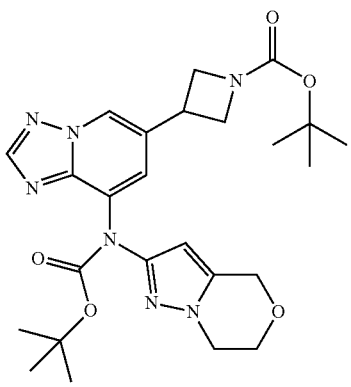

To a mixture of zinc (0.16 g, 2.5 mmol) in degassed DMA (3 mL) under nitrogen was added trimethylsilyl chloride (0.032 mL, 0.25 mmol) and 1,2-dibromoethane (0.032 g, 0.17 mmol). The mixture was stirred for about 15 min, and tert-butyl 3-iodoazetidine-1-carboxylate (0.35 g, 1.2 mmol) was added via syringe. The resulting mixture was stirred at rt for about 1.5 h to form the (1-(tert-butoxycarbonyl)azetidin-3-yl) zinc (II) iodide. tert-Butyl (6-bromo-[1,2,4]triazolo[1,5-a]pyridin-8-yl)(6,7-dihydro-4H-pyrazolo[5,1-c][1,4]oxazin-2-yl)carbamate (0.11 g, 0.25 mmol) was dissolved in DMA (5 mL), and degassed for about 5 min followed by the addition of PdCl2(dppf) (0.013 g, 0.017 mmol) and copper(I)iodide (0.056 g, 0.30 mmol) and then the addition of the previously generated solution of (1-(tert-butoxycarbonyl)azetidin-3-yl) zinc(II) iodide. The reaction was heated to about 80° C. for about 2 h. The reaction mixture was diluted with EtOAc (40 mL) and filtered through a nylon filter. Water (40 mL) was added, the layers were separated, the organic phase was washed with brine (3×40 mL)), and then dried over anhydrous Na$_2$SO$_4$. The solution was concentrated and the residue was purified by prep-TLC using DCM and MeOH (40:1) and tert-butyl 3-(8-((tert-butoxycarbonyl)(6,7-dihydro-4H-pyrazolo[51-c][1,4]oxazin-2-yl)amino)-[1,2,4]triazolo[1,5-a]pyridin-6-yl)azetidine-1-carboxylate (0.07 g, 41.5%) was obtained as a brown solid: LC/MS (Table 1, Method q) R$_t$=1.81 min.; MS m/z: 512 (M+H)$^+$.

Preparation #3: 1-(4-amino-1H-pyrazol-1-yl)-2-methylpropan-2-ol

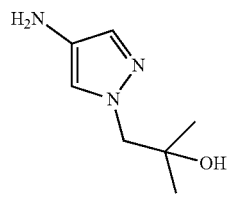

Step A: 2-methyl-1-(4-nitro-1H-pyrazol-1-yl)propan-2-ol

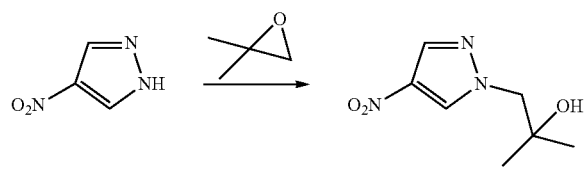

A round bottom flask was charged with 4-nitro-1H-pyrazole (4 g, 35.4 mmol), 2,2-dimethyloxirane (5.1 g, 70 mmol), and $Cs_2CO_3$ (23 g, 70 mmol). The reaction was heated to about 90° C. for about 12 h, cooled to ambient temperature, filtered, and the filtrate was concentrated under reduced pressure. The crude material was purified via silica chromatography eluting with EtOAc:petroleum ether (10:1 to 3:1) to afford 2-methyl-1-(4-nitro-1H-pyrazol-1-yl)propan-2-ol (4 g, 61% yield) as a yellow oil. LC/MS (Table 1, Method w) $R_t$=0.976 min.; MS m/z: 182 (M+H)$^+$.

Step B: 1-(4-amino-1H-pyrazol-1-yl)-2-methylpropan-2-ol

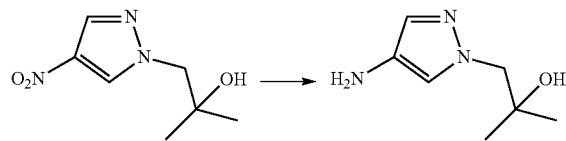

A round bottom flask was charged with 2-methyl-1-(4-nitro-1H-pyrazol-1-yl)propan-2-ol (1 g, 5.40 mmol) and Raney Nickel (1 g) in THF (40 mL). The reaction mixture stirred at about 20° C. for about 12 h, under an atmosphere of hydrogen. The reaction mixture was filtered through a pad of Celite® and concentrated under reduced pressure to afford 1-(4-amino-1H-pyrazol-1-yl)-2-methylpropan-2-ol (0.8 g, 95% yield) as a white solid. LC/MS (Table 1, Method w) $R_t$=0.155 min.; MS m/z: 156 (M+H)$^+$.

Preparation #4: 4-(4-amino-1H-pyrazol-1-yl)-2-methylbutan-2-ol

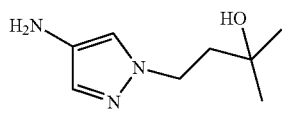

Step A: 3-hydroxy-3-methylbutyl methanesulfonate

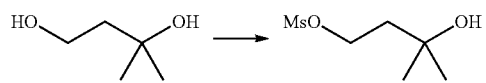

A round bottom flask was charged with 3-methylbutane-1,3-diol (10 g, 96 mmol) and TEA (20 mL, 144 mmol) in DCM (80 mL). A solution of methanesulfonyl chloride (12 g, 106 mmol) in DCM (50 mL) was added dropwise to the reaction mixture at about 0° C. The resulting mixture was stirred at about 0° C. for 4 h. The reaction was diluted with saturated aq. sodium bicarbonate (100 mL). The organic portion was dried over anhydrous $Na_2SO_4$, filtered, and concentrated under reduced pressure to give 3-hydroxy-3-methylbutyl methanesulfonate (12 g, 66% yield) as a yellow oil. $^1$H NMR (400 MHz, CHLOROFORM-d) δ=4.40 (t, J=7.1 Hz, 2H), 3.01 (s, 3H), 1.94 (t, J=7.1 Hz, 2H), 1.81 (s, 1H), 1.27 (s, 6H).

Step B: 2-methyl-4-(4-nitro-1H-pyrazol-1-yl)butan-2-ol

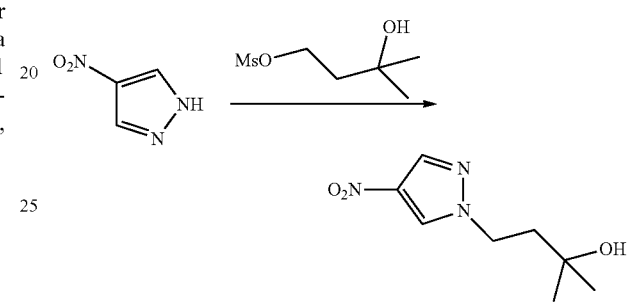

A round bottom flask was charged with 3-hydroxy-3-methylbutyl methanesulfonate (12 g, 66 mmol), $K_2CO_3$ (7.3 g, 53.1 mmol) and KI (4.4 g, 26.5 mmol) ACN (250 mL). 4-nitro-1H-pyrazole (3 g, 26.5 mmol) was added to the reaction mixture at about 15° C. The reaction was then heated to about 90° C. for about 12 h. The reaction mixture was cooled to ambient temperature, diluted with water (100 mL) and extracted with EtOAc (3×200 mL). The combined organic portion was dried over anhydrous $Na_2SO_4$, filtered, and concentrated under reduced pressure. The crude material was purified via silica chromatography eluting with: petroleum ether:EtOAc (30:1 to 1:1) to afford 2-methyl-4-(4-nitro-1H-pyrazol-1-yl)butan-2-ol (4.7 g, 89% yield) as a yellow oil. LC/MS (Table 1, Method w) $R_t$=0.807 min.; MS m/z: 200 (M+H)$^+$.

Step C: 4-(4-amino-1H-pyrazol-1-yl)-2-methylbutan-2-ol

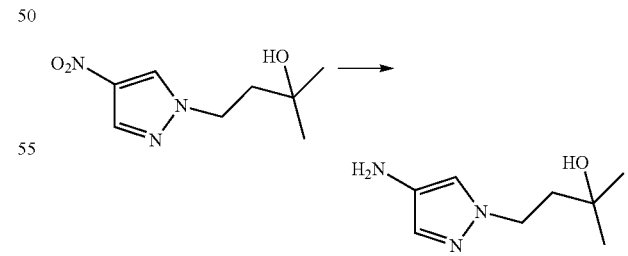

To a solution of 2-methyl-4-(4-nitro-1H-pyrazol-1-yl)butan-2-ol (0.5 g, 2.5 mmol) in THF (50 mL) was added Raney nickel (1 g, 17.04 mmol) at about 15° C. The reaction mixture stirred at about 15° C. for about 12 h, under an atmosphere of hydrogen. The reaction mixture was filtered through a pad of Celite® and concentrated under reduced pressure to afford 4-(4-amino-1H-pyrazol-1-yl)-2-methylbutan-2-ol (0.36 g, 80% yield) as a light pink solid. LC/MS (Table 1, Method w) R$_t$=0.162 min.; MS m/z: 170 (M+H)$^+$.

Preparation #5: 1-(2,2,6,6-tetramethyltetrahydro-2H-pyran-4-yl)-1H-pyrazol-4-amine

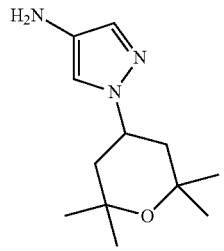 [SMILES: CC1(C)CC(n2cc(N)cn2)CC(C)(C)O1]

Step A: 2,2,6,6-tetramethyldihydro-2H-pyran-4(3H)-one

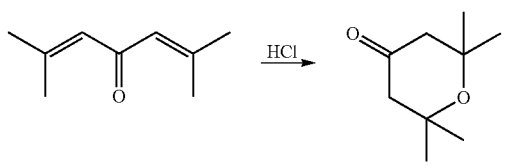

A round bottom flask was charged with 2,6-dimethyl hepta-2,5-dien-4-one (10 g, 72.4 mmol) and 1 M HCl (100 mL, 100 mmol). The reaction was stirred at about 40° C. for about 4 days. The reaction was extracted with DCM (3×100 mL). The organic portion was dried over anhydrous Na$_2$SO$_4$, filtered, and concentrated under reduced pressure to give 2,2,6,6-tetramethyldihydro-2H-pyran-4(3H)-one (10 g, 62% yield) as a yellow oil. $^1$H NMR (400 MHz, CHLOROFORM-d) δ=2.15-2.10 (m, 2H), 1.91-1.87 (m, 2H), 1.31 (s, 6H), 1.27 (s, 6H).

Step B: 2,2,6,6-tetramethyltetrahydro-2H-pyran-4-ol

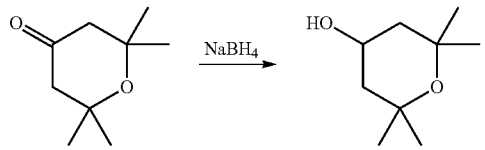

To a solution of 2,2,6,6-tetramethyldihydro-2H-pyran-4(3H)-one (2 g, 12.8 mmol) in MeOH (50 mL) was added portionwise NaBH$_4$ (0.97 g, 25.6 mmol) at about 0° C. The reaction stirred at about 0° C. for about 2 h. The reaction was diluted with saturated aq. NH$_4$Cl (50 mL) and extracted with DCM (2×50 mL). The organic portion was dried over anhydrous Na$_2$SO$_4$, filtered, and concentrated under reduced pressure to give 2,2,6,6-tetramethyltetrahydro-2H-pyran-4-ol (1.4 g, 48% yield) as a white wax. $^1$H NMR (400 MHz, CHLOROFORM-d) δ=4.1-4.05 (m, 1H), 1.92-1.87 (m, 2H), 1.71-1.68 (m, 2H), 1.25 (s, 6H), 1.23 (s, 6H).

Step C: 2,2,6,6-tetramethyltetrahydro-2H-pyran-4-yl methanesulfonate

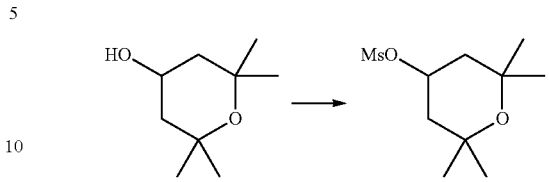

A round bottom flask was charged with 2,2,6,6-tetramethyltetrahydro-2H-pyran-4-ol (5.5 g, 34.8 mmol) and TEA (7.0 g, 69 mmol) in DCM (110 mL). Methanesulfonyl chloride (5.9 g, 52.1 mmol) was slowly added to the reaction mixture at about 0° C. over 20 minutes. The reaction warmed to about 20° C. over 30 minutes and stirred at about 20° C. for about 2 h. The reaction was diluted with water (100 mL) and extracted with DCM (3×100 mL). The organic portion was dried over anhydrous Na$_2$SO$_4$, filtered, and concentrated under reduced pressure to give 2,2,6,6-tetramethyltetrahydro-2H-pyran-4-yl methanesulfonate (8 g, crude) as a yellow oil. $^1$H NMR (400 MHz, CHLOROFORM-d) δ=5.1-5.09 (m, 1H), 3.03 (s, 3H), 2.1-2.07 (d, 2H), 1.59-1.54 (d, 2H), 1.30 (s, 6H), 1.25 (s, 6H).

Step D: 4-nitro-1-(2,2,6,6-tetramethyltetrahydro-2H-pyran-4-yl)-1H-pyrazole

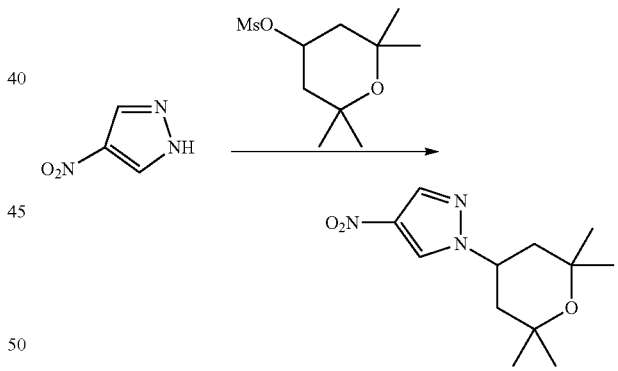

A round bottom flask was charged with 4-nitro-1H-pyrazole (1.2 g, 10.61 mmol), 2,2,6,6-tetramethyltetrahydro-2H-pyran-4-yl methanesulfonate (7.5 g, 31 mmol), and Cs$_2$CO$_3$ (6.9 g, 21.2 mmol) in DMF (30 mL). The reaction was heated to about 130° C. for about 12 h. The reaction was cooled to ambient temperature, diluted with water (100 mL) and extracted with EtOAc (3×100 mL). The organic portion was dried over anhydrous Na$_2$SO$_4$, filtered, and concentrated under reduced pressure. The crude material was purified via silica gel chromatography eluting with petroleum ether/EtOAc (20:1 to 5:1) to give 4-nitro-1-(2,2,6,6-tetramethyltetrahydro-2H-pyran-4-yl)-1H-pyrazole (0.6 g, 21% yield) as white solid. LC/MS (Table 1, Method w) R$_t$=1.37 min.; MS m/z: 254 (M+H)$^+$.

Step E: 1-(2,2,6,6-tetramethyltetrahydro-2H-pyran-4-yl)-1H-pyrazol-4-amine

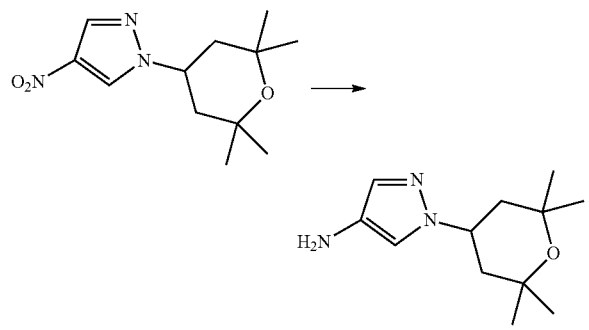

To a solution of 4-nitro-1-(2,2,6,6-tetramethyltetrahydro-2H-pyran-4-yl)-1H-pyrazole (0.3 g, 1.18 mmol) in THF (20 mL) was added Raney nickel (1 g, 17.04 mmol). The reaction mixture stirred at about 20° C. for about 12 h, under an atmosphere of hydrogen. The reaction mixture was filtered through a pad of Celite® and concentrated under reduced pressure to afford 1-(2,2,6,6-tetramethyltetrahydro-2H-pyran-4-yl)-1H-pyrazol-4-amine (0.25 g, 85% yield) as a white solid. LC/MS (Table 1, Method w) $R_t$=0.729 min.; MS m/z: 224 (M+H)$^+$.

Preparation #6: (trans)-4-(4-amino-1H-pyrazol-1-yl)cyclohexanol and (cis)-4-(4-amino-1H-pyrazol-1-yl)cyclohexanol

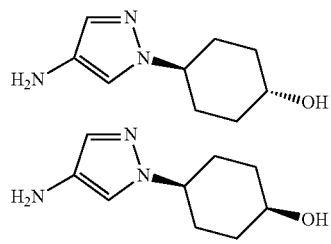

Step A: 4-hydroxycyclohexyl methanesulfonate

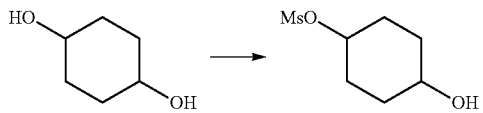 [SMILES: OC1CCC(O)CC1 ; CS(=O)(=O)OC1CCC(O)CC1]

A round bottom flask was charged with cyclohexane-1,4-diol (10 g, 86 mmol) and TEA (8.7 g, 86 mmol) in THF (200 mL). Methanesulfonyl chloride (3.9 g, 34 mmol) was slowly added to the reaction mixture at about 0° C. over 20 minutes. The reaction warmed to about 20° stirred for about 2 h. The reaction was diluted with water (150 mL) and extracted with EtOAc (3×150 mL). The organic portion was dried over anhydrous Na$_2$SO$_4$, filtered, and concentrated under reduced pressure to give 4-hydroxycyclohexyl methanesulfonate (6 g, 32% yield) as a yellow oil. $^1$H NMR (400 MHz, CHLOROFORM-d) δ=4.8-4.71 (m, 1H), 3.79-3.73 (m, 1H), 3.02 (s, 3H), 2.1-1.97 (m, 4H), 1.6-1.46 (m, 4H).

Step B: (trans)-4-(4-nitro-1H-pyrazol-1-yl)cyclohexanol and (cis)-4-(4-nitro-1H-pyrazol-1-yl)cyclohexanol

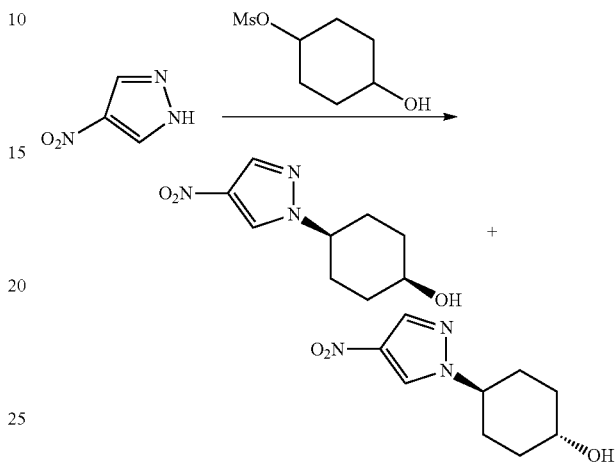

A round bottom flask was charged with 4-nitro-1H-pyrazole (2 g, 17.6 mmol), 4-hydroxycyclohexyl methanesulfonate (6 g, 30.9 mmol), and Cs$_2$CO$_3$ (11.5 g, 35.4 mmol) in DMF (60 mL). The reaction was heated to about 130° C. for about 12 h. The reaction was cooled to ambient temperature and concentrated under reduced pressure. The crude material was purified via silica gel chromatography eluting with petroleum ether/EtOAc (10:1 to 1:1) to give (trans)-4-(4-nitro-1H-pyrazol-1-yl)cyclohexanol (0.3 g, 8% yield). LC/MS (Table 1, Method w) $R_t$=1.08 min.; MS m/z: 211 (M+H)$^+$, and (cis)-4-(4-nitro-1H-pyrazol-1-yl)cyclohexanol (0.3 g, 8% yield).). LC/MS (Table 1, Method w) $R_t$=1.09 min.; MS m/z: 211 (M+H)$^+$

Step C: (trans)-4-(4-amino-1H-pyrazol-1-yl)cyclohexanol

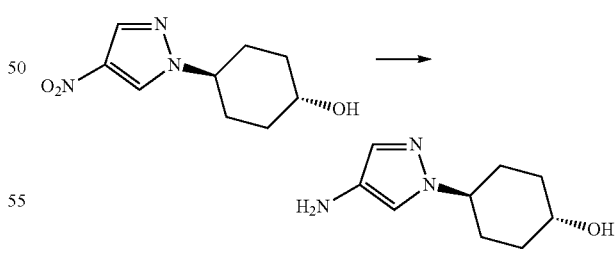

To a solution of (trans)-4-(4-nitro-1H-pyrazol-1-yl)cyclohexanol (0.15 g, 0.71 mmol) in THF (15 mL) was added Raney nickel (0.3 g). The reaction mixture stirred at about 20° C. for about 3 h, under an atmosphere of hydrogen. The reaction mixture was filtered through a pad of Celite® and concentrated under reduced pressure to afford (trans)-4-(4-amino-1H-pyrazol-1-yl)cyclohexanol (0.13 g, 91% yield) as a white solid. LC/MS (Table 1, Method w) $R_t$=0.162 min.; MS m/z: 182 (M+H)$^+$.

Step D: (cis)-4-(4-amino-1H-pyrazol-1-yl)cyclohexanol

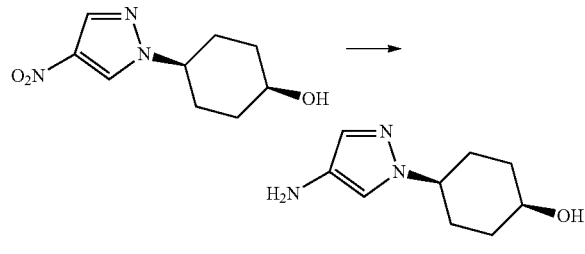

To a solution of (cis)-4-(4-nitro-1H-pyrazol-1-yl)cyclohexanol (0.15 g, 0.71 mmol) in THF (15 mL) was added Raney nickel (0.3 g). The reaction mixture stirred at about 20° C. for about 3 h, under an atmosphere of hydrogen. The reaction mixture was filtered through a pad of Celite® and concentrated under reduced pressure to afford (cis)-4-(4-amino-1H-pyrazol-1-yl)cyclohexanol (0.13 g, 91% yield) as a white solid. LC/MS (Table 1, Method w) $R_f$=0.210 min.; MS m/z: 182 (M+H)$^+$.

Preparation #7: (trans)-3-(4-amino-1H-pyrazol-1-yl)cyclohexanol

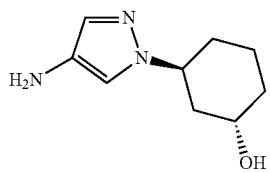 [SMILES: Nc1cnn([C@H]2CCC[C@H](O)C2)c1]

Step A:
3-((tert-butyldimethylsilyl)oxy)cyclohexanol

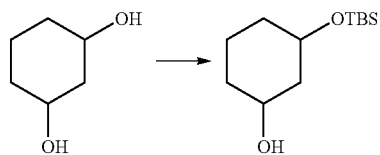 [SMILES: OC1CCCC(O)C1 ; CC(C)(C)[Si](C)(C)OC1CCCC(O)C1]

To a solution cyclohexane-1,3-diol (10 g, 86 mmol) and imidazole (8.9 g, 130 mmol) in THF (300 mL) was added tert-butylchlorodimethylsilane (5.2 g, 34.4 mmol). The reaction mixture stirred at about 15° C. for about 12 h. The solvent was removed under reduced pressure and the residue was diluted with water (100 mL). The material was extracted with EtOAc (2×200 mL), dried over anhydrous Na$_2$SO$_4$, filtered, and concentrated under reduced pressure to afford 3-((tert-butyldimethylsilyl)oxy)cyclohexanol (7.8 g, 37% yield) as a light yellow oil. $^1$H NMR (400 MHz, CHLOROFORM-d) δ=4.12-3.98 (m, 1H), 3.95-3.77 (m, 1H), 1.95-1.74 (m, 2H), 1.72-1.64 (m, 1H), 1.62-1.49 (m, 3H), 1.48-1.40 (m, 1H), 1.35-1.26 (m, 1H), 0.89-0.86 (m, 9H), 0.06 (d, J=3.1 Hz, 3H), 0.04-0.01 (m, 3H)

Step B: (trans)-3-((tert-butyldimethylsilyl)oxy)cyclohexyl)-4-nitro-1H-pyrazole and (cis)-3-((tert-butyldimethylsilyl)oxy)cyclohexyl)-4-nitro-1H-pyrazole

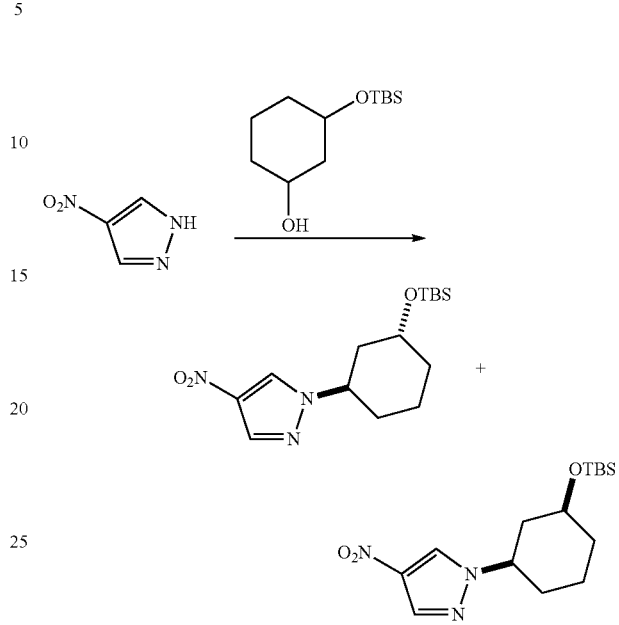

To a solution of 4-nitro-1H-pyrazole (3.6 g, 32.2 mmol), 3-((tert-butyldimethylsilyl)oxy)cyclohexanol (7.8 g, 32.2 mmol) and triphenylphosphine (12.6 g, 48.2 mmol) in THF (250 mL) was added a solution of DIAD (9.4 mL, 48.2 mmol) in THF (50 mL) at about 0° C. The reaction mixture warmed to about 15° C. and stirred for about 12 h. The solvent was removed under reduced pressure and the remaining residue was purified via silica gel chromatography eluting with petroleum ether/EtOAc (50:1 to 30:1) to give (trans)-3-((tert-butyldimethylsilyl)oxy)cyclohexyl)-4-nitro-1H-pyrazole (3.1 g, 29% yield). $^1$H NMR (400 MHz, CHLOROFORM-d) δ=8.14 (s, 1H), 8.07 (s, 1H), 4.56 (tt, J=3.7, 11.7 Hz, 1H), 4.28 (br. s., 1H), 2.13 (dd, J=1.5, 10.8 Hz, 2H), 1.96-1.86 (m, 2H), 1.78-1.66 (m, 3H), 1.50-1.40 (m, 1H), 0.92 (s, 9H), 0.10-0.04 (m, 6H) and (cis)-3-((tert-butyldimethylsilyl)oxy)cyclohexyl)-4-nitro-1H-pyrazole (1.84 g, 17% yield) $^1$H NMR (400 MHz, CHLOROFORM-d) δ=8.17 (s, 1H), 8.07 (s, 1H), 4.17 (tt, J=3.9, 12.0 Hz, 1H), 3.77-3.68 (m, 1H), 2.40-2.32 (m, 1H), 2.15 (d, J=12.3 Hz, 1H), 1.94 (dt, J=3.5, 6.6 Hz, 2H), 1.80-1.70 (m, 1H), 1.60 (dq, J=3.1, 12.2 Hz, 1H), 1.47-1.28 (m, 2H), 0.88 (s, 9H), 0.13-0.01 (m, 6H).

Step C: (trans)-3-(4-nitro-1H-pyrazol-1-yl)cyclohexanol

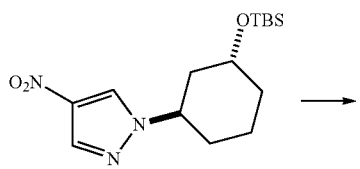

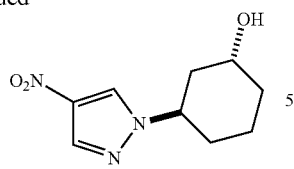

To a solution of (trans)-3-((tert-butyldimethylsilyl)oxy)cyclohexyl)-4-nitro-1H-pyrazole (1 g, 3.07 mmol) in MeOH (30 mL) was added a solution of HI (0.513 ml, 3.07 mmol) in MeOH (5 mL). The reaction mixture stirred at about 15° C. for about 12 h. The solvent was removed under reduced pressure and the remaining residue was partitioned between saturated aq. NaHCO$_3$ (30 mL) and EtOAc (100 mL). The organic layer was washed with saturated aq. sodium thiosulfate (2×30 mL), dried over Na$_2$SO$_4$, filtered, and concentrated under reduced pressure to give (trans)-3-(4-nitro-1H-pyrazol-1-yl)cyclohexanol (0.64 g, 94% yield) as a yellow solid. LC/MS (Table 1, Method w) R$_t$=1.07 min.; MS m/z: 212 (M+H)$^+$.

Step D: (trans)-3-(4-amino-1H-pyrazol-1-yl)cyclohexanol

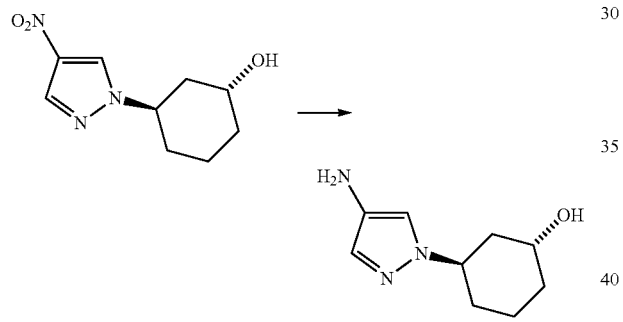

To a solution of (trans)-3-(4-nitro-1H-pyrazol-1-yl)cyclohexanol (0.3 g, 1.42 mmol) in THF (50 mL) was added Raney nickel (1 g, 17.04 mmol). The reaction mixture stirred at about 15° C. for about 12 h, under an atmosphere of hydrogen. The reaction mixture was filtered through a pad of Celite® and concentrated under reduced pressure to afford (trans)-3-(4-amino-1H-pyrazol-1-yl)cyclohexanol (0.23 g, 85% yield) as a light red solid. LC/MS (Table 1, Method w) R$_t$=0.198 min.; MS m/z: 182 (M+H)$^+$.

Preparation #8: (cis)-3-(4-amino-1H-pyrazol-1-yl)cyclohexanol

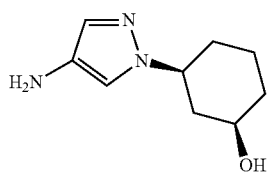 [SMILES: Nc1cnn([C@H]2CCC[C@@H](O)C2)c1]

Step A: (cis)-3-(4-nitro-1H-pyrazol-1-yl)cyclohexanol

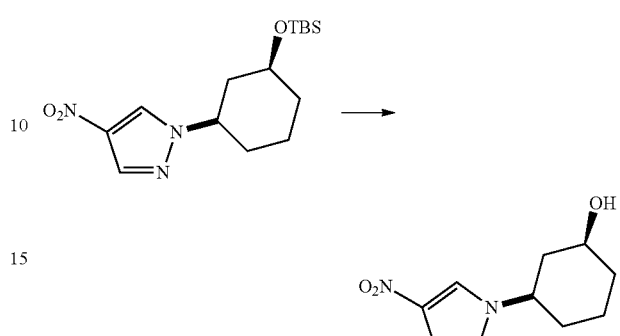

To a solution of (cis)-3-((tert-butyldimethylsilyl)oxy)cyclohexyl)-4-nitro-1H-pyrazole (0.9 g, 2.77 mmol, Preparation #7, Step B) in MeOH (30 mL) was added a solution of HI (0.54 ml, 3.32 mmol) in MeOH (5 mL). The reaction mixture stirred at about 15° C. for about 12 h. The solvent was removed under reduced pressure and the remaining residue was partitioned between saturated aq. NaHCO$_3$ (30 mL) and EtOAc (100 mL). The organic layer was washed with saturated aq. sodium thiosulfate (2×30 mL), dried over Na$_2$SO$_4$, filtered, and concentrated under reduced pressure to give (cis)-3-(4-nitro-1H-pyrazol-1-yl)cyclohexanol (0.54 g, 88% yield). LC/MS (Table 1, Method w) R$_t$=1.07 min.; MS m/z: 212 (M+H)$^+$.

Step B: (cis)-3-(4-amino-1H-pyrazol-1-yl)cyclohexanol

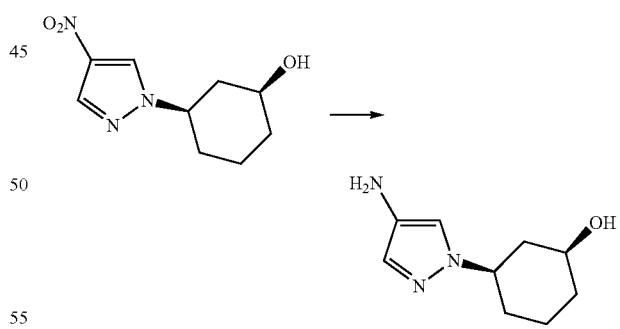

To a solution of (trans)-3-(4-nitro-1H-pyrazol-1-yl)cyclohexanol (0.54 g, 2.56 mmol) in THF (50 mL) was added Raney nickel (1 g, 17.04 mmol). The reaction mixture stirred at about 15° C. for about 12 h, under an atmosphere of hydrogen. The reaction mixture was filtered through a pad of Celite® and concentrated under reduced pressure to afford (cis)-3-(4-amino-1H-pyrazol-1-yl)cyclohexanol (0.41 g, 87% yield) as a pink solid. LC/MS (Table 1, Method w) R$_t$=0.232 min.; MS m/z: 182 (M+H)$^+$.

Preparation #9: ethyl 4-(4-amino-1H-pyrazol-1-yl)cyclohexanecarboxylate

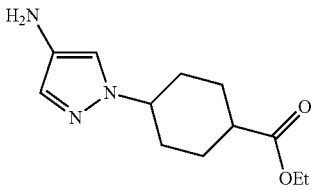 [SMILES: CCOC(=O)C1CCC(n2cc(N)cn2)CC1]

Step A: ethyl 4-(4-nitro-1H-pyrazol-1-yl)cyclohexanecarboxylate

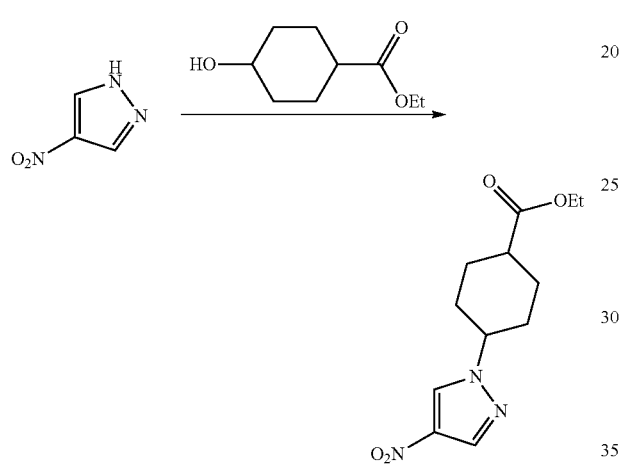

A round bottom flask was charged with ethyl 4-hydroxycyclohexanecarboxylate (4.1 g, 23.8 mmol), 4-nitro-1H-pyrazole (2.2 g, 19.0 mmol), and PPh$_3$ (6.2 g, 23.8 mmol) in THF (95 mL). The reaction was degassed with nitrogen for about 5 min. before the addition of DIAD (7.4 ml, 38.1 mmol). The reaction mixture was stirred at about 60° C. for about 16 h. The solvent was concentrated under reduced pressure. The crude material was purified via silica gel chromatography eluting with EtOAc/Heptanes (0-100%) to afford ethyl 4-(4-nitro-1H-pyrazol-1-yl)cyclohexanecarboxylate (5.0 g, quant yield). LC/MS (Table 1, Method h) R$_t$=2.22 min.; MS m/z: 268 (M+H)$^+$.

Step B: ethyl 4-(4-amino-1H-pyrazol-1-yl)cyclohexanecarboxylate

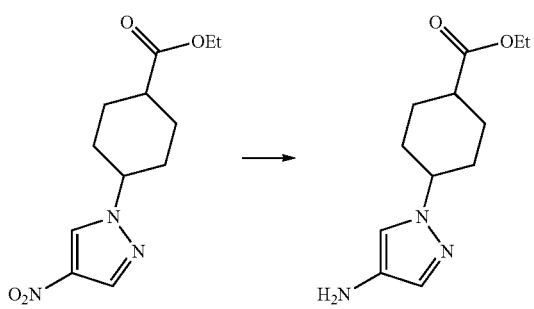 [SMILES: CCOC(=O)C1CCC(n2cc([N+](=O)[O-])cn2)CC1 ; CCOC(=O)C1CCC(n2cc(N)cn2)CC1]

A solution of ethyl 4-(4-nitro-1H-pyrazol-1-yl)cyclohexanecarboxylate (5.1 g, 18.9 mmol) in EtOH (95 mL) was passed through the H-Cube with a 10% Pd/C cartridge under 10 bar of hydrogen at 50° C. The reaction solution cycled through the reactor for 5 h. The solvent was concentrated under reduced pressure to afford ethyl 4-(4-amino-1H-pyrazol-1-yl)cyclohexanecarboxylate (4.5 g, quant yield). LC/MS (Table 1, Method h) R$_t$=1.30 min.; MS m/z: 238 (M+H)$^+$.

Preparation #10: tert-butyl 4-(4-amino-1H-pyrazol-1-yl)-2,6-dimethylpiperidine-1-carboxylate

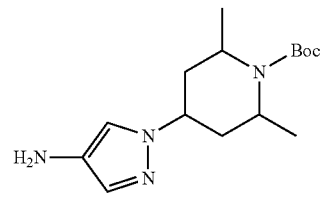

Step A: dimethyl 2,6-dimethyl-4-oxopiperidine-3,5-dicarboxylate

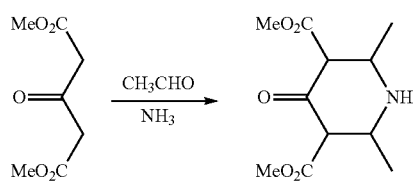

To a mixture of dimethyl 3-oxopentanedioate (100 g, 574 mmol) and acetaldehyde (65.8 g, 1.5 mol) was bubbled ammonia gas at −30° C. until the liquid was saturated. The solution was stored in the freezer for about 20 h. The yellow reside was purified by chromatography on silica gel eluting with (PE:EtOAc=10:1 to PE:EtOAc=1:2) to give dimethyl 2,6-dimethyl-4-oxopiperidine-3,5-dicarboxylate (120 g, 50% yield, 60% purity). $^1$H NMR (400 MHz, CHLOROFORM-d) 3.73-3.70 (m, 9H), 3.39-3.31 (m, 2H), 3.04-2.98 (m, 2H), 1.19 (d, J=6.2 Hz, 6H).

Step B: 2,6-dimethylpiperidin-4-one hydrochloride

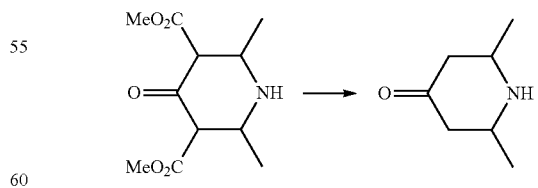

A solution of dimethyl 2,6-dimethyl-4-oxopiperidine-3,5-dicarboxylate (120 g, 286 mmol) in 10% aq. HCl (900 mL) was heated to about 110° C. for 24 hrs. The solvent was concentrated under reduced pressure to give 2,6-dimethylpiperidin-4-one hydrochloride (50 g, 80% yield), which was used for the next step directly. $^1$H NMR (400 MHz, DMSO-d$_6$) 10.15-9.80 (m, 2H), 3.82 (d, J=4.4 Hz, 1H), 3.59-3.45 (m, 1H), 2.75-2.60 (m, 2H), 2.47-2.34 (m, 2H), 1.38-1.27 (m, 6H)

Step C: tert-butyl 2,6-dimethyl-4-oxopiperidine-1-carboxylate

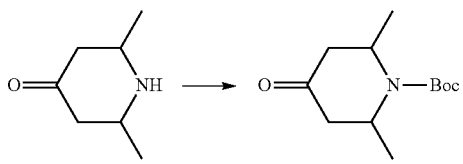

To a solution of 2,6-dimethylpiperidin-4-one hydrochloride (50 g, 281 mmol) in 1,4-dioxane (350 mL) and water (350 mL) was added Na$_2$CO$_3$ (59 g, 562 mmol) portionwise. Boc-anhydride (123 g, 562 mmol) was added and the resulting reaction mixture was stirred at about 15° C. for about 24 h. The solvent was concentrated under reduced pressure. The resulting residue was extracted with MTBE (3×400 mL) and the organic layer was washed with brine (300 mL) and dried over anhydrous Na$_2$SO$_4$. After evaporation, the crude product was purified by column chromatography on silica gel eluting with (PE to PE:EA=10:1) to afford tert-butyl 2,6-dimethyl-4-oxopiperidine-1-carboxylate (25 g, 38% yield), which was a mixture of Trans/Cis=2:1.

$^1$H NMR (400 MHz, CHLOROFORM-d) 4.66 (dd, J=4.9, 6.8 Hz, 2H), 4.32 (t, J=6.3 Hz, 1H), 2.79 (dd, J=6.5, 17.8 Hz, 1H), 2.66 (dd, J=7.6, 14.7 Hz, 2H), 2.31 (dd, J=1.6, 17.6 Hz, 1H), 2.24-2.17 (m, 2H), 1.43 (d, J=2.3 Hz, 15H), 1.23-1.17 (m, 10H).

Step D: tert-butyl 4-hydroxy-2,6-dimethylpiperidine-1-carboxylate

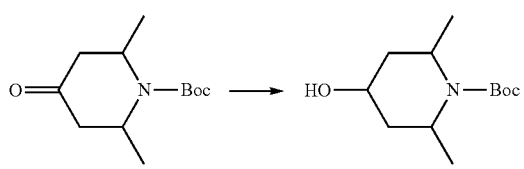 [SMILES: CC1CC(=O)CC(C)N1C(=O)OC(C)(C)C ; CC1CC(O)CC(C)N1C(=O)OC(C)(C)C]

To a solution of tert-butyl 2,6-dimethyl-4-oxopiperidine-1-carboxylate (25 g, 110 mmol) in EtOH (75 mL) was added NaBH$_4$ (6.24 g, 165 mmol) at about 0° C. The resulting solution was warmed to about 15° C. and stirred for about 4 h. The reaction mixture was cooled to about 0° C. before the addition of saturated aq. NH$_4$Cl (80 mL). The solvent was evaporated under reduced pressure and EtOAc (100 mL) was added to the residue. The two layers were separated and the aqueous layer was extracted with EtOAc (3×100 mL). The combined organic layers were dried over anhydrous Na$_2$SO$_4$, and evaporated to give tert-butyl 4-hydroxy-2,6-dimethylpiperidine-1-carboxylate (20 g, 79% yield) as a colorless oil. $^1$H NMR (400 MHz, CHLOROFORM-d) 4.47-4.37 (m, 1H), 4.31-4.13 (m, 2H), 4.01 (br. s., 1H), 3.94-3.82 (m, 1H), 2.25-2.14 (m, 1H), 2.09-1.99 (m, 2H), 1.98-1.79 (m, 2H), 1.63-1.53 (m, 2H), 1.45 (s, 13H), 1.39-1.28 (m, 6H), 1.23-1.12 (m, 2H).

Step E: tert-butyl 2,6-dimethyl-4-(4-nitro-1H-pyrazol-1-yl)piperidine-1-carboxylate

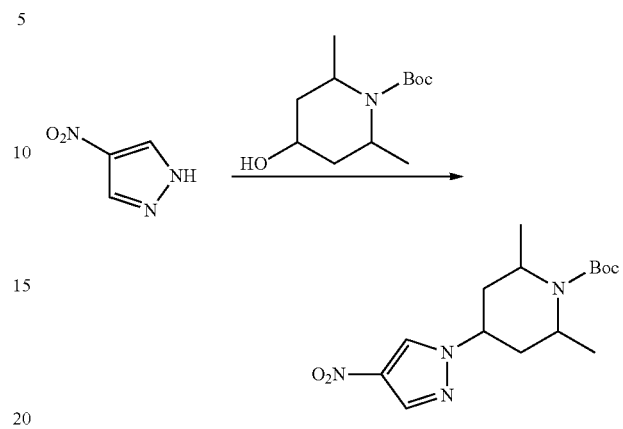

To a solution of tert-butyl 4-hydroxy-2,6-dimethylpiperidine-1-carboxylate (8.9 g, 38.8 mmol), 4-nitro-1H-pyrazole (4.39 g, 38.8 mmol), and PPh$_3$ (15.3 g, 58.2 mmol) in THF (150 ml) was added DIAD (11.3 mL, 58.2 mmol) dropwise. The reaction mixture stirred at about 0° C. for 10 minutes then warmed to about 30° C. and stirred for about 16 hrs. The reaction mixture was partitioned between EtOAc and brine. The organic portion was dried over anhydrous Na$_2$SO$_4$, filtered, and concentrated under reduced pressure. The crude material was purified via silica gel chromatography eluting with EtOAc/Petroleum ether (0-10%) to afford tert-butyl 2,6-dimethyl-4-(4-nitro-1H-pyrazol-1-yl)piperidine-1-carboxylate (7 g, 56% yield) as a white solid.

$^1$H NMR (400 MHz, CHLOROFORM-d) δ=8.19 (s, 1H), 8.10 (d, J=1.6 Hz, 1H), 4.77-4.46 (m, 3H), 3.89-3.76 (m, 1H), 2.43-2.24 (m, 1H), 2.16-1.90 (m, 4H), 1.49 (d, J=1.6 Hz, 11H), 1.46 (d, J=6.7 Hz, 2H), 1.38-1.27 (m, 6H)

Step F: tert-butyl 4-(4-amino-1H-pyrazol-1-yl)-2,6-dimethylpiperidine-1-carboxylate

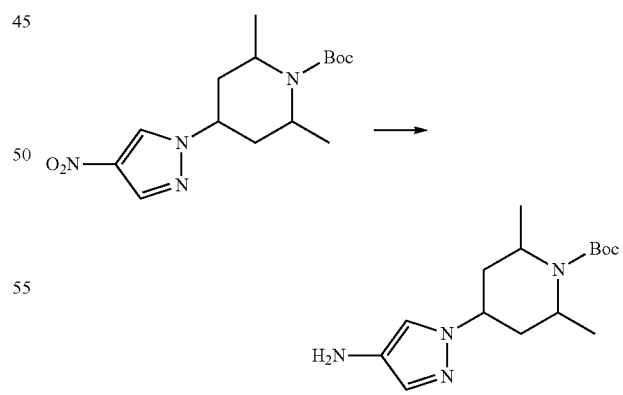

To a solution of tert-butyl 2,6-dimethyl-4-(4-nitro-1H-pyrazol-1-yl)piperidine-1-carboxylate (2 g, 6.17 mmol) in THF (50 mL) and NH$_4$OH (0.5 mL) was added Raney nickel (1.1 g, 18.1 mmol). The reaction mixture stirred at rt for about 2 h, under an atmosphere of hydrogen. The reaction mixture was filtered through a pad of Celite® and concentrated under reduced pressure to afford tert-butyl 4-(4- amino-1H-pyrazol-1-yl)-2,6-dimethylpiperidine-1-carboxylate (1.8 g, 99% yield). LC/MS (Table 1, Method w) $R_f$=0.96 min.; MS m/z: 295 (M+H)⁺.

General Procedure A: Nucleophilic Displacement of an Aryl or Heteroaryl Halide with an Amine To a microwave vessel, a vial, or a round bottom flask is added an aryl or heteroaryl halide (preferably 1 equiv), an amine or an amine salt (1-10 equiv, preferably 1.1-2 equiv), a solvent (such as 1,4-dioxane, MeCN, i-PrOH, n-PrOH, n-BuOH, toluene, DMSO, DMF, DMA or EtOH, preferably 1,4-dioxane [microwave] or i-PrOH [thermal heating]), and a base (such as $K_2CO_3$, $Na_2CO_3$, TEA or DIEA, preferably TEA, DIEA, or $K_2CO_3$, 1-5 equiv, preferably 2-4 equiv). Optionally the aryl or heteroaryl halide and the amine or amine salt are each separately dissolved in a solvent prior to combining. The reaction mixture is heated at about 40-220° C. thermally (preferably about 80-100° C.) for about 0.5-36 h (preferably about 8-24 h) or is subjected to microwave heating at about 100-200° C. (preferably about 130-150° C.) for about 0.5-8 h (preferably about 0.5-2 h). In cases where the reaction does not proceed to completion as monitored by TLC, LC/MS, or HPLC, the reaction may be resubjected to thermal heating at about 40-220° C. (preferably about 80-100° C.) for about 0.5-8 h (preferably about 1-2 h) or microwave heating at about 120-200° C. (preferably about 130-150° C.) for an additional about 1-8 h (preferably about 0.5-2 h) with the optional addition of more amine or amine salt (1-10 equiv, preferably 0.5-1.5 equiv) and/or base (such as $K_2CO_3$, $Na_2CO_3$, TEA or DIEA, preferably TEA, DIEA or $K_2CO_3$, 1-5 equiv, preferably 2-4 equiv). This process is repeated until the reaction proceeds no further. After cooling to ambient temperature, the reaction is worked up using one of the following methods. Method 1: The reaction is concentrated under reduced pressure. Method 2: A reaction mixture containing a precipitate may be filtered to collect the target compound, while optionally washing with organic solvent or solvents such as $Et_2O$, DCM and/or petroleum ether. Method 3: The reaction mixture is diluted with an organic solvent such as MeOH, silica gel is added, and the mixture is concentrated under reduced pressure to prepare for separation by chromatography with solid loading. Method 4: The reaction mixture is concentrated under reduced pressure prior to the addition of an organic solvent such as EtOAc or DCM and is then optionally washed with water and/or brine, dried over anhydrous $Na_2SO_4$ or $MgSO_4$, filtered or decanted, and concentrated under reduced pressure. Method 5: An organic solvent such as EtOAc or DCM is added with the optional addition of water or brine and the layers are separated. The aqueous layer is then optionally extracted with additional organic solvent such as EtOAc or DCM. The combined organic layers are optionally washed with brine or water, dried over anhydrous $MgSO_4$ or $Na_2SO_4$, filtered or decanted, and concentrated under reduced pressure.

Illustration of General Procedure A

Preparation #A.1: 8-((6-bromo-[1,2,4]triazolo[1,5-a]pyrazin-8-yl)amino)-4,5-dihydro-1H-benzo[b]azepin-2(3H)-one

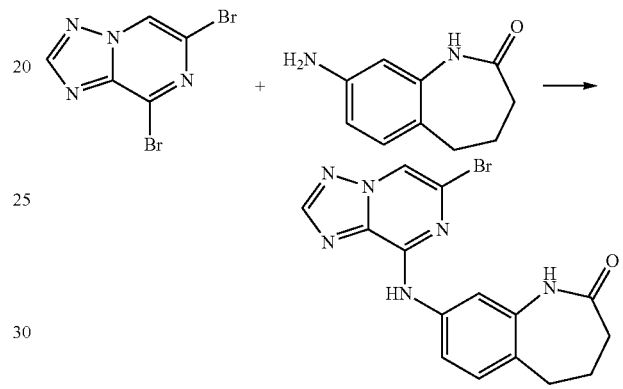

To a solution of 6,8-dibromo-[1,2,4]triazolo[1,5-a]pyrazine (0.200 g, 0.720 mmol, Ark Pharm) and 8-amino-4,5-dihydro-1H-benzo[b]-azepin-2(3H)-one (0.139 g, 0.792 mmol, Astatech) in i-PrOH (8 mL) was added DIEA (0.377 mL, 2.16 mmol). The mixture was heated to reflux for about 24 h. The resulting solution was cooled to rt and filtered to give 8-((6-bromo-[1,2,4]triazolo[1,5-a]pyrazin-8-yl)amino)-4,5-dihydro-1H-benzo[b]azepin-2(3H)-one (0.15 g, 56%) as a brown solid: ¹H NMR (DMSO-d6) δ 9.62 (s, 1H), 8.69 (s, 1H), 8.59 (s, 1H), 7.61-7.67 (m, 2H), 7.23 (d, J=8.4 Hz, 1H), 2.65 (t, J=6.4 Hz, 2H), 2.07-2.15 (m, 3H), 1.23 (m, 1H).

TABLE A1

Examples prepared from 8-bromo-6-cyclohexyl-[1,2,4]triazolo[1,5-α]pyrazine [Example #11, Step E] as described in General Procedure A.

| Amine | Product | Example # | $R_t$ min (Table 1, Method) | m/z ESI+ (M + H)⁺ | CSF-1R Enzyme $IC_{50}$ |
|---|---|---|---|---|---|
| 4-(4-amino-1H-pyrazol-1-yl)-2-methylbutan-2-ol [Preparation #4] | | A.1.1 | 3.15 (w) | 370 | A |

TABLE A1-continued

Examples prepared from 8-bromo-6-cyclohexyl-[1,2,4]triazolo[1,5-α]pyrazine [Example #11, Step E] as described in General Procedure A.

| Amine | Product | Example # | $R_t$ min (Table 1, Method) | m/z ESI+ $(M + H)^+$ | CSF-1R Enzyme $IC_{50}$ |
|---|---|---|---|---|---|
| 1-(tetrahydro-2H-pyran-4-yl)-1H-pyrazol-4-amine [WO2011/71716A1] | | A.1.2 | 3.26 (w) | 368 | A |
| 1-(2,2,6,6-tetramethyltetrahydro-2H-pyran-4-yl)-1H-pyrazol-4-amine [Preparation #5] | | A.1.3 | 3.42 (v) | 356 | A |
| 1-(oxetan-3-yl)-1H-pyrazol-4-amine [WO2014/194242A2] | | A.1.4 | 3.14 (w) | 340 | A |
| (trans)-4-(4-amino-1H-pyrazol-1-yl)cyclohexanol [Preparation #6] | | A.1.5 | 3.07 (v) | 356 | A |
| (cis)-4-(4-amino-1H-pyrazol-1-yl)cyclohexanol [Preparation #6] | | A.1.6 | 3.14 (v) | 356 | A |

TABLE A1-continued

Examples prepared from 8-bromo-6-cyclohexyl-[1,2,4]triazolo[1,5-α]pyrazine [Example #11, Step E] as described in General Procedure A.

| Amine | Product | Example # | $R_t$ min (Table 1, Method) | m/z ESI+ $(M + H)^+$ | CSF-1R Enzyme $IC_{50}$ |
|---|---|---|---|---|---|
| 1H-pyrazol-4-amine [CombiBlocks] | | A.1.7 | 1.96 (h) | 284 | A |
| ethyl 4-(4-amino-1H-pyrazol-1-yl)cyclohexanecarboxylate [Preparation #9] | | A.1.8 | 2.90 (h) | 438 | A |

General Procedure B: Buchwald-Hartwig Reaction of an Aryl or Heteroaryl Halide with an Amine A mixture of an aryl or heteroaryl halide (1.0 equiv), an amine (1 to 2.2 equiv, preferably 1 to 1.2 equiv), a palladium catalyst (such as $Pd_2dba_3$, $Pd(OAc)_2$, preferably $Pd(OAc)_2$; 0.01 to 1.0 equiv, preferably 0.04 to 0.1 equiv), a ligand (such as Xphos, Xantphos or tert-butyl-X-phos, preferably Xantphos or XPhos, 0.01 to 2.0 equiv, preferably 0.04 to 0.1 equiv) and a base (such as $K_2CO_3$, $Na_2CO_3$, $Cs_2CO_3$, $K_3PO_4$, NaOt-Bu, KOt-Bu, KOAc, KOH, preferably $Cs_2CO_3$ or $K_2CO_3$; 1 to 5 equiv, preferably 1 to 3 equiv) are added to a solvent (such as 1,4-dioxane, t-BuOH, preferably t-BuOH). The mixture is degassed under an inert atmosphere (such as nitrogen or argon, preferably nitrogen) and heated with conventional or microwave heating at about 80 to 150° C. (preferably about 85 to 95° C.) for about 2 to 24 h (preferably about 16 h). The mixture is cooled to rt. The mixture is optionally filtered through a media (such as silica gel or Celite®) which is rinsed with an appropriate solvent (such as EtOAc, 1,4-dioxane, THF, MeCN, DCM, $Et_2O$, MeOH, EtOH, DMSO, 1:1 MeOH/DMSO or 2:1 MeOH/DMSO, preferably MeOH/DMSO) and then the filtrate is optionally concentrated under reduced pressure or under a warm nitrogen stream to give a residue.

Illustration of General Procedure B

Preparation #B.1: 6-chloro-N-(1-methyl-1H-pyrazol-3-yl)-[1,2,4]triazolo[1,5-a]pyridin-8-amine

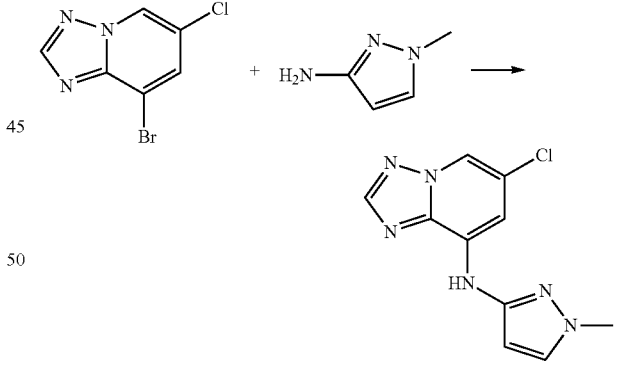

To a microwave vial was added 8-bromo-6-chloro-[1,2,4]triazolo[1,5-a]pyridine (0.70 g, 3.0 mmol, Example #1, Step A), 1-methyl-1H-pyrazol-3-amine (0.32 g, 3.3 mmol, Matrix Scientific), Xantphos (0.37 g, 0.63 mmol), $Pd(OAc)_2$ (0.068 g, 0.30 mmol), cesium carbonate (2.453 g, 7.53 mmol) and 1,4-dioxane (7 mL). The mixture was then heated in a microwave for about 1.5 h at about 120° C. The reaction mixture was cooled to rt, filtered, washed with DCM and MeOH. Silica gel (2 g) was added to the filtrate. The mixture was concentrated under reduced pressure and purified via silica gel chromatography eluting with 0-50% DCM/MeOH/$NH_4OH$ (90:9:1) in DCM. The product-containing fractions were combined and concentrated under reduced pressure and dried under vacuum at about 55° C. to give 6-chloro-N-(1-methyl-1H-pyrazol-3-yl)-[1,2,4]triazolo[1,5-a]pyridin-8-amine (0.55 g, 73%, 75% purity by NMR): LC/MS (Table 1, Method a) R$_t$=1.29 min.; MS m/z: 249 (M+H)$^+$.

General Procedure C: Reaction of an Aryl or Heteroaryl Halide with a Boronic Acid or Boronate Ester To a mixture of an aryl halide (preferably 1 equiv), a boronic acid or boronate ester (1-2.5 equiv, preferably 1.3-2.0 equiv), and an inorganic base (for example, potassium fluoride, sodium carbonate or cesium carbonate, preferably cesium carbonate; 1.1-16 equiv, preferably 2-3 equiv) in a solvent (for example THF, DME, DMF, 1,4-dioxane, DME/water, 1,4-dioxane/water, toluene/EtOH/water, THF/MeOH/water or 1,4-dioxane/EtOH/water; preferably THF/MeOH/water, 1,4-dioxane/EtOH/water or DME) is added a palladium catalyst (for example tris(benzylideneacetone)dipalladium(0), tetrakis(triphenylphosphine)palladium(0), bis(acetato)-triphenylphosphinepalladium(II), polymer-bound FibreCat™ 1032, SiliaCat DPP-Pd [Silicycle], (1,1'-bis(diphenyl-phosphino)ferrocene)dichloropalladium(II), or dichlorobis(triphenyl-phosphine)palladium(II); preferably tris(benzylideneacetone)di-palladium(0) or tetrakis-(triphenylphosphine)palladium(0), 0.01-0.20 equiv, preferably 0.1 equiv) and optionally a ligand (for example tricyclohexylphosphine, XPhos, Xantphos, tert-butyl-XPhos, or tri-t-butyl-phosphane; preferably no ligand, XPhos, or Xantphos (0.01-1.0 equiv, preferably 0.1-0.2 equiv) is added. The reaction mixture is heated at about 40-120° C. (preferably about 80-90° C.) for about 1-24 h (preferably about 2 h) thermally, or at about 100-200° C. (preferably about 120-150° C.) for about 5 min-3 h (preferably about 30 min) in a microwave. In cases where the reaction does not proceed to completion as monitored by TLC, HPLC, or LCMS, additional reagents and reactants can be optionally added and the reaction can be resubjected to heating for an additional about 5 min-3 h (preferably about 30 min) in the microwave or 1-24 h (preferably about 2 h) thermally at the same or higher temperature via the same or different heating method. This process is repeated until the reaction proceeds no further. The reaction mixture is allowed to cool to ambient temperature and is worked up using one of the following methods. Method 1. For reactions containing water, the reaction mixture may be optionally filtered then diluted with an organic solvent (such as DCM or EtOAc). The layers are separated, the organic solution is optionally washed with water and/or brine, dried over MgSO$_4$ or Na$_2$SO$_4$, filtered, and the solvent is removed under reduced pressure. Method 2. The reaction mixture is concentrated under reduced pressure. Method 3. The catalyst is removed by filtration and the filtrate is concentrated under reduced pressure or the filtrate is washed with water and/or brine, the layers are separated, the organic solution is dried over MgSO$_4$ or Na$_2$SO$_4$, filtered, and the solvent is removed under reduced pressure. Method 4. Water and/or MeOH is added and the resulting precipitate is collected via filtration.

Illustration of General Procedure C

Preparation #C.1: tert-butyl 3-(8-((2-oxo-2,3,4,5-tetrahydro-1H-benzo[b]azepin-8-yl)amino)-[1,2,4]triazolo[1,5-a]pyrazin-6-yl)-2,5-dihydro-1H-pyrrole-1-carboxylate

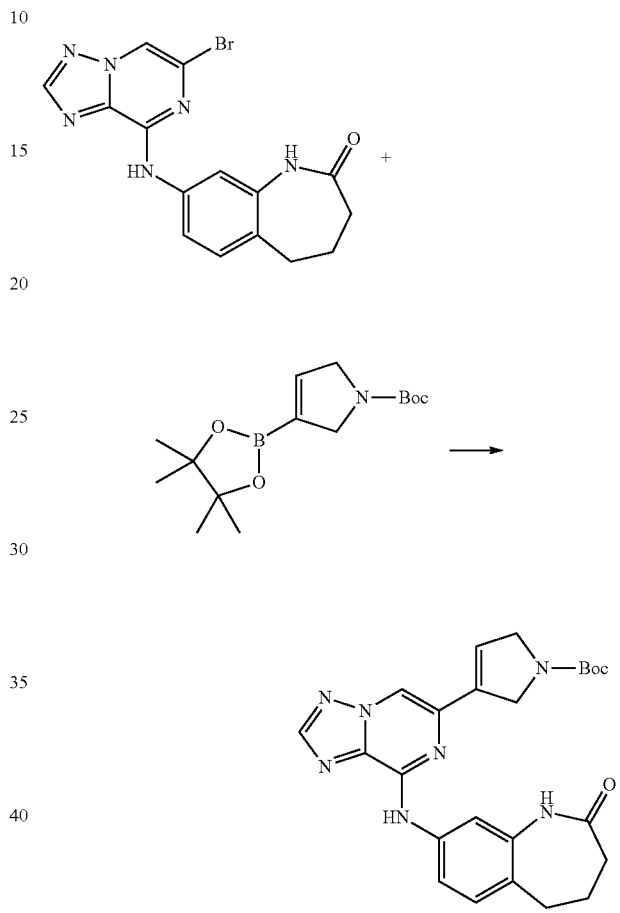

To a solution of 8-((6-bromo-[1,2,4]triazolo[1,5-a]pyrazin-8-yl)amino)-4,5-dihydro-1H-benzo[b]azepin-2(3H)-one (0.500 g, 1.34 mmol, Preparation #A.1) in DME (12 mL) was added tert-butyl 3-(4,4,5,5-tetramethyl-1,3,2-dioxaborolan-2-yl)-2,5-dihydro-1H-pyrrole-1-carboxylate (0.791 g, 2.68 mmol, Combi-Blocks), XPhos (0.058 mg, 0.134 mmol), tris(benzylideneacetone)di-palladium(0) (0.123 g, 0.134 mmol) and Cs$_2$CO$_3$ (1.30 g, 4.02 mmol). The mixture was heated at about 140° C. for about 30 min in a microwave reactor. The resulting solution was filtered and the solid was washed with DCM then washed with water and brine. The organic phase was dried over Na$_2$SO$_4$ and concentrated to give a crude solid, which was washed with MeOH to afford tert-butyl 3-(8-((2-oxo-2,3,4,5-tetrahydro-1H-benzo[b]azepin-8-yl)amino)-[1,2,4]triazolo[1,5-a]pyrazin-6-yl)-2,5-dihydro-1H-pyrrole-1-carboxylate (0.25 g, 40%) as a brown solid: $^1$H NMR (DMSO-d6) δ 10.05 (s, 1H), 9.65 (d, J=7.9 Hz, 1H), 8.60 (s, 1H), 8.50-8.38 (m, 1H), 7.82 (d, J=12.3 Hz, 1H), 7.71 (t, J=9.5 Hz, 1H), 7.20 (t, J=6.6 Hz, 1H), 6.68 (d, J=11.9 Hz, 1H), 4.44 (br s, 2H), 4.24 (br s, 2H), 2.64 (br s, 2H), 2.24-1.96 (m, 4H), 1.59-1.35 (s, 9H).

TABLE C1

Examples prepared from 6-bromo-N-(4-morpholinophenyl)-[1,2,4]triazolo[1,5-α]pyrazin-8-amine (prepared using B from 6,8-dibromo-[1,2,4]triazolo[1,5-α]pyrazine [Ark Pharm] and 4-morpholinoaniline) using General Procedure C

| Boronic acid or boronate | Product | Example # | $R_t$ min (Table 1, Method) | m/z ESI+ $(M+H)^+$ | Btk Enzyme $IC_{50}$ |
|---|---|---|---|---|---|
| N-(3-(4,4,5,5-tetramethyl-1,3,2-dioxaborolan-2-yl)benzyl)acrylamide (prepared using F from (3-(4,4,5,5-tetramethyl-1,3,2-dioxaborolan-2-yl)phenyl)methanamine [ChemMaker] and acryloyl chloride) | (structure) | C.1.1 | 1.59 (b) | 546 | C |

General Procedure D: Acidic Cleavage of a Boc-Protected Amine

To a solution of an N-Boc amine (1 equiv) in an organic solvent (such as DCM, DCE, EtOAc, 1,4-dioxane or MeOH, preferably DCM, EtOAc, MeOH or 1,4-dioxane) is added an acid (such as TFA or HCl (HCl could be commercially purchased or generated in situ with MeOH and acetyl chloride), preferably HCl; 2 to 100 equiv, preferably 25 to 50 equiv). The mixture is stirred at about 0 to 100° C. (preferably about 20 to 60° C.) for about 1 to 24 h (preferably about 1 to 12 h). Optionally, additional acid (2 to 35 equiv, preferably 20 to 25 equiv) may be added and the mixture stirred at about 0 to 100° C. (preferably about 20 to 60° C.) for about 1 to 24 h (preferably about 1 to 6 h). If a solid is present in the mixture, the mixture may be optionally filtered and the solid washed with an organic solvent such as 1,4-dioxane or $Et_2O$. The resulting solid is then optionally dried under reduced pressure to give the targeted compound. Alternatively, the mixture may be optionally concentrated in vacuo to give final compound. Alternatively, either the residue or the solution may be optionally partitioned between water and an organic solvent (such as EtOAc, $Et_2O$ or DCM). The organic layer is isolated and may be optionally washed in no particular order with water and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.

Illustration of General Procedure D

Preparation #D.1: 8-((6-(pyrrolidin-3-yl)-[1,2,4]triazolo[1,5-a]pyrazin-8-yl)amino)-4,5-dihydro-1H-benzo[b]azepin-2(3H)-one

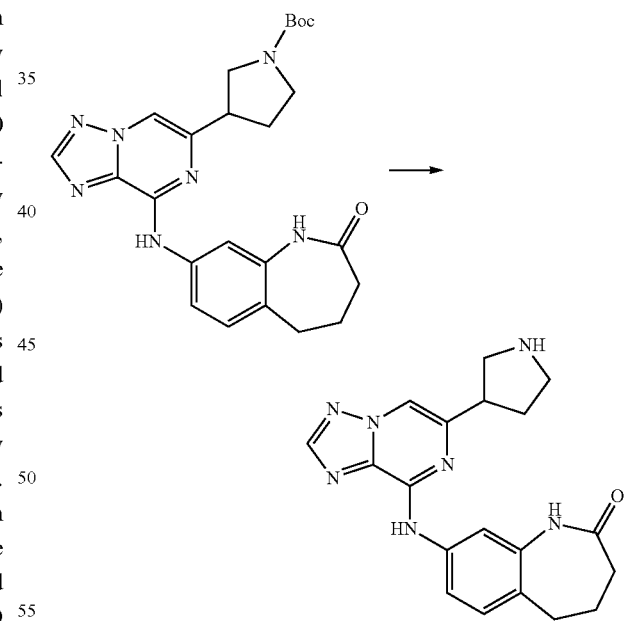

To a solution of 3-[8-(2-oxo-2,3,4,5-tetrahydro-1H-benzo[b]azepin-8-ylamino)-[1,2,4]triazolo[1,5-a]pyrazin-6-yl]-pyrrolidine-1-carboxylic acid methylamide (1.60 g, 3.45 mmol, Preparation #E.1) in EtOAc (20 mL) was added HCl/EtOAc (20 mL). The mixture was stirred for about 12 h at about 25° C. The resulting solution was concentrated under reduced pressure to give 8-((6-(pyrrolidin-3-yl)-[1,2,4]triazolo[1,5-a]pyrazin-8-yl)amino)-4,5-dihydro-1H-benzo[b]azepin-2(3H)-one (1.20 g, 96%) as a brown solid: LC/MS (Table 1, Method d) $R_t$=2.12 min; MS m/z: 364 $(M+H)^+$.

TABLE D1

Examples prepared using HCl as described in General Procedure D

| Carbamate | Product | Example # | R, min (Table 1, Method) | m/z ESI+ (M + H)+ | CSF-1R Enzyme IC50 |
|---|---|---|---|---|---|
| tert-butyl 4-(4-((6-cyclohexyl-[1,2,4]triazolo[1,5-α]pyrazin-8-yl)amino)-1H-pyrazol-1-yl)piperidine-1-carboxylate (prepared using A from 6,8-dibromo-[1,2,4]triazolo[1,5-a]pyrazine [ArkPharm] and tert-butyl 4-(4-amino-1H-pyrazol-1-yl)piperidine-1-carboxylate [Combiblocks], C with 2-(cyclohex-1-en-1-yl)-4,4,5,5-tetramethyl-1,3,2-dioxaborolane [Combiblocks], and E with Pd(OH)₂/C. | 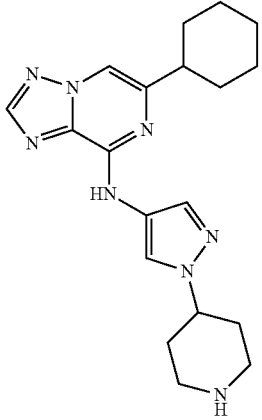 [SMILES: c1nc2c(Nc3cnn(C4CCNCC4)c3)nc(C3CCCCC3)cn2n1] | D.1.1 | 1.53 (h) | 367 | A |
| tert-butyl 4-(4-((6-(cyclopent-1-en-1-yl)-[1,2,4]triazolo[1,5-α]pyrazin-8-yl)amino)-1H-pyrazol-1-yl)piperidine-1-carboxylate (prepared using A from 6,8-dibromo-[1,2,4]triazolo[1,5-a]pyrazine [ArkPharm] and tert-butyl 4-(4-amino-1H-pyrazol-1-yl)piperidine-1-carboxylate [Combiblocks], C with 2-(cyclopent-1-en-1-yl)-4,4,5,5-tetramethyl-1,3,2-dioxaborolane [ArkPharm], and E with Pd(OH)₂/C. | 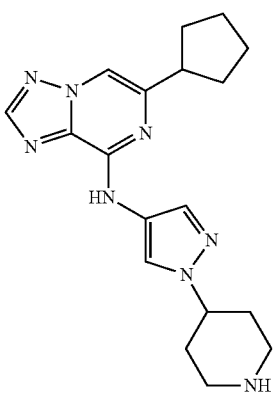 [SMILES: c1nc2c(Nc3cnn(C4CCNCC4)c3)nc(C3CCCC3)cn2n1] | D.1.2 | 1.42(h) | 353 | A |

General Procedure E: Hydrogenation of a Double Bond

A reaction vessel is charged with an alkene (1 equiv), neat or as a solution in an organic solvent or mixture of solvents (such as THF, EtOAc, MeOH, EtOH or MeOH/AcOH, preferably THF or MeOH) followed by addition of Pd(OH)₂ or Pd/C (0.005-3 equiv, preferably 2 equiv) either as a solid or in an organic solvent or mixture of solvents (such as AcOH, THF, EtOAc, MeOH, EtOH or MeOH/AcOH, preferably AcOH. Optionally the alkene is added to the Pd mixture. The reaction mixture is sparged with hydrogen. The mixture is stirred or shaken (preferably stirred when atmospheric hydrogen is used or shaken when higher pressures of hydrogen is used) under hydrogen at about atmospheric pressure to 60 psi (preferably about 50 psi) at about 20-60° C. (preferably ambient temperature) for about 0.5-5 days (preferably about 1-3 days). The reaction mixture is filtered through a pad of Celite® or a nylon membrane. The filter cake is rinsed with an organic solvent (such as THF, EtOAc, DCM, MeOH, or EtOH, preferably the reaction solvent) and the filtrate is concentrated under reduced pressure to give the targeted compound.

The reaction could also be carried in flow chemistry style, using H-cube, with same choices of solutions listed above. The reaction mixture as a solution is passed through Cat-cart® filled with Pd(OH)/C or Pd/C, under hydrogen from 1 bar to 80 bar (preferably about 40-60 bar) at about 20-80° C. (preferably 30-60° C.) for about 0.5-24 h (preferably about 8 h). The mixture is then concentrated under reduced pressure to give the targeted compound.

Illustration of General Procedure E

Preparation #E.1: tert-butyl 3-(8-((2-oxo-2,3,4,5-tetrahydro-1H-benzo[b]azepin-8-yl)amino)-[1,2,4]triazolo[1,5-a]pyrazin-6-yl)pyrrolidine-1-carboxylate

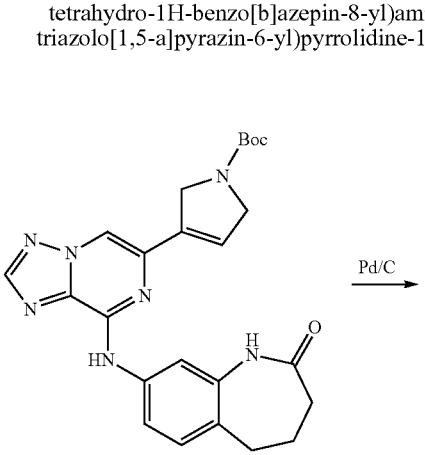

-continued

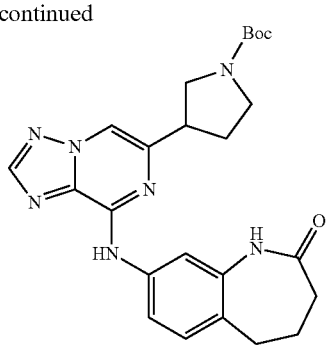

To solution of 3-[8-(2-oxo-2,3,4,5-tetrahydro-1H-benzo[b]azepin-8-ylamino)-[1,2,4]triazolo[1,5-a]pyrazin-6-yl]-2,5-dihydro-pyrrole-1-carboxylic acid tert-butyl ester (2.0 g, 4.33 mmol, Preparation #C.1) in MeOH (300 mL) and THF (60 mL) was added 10% Pd/C (2 g) and AcOH (30 mL). The suspension was stirred for about 72 h at about 25° C. under $H_2$ (50 psi) atmosphere. The resulting solution was filtered through Celite® and concentrated under reduced pressure to give tert-butyl 3-(8-((2-oxo-2,3,4,5-tetrahydro-1H-benzo[b]azepin-8-yl)amino)-[1,2,4]triazolo[1,5-a]pyrazin-6-yl)pyrrolidine-1-carboxylate (1.8 g, 90%): LC/MS (Table 1, Method c) $R_t$=1.40 min; MS m/z: 464 (M+H)$^+$.

TABLE E.1

Examples prepared using Pd/C or Pd(OH)$_2$/C as descibed in General Procedure E

| Olefin | Product | Example # | $R_1$ min (Table 1, Method) | m/z ESI+ (M + H)$^+$ | CSF-1R Enzyme IC$_{50}$ |
|---|---|---|---|---|---|
| 6-(cyclohex-1-en-1-yl)-N-(1-isopropyl-1H-pyrazol-4-yl)-[1,2,4]triazolo[1,5-a]pyrazin-8-amine(prepared using A from 6,8-dibromo-[1,2,4]triazolo[1,5-a]pyrazine [ArkPharm] and 1-isopropyl-1H-pyrazol-4-amine[Combiblocks], C with 2-(cyclohex-1-en-1-yl)-4,4,5,5-tetramethyl-1,3,2-dioxaborolane[Combiblocks] | | E.1.1 | 2.55 (h) | 326 | A |
| 6-(4,4-dimethylcyclohex-1-en-1-yl)-N-(1-methyl-1H-pyrazol-4-yl)-[1,2,4]triazolo[1,5-a]pyrazin-8-amine(prepared using A from 6,8-dibromo-[1,2,4]triazolo[1,5-a]pyrazine [ArkPharm] and 1-methyl-1H-pyrazol-4-amine, C with 2-(4,4-dimethylcyclohex-1-en-1-yl)-4,4,5,5-tetramethyl-1,3,2-dioxaborolane | | E.1.2 | 3.22 (t) | 326 | A |
| N-(1-methyl-1H-pyrazol-4-yl)-6-(4-methylcyclohex-1-en-1-yl)-[1,2,4]triazolo[1,5-a]pyrazin-8-amine(Prepared using A from 6,8-dibromo-[1,2,4]triazolo[1,5-a]pyrazine [ArkPharm] and 1-methyl-1H-pyrazol-4-amine, C with 4,4,5,5-tetramethyl-2-(4-methylcyclohex-1-en-1-yl)-1,3,2-dioxaborolane | | E.1.3 | 3.37 (t) | 312 | A |

TABLE E.1-continued

Examples prepared using Pd/C or Pd(OH)$_2$/C as descibed in General Procedure E

| Olefin | Product | Example # | R$_1$ min (Table 1, Method) | m/z ESI+ (M + H)$^+$ | CSF-1R Enzyme IC$_{50}$ |
|---|---|---|---|---|---|
| N-(1-methyl-1H-pyrazol-4-yl)-6-(4-methylcyclohex-1-en-1-yl)-[1,2,4]triazolo[1,5-a]pyrazin-8-amine(Prepared using A from 6,8-dibromo-[1,2,4]triazolo[1,5-a]pyrazine [ArkPharm] and 1-methyl-1H-pyrazol-4-amine, C with 4,4,5,5-tetramethyl-2-(4-methylcyclohex-1-en-1-yl)-1,3,2-dioxaborolane [CombiBlocks] | | E.1.4 | 3.39 (t) | 312 | A |
| N-(1-methyl-1H-pyrazol-4-yl)-6-(4-(trifluoromethyl)cyclohex-1-en-1-yl)-[1,2,4]triazolo[1,5-a]pyrazin-8-amine (Prepared using A from 6,8-dibromo-[1,2,4]triazolo[1,5-a]pyrazine [ArkPharm] and 1-methyl-1H-pyrazol-4-amine, C with 4,4,5,5-tetramehtyl-2-[4-(trifluoromethyl)-1-cylcohexen-1-yl]-1,3,2-dioxaborolane [Acentix] | | E.1.5 | 2.27 (h) | 366 | A |
| N-(6-(cyclohex-1-en-1-yl)-[1,2,4]triazolo[1,5-a]pyridin-8-yl)-6,7-dihydro-4H-pyrazolo[5,1-c][1,4]oxazin-2-amine (Prepared using B from 8-bromo-6-chloro-[1,2,4]triazolo[1,5-a]pyridine [Example #1, Step A] and 6,7-dihydro-4H-pyrazolo[5,1-c][1,4]oxazin-2-amine [Preparation #1], and C with 1-cyclohexenyl boronic acid [CombiBlocks] | | E.1.6 | 2.23 (h) | 339 | A |
| 6-(cyclohex-1-en-1-yl)-N-(5-methyl-4,5,6,7-tetrahydropyrazolo[1,5-a]pyrazin-2-yl)-[1,2,4]triazolo[1,5-a]pyridin-8-amine (Prepared using B from 8-bromo-6-chloro-[1,2,4]triazolo[1,5-a]pyridine [Example #1, Step A] and 5-methyl-4,5,6,7-tetrahydropyrazolo[1,5-a]pyrazin-2-amine[Astatech], and C with 1-cyclohexenyl boronic acid [CombiBlocks] | | E.1.7 | 2.09 (h) | 352 | A |

TABLE E.1-continued

Examples prepared using Pd/C or Pd(OH)$_2$/C as descibed in General Procedure E

| Olefin | Product | Example # | R$_t$ min (Table 1, Method) | m/z ESI+ (M + H)+ | CSF-1R Enzyme IC$_{50}$ |
|---|---|---|---|---|---|
| 6-(cyclopent-1-en-1-yl)-N-(1-methyl-1H-pyrazol-4-yl)-[1,2,4]triazolo[1,5-a]pyrazin-8-amine(Prepared using A from 6,8-dibromo-[1,2,4]triazolo[1,5-a]pyrazine [ArkPharm] and 1-methyl-1H-pyrazol-4-amine, C with 2-(cyclopent-1-en-1-yl)-4,4,5,5-tetramethyl-1,3,2-dioxaborolane[Combiblocks] | | E.1.8 | 2.82 (x) | 284 | A |
| 6-(cyclopent-1-en-1-yl)-N-(5-methyl-4,5,6,7-tetrahydropyrazolo[1,5-a]pyrazin-2-yl)-[1,2,4]triazolo[1,5-a]pyridin-8-amine(Prepared using B from 8-bromo-6-chloro-[1,2,4]triazolo[1,5-a]pyridine [Example #1, Step A] and 5-methyl-4,5,6,7-tetrahydropyrazolo[1,5-a]pyrazin-2-amine[Astatech], and C with 2-(cyclopent-1-en-1-yl)-4,4,5,5-tetramethyl-1,3,2-dioxaborolane[Combiblocks] | | E.1.9 | 1.80 (h) | 338 | A |
| 6-(cyclohex-1-en-1-yl)-N-(1-methyl-1H-pyrazol-4-yl)-[1,2,4]triazolo[1,5-a]pyrazin-8-amine(Prepared using A from 6,8-dibromo-[1,2,4]triazolo[1,5-a]pyrazine [ArkPharm] and 1-methyl-1H-pyrazol-4-amine [Astatech], C with 2-(cyclohex-1-en-1-yl)-4,4,5,5-tetramethyl-1,3,2-dioxaborolane[ArkPharm] | | E.1.10 | 2.22 (h) | 298 | A |

General Procedure F: Formation of an Amide from an Acid Chloride and an Amine or of a Carbamate from a Carbonochloridate and an Amine To a solution of an amine (1 equiv), optionally as a hydrochloride salt, in an organic solvent (such as DCM, DCE, DMF, DMA, NMP, THF, Et$_2$O or 1,4-dioxane, preferably DMA, DMF or DCM) at 0 to 25° C. (preferably rt) is added a base (such as TEA, DIEA or pyridine; 1 to 50 equiv, preferably pyridine 10 to 30 equiv or DIEA 2 to 3 equiv) and an acid chloride or a carbonochloridate (1 to 3 equiv, preferably 1.2 equiv). The mixture is allowed to stir at about 0 to 60° C. (preferably about 25 to 50° C.) for about 5 min to 20 h (preferably about 1 to 12 h). The mixture is optionally neutralized with AcOH. The mixture is optionally concentrated in vacuo to give the final compound. The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure F

Example #F.1: 8-((6-(1-acryloylpyrrolidin-3-yl)-[1,2,4]triazolo[1,5-a]pyrazin-8-yl)amino)-4,5-dihydro-1H-benzo[b]azepin-2(3H)-one

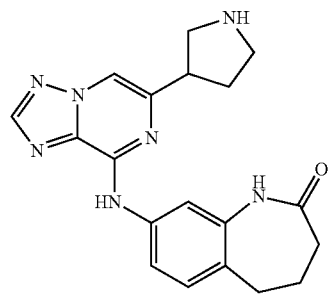

+

To a solution of 8-((6-(pyrrolidin-3-yl)-[1,2,4]triazolo[1,5-a]pyrazin-8-yl)amino)-4,5-dihydro-1H-benzo[b]azepin-2(3H)-one (0.090 g, 0.25 mmol, Preparation #D.1) in DCM (4 mL) was added DIEA (0.130 mL, 0.743 mmol) followed by acryloyl chloride (0.045 g, 0.495 mmol). The mixture was stirred for about 12 h at about 25° C. The resulting solution was concentrated under reduced pressure to give a crude product, which was purified by prep-HPLC (Table 1, Method i) to afford 8-((6-(1-acryloylpyrrolidin-3-yl)-[1,2,4]triazolo[1,5-a]pyrazin-8-yl)amino)-4,5-dihydro-1H-benzo[b]azepin-2(3H)-one (0.054 g, 52%) as a white solid. LC/MS (Table 1, Method d) $R_t$=2.62 min; MS m/z: 418 (M+H)$^+$. BTK enzyme IC$_{50}$=A.

TABLE F.1

Examples prepared using an acid chloride as described in General Procedure F

| Amine | Product | Example # | $R_t$ min (Table 1, Method) | m/z ESI+ (M + H)$^+$ | Btk enzyme IC$_{50}$ | CSF-1R enzyme IC$_{50}$ |
|---|---|---|---|---|---|---|
| 6-(3-(aminomethyl)phenyl)-N-(bicyclo[1.1.1]pentan-1-yl)-[1,2,4]triazolo[1,5-a]pyrazin-8-amine(prepared using A from 6,8-dibromo-[1,2,4]triazolo[1,5-a]pyrazine[Ark Pharm] and bicyclo[1.1.1]pentan-1-amine hydrochloride[AKos], C with (3-(4,4,5,5-tetramethyl-1,3,2-dioxaborolan-2-yl)phenyl)methanamine hydrochloride) | | F.1.1 | 2.89 (e) | 361 | B | NT |
| 6-(3-aminophenyl)-N-(bicyclo[1.1.1]pentan-1-yl)-[1,2,4]triazolo[1,5-a]pyrazin-8-amine(prepared using A from 6,8-dibromo-[1,2,4]triazolo[1,5-a]pyrazine[Ark Pharm] and bicyclo[1.1.1]pentan-1-amine hydrochloride[AKos], C with 3-(4,4,5,5-tetramethyl-1,3,2-dioxaborolan-2-yl)aniline) | | F.1.2 | 3.01 (e) | 347 | B | NT |

TABLE F.1-continued

Examples prepared using an acid chloride as described in General Procedure F

| Amine | Product | Example # | $R_t$ min (Table 1, Method) | m/z ESI+ $(M + H)^+$ | Btk enzyme $IC_{50}$ | CSF-1R enzyme $IC_{50}$ |
|---|---|---|---|---|---|---|
| 6-(2-aminophenyl)-N-(bicyclo[1.1.1]pentan-1-yl)-[1,2,4]triazolo[1,5-a]pyrazin-8-amine(prepared using A from 6,8-dibromo-[1,2,4]triazolo[1,5-a]pyrazine[Ark Pharm] and bicyclo[1.1.1]pentan-1-amine hydrochloride[AKos], C with 2-(4,4,5,5-tetramethyl-1,3,2-dioxaborolan-2-yl)aniline) | | F.1.3 | 3.08 (e) | 347 | C | NT |
| 8-((6-(piperidin-3-yl)-[1,2,4]triazolo[1,5-a]pyrazin-8-yl)amino)-4,5-dihydro-1H-benzo[b]azepin-2(3H)-one (prepared using A from 6,8-dibromo-[1,2,4]triazolo[1,5-a]pyrazine[Ark Pharm] and 8-amino-4,5-dihydro-1H-benzo[b]azepin-2(3H)-one [AstaTech], C with tert-butyl 3-(4,4,5,5-tetramethyl-1,3,2-dioxaborolan-2-yl)-5,6-dihydropyridine-1(2H)-carboxylate[Anichem], E with Pd/C, D with TFA) | | F.1.4 | 2.60 (f) | 432 | A | NT |
| 7-((6-(3-aminophenyl)-[1,2,4]triazolo[1,5-a]pyrazin-8-yl)amino)-4,5-dihydro-1H-benzo[b]azepin-2(3H)-one 2,2,2-trifluoroacetate (prepared using A from 6,8-dibromo-[1,2,4]triazolo[1,5-a]pyrazine[Ark Pharm] and 8-amino-4,5-dihydro-1H-benzo[b]azepin-2(3H)-one [AstaTech], C with 3-(4,4,5,5-tetramethyl-1,3,2-dioxaborolan-2-yl)aniline) | | F.1.5 | 3.03 (d) | 440 | A | NT |
| 8-((6-(3-(aminomethyl)phenyl)-[1,2,4]triazolo[1,5-a]pyrazin-8-yl)amino)-4,5-dihydro-1H-benzo[b]azepin-2(3H)-one (prepared using A from 6,8-dibromo-[1,2,4]triazolo[1,5-a]pyrazine[Ark Pharm] and 8-amino-4,5-dihydro-1H-benzo[b]azepin-2(3H)-one [AstaTech], C from (3-(4,4,5,5-tetramethyl-1,3,2-dioxaborolan-2-yl)phenyl)methanamine hydrochloride) | | F.1.6 | 2.85 (d) | 454 | B | NT |

TABLE F.1-continued

Examples prepared using an acid chloride as described in General Procedure F

| Amine | Product | Example # | R$_t$ min (Table 1, Method) | m/z ESI+ (M + H)$^+$ | Btk enzyme IC$_{50}$ | CSF-1R enzyme IC$_{50}$ |
|---|---|---|---|---|---|---|
| N-(6-methoxypyridazin-3-yl)-6-(pyrrolidin-3-yl)-[1,2,4]triazolo[1,5-a]pyridin-8-amine(prepared using B from 8-bromo-6-chloro-[1,2,4]triazolo[1,5-a]pyridine [Example #1, Step A] and 4-morpholinopyridin-2-amine [Matrix], C with tert-butyl 3-(4,4,5,5-tetramethyl-1,3,2-dioxaborolan-2-yl)-2,5-dihydro-1H-pyrrole-1-carboxylate [Combi-Blocks], E with Pd/C, D with TFA) | | F.1.7 | 0.62 (d) | 420 | C | NT |
| N-(3,4-dimethoxyphenyl)-6-(pyrrolidin-3-yl)-[1,2,4]triazolo[1,5-a]pyrazin-8-amine(prepared using A from 6,8-dibromo-[1,2,4]triazolo[1,5-a]pyrazine[ArkPharm] and 3,4-dimethoxyaniline, C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, D with HCl) | | F.1.8 | 2.69 (e) | 395 | B | NT |
| (R)-8-((6-(pyrrolidin-3-yl)imidazo[1,2-a]pyrazin-8-yl)amino)-4,5-dihydro-1H-benzo[b]azepin-2(3H)-one (prepared using A from 6,8-dibromoimidazo[1,2-a]pyrazine and 8-amino-4,5-dihydro-1H-benzo[b]azepin-2(3H)-one[AstaTech], C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, G [Table 2, Method 1], D with TFA) | | F.1.9 | 2.45 (d) | 417 | A | NT |
| (S)-8-((6-(pyrrolidin-3-yl)imidazo[1,2-a]pyrazin-8-yl)amino)-4,5-dihydro-1H-benzo[b]azepin-2(3H)-one (prepared using A from 6,8-dibromoimidazo[1,2-a]pyazine and 8-amino-4,5-dihydro-1H-benzo[b]azepin-2(3H)-one[AstaTech], C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, G[Table 2, Method 1], D with TFA) | | F.1.10 | 2.45 (d) | 417 | B | NT |

TABLE F.1-continued

Examples prepared using an acid chloride as described in General Procedure F

| Amine | Product | Example # | $R_t$ min (Table 1, Method) | m/z ESI+ $(M + H)^+$ | Btk enzyme $IC_{50}$ | CSF-1R enzyme $IC_{50}$ |
|---|---|---|---|---|---|---|
| (S)-N-(3,4-dimethoxyphenyl)-6-(pyrrolidin-3-yl)-[1,2,4]triazolo[1,5-a]pyrazin-8-amine(prepared using D from Example #3, Step A with HCl) | | F.1.11 | 2.40 (e) | 395 | B | NT |
| (R)-N-(3,4-dimethoxyphenyl)-6-(pyrrolidin-3-yl)-[1,2,4]triazolo[1,5-a]pyrazin-8-amine (prepared using D from Example #3, Step A with HCl) | | F.1.112 | 2.40 (e) | 395 | C | NT |
| 7-((6-(pyrrolidin-3-yl)-[1,2,4]triazolo[1,5-a]pyrazin-8-yl)amino)-3,4-dihydroquinolin-2(1H)-one (prepared using A from 6,8-dibromo-[1,2,4]triazolo[1,5-a]pyrazine[Ark Pharm] and 7-amino-3,4-dihydroquinolin-2(1H)-one [AstaTech], C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, D with TFA) | | F.1.13 | 2.59 (d) | 404 | B | NT |
| 6-((6-(1-acryloylpyrrolidin-3-yl)-[1,2,4]triazolo[1,5-a]pyrazin-8-yl)amino)-2H-benzo[b][1,4]oxazin-3(4H)-one (prepared from 6,8-dibromo-[1,2,4]triazolo[1,5-a]pyrazine[Ark Pharm] and 6-amino-2H-benzo[b][1,4]oxazin-3(4H)-one[Bionet], C with tert-butyl 3-(4,4,5,5-tetramethyl-1,3,2-dioxaborolan-2-yl)-2,5-dihydro-1H-pyrrole-1- | | F.1.14 | 2.60 (d) | 406 | N | NT |

TABLE F.1-continued

Examples prepared using an acid chloride as described in General Procedure F

| Amine | Product | Example # | R$_t$ min (Table 1, Method) | m/z ESI+ (M + H)+ | Btk enzyme IC$_{50}$ | CSF-1R enzyme IC$_{50}$ |
|---|---|---|---|---|---|---|
| carboxylate[Combi-Blocks], E with Pd/C, D with TFA) | | | | | | |
| 8-((6-(pyrrolidin-3-yl)-[1,2,4]triazolo[1,5-a]pyridin-8-yl)amino)-4,5-dihydro-1H-benzo[b]azepin-2(3H)-one trifluoroacetate(prepared using B from 8-bromo-6-chloro-[1,2,4]triazolo[1,5-a]pyridine[Example #1, Step A] and 8-amino-4,5-dihydro-1H-benzo[b]azepin-2(3H)-one[AstaTech], C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, D with TFA) | 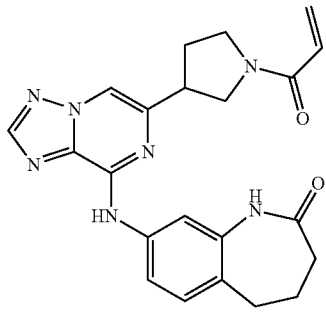 [SMILES: C=CC(=O)N1CCC(c2cn3ncnc3c(Nc3ccc4c(c3)NC(=O)CCC4)n2)C1] | F.1.15 | 1.76 (e) | 417 | B | NT |
| N-methyl-6-(pyrrolidin-3-yl)-[1,2,4]triazolo[1,5-a]pyrazin-8-amine(prepared using A from 6,8-dibromo-[1,2,4]triazolo[1,5-a]pyrazine[Ark Pharm] and methylamine, C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, D with TFA) | 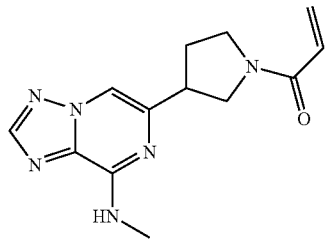 [SMILES: C=CC(=O)N1CCC(c2cn3ncnc3c(NC)n2)C1] | F.1.16 | 1.04 (f) | 273 | C | NT |
| N-(2-methoxyethyl)-6-(pyrrolidin-3-yl)-[1,2,4]triazolo[1,5-a]pyrazin-8-amine (prepared using A from 6,8-dibromo-[1,2,4]triazolo[1,5-a]pyrazine[Ark Pharm] and 2-methoxyethanamine, C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, D with TFA) | 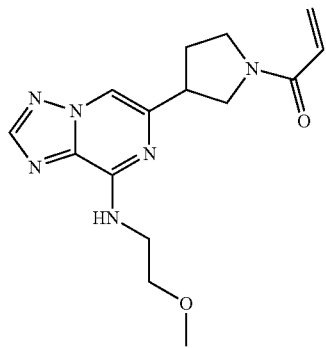 [SMILES: C=CC(=O)N1CCC(c2cn3ncnc3c(NCCOC)n2)C1] | F.1.7 | 1.50 (f) | 317 | C | NT |
| N-(6-morpholinopyridin-3-yl)-6-(piperidin-3-yl)-[1,2,4]triazolo[1,5-a]pyrazin-8-amine (prepared using A from 6,8-dibromo-[1,2,4]triazolo[1,5-a]pyrazine[Ark Pharm] and 6-morpholinopyridin-3-amine, C with tert-butyl 3-(4,4,5,5-tetramethyl-1,3,2-dioxaborolan-2-yl)-5,6-dihydropyridine-1(2H)-carboxylate[Anichem], E with Pd/C, D with TFA) | 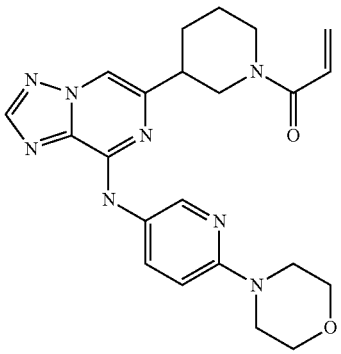 [SMILES: C=CC(=O)N1CCCC(c2cn3ncnc3c(Nc3ccc(N4CCOCC4)nc3)n2)C1] | F.1.18 | 1.23 (f) | 435 | B | NT |

TABLE F.1-continued

Examples prepared using an acid chloride as described in General Procedure F

| Amine | Product | Example # | $R_t$, min (Table 1, Method) | m/z ESI+ $(M + H)^+$ | Btk enzyme $IC_{50}$ | CSF-1R enzyme $IC_{50}$ |
|---|---|---|---|---|---|---|
| N-(2-methoxyethyl)-6-(pyrrolidin-3-yl)-[1,2,4]triazolo[1,5-a]pyrazin-8-amine (prepared using A from 6,8-dibromo-[1,2,4]triazolo[1,5-a]pyrazine[Ark Pharm] and 6-morpholinopyridin-3-amine, C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, D with TFA) | 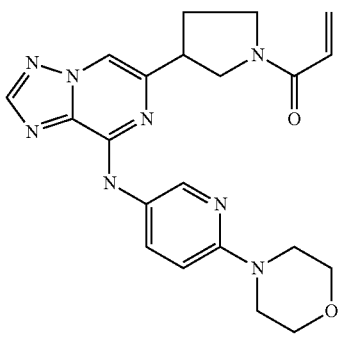 [SMILES: C=CC(=O)N1CCC(c2cn3ncnc3c(Nc3ccc(N4CCOCC4)nc3)n2)C1] | F.1.19 | 1.16 (f) | 421 | B | NT |
| N-(2-methoxyethyl)-6-(pyrrolidin-3-yl)-[1,2,4]triazolo[1,5-a]pyrazin-8-amine (prepared using A from 6,8-dibromo-[1,2,4]triazolo[1,5-a]pyrazine[Ark Pharm] and 1-(4-aminophenyl)-3-methylimidazolidin-2-one [Chembridge], C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, D with HCl) | 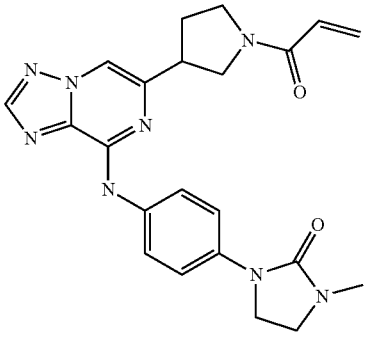 [SMILES: C=CC(=O)N1CCC(c2cn3ncnc3c(Nc3ccc(N4CCN(C)C4=O)cc3)n2)C1] | F.1.20 | 1.37 (f) | 433 | B | NT |
| N-(1-methyl-1H-pyrazol-3-yl)-6-(piperidin-3-yl)-[1,2,4]triazolo[1,5-a]pyridin-8-amine(prepared using B from 8-bromo-6-chloro-[1,2,4]triazolo[1,5-a]pyridine [Example #1, Step A] and 1-methyl-1H-pyrazol-3-amine, C with tert-butyl 3-(4,4,5,5-tetramethyl-1,3,2-dioxaborolan-2-yl)-5,6-dihydropyridine-1(2H)-carboxylate[Anichem], E with Pd/C, D with TFA) | 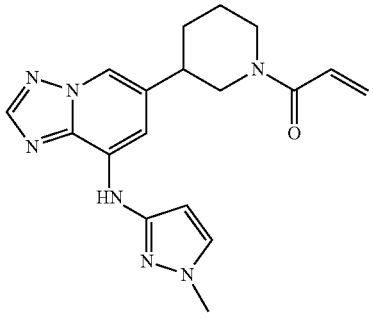 [SMILES: C=CC(=O)N1CCCC(c2cc(Nc3ccn(C)n3)c3ncnn3c2)C1] | F.1.21 | 2.56 (d) | 352 | B | NT |
| N-(1-methyl-1H-pyrazol-4-yl)-6-(pyrrolidin-3-yl)-[1,2,4]triazolo[1,5-a]pyrazin-8-amine(prepared using A from 6,8-dibromo-[1,2,4]triazolo[1,5-a]pyrazine[Ark Pharm] and 1-methyl-1H-pyrazol-4-amine, C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, D with TFA) | 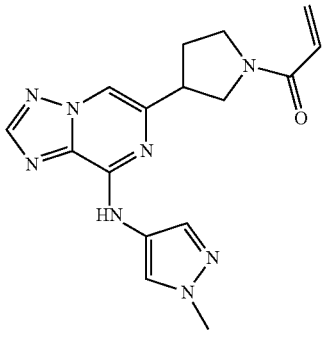 [SMILES: C=CC(=O)N1CCC(c2cn3ncnc3c(Nc3cnn(C)c3)n2)C1] | F.1.22 | 2.38 (d) | 339 | A | NT |

TABLE F.1-continued

Examples prepared using an acid chloride as described in General Procedure F

| Amine | Product | Example # | $R_t$ min (Table 1, Method) | m/z ESI+ $(M + H)^+$ | Btk enzyme $IC_{50}$ | CSF-1R enzyme $IC_{50}$ |
|---|---|---|---|---|---|---|
| N-(1-methyl-1H-pyrazol-3-yl)-6-(pyrrolidin-3-yl)-[1,2,4]triazolo[1,5-a]pyrazin-8-amine (prepared using A from 6,8-dibromo-[1,2,4]triazolo[1,5-a]pyrazine[ArkPharm] and 1-methyl-1H-pyrazol-3-amine, C with tert-butyl 3-(4,4,5,5-tetramethyl-1,3,2-dioxaborolan-2-yl)-2,5-dihydro-1H-pyrrole-1-carboxylate, E with Pd(OH)$_2$/C, D with HCl) | | F.1.23 | 1.40 (h) | 339 | C | NT |
| (S)-N-(6-(piperidin-3-yl)-[1,2,4]triazolo[1,5-a]pyridin-8-yl)-6,7-dihydro-4H-pyrazolo[5,1-c][1,4]oxazin-2-amine (prepared from Example #5, Step C, using D with HCl) | | F1.24 | 1.58 (h) | 394 | C | NT |
| (R)-N-(1-methyl-1H-pyrazol-4-yl)-6-(pyrrolidin-3-yl)-[1,2,4]triazolo[1,5-a]pyrazin-8-amine (prepared from Example #6, Step C using D with HCl) | | F1.25 | 1.42 (h) | 339 | C | NT |
| N-(6-(pyrrolidin-3-yl)-[1,2,4]triazolo[1,5-a]pyridin-8-yl)-6,7-dihydro-4H-pyrazolo[5,1-c][1,4]oxazin-2-amine amine(prepared using B from tert-butyl 3-(8-chloro-[1,2,4]triazolo[1,5-a]pyridin-6-yl)piperidine-1-carboxylate[prepared using C with 6-bromo-8-chloro-[1,2,4]triazolo[1,5-a]pyridine[Example #1, Step A] and tert-butyl 3-(4,4,5,5-tetramethyl-1,3,2-dioxaborolan-2-yl)-2,5-dihydro-1H-pyrrole-1-carboxylate[Cobmi-Blocks], E with Pt/C] and 6,7-dihydro-4H-pyrazolo[5,1-c][1,4]oxazin-2-amine [Preparation #1], D with TFA) | | F1.26 | 0.66 (a) | 380 | A | NT |

TABLE F.1-continued

Examples prepared using an acid chloride as described in General Procedure F

| Amine | Product | Example # | $R_t$ min (Table 1, Method) | m/z ESI+ $(M + H)^+$ | Btk enzyme $IC_{50}$ | CSF-1R enzyme $IC_{50}$ |
|---|---|---|---|---|---|---|
| N-(6-morpholinopyridazin-3-yl)-6-(piperidin-3-yl)-[1,2,4]triazolo[1,5-a]pyridin-8-amine(prepared using B from tert-butyl 3-(8-chloro-[1,2,4]triazolo[1,5-a]pyridin-6-yl)piperidine-1-carboxylate[prepared using C with 6-bromo-8-chloro-[1,2,4]triazolo[1,5-a]pyridine[Example #1, Step A] and tert-butyl 3-(4,4,5,5-tetramethyl-1,3,2-dioxaborolan-2-yl)-5,6-dihydropyridine-1(2H)-carboxylate[Anichem], E with Pt/C] and 3-amino-6-(morpholin-4-yl)pyridazine (Matrix), D with TFA) | | F.1.27 | 1.13 (e) | 435 | NT | NT |
| N-(5-morpholinopyridin-2-yl)-6-(piperidin-3-yl)-[1,2,4]triazolo[1,5-a]pyridin-8-amine(prepared using B from tert-butyl 3-(8-chloro-[1,2,4]triazolo[1,5-a]pyridin-6-yl)piperidine-1-carboxylate[prepared using C with 6-bromo-8-chloro-[1,2,4]triazolo[1,5-a]pyridine[Example #1, Step A] and tert-butyl 3-(4,4,5,5-tetramethyl-1,3,2-dioxaborolan-2-yl)-5,6-dihydropyridine-1(2H)-carboxylate[Anichem], E with Pt/C] and 5-morpholinopyridin-2-amine (Oakwood), D with TFA) | | F.128 | 1.10 (a) | 434 | B | NT |
| N-(6-morpholinopyridin-2-yl)-6-(piperidin-3-yl)-[1,2,4]triazolo[1,5-a]pyridin-8-amine(prepared using B from tert-butyl 3-(8-chloro-[1,2,4]triazolo[1,5-a]pyridin-6-yl)piperidine-1-carboxylate[prepared using C with 6-bromo-8-chloro-[1,2,4]triazolo[1,5-a]pyridine[Example #1, Step A] and tert-butyl 3-(4,4,5,5-tetramethyl-1,3,2-dioxaborolan-2-yl)-5,6-dihydropyridine-1(2H)-carboxylate[Anichem], E with Pt/C] and 6-morpholinopyridin-2-amine (Combi-Phos), D with TFA) | | F.1.29 | 2.02 (e) | 434 | B | NT |

TABLE F.1-continued

Examples prepared using an acid chloride as described in General Procedure F

| Amine | Product | Example # | $R_t$ min (Table 1, Method) | m/z ESI+ $(M + H)^+$ | Btk enzyme $IC_{50}$ | CSF-1R enzyme $IC_{50}$ |
|---|---|---|---|---|---|---|
| N-(6-piperidin-3-yl)-[1,2,4]triazolo[1,5-a]pyridin-8-yl)-6,7-dihydro-4H-pyrazolo[5,1-c][1,4]oxazin-2-amine (prepared using B from tert-butyl 3-(8-chloro-[1,2,4]triazolo[1,5-a]pyridin-6-yl)piperidine-1-carboxylate[prepared using C with 6-bromo-8-chloro-[1,2,4]triazolo[1,5-a]pyridine[Example #1, Step A] and tert-butyl 3-(4,4,5,5-tetramethyl-1,3,2-dioxaborolan-2-yl)-5,6-dihydropyridine-1(2H)-carboxylate[Anichem], E with Pt/C] and 6,7-dihydro-4H-pyrazolo[5,1-c][1,4]oxazin-2-amine [Preparation #1], D with TFA) | | F1.30 | 1.75 (e) | 394 | B | NT |
| 3-isopropyl-N-(6-(piperidin-3-yl)-[1,2,4]triazolo[1,5-a]pyridin-8-yl)-1,2,4-oxadiazol-5-amine(prepared using B from tert-butyl 3-(8-chloro-[1,2,4]triazolo[1,5-a]pyridin-6-yl)piperidine-1-carboxylate[prepared using C with 6-bromo-8-chloro-[1,2,4]triazolo[1,5-a]pyridine[Example #1, Step A] and tert-butyl 3-(4,4,5,5-tetramethyl-1,3,2-dioxaborolan-2-yl)-5,6-dihydropyridine-1(2H)-carboxylate[Anichem], E with Pt/C] and 3-isopropyl-1,2,4-oxadiazol-5-amine (Ark Pharm), D with TFA) | | F1.31 | 1.95 (e) | 382 | C | NT |
| 3-methyl-N-(6-(piperidin-3-yl)-[1,2,4]triazolo[1,5-a]pyridin-8-yl)-1,2,4-oxadiazol-5-amine(prepared using B from tert-butyl 3-(8-chloro-[1,2,4]triazolo[1,5-a]pyridin-6-yl)piperidine-1-carboxylate[prepared using C with 6-bromo-8-chloro-[1,2,4]triazolo[1,5-a]pyridine[Example #1, Step A] and tert-butyl 3-(4,4,5,5-tetramethyl-1,3,2-dioxaborolan-2-yl)-5,6-dihydropyridine-1(2H)-carboxylate[Anichem], E with Pt/C] and 3-methyl-1,2,4-oxadiazol-5-amine(Matrix), D with TFA) | | F1.32 | 1.27 (e) | 354 | C | NT |

TABLE F.1-continued

Examples prepared using an acid chloride as described in General Procedure F

| Amine | Product | Example # | $R_t$, min (Table 1, Method) | m/z ESI+ $(M + H)^+$ | Btk enzyme $IC_{50}$ | CSF-1R enzyme $IC_{50}$ |
|---|---|---|---|---|---|---|
| (S)-N-(6-(pyrrolidin-3-yl)-[1,2,4]triazolo[1,5-a]pyridin-8-yl)-6,7-dihydro-4H-pyrazolo[5,1-c][1,4]oxazin-2-amine (prepared using B from -[1,2,4]triaozlo[1,5-a]pyridine[Example #1, Step A] and 6,7-dihydro-4H-pyrazolo[5,1-c][1,4]oxazin-2-amine [Preparation #1], C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, G [Table 2, Method 7], D with HCl) | | F1.33 | 1.42 (l) | 380 | C | NT |
| 6-((1R,3S)-3-aminocyclopentyl)-N-(1-methyl-1H-pyrazol-3-yl)-[1,2,4]triazolo[1,5-a]pyridin-8-amine hydrochloride (prepared using Example #7, Step E using(2S,5S)-5-benzyl-3-methyl-2-(5-methlfuran-2-yl)imidazolidin-4-one, then Example #7, Step F, D with HCl) | | F1.34 | 1.49 (a) | 352 | B | NT |
| 6-(cis-3-aminocyclohexyl)-N-(1-methyl-1H-pyrazol-3-yl)-[1,2,4]triazolo[1,5-a]pyridin-8-amine(prepared using B from 8-bromo-6-chloro-[1,2,4]triazolo[1,5-a]pyridine[Example #1, Step A] and 1-methyl-1H-pyrazol-3-amine, C with [3-(4,4,5,5-tetramethyl[1,3,2]dioxaborolan-2-yl)-cyclohex-3-enyl]-carbamic acid tert-butyl ester and [3-(4,4,5,5-tetramethyl-[1,3,2]dioxaborolan-2-yl)-cyclohex-2-enyl]-carbamic acid tert-butyl ester [prepared according to U.S. 2009/0197864], E with Pd/C, D with HCl) | | F1.35 | 2.62 (b) | 366 | A | NT |

TABLE F.1-continued

Examples prepared using an acid chloride as described in General Procedure F

| Amine | Product | Example # | $R_t$ min (Table 1, Method) | m/z ESI+ $(M + H)^+$ | Btk enzyme $IC_{50}$ | CSF-1R enzyme $IC_{50}$ |
|---|---|---|---|---|---|---|
| 6-(t-3-aminocyclohexyl)-N-(1-methyl-1H-pyrazol-3-yl)-[1,2,4]triazolo[1,5-a]pyridin-8-amine(prepared using B from 8-bromo-6-chloro-[1,2,4]triazolo[1,5-a]pyridine [Example #1, Step A] and 1-methyl-1H-pyrazol-3-amine, C with [3-(4,4,5,5-tetramethyl[1,3,2]dioxaborolan-2-yl)-cyclohex-3-enyl]-carbamic acid tert-butyl ester and [3-(4,4,5,5-tetramethyl-[1,3,2]dioxaborolan-2-yl)-cyclohex-2-enyl]-carbamic acid tert-butyl ester [prepared according to U.S. 2009/0197864], E with Pd/C, D with HCl) | | F.1.36 | 2.64 (d) | 366 | B | NT |
| (S)-N-(1-methyl-1H-pyrazol-3-yl)-6-(pyrrolidin-3-yl)-[1,2,4]triazolo[1,5-a]pyridin-8-amine(prepared using C from tert-butyl 3-(4,4,5,5-tetramethyl-1,3,2-dioxaborolan-2-yl)-2,5-dihydro-1H-pyrrole-1-carboxylate[Combi-Blocks] and Preparation #B.1, E with Pd/C, G [Table 2, Method 10], D with HCl) | | F.1.37 | 1.43 (h) | 338 | C | NT |
| (R)-N-(1-methyl-1H-pyrazol-3-yl)-6-(pyrrolidin-3-yl)-[1,2,4]triazolo[1,5-a]pyridin-8-amine(prepared using C from tert-butyl 3-(4,4,5,5-tetramethyl-1,3,2-dioxaborolan-2-yl)-2,5-dihydro-1H-pyrrole-1-carboxylate[Combi-Blocks] and Preparation #B.1, E with Pd/C, G[Table 2, Method 10], D with HCl) | | F.1.38 | 1.43 (h) | 338 | A | NT |
| (S)-N-(5-methyl-4,5,6,7-tetrahydropyrazolo[1,5-a]pyrazin-2-yl)-6-(pyrrolidin-3-yl)-[1,2,4]triazolo[1,5-a]pyridin-8-amine hydrochloride (prepared using B from Example #1, Step A and 5-methyl-4,5,6,7-tetrahydropyrazolo[1,5-a]pyrazin-2-amine [Astatech], C with tert-butyl 3-(4,4,5,5-tetramethyl-1,3,2-dioxaborolan-2-yl)-2,5-dihydro-1H-pyrrole-1-carboxylate[Combi-Blocks], E with Pd/C, G[Table 2, Method 11], D) | | F.1.39 | 1.37 (m) | 393 | A | NT |

TABLE F.1-continued

Examples prepared using an acid chloride as described in General Procedure F

| Amine | Product | Example # | $R_t$ min (Table 1, Method) | m/z ESI+ $(M + H)^+$ | Btk enzyme $IC_{50}$ | CSF-1R enzyme $IC_{50}$ |
|---|---|---|---|---|---|---|
| (S)-N-(5-methyl-4,5,6,7-tetrahydropyrazolo[1,5-a]pyrazin-2-yl)-6-(piperidin-3-yl)-[1,2,4]triazolo[1,5-a]pyridin-8-amine hydrochloride(prepared using B from Example #1, Step A and 5-methyl-4,5,6,7-tetrahydropyrazolo[1,5-a]pyrazin-2-amine [Astatech], C with tert-butyl 3-(4,4,5,5-tetramethyl-1,3,2-dioxaborolan-2-yl)-5,6-dihydropyridine-1(2H)-carboxylate[Anichem], E with Pd(OH)2, G[Table 2, Method 12], D) | | F.1.40 | 1.49 (n) | 407 | A | NT |
| N-(6-(pyrrolidin-3-yl)imidazo[1,2-b]pyridazin-8-yl)-6,7-dihydro-4H-pyrazolo[5,1-c][1,4]oxazin-2-amine, hydrochloric acid (prepared using B from 8-bromo-6-chloroimidazo[1,2-b]pyridazine, hydrochloric acid[Astatech] and Preparation #1, C with tert-butyl 3-(4,4,5,5-tetramethyl-1,3,2-dioxaborolan-2-yl)-2,5-dihydro-1H-pyrrole-1-carboxylate[Combi-Blocks], E with Pd(OH)$_2$, D) | | F.1.41 | 1.47 (a) | 380 | A | NT |
| N-(6-(azetidin-3-yl)-[1,2,4]triazolo[1,5-a]pyridin-8-yl)-6,7-dihydro-4H-pyrazolo[5,1-c][1,4]oxazin-2-amine hydrochloride (prepared using D from Preparation #2) | | F.1.42 | 1.34 (o) | 366 | A | NT |
| 6-cyclohexyl-N-(1-(piperidin-4-yl)-1H-pyrazol-4-yl)-[1,2,4]triazolo[1,5-a]pyrazin-8-amine hydrochloride(prepared using A from 6,8-dibromo-[1,2,4]triazolo[1,5-a]pyrazine [ArkPharm] and tert-butyl 4-(4-amino-1H-pyrazol-1-yl)piperidine-1-carboxylate[Combiblocks], C with 2-(cyclohex-1-en-1-yl)-4,4,5,5-tetramethyl-1,3,2-dioxaborolane [Combiblocks], E with Pd(OH)$_2$/C, and D with HCl. | | F.1.43 | 2.00 (h) | 409 | NT | A |

TABLE F.1-continued

Examples prepared using an acid chloride as described in General Procedure F

| Amine | Product | Example # | $R_t$ min (Table 1, Method) | m/z ESI+ $(M + H)^+$ | Btk enzyme $IC_{50}$ | CSF-1R enzyme $IC_{50}$ |
|---|---|---|---|---|---|---|
| 6-cyclohexyl-N-(1-(piperidin-4-yl)-1H-pyrazol-4-yl)-[1,2,4]triazolo[1,5-a]pyrazin-8-amine hydrochloride(prepared using A from 6,8-dibromo-[1,2,4]triazolo[1,5-a]pyrazine [ArkPharm] and tert-butyl 4-(4-amino-1H-pyrazol-1-yl)piperidine-1-carboxylate[Combiblocks], C with 2-(cyclohex-1-en-1-yl)-4,4,5,5-tetramethyl-1,3,2-dioxaborolane [Combiblocks], E with Pa(OH)$_2$/C, and D with HCl. | | F.1.44 | 1.99 (h) | 424 | NT | A |

General Procedure G: Chiral Preparative HPLC Separation of Stereoisomers

A racemic mixture of compound is subjected to chiral purification using preparative HPLC. The representative gradients using mobile phases A and B are described in Table 2, Methods (1-6). When indicated, methods (1-6) from Table 2, were employed respectively for the chiral separation of the racemic mixtures.

Illustration of General Procedure G

Preparation #G.1 and #G.2: (S)-tert-butyl 3-(8-((1-methyl-1H-pyrazol-4-yl)amino)-[1,2,4]triazolo[1,5-a]pyrazin-6-yl)pyrrolidine-1-carboxylate and (R)-tert-butyl 3-(8-((1-methyl-1H-pyrazol-4-yl)amino)-[1,2,4]triazolo[1,5-a]pyrazin-6-yl)pyrrolidine-1-carboxylate

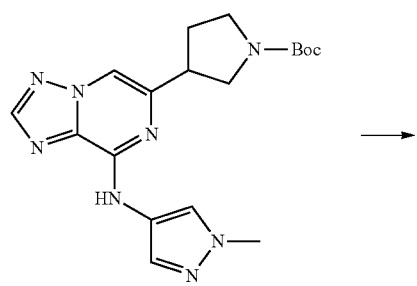

→

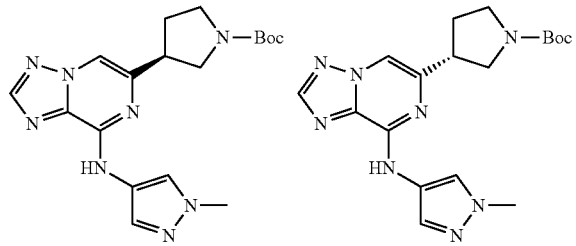

A racemic mixture of tert-butyl 3-(8-((1-methyl-1H-pyrazol-4-yl)amino)-[1,2,4]triazolo[1,5-a]pyrazin-6-yl)pyrrolidine-1-carboxylate (Example #6, step C) was separated via chiral prep (Table 2, Method 6) to give (S)-tert-butyl 3-(8-((1-methyl-1H-pyrazol-4-yl)amino)-[1,2,4]triazolo[1,5-a]pyrazin-6-yl)pyrrolidine-1-carboxylate (0.435 g, 40.2%, OR=negative) and (R)-tert-butyl 3-(8-((1-methyl-1H-pyrazol-4-yl)amino)-[1,2,4]triazolo[1,5-a]pyrazin-6-yl)pyrrolidine-1-carboxylate (0.442 g, 40.9%, OR=positive) [Stereochemistry is arbitrarily assigned]: LC/MS (Table 1, Method 1) $R_t$=1.96 min.; MS m/z: 385 $(M+H)^+$.

TABLE G.1

Examples prepared using chiral SFC (Table 2, Method 17 or 18) from General Procedure G

| Racemate | Products | Example # | $R_t$ min (Table 1, Method) | $R_t$ min (Table 2, Method) | m/z ESI+ $(M + H)^+$ | CSF-1R enzyme $IC_{50}$ |
|---|---|---|---|---|---|---|
| (trans)-3-(4-((6-cyclohexyl-[1,2,4]triazolo[1,5-a]pyrazin-8-yl)amino)-1H-pyrazol-1-yl)cyclohexanol (prepared using A from 8-bromo-6-cyclohexyl-[1,2,4]triazolo[1,5-a]pyrazine[Example #11, Step E] and (trans)-3-(4-amino-1H-pyrazol-1-yl)cyclohexanol [Preparation #7] | | G.1.1 | 1.45 (v) | 1.86 (17) | 382 | A |
| (trans)-3-(4-((6-cyclohexyl-[1,2,4]triazolo[1,5-a]pyrazin-8-yl)amino)-1H-pyrazol-1-yl)cyclohexanol (prepared using A from 8-bromo-6-cyclohexyl-[1,2,4]triazolo[1,5-a]pyrazine[Example #11, Step D] and (trans)-3-(4-amino-1H-pyrazol-1-yl)cyclohexanol [Preparation #7] | | G.1.2 | 3.23 (v) | 1.98 (17) | 382 | A |
| (cis)-3-(4-((6-cyclohexyl-[1,2,4]triazolo[1,5-a]pyrazin-8-yl)amino)-1H-pyrazol-1-yl)cyclohexanol (prepared using A from 8-bromo-6-cyclohexyl-[1,2,4]triazolo[1,5-a]pyrazine[Example #11, Step D] and (cis)-3-(4-amino-1H-pyrazol-1-yl)cyclohexanol [Preparation #8] | | G.1.3 | 3.23 (v) | 2.10 (18) | 382 | A |
| (cis)-3-(4-((6-cyclohexyl-[1,2,4]triazolo[1,5-a]pyrazin-8-yl)amino)-1H-pyrazol-1-yl)cyclohexanol (prepared using A from 8-bromo-6-cyclohexyl-[1,2,4]triazolo[1,5-a]pyrazine[Example #11, Step D] and (cis)-3-(4-amino-1H-pyrazol-1-yl)cyclohexanol [Preparation #8] | | G.1.4 | 3.13 (v) | 2.29 (18) | 382 | A |

General Procedure H: Formation of a Sulfonamide from a Sulfonyl Chloride and an Amine To a solution of an amine (preferably 1 equiv) and a base (such as pyridine, DIEA or TEA; 1.1-5 equiv, preferably 2-3 equiv DIEA) in an organic solvent (for example, DMA, DMF or THF, preferably DMA) at about 0° C. is added a sulfonyl chloride (1.0-1.2 equiv). After about 5-120 min (preferably 10-30 min), the reaction mixture is added slowly into ice water while stirring. If a precipitate is present after the ice melted completely, the resulting solid is collected via vacuum filtration to give crude product. Alternatively an extractive work up or concentration of the reaction mixture under reduced pressure may be done.

Illustration of General Procedure H

Example #H.1: (S)—N-(3,4-dimethoxyphenyl)-6-(1-(vinylsulfonyl)pyrrolidin-3-yl)-[1,2,4]triazolo[1,5-a]pyrazin-8-amine

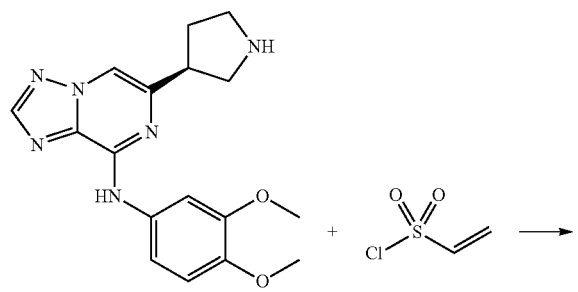

To a solution of (S)—N-(3,4-dimethoxyphenyl)-6-(pyrrolidin-3-yl)-[1,2,4]triazolo[1,5-a]pyrazin-8-amine (0.073 g, 0.21 mmol, Example #3, Step B) and DIEA (0.093 mL, 0.54 mmol) in DMA (1.5 mL) at about 0° C. was added ethenesulfonyl chloride (0.025 mL, 0.22 mmol). After about 20 min, the reaction mixture was added slowly into ice water (~10 mL) while stirring. After the ice melted completely, the resulting solid was collected via vacuum filtration and dried under vacuum at 55° C. to give impure product. The solid was triturated with MeOH (1 mL). The resulting solid was collected via vacuum filtration while washing with additional MeOH (1 mL) and dried under vacuum at 55° C. to give solid with little change in purity by LCMS. The filtrate and solid were recombined, concentrated under reduced pressure and purified via silica gel chromatography eluting with 0-5% MeOH in DCM. The product-containing fraction was concentrated under reduced pressure and dried under vacuum at about 55° C. to give (S)—N-(3,4-dimethoxyphenyl)-6-(1-(vinylsulfonyl)pyrrolidin-3-yl)-[1,2,4]triazolo[1,5-a]pyrazin-8-amine (0.024 g, 26%) as a white solid: LC/MS (Table 1, Method e) $R_t$=2.00 min.; MS m/z: 431 (M+H)$^+$. BTK enzyme IC$_{50}$=A General Procedure I: Formation of a Cyanamide from an Amine with Cyanogen Bromide To a mixture of an amine (preferably 1 equiv) and a base (such as cesium carbonate or TEA; 1-10 equiv, preferably 1-5 equiv) in a solvent such as DCM, DMA, THF or DMF (preferably DMA or THF) at about −5 to 25° C. (preferably 0° C.) is added cyanogen bromide (1-3 equivalents, preferably 1.1-2.2 equiv). The reaction temperature is maintained or is allowed to warm. After about 5-120 min, the reaction mixture is diluted with water (10 mL) and extracted (for example with DCM). The combined organic layers is optionally washed with brine, dried over Na$_2$SO$_4$ or MgSO$_4$, filtered, and concentrated under reduced pressure.

Illustration of General Procedure I

Example #I.1: 3-(8-((1-methyl-1H-pyrazol-3-yl)amino)-[1,2,4]triazolo[1,5-a]pyridin-6-yl)pyrrolidine-1-carbonitrile

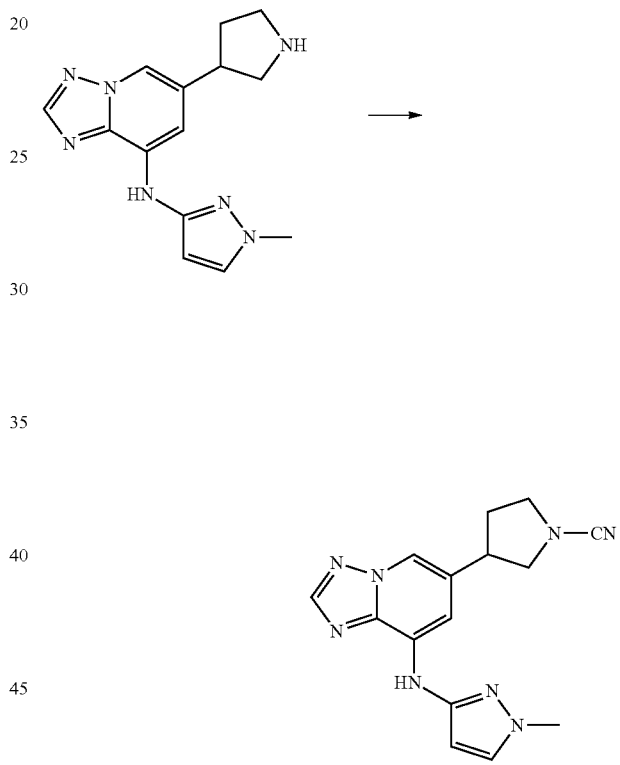

To a mixture of N-(1-methyl-1H-pyrazol-3-yl)-6-(pyrrolidin-3-yl)-[1,2,4]triazolo[1,5-a]pyridin-8-amine (0.10 g, 0.35 mmol) and cesium carbonate (0.460 g, 1.41 mmol) in DMA (3.0 mL) at about 0° C. was added cyanogen bromide (0.075 g, 0.71 mmol). The reaction bath was allowed to warm to about 10° C. After about 30 min, diluted with water (10 mL) and extracted with DCM (3×15 mL). The combined organic layers were washed with brine (15 mL), dried over MgSO$_4$, filtered, and concentrated under reduced pressure. The residue was dissolved in DCM for purification via silica gel chromatography eluting with 0-50% DCM/MeOH/NH$_4$OH (90:9:1) in DCM to give 3-(8-((1-methyl-1H-pyrazol-3-yl)amino)-[1,2,4]triazolo[1,5-a]pyridin-6-yl)pyrrolidine-1-carbonitrile (0.076 g, 70%) as a pale yellow solid after drying under vacuum at about 55° C. LC/MS (Table 1, Method e) $R_t$=1.43 min.; MS m/z: 309 (M+H)$^+$. BTK enzyme IC$_{50}$=B

TABLE I.1

Examples prepared from cyanogen bromide using General Procedure I

| Amine | Product | Example # | R$_t$ min (Table 1, Method) | m/z ESI+ (M + H)$^+$ | BTK enzyme IC$_{50}$ |
|---|---|---|---|---|---|
| N-(1-methyl-1H-pyrazol-3-yl)-6-(piperidin-3-yl)-[1,2,4]triazolo[1,5-a]pyridin-8-amine(prepared using B from 8-bromo-6-chloro-[1,2,4]triazolo[1,5-a]pyridine [Example #1, Step A] and 1-methyl-1H-pyrazol-3-amine, C with tert-butyl 3-(4,4,5,5-tetramethyl-1,3,2-dioxaborolan-2-yl)-5,6-dihydropyridine-1(2H)-carboxylate[Anichem], E with Pd/C, D with TFA) | | I.1.1 | 1.63 (e) | 323 | B |
| N-(1-methyl-1H-pyrazol-4-yl)-6-(pyrrolidin-3-yl)-[1,2,4]triazolo[1,5-a]pyrazin-8-amine(prepared from 6,8-dibromo-[1,2,4]triazolo[1,5-a]pyrazine[Ark Pharm] and 1-methyl-1H-pyrazol-4-amine, C with tert-butyl 3-(4,4,5,5-etramethyl-1,3,2-dioxaborolan-2-yl)-2,5-dihydro-1H-pyrrole-1-carboxylate[Combi-Blocks], E with Pd/C, D with TFA) | | I.1.2 | 1.44 (e) | 310 | B |
| N-(6-(piperidin-3-yl)-[1,2,4]triazolo[1,5-a]pyridin-8-yl)-6,7-dihydro-4H-pyrazolo[5,1-c][1,4]oxazin-2-amine(prepared using B form tert-butyl 3-(8-chloro-[1,2,4]triazolo[1,5-a]pyridin-6-yl)piperidine-1-carboxylate [prepared using C with 6-bromo-8-chloro-[1,2,4]triazolo[1,5-a]pyridine [Example #1, Step A] and tert-butyl 3-(4,4,5,5-tetramethyl-1,3,2-dioxaborolan-2-yl)-5,6-dihydropyridine-1(2H)-carboxylate[Anichem], E with Pt/C] and 6,7-dihydro-4H-pyrazolo[5,1-c][1,4]oxazin-2-amine[Preparation #1], D with TFA) | | I.1.3 | 1.66 (e) | 365 | B |
| 6-(trans-3-aminocyclohexyl)-N-(1-methyl-1H-pyrazol-3-yl)-[1,2,4]triazolo[1,5-a]pyridin-8-amine(prepared using B from 8-bromo-6-chloro-[1,2,4]triazolo[1,5-a]pyridine [Example #1, Step A] and 1-methyl-1H-pyrazol-3-amine, C with [3-(4,4,5,5-tetramethyl[1,3,2]dioxaborolan-2-yl)-cyclohex-3-ethyl]-carbamic acid tert-butyl ester and [3-(4,4,5,5-tetramethyl-[1,3,2]dioxaborolan-2-yl)-cyclohex-2-enyl]-carbamic acid tert-butyl ester[prepared according to U.S. 2009/0197864], E with Pd/C, D with HCl) | | I.1.4 | 2.48 (f) | 337 | B |

123

Example #1. 1-(3-(8-((1-methyl-1H-pyrazol-3-yl)amino)-[1,2,4]triazolo[1,5-a]pyridin-6-yl)pyrrolidin-1-yl)prop-2-en-1-one

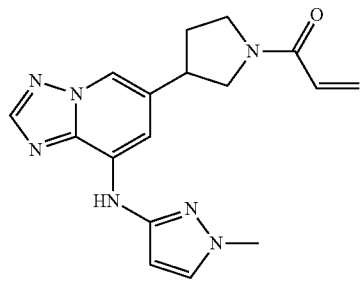 [SMILES: C=CC(=O)N1CCC(c2cc(Nc3ccn(C)n3)c3ncnn3c2)C1]

Step A: 8-bromo-6-chloro-[1,2,4]triazolo[1,5-a]pyridine

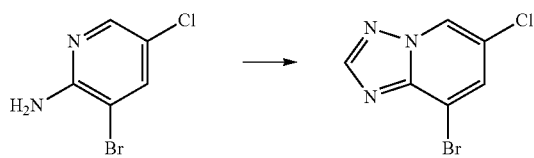 [SMILES: Nc1ncc(Cl)cc1Br ; Clc1cc(Br)c2ncnn2c1]

To a solution of 2-amino-3-bromo-5-chloropyridine (10.0 g, 48.2 mmol, Ark Pharm) in N,N-dimethylformamide (20 mL) was added DMF-DMA (17.2 g, 145 mmol) and the mixture was stirred at 130° C. for about 18 h. The mixture was cooled and evaporated to dryness. To an ice cooled stirring solution of the brown solid in MeOH (80.0 mL) and pyridine (7.80 mL, 96 mmol) was added hydroxylamine-o-sulfonic acid (7.63 g, 67.5 mmol). The reaction was allowed to warm to about 25° C. and stirred for about 18 h. The mixture was evaporated and the solid residue was dissolved in DCM (150 mL) and washed with saturated sodium bicarbonate (200 mL), water (200 mL) and brine (200 mL). The organic mixture was filtered through a Biotage phase separator to remove residual water and evaporated to dryness to give 8-bromo-6-chloro-[1,2,4]triazolo[1,5-a]pyridine as an orange solid, which was used in the next step without further purification. (6.1 g, 64% crude): $^1$H NMR (CDCl$_3$) δ 8.65 (d, J=1.8 Hz, 1H), 8.39 (s, 1H), 7.80 (d, J=1.7 Hz, 1H).

Step B. 6-chloro-N-(1-methyl-1H-pyrazol-3-yl)-[1,2,4]triazolo[1,5-a]pyridin-8-amine

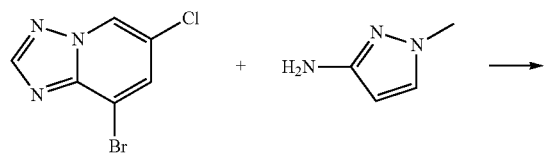

124

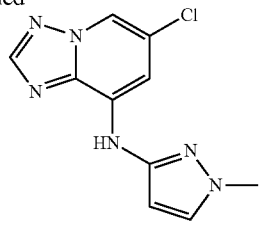

To a microwave vial was added 8-bromo-6-chloro-[1,2,4]triazolo[1,5-a]pyridine (1.59 g, 6.84 mmol, Example #1, Step A), 1-methyl-1H-pyrazol-3-amine (0.731 g, 7.52 mmol, Matrix Scientific), Xantphos (0.831 g, 1.44 mmol), palladium(II) acetate (0.154 g, 0.684 mmol), cesium carbonate (5.57 g, 17.1 mmol) and 1,4-dioxane (12 mL). The mixture was then heated in a microwave for about 1.5 h at about 120° C. The reaction was cooled to rt and concentrated under reduced pressure. The residue was sonicated with MeOH (10 mL) to give a uniform suspension, followed by filtration. LC/MS indicated impure product in both solid and filtrate. The solid and filtrate were combined, concentrated under reduced pressure, redissolved in DCM/MeOH (3:1; 250 mL), followed by addition of Silica gel. The suspension was concentrated under reduced pressure, purified via silica gel chromatography eluting with 0-60% DCM/MeOH/NH$_4$OH (90:9:1) in DCM. The product-containing fractions were combined and concentrated under reduced pressure to give 6-chloro-N-(1-methyl-1H-pyrazol-3-yl)-[1,2,4]triazolo[1,5-a]pyridin-8-amine (1.63 g, ~96%, ~86% purity by NMR): LC/MS (Table 1, Method e) R$_f$=2.33 min.; MS m/z: 248 (M+H)$^+$.

Step C. tert-butyl 3-(8-((1-methyl-1H-pyrazol-3-yl)amino)-[1,2,4]triazolo[1,5-a]pyridin-6-yl)-2,5-dihydro-1H-pyrrole-1-carboxylate

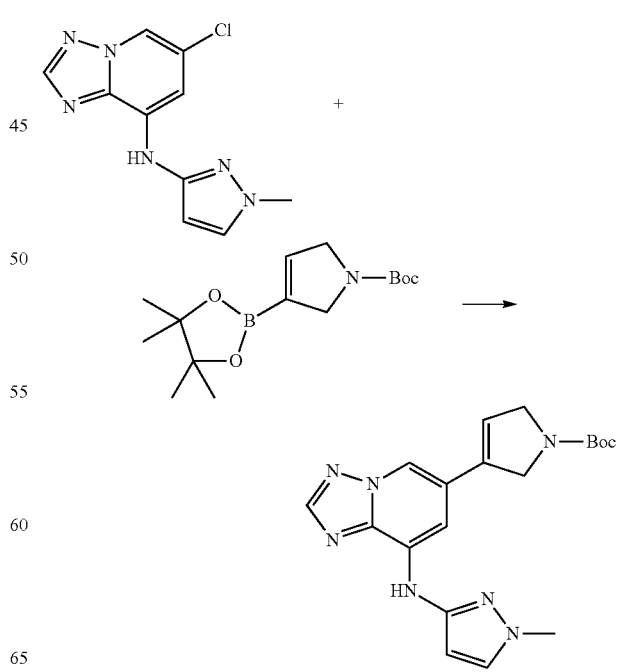

To a 10 mL microwave tube were added 6-chloro-N-(1-methyl-1H-pyrazol-3-yl)-[1,2,4]triazolo[1,5-a]pyridin-8-amine (0.21 g, 0.84 mmol), tert-butyl 3-(4,4,5,5-tetramethyl-1,3,2-dioxaborolan-2-yl)-2,5-dihydro-1H-pyrrole-1-carboxylate (0.35 g, 1.2 mmol, Combi-Blocks), THF (5 mL), MeOH (1 mL) and sodium carbonate (1.27 mL, 2.53 mmol). The mixture was sparged with nitrogen, then 1,1'-bis(diphenylphosphino)ferrocene-palladium(II)dichloride dichloromethane complex (0.069 g, 0.084 mmol) was added. The vial was sealed. The mixture was heated in a microwave at about 130° C. for about 1 h. The reaction mixture was filtered through Celite®, washed with DCM and MeOH. The filtrate was concentrated under reduced pressure. The crude product was purified via silica gel chromatography eluting with 0-80% DCM/MeOH/NH$_4$OH (90:9:1) in DCM. The product-containing fractions were combined, concentrated under reduced pressure, triturated with MeOH (1 mL). The resulting solid was collected via vacuum filtration, washed with additional MeOH (5 mL) and then dried under vacuum at about 55° C. to give tert-butyl 3-(8-((1-methyl-1H-pyrazol-3-yl)amino)-[1,2,4]triazolo[1,5-a]pyridin-6-yl)-2,5-dihydro-1H-pyrrole-1-carboxylate (0.17 g, 53%): LC/MS (Table 1, Method e) R$_t$=3.09 min.; MS m/z: 382 (M+H)$^+$.

Step D. tert-butyl 3-(8-((1-methyl-1H-pyrazol-3-yl)amino)-[1,2,4]triazolo[1,5-a]pyridin-6-yl)pyrrolidine-1-carboxylate

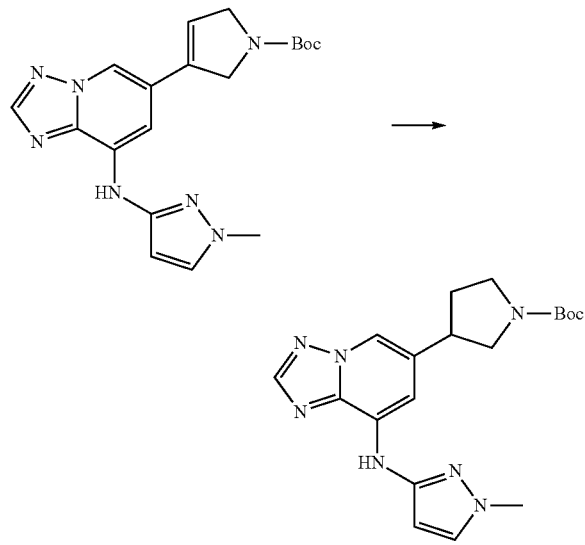

tert-Butyl 3-(8-((1-methyl-1H-pyrazol-3-yl)amino)-[1,2,4]triazolo[1,5-a]pyridin-6-yl)-2,5-dihydro-1H-pyrrole-1-carboxylate (1.40 g, 3.67 mmol), MeOH (100 mL), THF (5 mL), AcOH (5 mL) were added to dry 10% Pd/C (0.450 g, 0.423 mmol) in a 250 mL stainless steel pressure bottle. The reaction mixture was stirred at rt for about 16 h with 30 psi of H$_2$. Analytical HPLC indicated starting material and product present. Dry 10% Pd/C (0.450 g, 0.423 mmol) was added and hydrogenation continued at rt for about 4 days. The mixture was filtered through a nylon membrane and concentrated under reduced pressure. The residue was purified via silica gel chromatography eluting with 0-50% DCM/MeOH/NH$_4$OH (90:9:1) in DCM. The product-containing fractions were combined and concentrated under reduced pressure and dried under vacuum at about 55° C. to give tert-butyl 3-(8-((1-methyl-1H-pyrazol-3-yl)amino)-[1,2,4]triazolo[1,5-a]pyridin-6-yl)pyrrolidine-1-carboxylate (0.752 g, 52%): LC/MS (Table 1, Method e) R$_t$=2.21 min.; MS m/z: 384 (M+H)$^+$.

Step E. N-(1-methyl-1H-pyrazol-3-yl)-6-(pyrrolidin-3-yl)-[1,2,4]triazolo[1,5-a]pyridin-8-amine

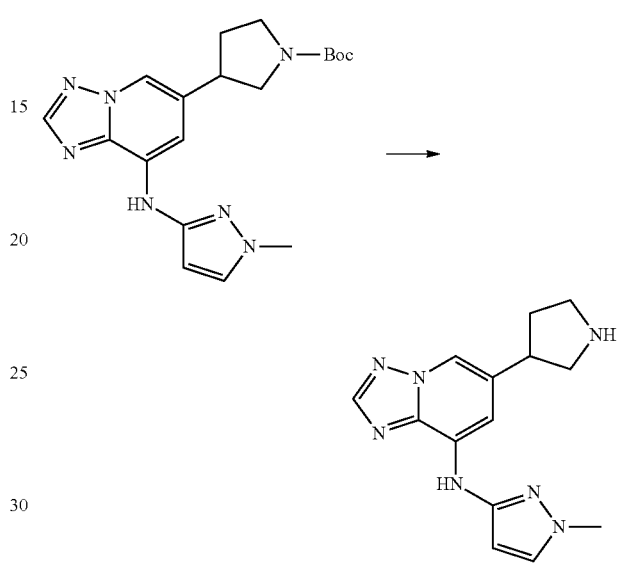

To a solution of tert-butyl 3-(8-((1-methyl-1H-pyrazol-3-yl)amino)-[1,2,4]triazolo[1,5-a]pyridin-6-yl)pyrrolidine-1-carboxylate (0.076 g, 0.20 mmol) in MeOH (0.75 mL) was added HCl (4M in 1,4-dioxane, 0.75 mL, 3.00 mmol). The reaction was stirred at rt for about 3.5 h and then concentrated under reduced pressure. The residue was purified via silica gel chromatography eluting with 0-100% DCM/MeOH/NH$_4$OH (90:9:1) in DCM. The product-containing fractions were combined, concentrated under reduced pressure and dried under vacuum at about 55° C. to give N-(1-methyl-1H-pyrazol-3-yl)-6-(pyrrolidin-3-yl)-[1,2,4]triazolo[1,5-a]pyridin-8-amine (0.061 g, ~109%, ~91% by NMR) which was used in the next step without further purification: LC/MS (Table 1, Method e) R$_t$=0.63 min.; MS m/z: 284 (M+H)$^+$.

Step F. 1-(3-(8-((1-methyl-1H-pyrazol-3-yl)amino)-[1,2,4]triazolo[1,5-a]pyridin-6-yl)pyrrolidin-1-yl)prop-2-en-1-one

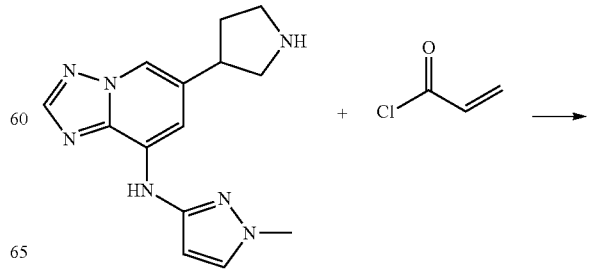

127

-continued

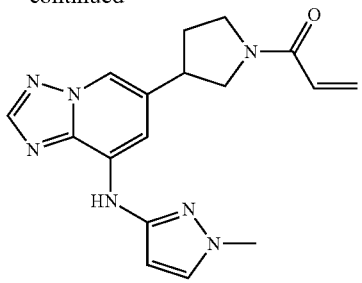

To a solution of N-(1-methyl-1H-pyrazol-3-yl)-6-(pyrrolidin-3-yl)-[1,2,4]triazolo[1,5-a]pyridin-8-amine (0.143 g, 0.505 mmol) and N-ethyl-N-isopropylpropan-2-amine (0.220 mL, 1.26 mmol) in DMA (2.5 mL) at about 0° C. was added acryloyl chloride (0.043 mL, 0.530 mmol). After about 2 min, the ice bath was removed and the reaction was allowed to stir at rt. After about 25 min, the reaction mixture was added diluted with water (10 mL), extracted with DCM (3×10 mL). The combined organic layers were washed with brine, dried over $MgSO_4$, filtered, and concentrated under reduced pressure. The crude product was purified via silica gel chromatography eluting with 50-100% EtOAc in DCM with long hold at 100% EtOAc. The product-containing fractions were combined, concentrated under reduced pressure, and dried under vacuum at about 55° C. to give 1-(3-(8-((1-methyl-1H-pyrazol-3-yl)amino)-[1,2,4]triazolo[1,5-a]pyridin-6-yl)pyrrolidin-1-yl)prop-2-en-1-one (0.11 g, 65%) as a white foam: LC/MS (Table 1, Method e) $R_t$=1.56 min.; MS m/z: 338 (M+H)⁺. BTK enzyme IC₅₀=A Example #2: 1-(3-(8-(6-Methoxypyridazin-3-ylamino)-[1,2,4]triazolo[1,5-a]pyridin-6-yl)pyrrolidin-1-yl)prop-2-en-1-one trifluoroacetate

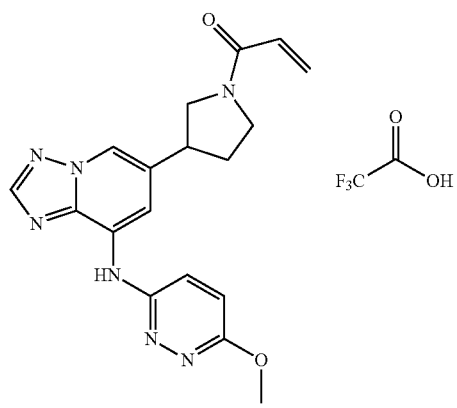 [SMILES: C=CC(=O)N1CCC(c2cc(Nc3ccc(OC)nn3)c3ncnn3c2)C1 ; O=C(O)C(F)(F)F]

128

Step A: 6-chloro-N-(6-methoxypyridazin-3-yl)-[1,2,4]triazolo[1,5-a]pyridin-8-amine

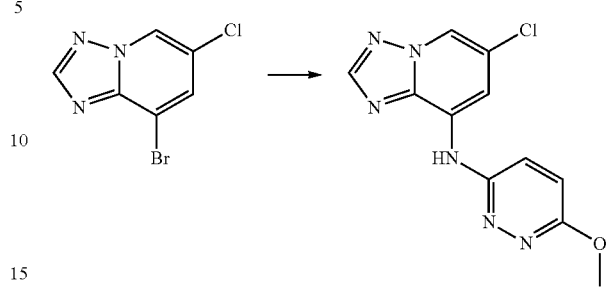

To a microwave tube were added 8-bromo-6-chloro-[1,2,4]triazolo[1,5-a]pyridine (1.00 g, 4.30 mmol, Example #1, Step A), 6-methoxypyridazin-3-amine (0.538 g, 4.30 mmol), Xantphos (0.523 g, 0.903 mmol), Pd(OAc)₂ (0.097 g, 0.43 mmol), cesium carbonate (2.80 g, 8.60 mmol) and 1,4-dioxane (15 mL). The reaction was degassed with vacuum and back filled with nitrogen. The vessel was sealed and heated for about 1.5 h at about 120° C. in a microwave oven. The mixture was cooled, filtered through Celite® and concentrated. The resulting residue was purified via silica gel chromatography eluting with a gradient of 20-70% EtOAc in hexane to give 6-chloro-N-(6-methoxypyridazin-3-yl)-[1,2,4]triazolo[1,5-a]pyridin-8-amine (0.500 g, 42%); ¹H NMR (CDCl₃) δ 8.84 (d, J=1.7 Hz, 1H), 8.30-8.20 (m, 2H), 7.65 (s, 1H), 7.09 (t, J=6.8 Hz, 1H), 7.00 (dd, J=12.4, 6.7 Hz, 1H), 4.12 (d, J=7.1 Hz, 3H).

Step B: tert-butyl 3-(8-(6-methoxypyridazin-3-ylamino)-[1,2,4]triazolo[1,5-a]pyridin-6-yl)-2,5-dihydro-1H-pyrrole-1-carboxylate

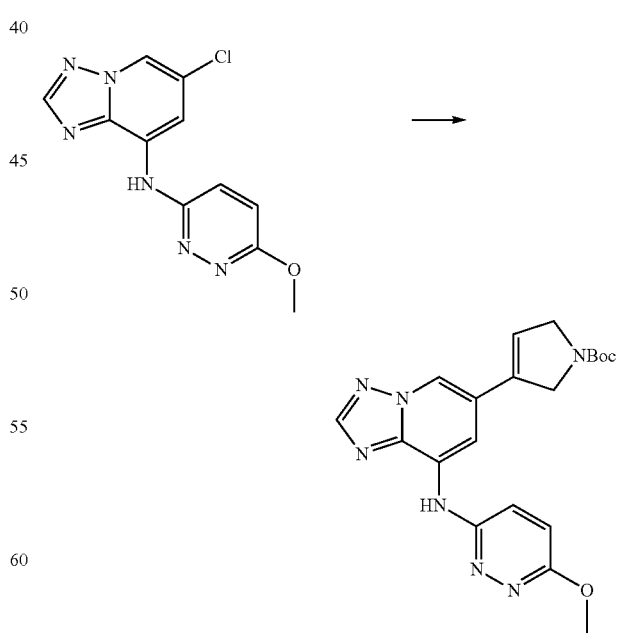

To a mixture of 6-chloro-N-(6-methoxypyridazin-3-yl)-[1,2,4]triazolo[1,5-a]pyridin-8-amine (3.45 g, 12.47 mmol), tert-butyl 3-(4,4,5,5-tetramethyl-1,3,2-dioxaborolan-2-yl)-

2,5-dihydro-1H-pyrrole-1-carboxylate (5.52 g, 18.7 mmol, Combi-Blocks), potassium carbonate (3.45 g, 24.9 mmol) 1,4-dioxane (100 mL), and water (50 mL) were added Pd$_2$(dba)$_3$ (1.14 g, 1.25 mmol) and dicyclohexyl(2',4',6'-triisopropyl-[1,1'-biphenyl]-2-yl)phosphine (0.594 g, 1.25 mmol) under nitrogen. The mixture was heated at about 100° C. under nitrogen for about 16 h. The reaction mixture was partitioned between water and DCM. The organic layer was concentrated and purified via silica gel chromatography eluting with a gradient of 20-80% EtOAc in hexane to give tert-butyl 3-(8-((6-methoxypyridazin-3-yl)amino)-[1,2,4]triazolo[1,5-a]pyridin-6-yl)-2,5-dihydro-1H-pyrrole-1-carboxylate (3.2 g, 62%) as a white solid. LC/MS (Table 1, Method d) R$_t$=1.38 min; MS m/z: 410 (M+H)$^+$.

Step C: tert-butyl 3-(8-(6-methoxypyridazin-3-ylamino)-[1,2,4]triazolo[1,5-a]pyridin-6-yl)pyrrolidine-1-carboxylate Step D: N-(6-methoxypyridazin-3-yl)-6-(pyrrolidin-3-yl)-[1,2,4]triazolo[1,5-a]pyridin-8-amine

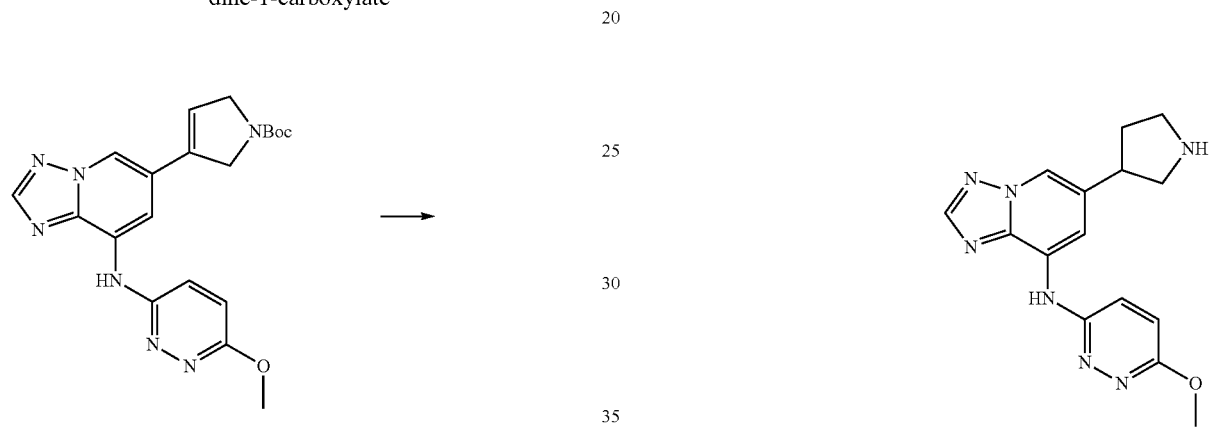

To a solution of tert-butyl 3-(8-(6-methoxypyridazin-3-ylamino)-[1,2,4]triazolo[1,5-a]pyridin-6-yl)-2,5-dihydro-1H-pyrrole-1-carboxylate (0.20 g, 0.49 mmol) in THF (120 mL) was added 10% Pd/C (0.50 g, 0.47 mmol). The mixture was stirred at rt under about 25 psi of H$_2$ for about 24 h. The mixture was filtered and concentrated under reduced pressure to give tert-butyl 3-(8-((6-methoxypyridazin-3-yl)amino)-[1,2,4]triazolo[1,5-a]pyridin-6-yl)pyrrolidine-1-carboxylate (0.18 g, 90%). LC/MS (Table 1, Method d) R$_t$=1.01 min; MS m/z: 412 (M+H)$^+$.

To a solution of tert-butyl 3-(8-(((6-methoxypyridazin-3-yl)amino)-[1,2,4]triazolo[1,5-a]pyridin-6-yl)pyrrolidine-1-carboxylate (0.600 g, 1.46 mmol) in DCM (360 mL) was added TFA (12 mL, 156 mmol). The mixture was stirred at rt for about 6 h. The mixture was concentrated to give N-(6-methoxypyridazin-3-yl)-6-(pyrrolidin-3-yl)-[1,2,4]triazolo[1,5-a]pyridin-8-amine which was used in next step without further purification. (0.50 g, 100% crude); LC/MS (Table 1, Method d) R$_t$=1.46 min; MS m/z: 312 (M+H)$^+$.

Step E: 1-(3-(8-(6-methoxypyridazin-3-ylamino)-[1,2,4]triazolo[1,5-a]pyridin-6-yl)pyrrolidin-1-yl)prop-2-en-1-one trifluoroacetate

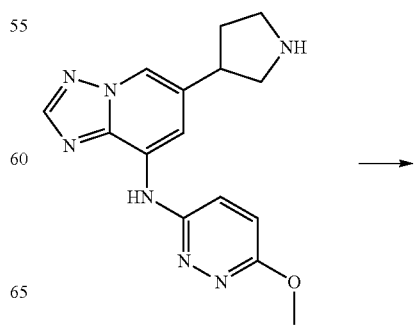

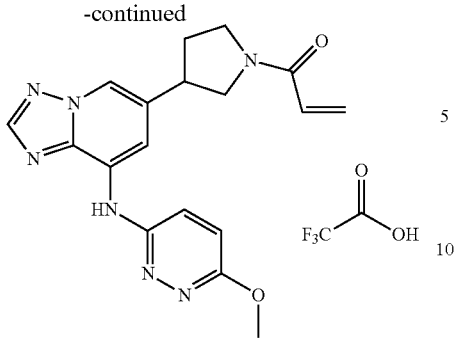

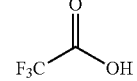

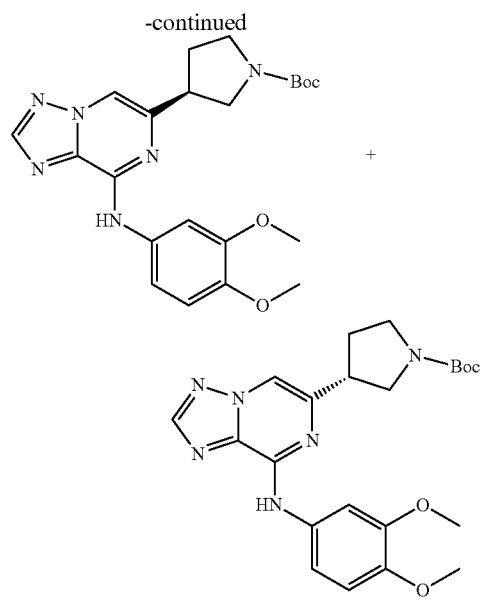

To a solution of N-(6-methoxypyridazin-3-yl)-6-(pyrrolidin-3-yl)-[1,2,4]triazolo[1,5-a]pyridin-8-amine (0.080 g, 0.26 mmol) and TEA (0.143 mL, 1.03 mmol) in DCM (2 mL) was added acryloyl chloride (0.023 g, 0.257 mmol) at about 0° C. The mixture was stirred at rt overnight. Water was added to quench the reaction. The reaction mixture was partitioned between water and DCM. The organic layer was concentrated and purified by prep-HPLC (Table 1, Method z) to give 1-(3-(8-(6-methoxypyridazin-3-ylamino)-[1,2,4]triazolo[1,5-a]pyridin-6-yl)pyrrolidin-1-yl)prop-2-en-1-one trifluoroacetate. (0.049 g, 52%); LC/MS (Table 1, Method d) $R_t$=2.29 min; MS m/z: 366 (M+H)$^+$. BTK enzyme IC$_{50}$=B Example #3. (S)—N-(3,4-dimethoxyphenyl)-6-(1-(vinylsulfonyl)pyrrolidin-3-yl)-[1,2,4]triazolo[1,5-a]pyrazin-8-amine

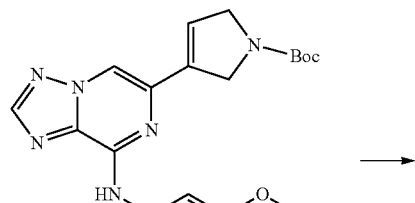

Step A. (S)-tert-butyl 3-(8-((3,4-dimethoxyphenyl)amino)-[1,2,4]triazolo[1,5-a]pyrazin-6-yl)pyrrolidine-1-carboxylate and (R)-tert-butyl 3-(8-((3,4-dimethoxyphenyl)amino)-[1,2,4]triazolo[1,5-a]pyrazin-6-yl)pyrrolidine-1-carboxylate

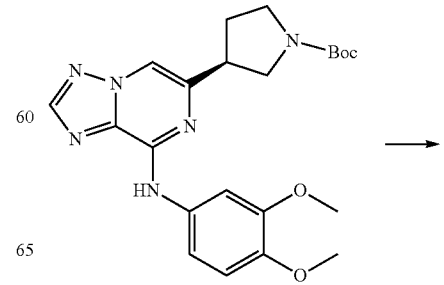

To dry 10% Pd/C (0.50 g, 0.40 mmol) in a 250 mL stainless steel pressure bottle was added tert-butyl 3-(8-((3,4-dimethoxyphenyl)amino)-[1,2,4]triazolo[1,5-a]pyrazin-6-yl)-2,5-dihydro-1H-pyrrole-1-carboxylate (1.00 g, 2.28 mmol, prepared using B with 6,8-dibromo-[1,2,4]triazolo[1,5-a]pyrazine [Ark Pharm], C with tert-butyl 3-(4,4,5,5-tetramethyl-1,3,2-dioxaborolan-2-yl)-2,5-dihydro-1H-pyrrole-1-carboxylate [Combi-Blocks]), MeOH (100 mL) and AcOH (4 mL). The reaction mixture was stirred under 50 psi of H$_2$ at rt. After 3 days, the mixture was filtered through a nylon membrane and concentrated under reduced pressure. The crude material was purified via silica gel chromatography eluting with 0-100% DCM/MeOH/NH$_4$OH (950:45:5) in DCM. The product-containing fractions were combined, concentrated under reduced pressure, dried under vacuum at about 70° C. to give a racemic mixture of products (0.72 g). The compound was separated via chiral prep-SFC (Table 2, Method 2) to give (S)-tert-butyl 3-(8-((3,4-dimethoxyphenyl)amino)-[1,2,4]triazolo[1,5-a]pyrazin-6-yl)pyrrolidine-1-carboxylate (0.26 g, 26%) and (R)-tert-butyl 3-(8-((3,4-dimethoxyphenyl)amino)-[1,2,4]triazolo[1,5-a]pyrazin-6-yl)pyrrolidine-1-carboxylate (0.32 g, 32%) [Stereochemistry is arbitrarily assigned]. LC/MS (Table 1, Method e) $R_t$=1.45 min.; MS m/z: 441 (M+H)$^+$.

Step B. (S)—N-(3,4-dimethoxyphenyl)-6-(pyrrolidin-3-yl)-[1,2,4]triazolo[1,5-a]pyrazin-8-amine

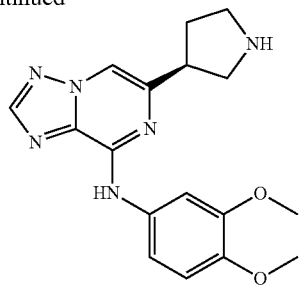

To a solution of (S)-tert-butyl 3-(8-((3,4-dimethoxyphenyl)amino)-[1,2,4]triazolo[1,5-a]pyrazin-6-yl)pyrrolidine-1-carboxylate (0.25 g, 0.568 mmol, stereochemistry assigned arbitrarily) in MeOH (2.0 mL) was added HCl (4M in 1,4-dioxane, 2.0 mL, 8.00 mmol). The reaction mixture was stirred at rt for about 4 h, then concentrated under reduced pressure. The residue was dissolved in DCM/MeOH/NH$_4$OH and concentrated onto silica gel (1 g) for purification via silica gel eluting with 0-100% DCM/MeOH/NH$_4$OH (90:9:1) in DCM with long hold at 100% DCM/MeOH/NH$_4$OH (90:9:1). The product-containing fractions were combined, concentrated, and dried under vacuum at about 70° C. to give (S)—N-(3,4-dimethoxyphenyl)-6-(pyrrolidin-3-yl)-[1,2,4]triazolo[1,5-a]pyrazin-8-amine (0.15 g, 78%) as an off-white solid: LC/MS (Table 1, Method e) R$_t$=1.45 min.; MS m/z: 341 (M+H)$^+$.

Step C. (S)—N-(3,4-dimethoxyphenyl)-6-(1-(vinylsulfonyl)pyrrolidin-3-yl)-[1,2,4]triazolo[1,5-a]pyrazin-8-amine

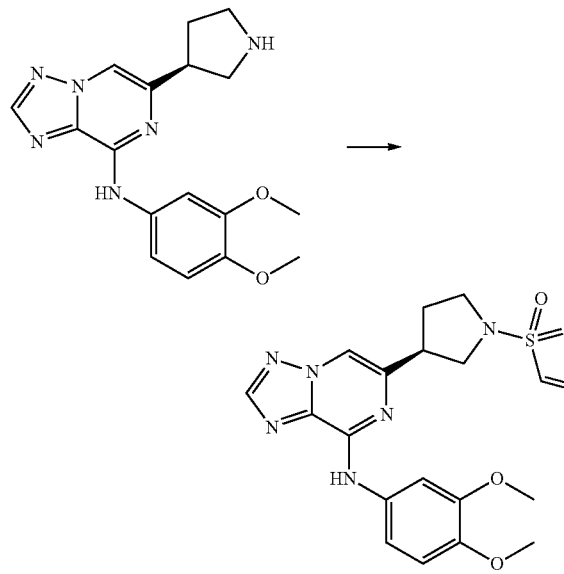

To a solution of (S)—N-(3,4-dimethoxyphenyl)-6-(pyrrolidin-3-yl)-[1,2,4]triazolo[1,5-a]pyrazin-8-amine (0.073 g, 0.21 mmol) and DIEA (0.093 mL, 0.54 mmol) in DMA (1.5 mL) at about 0° C. was added ethenesulfonyl chloride (0.025 mL, 0.22 mmol). After about 20 min, the reaction mixture was added slowly into ice water (~10 mL) while stirring. After the ice melted completely, the resulting solid was collected via vacuum filtration and dried under vacuum at 55° C. to give impure product. The solid was triturated with MeOH (1 mL). The resulting solid was collected via vacuum filtration while washing with additional MeOH (1 mL) and dried under vacuum at 55° C. to give solid with little change in purity by LCMS. The filtrate and solid were recombined, concentrated under reduced pressure and purified via silica gel chromatography eluting with 0-5% MeOH in DCM. The product-containing fraction was concentrated under reduced pressure and dried under vacuum at about 55° C. to give (S)—N-(3,4-dimethoxyphenyl)-6-(1-(vinylsulfonyl)pyrrolidin-3-yl)-[1,2,4]triazolo[1,5-a]pyrazin-8-amine (0.024 g, 26%) as a white solid: LC/MS (Table 1, Method e) R$_t$=2.00 min.; MS m/z: 431 (M+H)$^+$. BTK enzyme IC$_{50}$=A.

Example #4: 1-{(R)-3-[8-(6,7-Dihydro-4H-pyrazolo [5,1-c][1,4]oxazin-2-ylamino)-[1,2,4]triazolo[1,5-a] pyridin-6-yl]-pyrrolidin-1-yl}-propenone

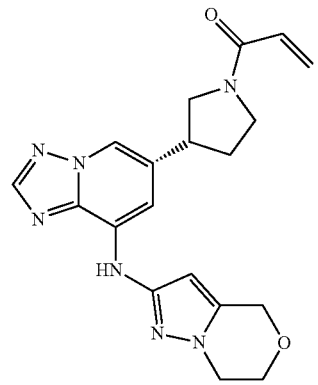

Step A: N-(6-chloro-[1,2,4]triazolo[1,5-a]pyridin-8-yl)-6,7-dihydro-4H-pyrazolo[5,1-c][1,4]oxazin-2-amine

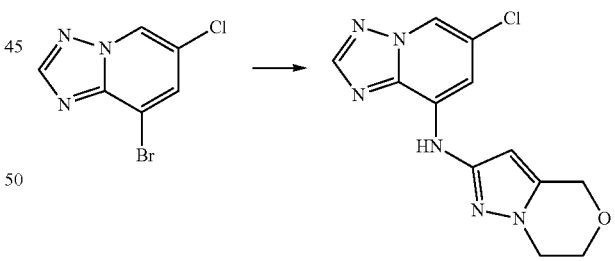

A flask was charged with 1,4-dioxane (129 mL) and degassed with nitrogen for 10 min before the addition of 8-bromo-6-chloro-[1,2,4]triazolo[1,5-a]pyridine (21.5 g, 64.7 mmol, Example #1, Step A), 6,7-dihydro-4H-pyrazolo [5,1-c][1,4]oxazin-2-amine (9.91 g, 71.2 mmol, Preparation #1), (9,9-dimethyl-9H-xanthene-4,5-diyl)bis(diphenylphosphine) (6.74 g, 11.65 mmol), diacetoxypalladium (1.308 g, 5.83 mmol), and cesium carbonate (63.3 g, 194 mmol). The reaction mixture was degassed with nitrogen for about 10 min., and then heated to about 120° C. for about 1 h. The reaction cooled to ambient temperature and 400 mL of water was slowly added and stirred vigorously. The resulting precipitate was filtered and dried in the vacuum oven overnight to afford N-(6-chloro-[1,2,4]triazolo[1,5-a]pyridin-8-yl)-6,7-dihydro-4H-pyrazolo[5,1-c][1,4]oxazin-2-amine (23.8 g, 102%, 85% purity): LC/MS (Table 1, Method 1) R$_t$=1.79 min.; MS m/z: 292, 294 (M+H)$^+$.

Step B: tert-butyl 3-(8-((6,7-dihydro-4H-pyrazolo[5,1-c][1,4]oxazin-2-yl)amino)-[1,2,4]triazolo[1,5-a]pyridin-6-yl)-2,5-dihydro-1H-pyrrole-1-carboxylate

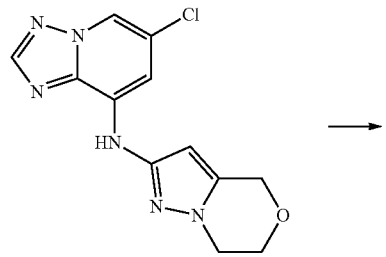

An oven-dried 2 L 3-necked flask was charged with N-(6-chloro-[1,2,4]triazolo[1,5-a]pyridin-8-yl)-6,7-dihydro-4H-pyrazolo[5,1-c][1,4]oxazin-2-amine (23 g, 79 mmol), tert-butyl 3-(4,4,5,5-tetramethyl-1,3-dioxolan-2-yl)-2,5-dihydro-1H-pyrrole-1-carboxylate (40.0 g, 134 mmol, Combi Blocks), 1,4-dioxane (330 mL) and a solution of potassium phosphate (40.3 g, 190 mmol) in water (66.0 mL). The reaction was sparged with argon for 25 min, followed by the addition of Xphos palladacycle G1 (2.92 g, 3.96 mmol). The reaction mixture was sparged with argon for about 30 min then heated to about 60° C. for about 80 min. The reaction cooled to ambient temperature and about 400 mL of water was slowly added to the reaction mixture. The resulting precipitate was collected via filtration and dried in the vacuum oven. The filter cake was taken up in DCM (1 L) and washed with brine (350 mL), dried over anhydrous MgSO$_4$, filtered, and concentrated under reduced pressure. The solid was then triturated with about 200 mL of ditheylether. The resulting precipitate was collected via filtration and dried in the vac oven to afford tert-butyl 3-(8-((6,7-dihydro-4H-pyrazolo[5,1-c][1,4]oxazin-2-yl)amino)-[1,2,4]triazolo[1,5-a]pyridin-6-yl)-2,5-dihydro-1H-pyrrole-1-carboxylate (31.3 g, 93%): LC/MS (Table 1, Method 1) R$_t$=2.10 min.; MS m/z: 424 (M+H)$^+$.

Step C: (R)-tert-butyl 3-(8-((6,7-dihydro-4H-pyrazolo[5,1-c][1,4]oxazin-2-yl)amino)-[1,2,4]triazolo[1,5-a]pyridin-6-yl)pyrrolidine-1-carboxylate and (S)-tert-butyl 3-(8-((6,7-dihydro-4H-pyrazolo[5,1-c][1,4]oxazin-2-yl)amino)-[1,2,4]triazolo[1,5-a]pyridin-6-yl)pyrrolidine-1-carboxylate

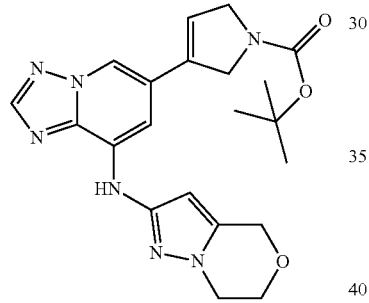

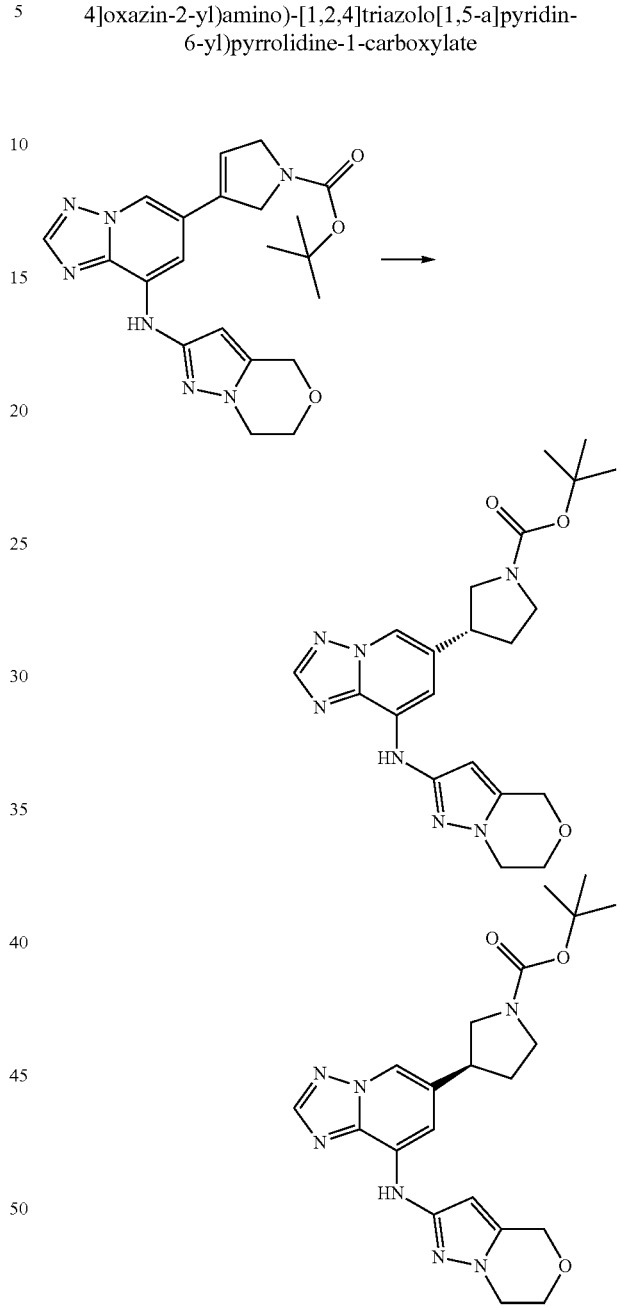

EtOH (0.50 mL) was added to tert-butyl 3-(8-((6,7-dihydro-4H-pyrazolo[5,1-c][1,4]oxazin-2-yl)amino)-[1,2,4]triazolo[1,5-a]pyridin-6-yl)-2,5-dihydro-1H-pyrrole-1-carboxylate (5.24 mg, 0.012 mmol) and 20% wt. palladium hydroxide on carbon (1.06 mg, 7.55 μmol) in a 4 mL pressure bottle. The mixture was stirred under 60 psi of hydrogen at about 50° C. for about 2 h. The catalyst was filtered off through a pad of Celite® and the remaining solvent was concentrated under reduced pressure. The crude reaction mixture was purified by silica gel chromatography eluting with 10-60% EtOAc/DCM to afford tert-butyl 3-(8-((6,7-dihydro-4H-pyrazolo[5,1-c][1,4]oxazin-2-yl)amino)-

[1,2,4]triazolo[1,5-a]pyridin-6-yl)pyrrolidine-1-carboxylate (14.5 g, 47%). The racemic mixture was then purified via chiral preparative HPLC (Table 2, Method 9) to afford (R)-tert-butyl 3-(8-((6,7-dihydro-4H-pyrazolo[1,5-c][1,4]oxazin-2-yl)amino)-[1,2,4]triazolo[1,5-a]pyridin-6-yl)pyrrolidine-1-carboxylate (3.79 g, 12%, OR=+) and (S)-tert-butyl 3-(8-((6,7-dihydro-4H-pyrazolo[5,1-c][1,4]oxazin-2-yl)amino)-[1,2,4]triazolo[1,5-a]pyridin-6-yl)pyrrolidine-1-carboxylate (4.67, 15%, OR=−): LC/MS (Table 1, Method 1) $R_f$=2.03 min.; MS m/z: 426 (M+H)$^+$.

Step D: (R)-1-(3-(8-((6,7-dihydro-4H-pyrazolo[5,1-c][1,4]oxazin-2-yl)amino)-[1,2,4]triazolo[1,5-a]pyridin-6-yl)pyrrolidin-1-yl)prop-2-en-1-one

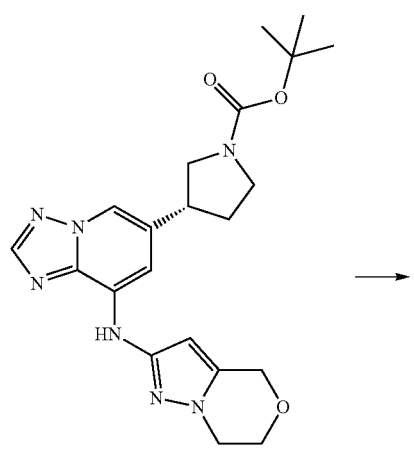

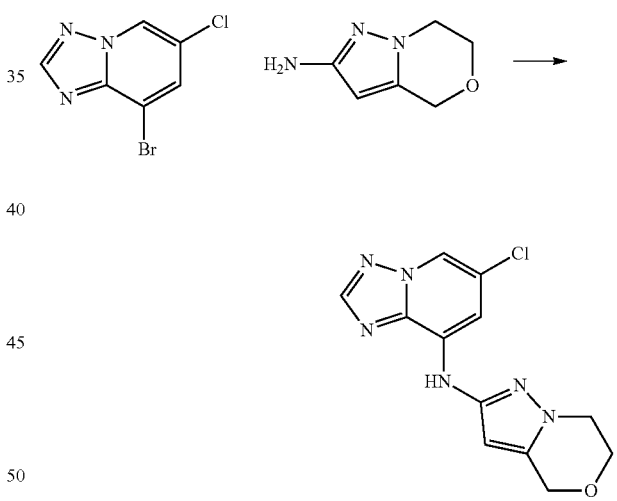

A flask was charged with (R)-tert-butyl 3-(8-((6,7-dihydro-4H-pyrazolo[5,1-c][1,4]oxazin-2-yl)amino)-[1,2,4]triazolo[1,5-a]pyridin-6-yl)pyrrolidine-1-carboxylate (3.7 g, 8.70 mmol) and 1,4-dioxane (43 mL) with hydrogen chloride (4 N in 1,4-dioxane, 21 mL, 87 mmol). The reaction was heated to about 35° C. for about 90 min. The solvent was concentrated under reduced pressure. The remaining residue was taken up in DCM (43 mL) and cooled to about −40° C., followed by the addition of N-ethyl-N-isopropylpropan-2-amine (7.59 mL, 43.5 mmol) and acryloyl chloride (0.918 mL, 11.30 mmol). The reaction stirred at about −40° C. for about 10 min. The solvent was concentrated under reduced pressure. The crude residue was purified by silica gel chromatography eluting with 0-8% MeOH/DCM. The compound was then recrystallized from MeCN using 10:1 volume ratio to afford (R)-1-(3-(8-((6,7-dihydro-4H-pyrazolo[5,1-c][1,4]oxazin-2-yl)amino)-[1,2,4]triazolo[1,5-a]pyridin-6-yl)pyrrolidin-1-yl)prop-2-en-1-one (2.4 g, 72.7% OR=+): LC/MS (Table 1, Method 1) $R_f$=1.41 min.; MS m/z: 380 (M+H)$^+$. BTK enzyme IC$_{50}$=A Example #5. (R)-1-(3-(8-((6,7-dihydro-4H-pyrazolo[5,1-c][1,4]oxazin-2-yl)amino)-[1,2,4]triazolo[1,5-a]pyridin-6-yl)piperidin-1-yl)prop-2-en-1-one

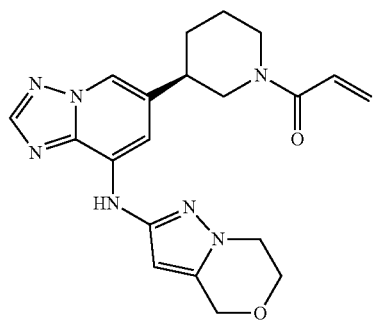

Step A. N-(6-chloro-[1,2,4]triazolo[1,5-a]pyridin-8-yl)-6,7-dihydro-4H-pyrazolo[5,1-c][1,4]oxazin-2-amine

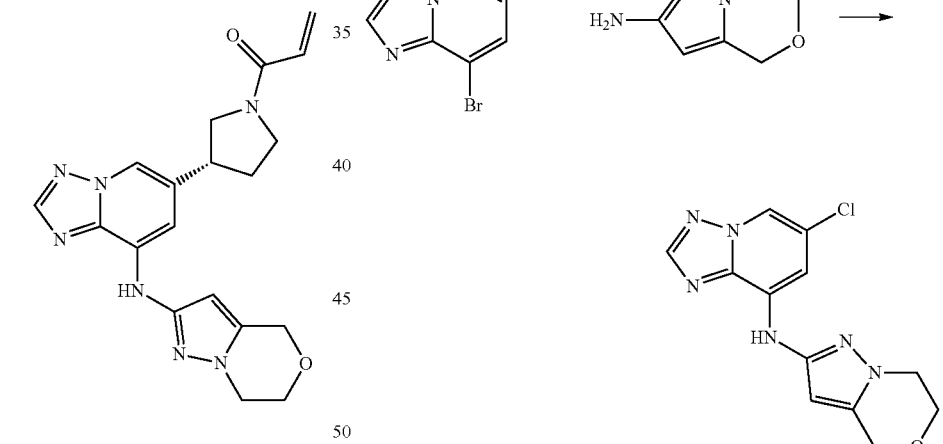

8-Bromo-6-chloro-[1,2,4]triazolo[1,5-a]pyridine (0.500 g, 2.151 mmol, Example #1, Step A), 6,7-dihydro-4H-pyrazolo[5,1-c][1,4]oxazin-2-amine (0.329 g, 2.366 mmol, Preparation #1), Xantphos (0.261 g, 0.452 mmol), Pd(OAc)$_2$ (0.048 g, 0.215 mmol) and Cs$_2$CO$_3$ (1.752 g, 5.38 mmol) in 1,4-dioxane (5 mL) was sparged with nitrogen. The solution was then heated in a microwave at about 120° C. for about 1.5 h. The reaction mixture was cooled to rt, partitioned between DCM (3×20 mL) and water (20 mL). The organic layers were combined, concentrated, purified via silica gel eluting with 20-60% EtOAc in heptanes to give N-(6-chloro-[1,2,4]triazolo[1,5-a]pyridin-8-yl)-6,7-dihydro-4H-pyrazolo[5,1-c][1,4]oxazin-2-amine (0.348 g, 55.7%): LC/MS (Table 1, Method 1) $R_f$=1.82 min.; MS m/z: 291 (M+H)$^+$.

Step B. tert-butyl 3-(8-(((6,7-dihydro-4H-pyrazolo[5,1-c][1,4]oxazin-2-yl)amino)-[1,2,4]triazolo[1,5-a]pyridin-6-yl)-5,6-dihydropyridine-1(2H)-carboxylate

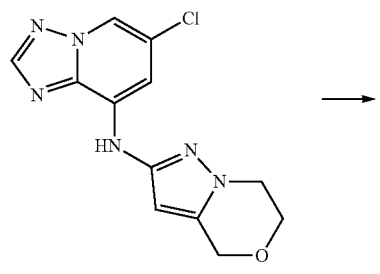

Step C. (S)-tert-butyl 3-(8-(((6,7-dihydro-4H-pyrazolo[5,1-c][1,4]oxazin-2-yl)amino)-[1,2,4]triazolo[1,5-a]pyridin-6-yl)piperidine-1-carboxylate and (R)-tert-butyl 3-(8-(((6,7-dihydro-4H-pyrazolo[5,1-c][1,4]oxazin-2-yl)amino)-[1,2,4]triazolo[1,5-a]pyridin-6-yl)piperidine-1-carboxylate

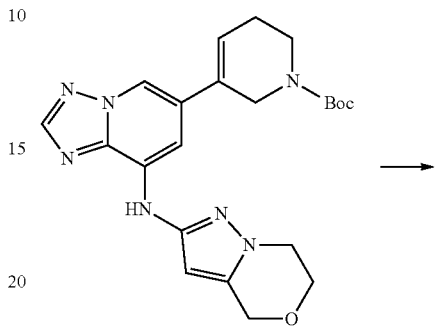

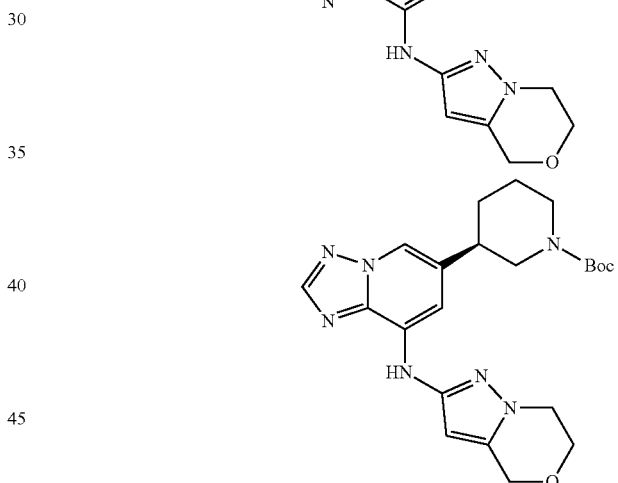

To a 10 mL microwave tube were added N-(6-chloro-[1,2,4]triazolo[1,5-a]pyridin-8-yl)-6,7-dihydro-4H-pyrazolo[5,1-c][1,4]oxazin-2-amine (0.576 g, 1.981 mmol), tert-butyl 3-(4,4,5,5-tetramethyl-1,3,2-dioxaborolan-2-yl)-5,6-dihydropyridine-1(2H)-carboxylate (0.858 g, 2.77 mmol, Anichem), THF (3 mL), MeOH (0.600 mL) and 2 M aqueous sodium carbonate solution (2.97 mL, 5.94 mmol). The mixture was sparged with nitrogen, followed by addition of 1,1'-bis(diphenylphosphino)ferrocene-palladium(II) dichloride dichloromethane complex (0.162 g, 0.198 mmol). The vial was sealed and sparged with nitrogen again. The reaction mixture was heated in microwave at about 130° C. for about 1 h. The reaction mixture was filtered through Celite®, washed with DCM and MeOH, concentrated under reduced pressure. The resulting residue was purified via silica gel chromatography eluting with 0-10% DCM/MeOH to give tert-butyl 3-(8-(((6,7-dihydro-4H-pyrazolo[5-c][1,4]oxazin-2-yl)amino)-[1,2,4]triazolo[1,5-a]pyridin-6-yl)-5,6-dihydropyridine-1(2H)-carboxylate (0.704 g, 65.0%) as a light brown solid: LC/MS (Table 1, Method 1) $R_t$=2.19 min.; MS m/z: 438 (M+H)$^+$.

A solution of tert-butyl 3-(8-(((6,7-dihydro-4H-pyrazolo[5,1-c][1,4]oxazin-2-yl)amino)-[1,2,4]triazolo[1,5-a]pyridin-6-yl)-5,6-dihydropyridine-1(2H)-carboxylate (0.704 g, 1.609 mmol) in THF (15 mL), MeOH (15 mL) and AcOH (10 mL) was passed through H-cube with Pearlman's catalyst Catcart® at about 45° C. under about 50 bar of H$_2$ for about 16 h. LC/MS showed complete conversion. The solvent was concentrated under reduced pressure. The racemic mixture was then separated via chiral prep HPLC (Table 2, Method 7) to give (S)-tert-butyl 3-(8-(((6,7-dihydro-4H-pyrazolo[5,1-c][1,4]oxazin-2-yl)amino)-[1,2,4]triazolo[1,5-a]pyridin-6-yl)piperidine-1-carboxylate (0.050 g, 7.07%) and (R)-tert-butyl 3-(8-(((6,7-dihydro-4H-pyrazolo[5,1-c][1,4]oxazin-2-yl)amino)-[1,2,4]triazolo[1,5-a]pyridin-6-yl)piperidine-1-carboxylate (0.053 g, 7.49%) [Stereochemistry is arbitrarily assigned]. LC/MS (Table 1, Method 1) $R_t$=2.17 min.; MS m/z: 440 (M+H)$^+$.

141

Step D. (R)—N-(6-(piperidin-3-yl)-[1,2,4]triazolo[1,5-a]pyridin-8-yl)-6,7-dihydro-4H-pyrazolo[5,1-c][1,4]oxazin-2-amine

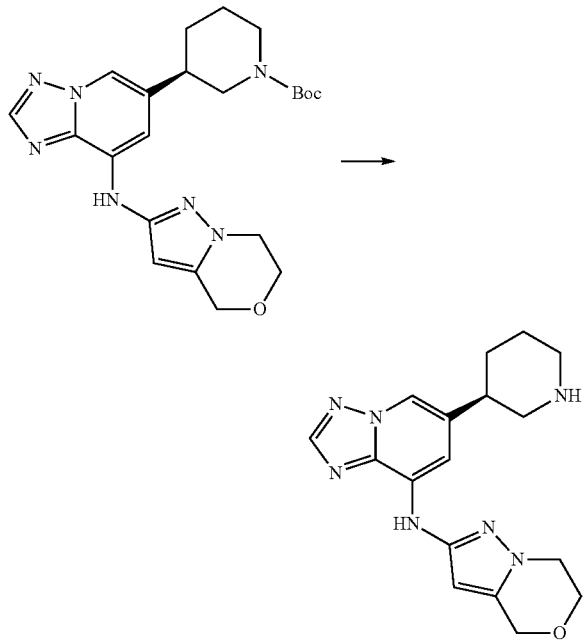

A flask was charged with MeOH (3.0 mL) and cooled to about 0° C. Acetyl chloride (0.364 mL, 5.12 mmol) was added dropwise. The mixture was stirred at rt for about 2 h. The solution was then added to (R)-tert-butyl 3-(8-((6,7-dihydro-4H-pyrazolo[5,1-c][1,4]oxazin-2-yl)amino)-[1,2,4]triazolo[1,5-a]pyridin-6-yl)piperidine-1-carboxylate (0.050 g, 0.114 mmol). The reaction mixture was stirred at rt overnight. The reaction mixture was concentrated to give (R)—N-(6-(piperidin-3-yl)-[1,2,4]triazolo[1,5-a]pyridin-8-yl)-6,7-dihydro-4H-pyrazolo[5,1-c][1,4]oxazin-2-amine as a light yellow solid. LC/MS (Table 1, Method l) $R_t$=1.12 min; MS m/z: 340 (M+H)$^+$. The crude material was used in the next step without further purification.

Step E. (R)-1-(3-(8-((6,7-dihydro-4H-pyrazolo[5,1-c][1,4]oxazin-2-yl)amino)-[1,2,4]triazolo[1,5-a]pyridin-6-yl)piperidin-1-yl)prop-2-en-1-one

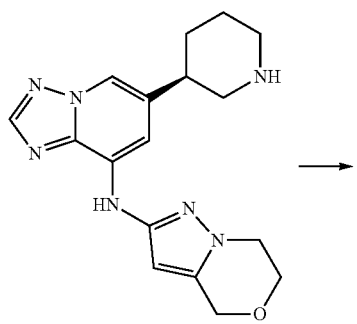

142

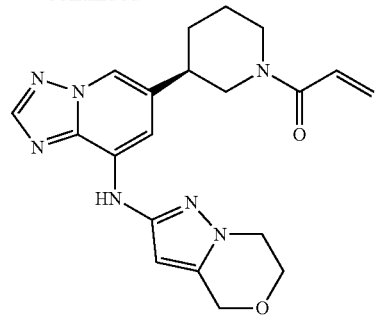 [SMILES: C=CC(=O)N1CCC[C@H](c2cc(Nc3cc4n(n3)CCOC4)c3ncnn3c2)C1]

A flask was charged with (R)—N-(6-(piperidin-3-yl)-[1,2,4]triazolo[1,5-a]pyridin-8-yl)-6,7-dihydro-4H-pyrazolo[5,1-c][1,4]oxazin-2-amine (0.039 g, 0.115 mmol) and TEA (0.072 mL, 0.517 mmol) in THF (1.1 mL). The reaction mixture was cooled to about 0° C. in an ice-bath. Acryloyl chloride (0.01 mL, 0.126 mmol) was added. The mixture was stirred for about 20 min, then was diluted with water (1.0 mL). The reaction mixture was purified by prep-HPLC (Table 1, Method k) to afford (R)-1-(3-(8-((6,7-dihydro-4H-pyrazolo[5,1-c][1,4]oxazin-2-yl)amino)-[1,2,4]triazolo[1,5-a]pyridin-6-yl)piperidin-1-yl)prop-2-en-1-one (0.016 g, 35%, OR=+) as an off-white solid: LC/MS (Table 1, Method h) $R_t$=1.58 min; MS m/z: 394 (M+H)$^+$. BTK enzyme IC$_{50}$=A.

Example #6. (S)-1-(3-(8-((1-methyl-1H-pyrazol-4-yl)amino)-[1,2,4]triazolo[1,5-a]pyrazin-6-yl)pyrrolidin-1-yl)prop-2-en-1-one

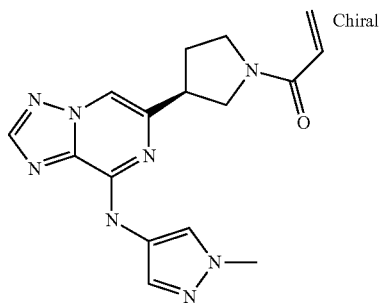 [SMILES: C=CC(=O)N1CC[C@H](c2cn3ncnc3c(Nc3cnn(C)c3)n2)C1]

Step A. 6-bromo-N-(1-methyl-1H-pyrazol-4-yl)-[1,2,4]triazolo[1,5-a]pyrazin-8-amine

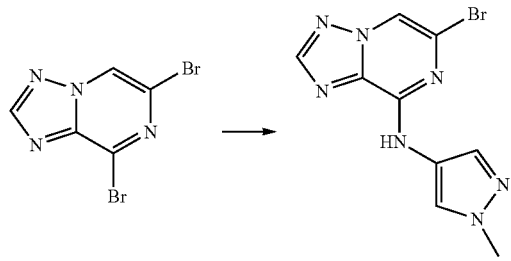 [SMILES: Brc1cn2ncnc2c(Br)n1 ; Cn1cc(Nc2nc(Br)cn3ncnc23)cn1]

To a mixture of NaH (0.864 g, 60%, 36 mmol) in THF (50 mL) was added 1-methyl-1H-pyrazol-4-amine (2.097 g, 21.59 mmol). The mixture was stirred for about 0.5 h at about 0° C. A solution of 6,8-dibromo-[1,2,4]triazolo[1,5-a]pyrazine (5 g, 17.99 mmol, Ark Pharm) in THF (30 mL) was added slowly and the reaction mixture was stirred for 1 h at 0° C. Water (5 mL) was added. The mixture was concentrated to dryness. Additional two reaction mixtures were set up following the above method. All three batches were combined, water (100 mL) was added. The mixture was extracted with EtOAc (3×500 mL). The organic phase was dried over $Na_2SO_4$, concentrated under reduced pressure, purified via silica gel chromatography eluting with 25-50% EtOAc/PE to give 6-bromo-N-(1-methyl-1H-pyrazol-4-yl)-[1,2,4]triazolo[1,5-a]pyrazin-8-amine (12 g, 76%) as a white solid: $^1$H NMR (400 MHz, DMSO-D6) δ ppm δ 10.71 (s, 1H), 8.59-8.56 (d, J=12, 2H), 8.07 (s, 1H), 7.76 (s, 1H), 3.86 (s, 3H).

Step B. tert-butyl 3-(8-(1-methyl-1H-pyrazol-4-ylamino)-[1,2,4]triazolo[1,5-a]pyrazin-6-yl)-2,5-dihydro-1H-pyrrole-1-carboxylate

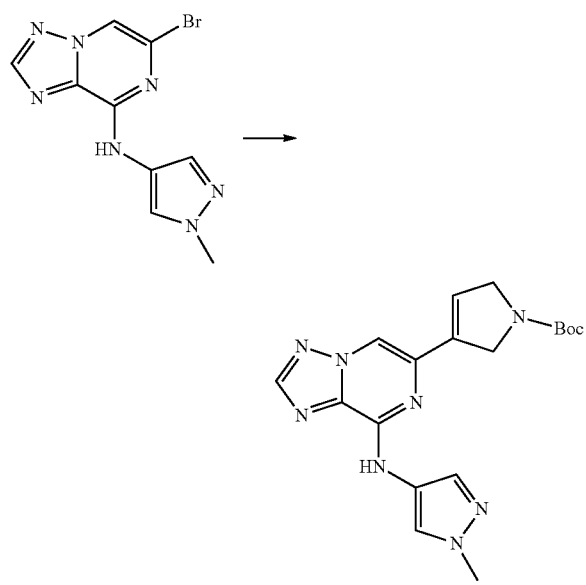 [SMILES: Cn1cc(Nc2nc(Br)cn3ncnc23)cn1 ; Cn1cc(Nc2nc(C3=CCN(C(=O)OC(C)(C)C)C3)cn3ncnc23)cn1]

To a solution of 6-bromo-N-(1-methyl-1H-pyrazol-4-yl)-[1,2,4]triazolo[1,5-a]pyrazin-8-amine (5 g, 17 mmol) in 1,4-dioxane (90 mL) and water (30 mL) was added tert-butyl 3-(4,4,5,5-tetramethyl-1,3,2-dioxaborolan-2-yl)-2,5-dihydro-1H-pyrrole-1-carboxylate (10.04 g, 34 mmol, Combi-Blocks), $Cs_2CO_3$ (16.62 g, 51 mmol) and $Pd(PPh_3)_2Cl_2$ (0.747 g, 1.7 mmol). The mixture was stirred for about 12 h at about 120° C. under $N_2$ protection. The reaction mixture was concentrated under reduced pressure. The residue was purified via silica gel chromatography eluting with 25-50% EtOAc in PE to give tert-butyl 3-(8-(1-methyl-1H-pyrazol-4-ylamino)-[1,2,4]triazolo[1,5-a]pyrazin-6-yl)-2,5-dihydro-1H-pyrrole-1-carboxylate (4.5 g, 69%) as a white solid: $^1$H NMR (400 MHz, DMSO-D6) δ ppm 10.31-10.30 (d, J=4, 1H), 8.55 (s, 1H), 8.37-8.30 (d, J=28, 1H), 8.13-8.10 (d, J=12, 1H), 7.79-7.75 (d, J=16, 1H), 6.67-6.64 (d, J=12, 1H), 4.46-4.43 (d, J=12, 2H), 4.25 (s, 2H), 3.30 (s, 3H), 1.46-1.44 (d, J=8, 9H).

Step C. tert-butyl 3-(8-(1-methyl-1H-pyrazol-4-ylamino)-[1,2,4]triazolo[1,5-a]pyrazin-6-yl)pyrrolidine-1-carboxylate

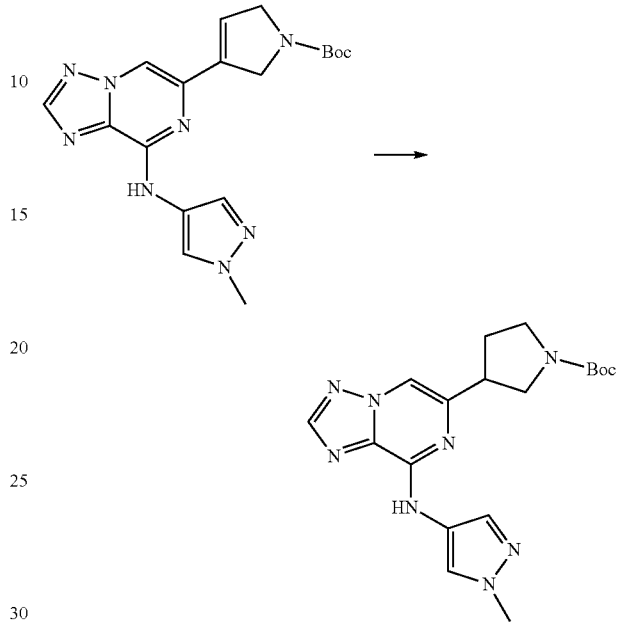

To a solution of tert-butyl 3-(8-(1-methyl-1H-pyrazol-4-ylamino)-[1,2,4]triazolo[1,5-a]pyrazin-6-yl)-2,5-dihydro-1H-pyrrole-1-carboxylate (4.5 g, 11.77 mmol) in THF (500 mL) was added Pd/C (4.5 g, 10%, 4.23 mmol) under protection of argon. The reaction mixture was stirred for about 12 h at room temperature under $H_2$ (about 14 psi). The reaction mixture was filtered through a pad of Celite®, and the filtrate was concentrated under reduced pressure to give tert-butyl 3-(8-(1-methyl-1H-pyrazol-4-ylamino)-[1,2,4]triazolo[1,5-a]pyrazin-6-yl)pyrrolidine-1-carboxylate (4.16 g, 92%) as a white solid: LC/MS (Table 1, Method d) $R_t$=2.94 min; MS m/z: 385 (M+H)$^+$.

Step D. (S)-tert-butyl 3-(8-((1-methyl-1H-pyrazol-4-yl)amino)-[1,2,4]triazolo[1,5-a]pyrazin-6-yl)pyrrolidine-1-carboxylate and (R)-tert-butyl 3-(8-((1-methyl-1H-pyrazol-4-yl)amino)-[1,2,4]triazolo[1,5-a]pyrazin-6-yl)pyrrolidine-1-carboxylate

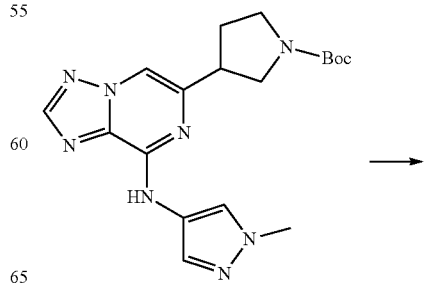

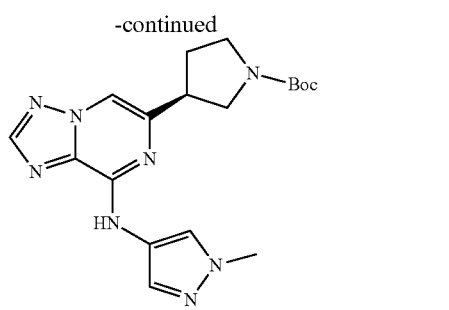

tert-Butyl 3-(8-(1-methyl-1H-pyrazol-4-ylamino)-[1,2,4]triazolo[1,5-a]pyrazin-6-yl)pyrrolidine-1-carboxylate was separated via chiral prep HPLC (Table 2, Method 6) to give (S)-tert-butyl 3-(8-((1-methyl-1H-pyrazol-4-yl)amino)-[1,2,4]triazolo[1,5-a]pyrazin-6-yl)pyrrolidine-1-carboxylate (0.435 g, 40.2%, OR=+) and (R)-tert-butyl 3-(8-((1-methyl-1H-pyrazol-4-yl)amino)-[1,2,4]triazolo[1,5-a]pyrazin-6-yl)pyrrolidine-1-carboxylate (0.442 g, 40.9%, OR=−) both as white solids. [Stereochemistry is arbitrarily assigned]. LC/MS (Table 1, Method 1) $R_t$=1.96 min.; MS m/z: 385 (M+H)$^+$.

Step E. (S)—N-(1-methyl-1H-pyrazol-4-yl)-6-(pyrrolidin-3-yl)-[1,2,4]triazolo[1,5-a]pyrazin-8-amine

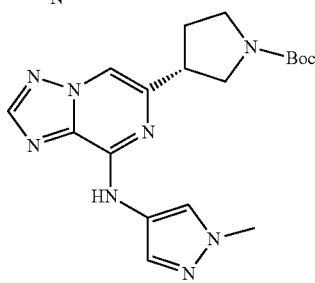

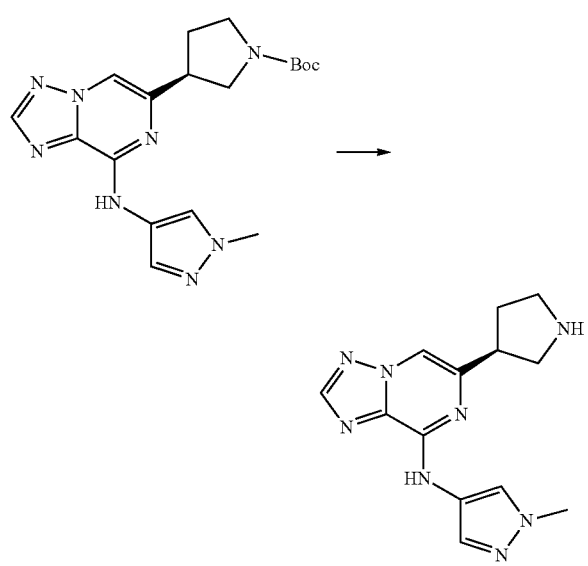

A flask was charged with MeOH (30 mL) and cooled to about 0° C. Acetyl chloride (3.60 mL, 50.9 mmol) was added dropwise. The mixture was stirred at rt for about 2 h. The solution was then added to (S)-tert-butyl 3-(8-((1-methyl-1H-pyrazol-4-yl)amino)-[1,2,4]triazolo[1,5-a]pyrazin-6-yl)pyrrolidine-1-carboxylate (0.435 g, 1.132 mmol). The reaction mixture was stirred at rt for about 3 h. Solvent was removed to give (S)—N-(1-methyl-1H-pyrazol-4-yl)-6-(pyrrolidin-3-yl)-[1,2,4]triazolo[1,5-a]pyrazin-8-amine as an off-white solid. LC/MS (Table 1, Method 1) $R_t$=0.99 min; MS m/z: 285 (M+H)$^+$. The crude material was used in the next without further purification.

Step F. (S)-1-(3-(8-((1-methyl-1H-pyrazol-4-yl)amino)-[1,2,4]triazolo[1,5-a]pyrazin-6-yl)pyrrolidin-1-yl)prop-2-en-1-one

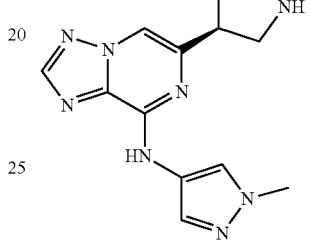

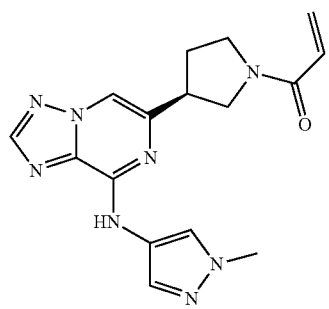

To a solution of (S)—N-(1-methyl-1H-pyrazol-4-yl)-6-(pyrrolidin-3-yl)-[1,2,4]triazolo[1,5-a]pyrazin-8-amine (0.200 g, 0.703 mmol), TEA (0.49 mL, 3.52 mmol) in DMF (3.5 mL) was added acryloyl chloride (0.057 mL, 0.703 mmol). The reaction mixture was stirred at rt for about 30 min. Water (1.5 mL) was added to quench the reaction. The mixture was purification by prep-HPLC (Table 1, Method k) to give (S)-1-(3-(8-((1-methyl-1H-pyrazol-4-yl)amino)-[1,2,4]triazolo[1,5-a]pyrazin-6-yl)pyrrolidin-1-yl)prop-2-en-1-one (0.075 g, 31%, OR=+) as a white solid: LC/MS (Table 1, Method h) $R_t$=1.42 min; MS m/z: 339 (M+H)$^+$. BTK enzyme IC$_{50}$=A.

Example #7: N-((1R,3S)-3-(8-((1-methyl-1H-pyrazol-3-yl)amino)-[1,2,4]triazolo[1,5-a]pyridin-6-yl)cyclopentyl)acrylamide

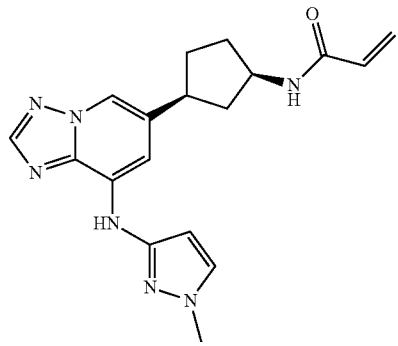 [SMILES: C=CC(=O)N[C@@H]1CC[C@H](c2cc(Nc3ccn(C)n3)c3ncnn3c2)C1]

Step A: 6-Chloro-N-(1-methyl-1H-pyrazol-3-yl)-[1,2,4]triazolo[1,5-a]pyridin-8-amine

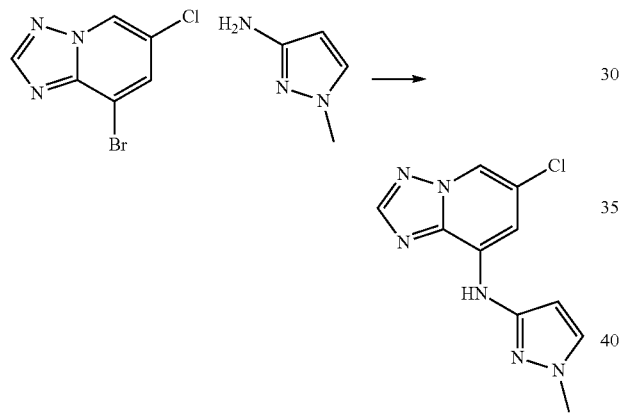

Cesium carbonate (42.0 g, 129 mmol) was added to 1,4-dioxane (238 mL) to give a white suspension. The mixture was degassed with nitrogen, then 8-bromo-6-chloro-[1,2,4]triazolo[1,5-a]pyridine (10 g, 43.0 mmol) (Example #1 Step A), (9,9-dimethyl-9H-xanthene-4,5-diyl)bis(diphenylphosphine) (4.98 g, 8.60 mmol) and 1-methyl-1H-pyrazol-3-amine (3.66 mL, 43.0 mmol) (Combi-Blocks) were each added sequentially rapidly to the mixture. The mixture was degassed with nitrogen, diacetoxypalladium (0.966 g, 4.30 mmol) was added. The mixture was further degassed with nitrogen and heated at about 120° C. for about 1 h. The mixture was allowed to cool to room temperature and EtOAc (250 mL) was added. The mixture was stirred and filtered through Celite®, washed with EtOAc (5×50 mL), and concentrated to give black syrup, which was partitioned between DCM (250 mL) and water (100 mL). The organic layer was drained, the aqueous layer was extracted by DCM (100 mL), the combined DCM layers were dried over sodium sulfate, filtered and concentrated to afford black syrup, which was deposited on silica gel (75 g), purified by silica gel chromatography eluting with a gradient of 20-55% EtOAc/heptane to afford 6-chloro-N-(1-methyl-1H-pyrazol-3-yl)-[1,2,4]triazolo[1,5-a]pyridin-8-amine (6.9 g, 64.5%): LC/MS (Table 1, Method a) $R_t$=1.81 min; MS m/z 249 (M+H)$^+$.

Step B: tert-butyl (6-chloro-[1,2,4]triazolo[1,5-a]pyridin-8-yl)(1-methyl-1H-pyrazol-3-yl)carbamate

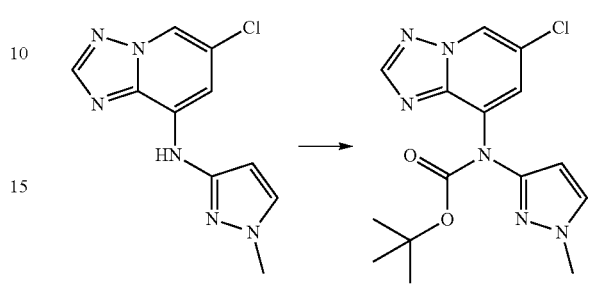

6-Chloro-N-(1-methyl-1H-pyrazol-3-yl)-[1,2,4]triazolo[1,5-a]pyridin-8-amine (5 g, 20.11 mmol) and di-tert-butyl dicarbonate (8.78 g, 40.2 mmol) in DCM (101 mL) were combined give a pale yellow solution. N,N-Dimethylpyridin-4-amine (0.123 g, 1.005 mmol) was added and the reaction mixture was stirred at rt for about 18 h. The mixture was concentrated to give a yellow solid which was mixed with EtOAc (200 mL) and 2-MeTHF (50 mL), washed with citric acid (10% in water, 2×75 mL), saturated aqueous sodium bicarbonate (4×60 mL) and brine (60 mL). To the organic layer was added DCM (100 mL), and the solution was dried over magnesium sulfate (13.7 g), filtered and concentrated to afford tert-butyl (6-chloro-[1,2,4]triazolo[1,5-a]pyridin-8-yl)(1-methyl-1H-pyrazol-3-yl)carbamate (7.11 g, 100%): LC/MS (Table 1, Method a) $R_t$=1.94 min; MS m/z 349 (M+H)$^+$.

Step C: tert-butyl (1-methyl-1H-pyrazol-3-yl)(6-(4,4,5,5-tetramethyl-1,3,2-dioxaborolan-2-yl)-[1,2,4]triazolo[1,5-a]pyridin-8-yl)carbamate

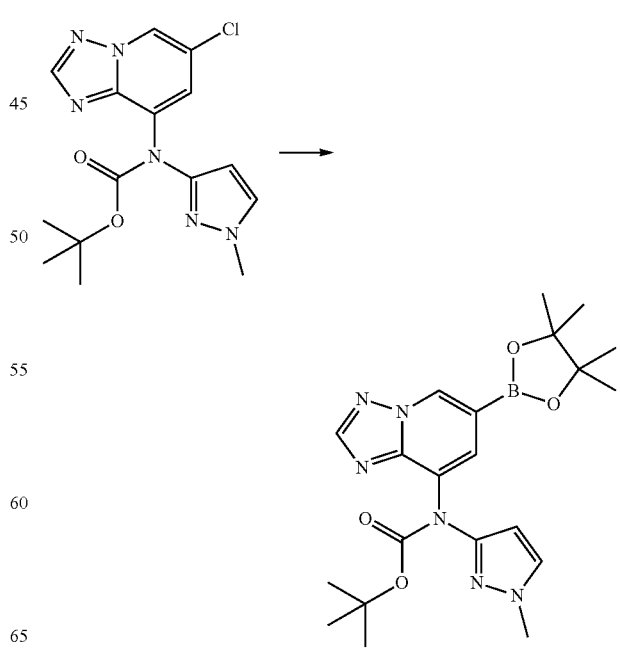

Potassium acetate (5.99 g, 61.1 mmol) and tert-butyl (6-chloro-[1,2,4]triazolo[1,5-a]pyridin-8-yl)(1-methyl-1H-pyrazol-3-yl)carbamate (7.1 g, 20.36 mmol) was added in 1,4-dioxane (70.9 mL) to give an orange suspension. The mixture was degassed with nitrogen then bis(pinacolato) diboron (12.92 g, 50.9 mmol) and XPhos (0.776 g, 1.628 mmol) were added sequentially rapidly to the mixture. The mixture was degassed with nitrogen, Pd$_2$(dba)$_3$ (0.373 g, 0.407 mmol) was added, the mixture was degassed with nitrogen, then it was heated at about 110° C. for about 18 h. The reaction mixture was allowed to cool to rt and DCM (30 mL) was added and stirred, the mixture was diluted with EtOAc (100 mL), filtered through Celite®, and washed by EtOAc (5×30 mL), and concentrated to afford a red solid. The solid was dissolved in DCM (120 mL) and heptane (120 mL), the red solution was concentrated under reduced pressure to remove most DCM and some heptane. The resulting suspension was filtered, washed with heptane (3×10 mL), dried in a vacuum oven to afford tert-butyl (1-methyl-1H-pyrazol-3-yl)(6-(4,4,5,5-tetramethyl-1,3,2-dioxaborolan-2-yl)-[1,2,4]triazolo[1,5-a]pyridin-8-yl)carbamate (8.765 g, 98%): LC/MS (Table 1, Method a) R$_f$=1.42 min; MS m/z 441 (M+H)$^+$.

Step D: tert-butyl (1-methyl-1H-pyrazol-3-yl)(6-(3-oxocyclopent-1-en-1-yl)-[1,2,4]triazolo[1,5-a]pyridin-8-yl)carbamate

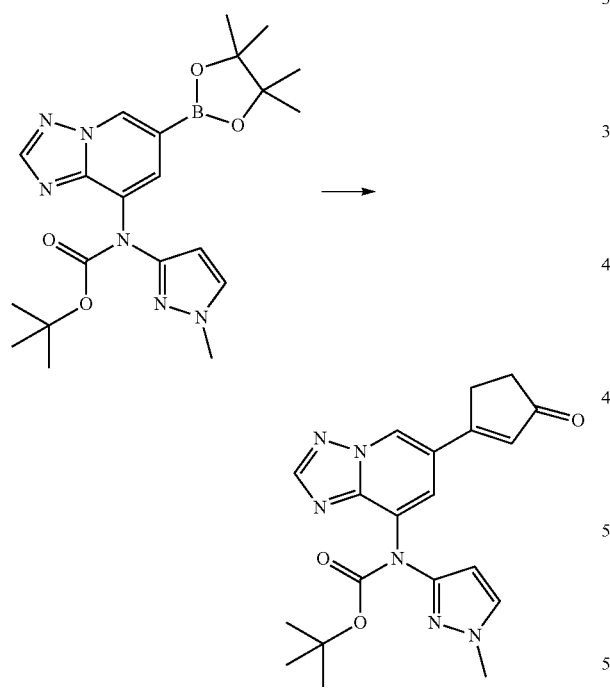

tert-Butyl (1-methyl-1H-pyrazol-3-yl)(6-(4,4,5,5-tetramethyl-1,3,2-dioxaborolan-2-yl)-[1,2,4]triazolo[1,5-a]pyridin-8-yl)carbamate (3.8 g, 8.63 mmol) was added to 1,4-dioxane (28.8 mL) to give cloudy yellow solution. Potassium phosphate (5.50 g, 25.9 mmol) in water (9.59 mL) was added to the solution. The reaction mixture was degassed with nitrogen, XPhos palladacycle (0.319 g, 0.432 mmol) was added and degassed with nitrogen; then a solution of 3-bromocyclopent-2-enone (2.62 mL, 23.91 mmol) (SynTech) in 1,4-dioxane (3×6 mL) were added rapidly. The mixture was degassed with nitrogen, then heated at about 60° C. for about 18 h. The reaction mixture was cooled to room temperature and diluted with DCM (100 mL), filtered through Celite®, washed with DCM (5×30 mL), concentrated to give a brown syrup, which was deposited on silica gel (20 g), purified by silica gel chromatography eluting with a gradient of 2 to 5% MeOH/DCM to afford tert-butyl (1-methyl-1H-pyrazol-3-yl)(6-(3-oxocyclopent-1-en-1-yl)-[1,2,4]triazolo[1,5-a]pyridin-8-yl)carbamate (2.54 g, 73%): LC/MS (Table 1, Method a) R$_f$=1.63 min; MS m/z 395 (M+H)$^+$.

Step E: (S)-tert-butyl (1-methyl-1H-pyrazol-3-yl)(6-(3-oxocyclopentyl)-[1,2,4]triazolo[1,5-a]pyridin-8-yl)carbamate

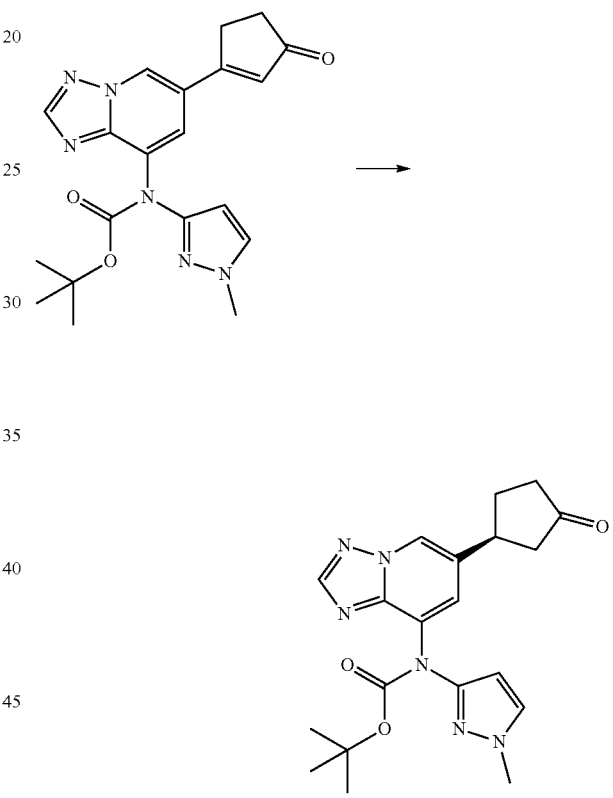

(2R,5R)-5-Benzyl-3-methyl-2-(5-methylfuran-2-yl)imidazolidin-4-one (0.014 g, 0.051 mmol) and tert-butyl (1-methyl-1H-pyrazol-3-yl)(6-(3-oxocyclopent-1-en-1-yl)-[1,2,4]triazolo[1,5-a]pyridin-8-yl)carbamate (0.1 g, 0.254 mmol) were added to THF (0.507 mL) to give a yellow suspension. The mixture was cooled to about 0° C. in an ice bath. Diethyl 2,6-dimethyl-1,4-dihydropyridine-3,5-dicarboxylate (0.077 g, 0.304 mmol) and trichloroacetic acid (5.11 µL, 0.051 mmol) were added. The mixture was stirred for about 44 h, the cooling bath was warmed up by ambient air. Then the crude was purified by silica gel chromatography eluting with a gradient of 0 to 5% MeOH/DCM to afford (S)-tert-butyl (1-methyl-1H-pyrazol-3-yl)(6-(3-oxocyclopentyl)-[1,2,4]triazolo[1,5-a]pyridin-8-yl)carbamate (0.088 g, 88%, OR=negative) [Stereochemistry is arbitrarily assigned]: LC/MS (Table 1, Method a) R$_f$=1.65 min; MS m/z 397 (M+H)$^+$.

Step F: tert-butyl (6-((1S,3R)-3-((R)-1,1-dimethylethylsulfinamido)cyclopentyl)-[1,2,4]triazolo[1,5-a]pyridin-8-yl)(1-methyl-1H-pyrazol-3-yl)carbamate

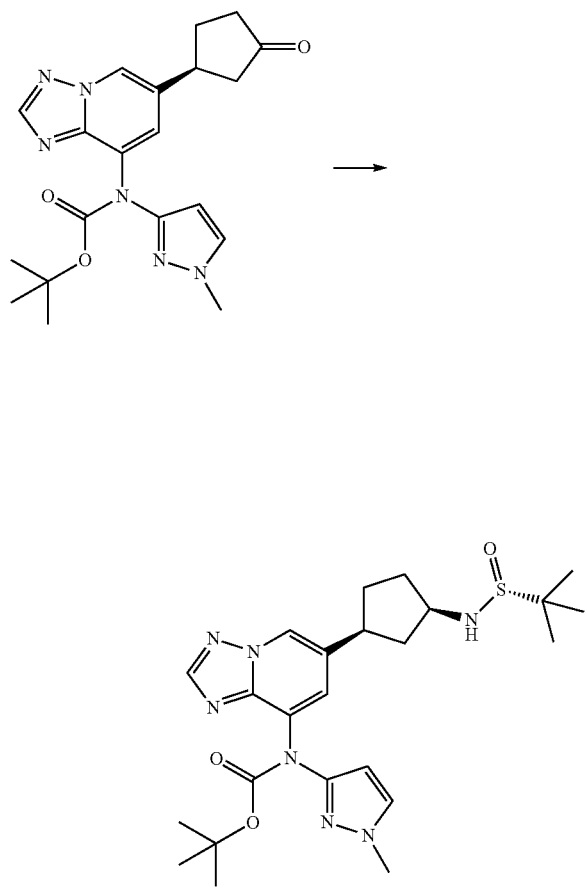

(S)-tert-butyl (1-methyl-1H-pyrazol-3-yl)(6-(3-oxocyclopentyl)-[1,2,4]triazolo[1,5-a]pyridin-8-yl)carbamate (14 g, 35.3 mmol) and (R)-2-methylpropane-2-sulfinamide (6.42 g, 53.0 mmol) were added in THF (72.7 mL) to give an orange solution. The mixture was degassed with nitrogen, then tetraethoxytitanium (24.17 g, 106 mmol) was added, the solution was heated at about 50° C. for about 18 h. The reaction mixture was cooled to rt, then the solution was cooled to about −50° C. in a dry ice/MeCN bath, sodium borohydride (1.924 g, 50.9 mmol) was added in one portion; the reaction mixture was stirred and the cooling bath was warmed up gradually over 4 h period. The resulting red solution was added dropwise into stirring aqueous sodium chloride solution (24%, 400 mL). THF (100 mL) and 2-MeTHF (200 mL) were added and the solution was stirred for about 1 h, The top organic layer was decanted by suction, the aqueous suspension was added 2-MeTHF (200 mL) and stirred for about 30 min, then it was filtered through Celite®, washed by 2-MeTHF (4×50 mL), the filtrate was partitioned, the organic layers were combined, washed by saturated aqueous sodium bicarbonate (2×100 mL) and brine (100 mL), dried over magnesium sulfate, filtered and concentrated to afford 20 g yellow solid, which was purified by silica gel chromatography eluting with a gradient of 0 to 6.5% MeOH/DCM to afford 14.6 g yellow solid. The mixture was separated via chiral prep (Table 2, Method 8) to give tert-butyl (6-((1S,3R)-3-((R)-1,1-dimethylethylsulfinamido)cyclopentyl)-[1,2,4]triazolo[1,5-a]pyridin-8-yl)(1-methyl-1H-pyrazol-3-yl)carbamate (7.0 g, 39.5%, OR=negative) [Stereochemistry is arbitrarily assigned]: LC/MS (Table 1, Method a) $R_t$=1.90 min; MS m/z 502 (M+H)$^+$.

Step G: 6-((1S,3R)-3-aminocyclopentyl)-N-(1-methyl-1H-pyrazol-3-yl)-[1,2,4]triazolo[1,5-a]pyridin-8-amine hydrochloride

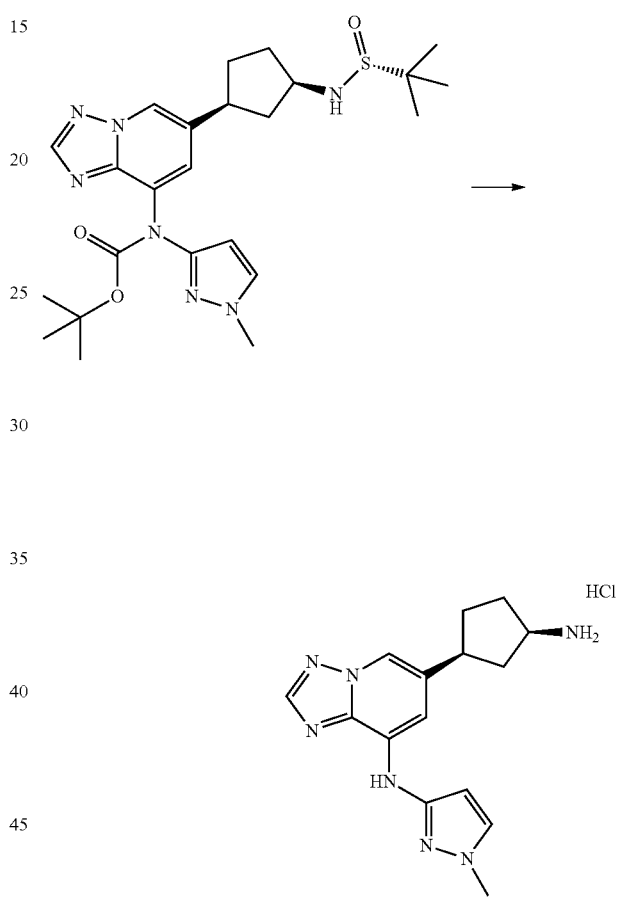

tert-Butyl (6-((1S,3R)-3-((R)-1,1-dimethylethylsulfinamido)cyclopentyl)-[1,2,4]triazolo[1,5-a]pyridin-8-yl)(1-methyl-1H-pyrazol-3-yl)carbamate (5.5 g, 10.96 mmol) was added in MeOH (22.02 mL) to give a pale yellow solution. The solution was cooled to about 0° C. in an ice bath. Hydrochloric acid (3.0 M in cyclopentyl methyl ether) (43.9 mL, 132 mmol) was added dropwise via addition funnel. The ice bath was removed after stirring for about 1 h, then the mixture was stirred at rt for about 18 h. Ether (100 mL) was added and the solution was stirred for 1 h. To the suspension was added ether (50 mL) and the mixture was filtered. The collected solid was rinsed with ether (5×20 mL), dried over 1 h to afford 6-((1S,3R)-3-aminocyclopentyl)-N-(1-methyl-H pyrazol-3-yl)-[1,2,4]triazolo[1,5-a]pyridin-8-amine hydrochloride: LC/MS (Table 1, Method a) $R_t$=1.04 min; MS m/z 298 (M+H)$^+$. It was used as is in next step.

153

Step H: N-((1R,3S)-3-(8-((1-methyl-1H-pyrazol-3-yl)amino)-[1,2,4]triazolo[1,5-a]pyridin-6-yl)cyclopentyl)acrylamide

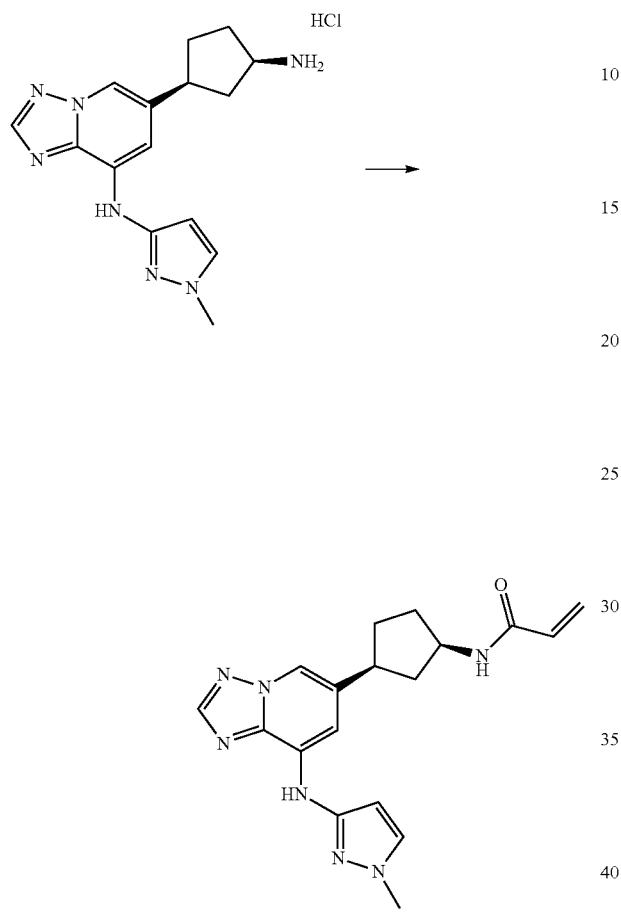

6-((1S,3R)-3-Aminocyclopentyl)-N-(1-methyl-1H-pyrazol-3-yl)-[1,2,4]triazolo[1,5-a]pyridin-8-amine hydrochloride (3.66 g, 10.96 mmol) was added in 2-MeTHF (60 mL) to give a white suspension. The mixture was cooled to about 0° C. in an ice bath. A solution of potassium hydrogenphosphate (22.91 g, 132 mmol) in water (70 mL) was added dropwise via dropping funnel and the mixture was stirred for about 10 min. A solution of acryloyl chloride (0.890 mL, 10.96 mmol) in 2-MeTHF (10 mL) was added dropwise via syringe over about 15 min, the reaction mixture was stirred at about 0° C. for about 30 min. The mixture was partitioned, the aqueous layer was drained, the organic layer was washed by saturated aqueous sodium bicarbonate (2×50 mL), brine (50 mL), dried over sodium sulfate, filtered and concentrated to afford 3.63 g pale yellow solid. MeCN (40 mL) was added and the suspension was stirred for about 1 h, then it was filtered, the collected solid was rinsed by ice-cold MeCN (4×10 mL), pentane (7×20 mL) to afford N-((1R,3S)-3-(8-((1-methyl-1H-pyrazol-3-yl)amino)-[1,2,4]triazolo[1,5-a]pyridin-6-yl)cyclopentyl)acrylamide (2.5 g, 64.9% OR=positive) [Stereochemistry is arbitrarily assigned]: LC/MS (Table 1, Method a) $R_t$=1.48 min; MS m/z 352 (M+H)$^+$. BTK enzyme IC$_{50}$=A

154

Example #8: N-((1R,3S)-3-(8-((6,7-dihydro-4H-pyrazolo[5,1-c][1,4]oxazin-2-yl)amino)-[1,2,4]triazolo[1,5-a]pyridin-6-yl)cyclopentyl)acrylamide and N-((1S,3R)-3-(8-((6,7-dihydro-4H-pyrazolo[5,1-c][1,4]oxazin-2-yl)amino)-[1,2,4]triazolo[1,5-a]pyridin-6-yl)cyclopentyl)acrylamide

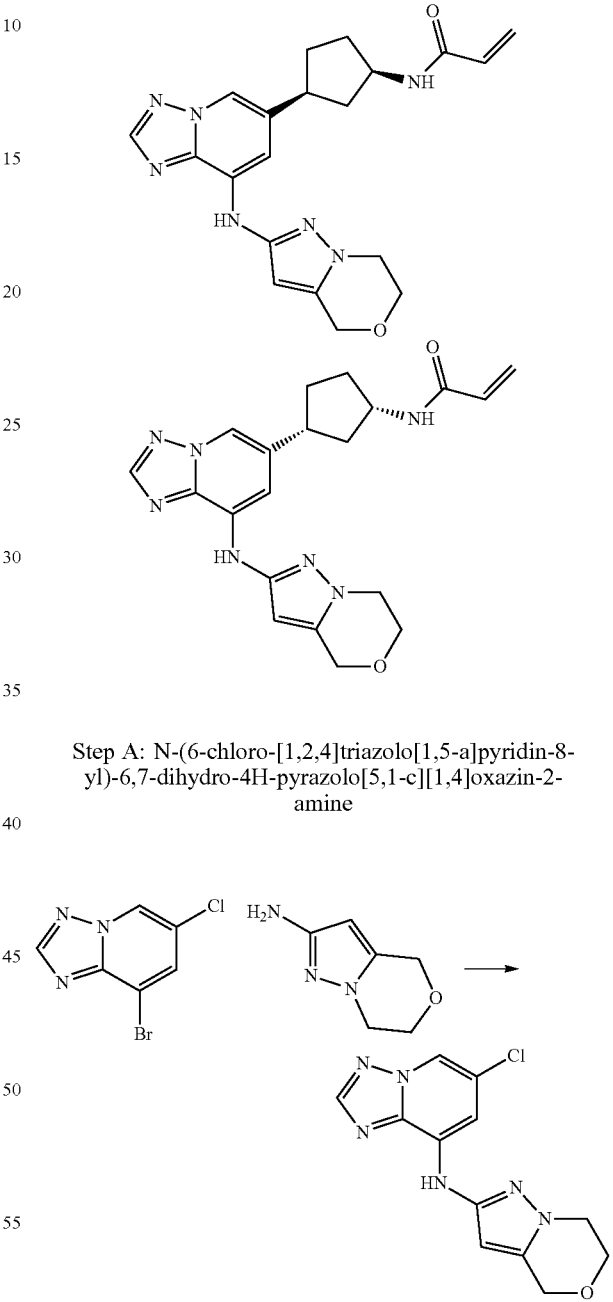

Step A: N-(6-chloro-[1,2,4]triazolo[1,5-a]pyridin-8-yl)-6,7-dihydro-4H-pyrazolo[5,1-c][1,4]oxazin-2-amine To a microwave reaction vial were added tert-butyl 8-bromo-6-chloro-[1,2,4]triazolo[1,5-a]pyridine (1.0 g, 4.3 mmol, Example #1, Step A), 6,7-dihydro-4H-pyrazolo[5,1-c][1,4]oxazin-2-amine (0.658 g, 4.73 mmol, Preparation #1), 1,4-dioxane (10 mL), Cs$_2$CO$_3$ (2.80 g, 8.60 mmol), Xantphos (0.124 g, 0.215 mmol) and Pd$_2$(dba)$_3$ (0.197 g, 0.215 mmol), The reaction vial was flushed with nitrogen, capped, stirred and heated to about 120° C. in a Biotage microwave reactor for about 3 h. The reaction mixture was diluted with DCM (80 mL) and water (50 mL). The organic layer was separated, washed with water (50 mL), brine (50 mL), and dried over Na$_2$SO$_4$. The organic layer was filtered, concentrated under reduced pressure and purified via silica gel chromatography eluting with 5% MeOH in DCM to afford N-(6-chloro-[1,2,4]triazolo[1,5-a]pyridin-8-yl)-6,7-dihydro-4H-pyrazolo[5,1-c][1,4]oxazin-2-amine (0.85 g, 61.2%) as a yellow solid: LC/MS (Table 1, Method m) R$_t$=1.56 min; MS m/z 291 (M+H)$^+$.

Step B: tert-butyl (6-chloro-[1,2,4]triazolo[1,5-a]pyridin-8-yl)(6,7-dihydro-4H-pyrazolo[5,1-c][1,4]oxazin-2-yl)carbamate

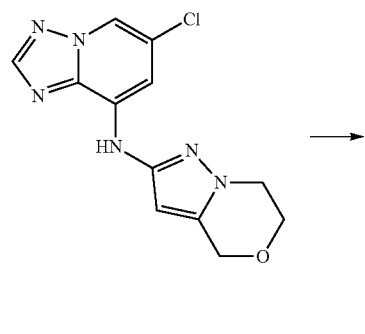

A mixture of N-(6-chloro-[1,2,4]triazolo[1,5-a]pyridin-8-yl)-6,7-dihydro-4H-pyrazolo[5,1-c][1,4]oxazin-2-amine (2.0 g, 6.9 mmol), BoC$_2$O (4.79 mL, 20.6 mmol), TEA (2.88 mL, 20.6 mmol) and DMAP (0.840 g, 6.88 mmol) in DCM (100 mL) was stirred at rt overnight. The organic layer was washed with saturated NH$_4$Cl (3×50 mL). The organic layer was dried with Na$_2$SO$_4$, filtered and concentrated under reduced pressure. The crude product was recrystallized from petroleum ether (60-90° C.) to give tert-butyl (6-chloro-[1,2,4]triazolo[1,5-a]pyridin-8-yl)(6,7-dihydro-4H-pyrazolo[5,1-c][1,4]oxazin-2-yl)carbamate (2.5 g, 86%) as a yellow solid: LC/MS (Table 1, Method n) R$_t$=1.72 min; MS m/z 391 (M+H)$^+$.

Step C: tert-butyl (6,7-dihydro-4H-pyrazolo[5,1-c][1,4]oxazin-2-yl)(6-(3-oxocyclopent-1-en-1-yl)-[1,2,4]triazolo[1,5-a]pyridin-8-yl)carbamate

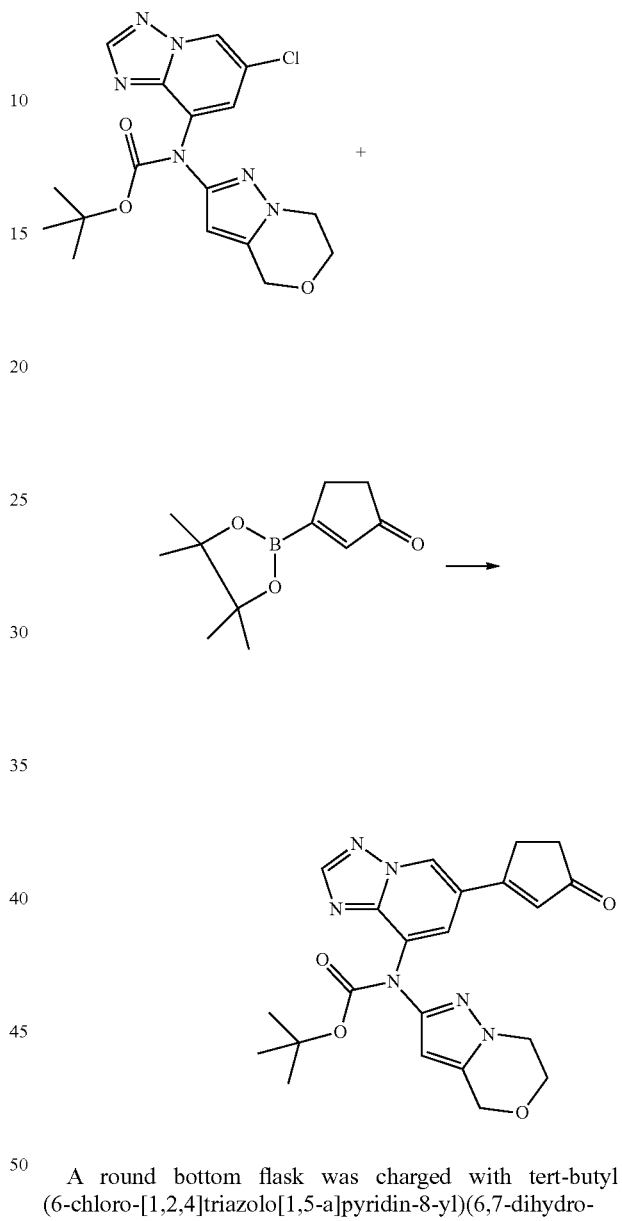

A round bottom flask was charged with tert-butyl (6-chloro-[1,2,4]triazolo[1,5-a]pyridin-8-yl)(6,7-dihydro-4H-pyrazolo[5,1-c][1,4]oxazin-2-yl)carbamate (0.05 g, 0.13 mmol), dicyclohexyl(2',6'-dimethoxy-[1,1'-biphenyl]-2-yl)phosphine (0.016 g, 0.038 mmol), potassium phosphate (0.081 g, 0.38 mmol), water (0.4 mL) and toluene (4 mL). The reaction mixture was degassed with nitrogen followed by the addition of 3-(4,4,5,5-tetramethyl-1,3,2-dioxaborolan-2-yl)cyclopent-2-enone (0.035 g, 0.17 mmol, US20120077814) and Pd$_2$(dba)$_3$ (0.012 g, 0.013 mmol). The suspension was heated in a Biotage microwave at about 100° C. for about 2 h. The mixture was purified by column chromatography (DCM:MeOH=40:1) to give tert-butyl (6,7-dihydro-4H-pyrazolo[5,1-c][1,4]oxazin-2-yl)(6-(3-oxocyclopent-1-en-1-yl)-[1,2,4]triazolo[1,5-a]pyridin-8-yl)carbamate (0.03 g, 53.7%): LC/MS (Table 1, Method r) R$_t$=1.57 min; MS m/z 437 (M+H)$^+$.

Step D: tert-butyl (6,7-dihydro-4H-pyrazolo[5,1-c][1,4]oxazin-2-yl)(6-(3-oxocyclopentyl)-[1,2,4]triazolo[1,5-a]pyridin-8-yl)carbamate

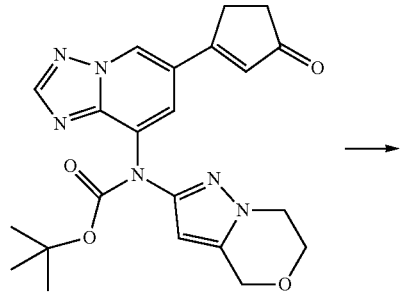

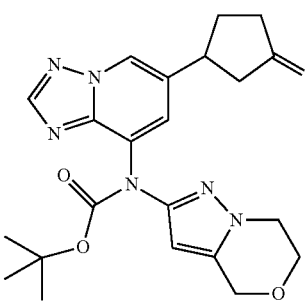

A round bottom flask was charged with tert-butyl (6,7-dihydro-4H-pyrazolo[1,5-c][1,4]oxazin-2-yl)(6-(3-oxocyclopent-1-en-1-yl)-[1,2,4]triazolo[1,5-a]pyridin-8-yl)carbamate (0.04 g, 0.09 mmol) in MeOH (15 mL) followed by the addition of 10% Pd/C (0.010 g, 0.092 mmol). The suspension was stirred under an atmosphere of hydrogen at rt for 1 day. The suspension was filtered, and the filtrate was concentrated under reduced pressure to give tert-butyl (6,7-dihydro-4H-pyrazolo[5,1-c][1,4]oxazin-2-yl)(6-(3-oxocyclopentyl)-[1,2,4]triazolo[1,5-a]pyridin-8-yl)carbamate (0.03 g 75%): LC/MS (Table 1, Method r) $R_t$=1.57 min; MS m/z 439 (M+H)$^+$.

Step E: tert-butyl (6-(3-(benzylamino)cyclopentyl)-[1,2,4]triazolo[1,5-a]pyridin-8-yl)(6,7-dihydro-4H-pyrazolo[5,1-c][1,4]oxazin-2-yl)carbamate

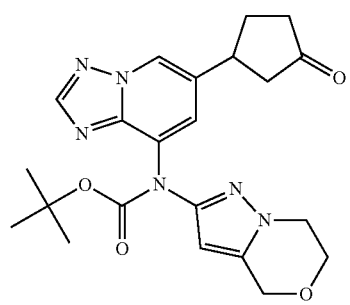

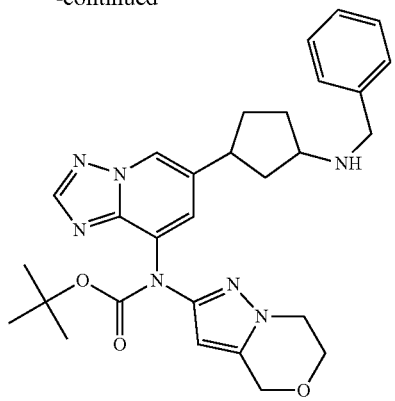

A solution of tert-butyl (6,7-dihydro-4H-pyrazolo[5,1-c][1,4]oxazin-2-yl)(6-(3-oxocyclopentyl)-[1,2,4]triazolo[1,5-a]pyridin-8-yl)carbamate (0.080 g, 0.18 mmol) in DCM (10 mL) was treated with AcOH (0.01 mL, 0.182 mmol) followed by phenylmethanamine (0.098 g, 0.91 mmol). After stirring for about 20 min at rt under nitrogen, sodium triacetoxyborohydride (0.193 g, 0.912 mmol) was added and stirring was continued overnight. MeOH (2 mL), DCM (10 mL) and saturated NaCl (10 mL) were added and the layers were separated. The aqueous layer was extracted with DCM (10 mL). The product was purified by Prep-TLC to give tert-butyl (6-(3-(benzylamino)cyclopentyl)-[1,2,4]triazolo[1,5-a]pyridin-8-yl)(6,7-dihydro-4H-pyrazolo[1,5-c][1,4]oxazin-2-yl)carbamate (0.03 g, 27.9%): LC/MS (Table 1, Method m) $R_t$=1.81, 1.83 min; MS m/z 530 (M+H)$^+$.

Step F: tert-butyl (6-(3-aminocyclopentyl)-[1,2,4]triazolo[1,5-a]pyridin-8-yl)(6,7-dihydro-4H-pyrazolo[5,1-c][1,4]oxazin-2-yl)carbamate

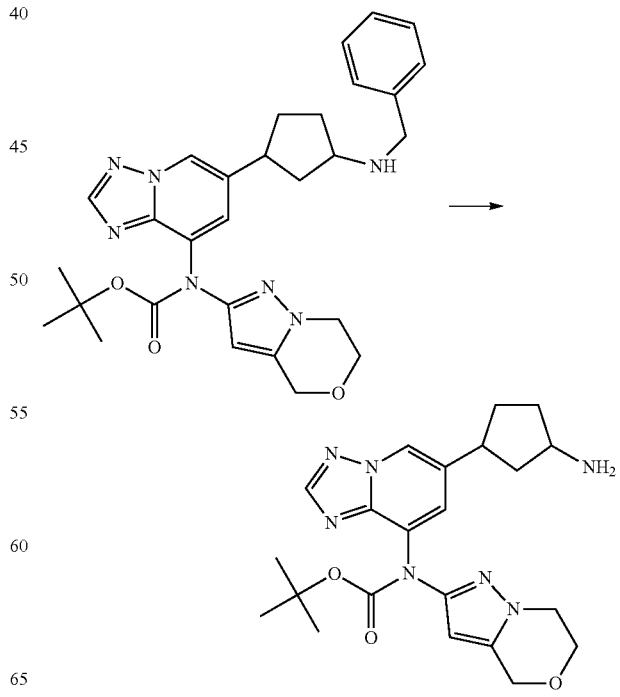

A mixture of tert-butyl (6-(3-(benzylamino)cyclopentyl)-[1,2,4]triazolo[1,5-a]pyridin-8-yl)(6,7-dihydro-4H-pyrazolo[5,1-c][1,4]oxazin-2-yl)carbamate (0.04 0 g, 0.076 mmol), 10% Pd/C (0.10 g, 0.944 mmol) and ammonium formate (0.30 g, 4.8 mmol) in MeOH (20 mL) were refluxed under nitrogen for about 2 h. The reaction mixture was cooled, filtered through Celite®, and concentrated. The residue was diluted with saturated NaCl (30 mL) and extracted with DCM (3×30 mL). The combined organic layers were washed with water (50 mL) and brine (50 mL), then were dried over anhydrous sodium sulfate, filtered and concentrated to give crude tert-butyl (6-(3-aminocyclopentyl)-[1,2,4]triazolo[1,5-a]pyridin-8-yl)(6,7-dihydro-4H-pyrazolo[5,1-c][1,4]oxazin-2-yl)carbamate (0.025 g, 52.7%): LC/MS (Table 1, Method m) $R_t$=1.39 min; MS m/z 440 (M+H)$^+$.

Step G: N-(6-(3-aminocyclopentyl)-[1,2,4]triazolo[1,5-a]pyridin-8-yl)-6,7-dihydro-4H-pyrazolo[5,1-c][1,4]oxazin-2-amine

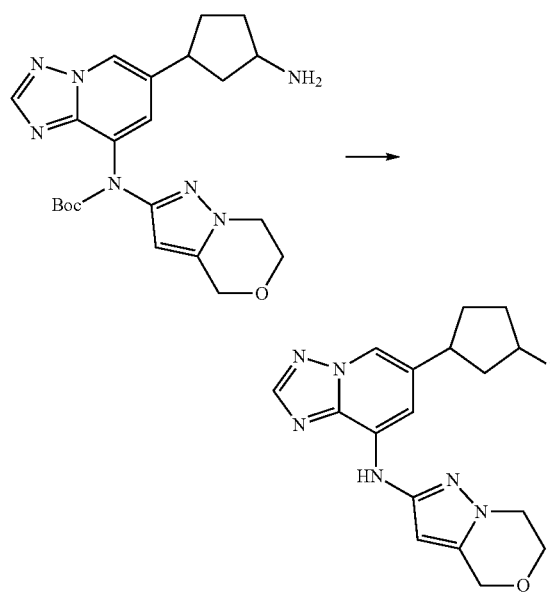

A round bottom flask was charged with tert-butyl (6-(3-aminocyclopentyl)-[1,2,4]triazolo[1,5-a]pyridin-8-yl)(6,7-dihydro-4H-pyrazolo[5,1-c][1,4]oxazin-2-yl)carbamate (0.120 g, 0.273 mmol) and MeOH (6 mL). A solution of 4M HCl in dioxane (0.010 mL, 0.28 mmol) was added and the reaction was stirred at rt for about 4 h. The solution was concentrated to dryness to give N-(6-(3-aminocyclopentyl)-[1,2,4]triazolo[1,5-a]pyridin-8-yl)-6,7-dihydro-4H-pyrazolo[5,1-c][1,4]oxazin-2-amine (0.085 g, 60%): LC/MS (Table 1, Method m) $R_t$=1.24 min; MS m/z 340 (M+H)$^+$.

Step H: N-(3-(8-((6,7-dihydro-4H-pyrazolo[5,1-c][1,4]oxazin-2-yl)amino)-[1,2,4]triazolo[1,5-a]pyridin-6-yl)cyclopentyl)acrylamide

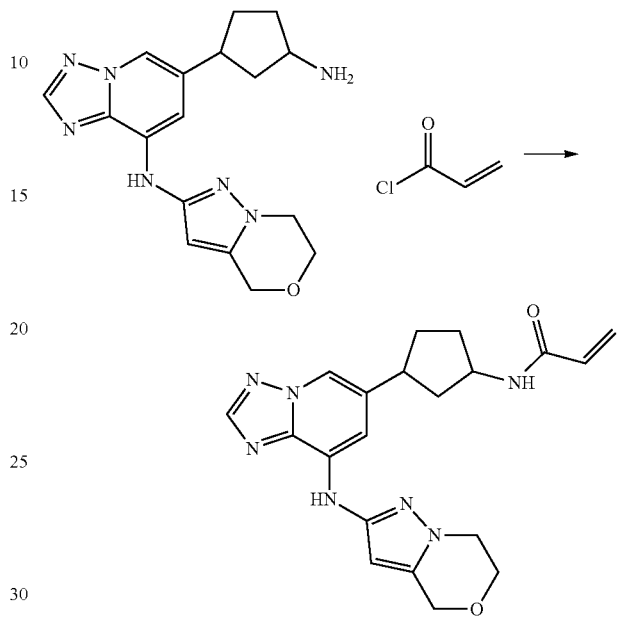

A round bottom flask was charged with N-(6-(3-aminocyclopentyl)-[1,2,4]triazolo[1,5-a]pyridin-8-yl)-6,7-dihydro-4H-pyrazolo[5,1-c][1,4]oxazin-2-amine hydrochloride (0.102 g, 0.271 mmol) and DCM (6 mL) and the solution was cooled to about 0° C. To the flask was added TEA (0.378 mL, 2.71 mmol) and the solution was stirred for about 10 min followed by the dropwise addition of a solution of acryloyl chloride (0.032 g, 0.353 mmol) in DCM (0.1 mL). The mixture was stirred for about 20 min. The reaction solution was then concentrated under reduced pressure to give N-(3-(8-((6,7-dihydro-4H-pyrazolo[5,1-c][1,4]oxazin-2-yl)amino)-[1,2,4]triazolo[1,5-a]pyridin-6-yl)cyclopentyl)acrylamide (0.05 g, 46.8%): LC/MS (Table 1, Method m) $R_t$=1.42 min; MS m/z 394 (M+H)$^+$.

Step I: N-((1R,3S)-3-(8-((6,7-dihydro-4H-pyrazolo[5,1-c][1,4]oxazin-2-yl)amino)-[1,2,4]triazolo[1,5-a]pyridin-6-yl)cyclopentyl)acrylamide and N-((1S,3R)-3-(8-((6,7-dihydro-4H-pyrazolo[5,1-c][1,4]oxazin-2-yl)amino)-[1,2,4]triazolo[1,5-a]pyridin-6-yl)cyclopentyl)acrylamide

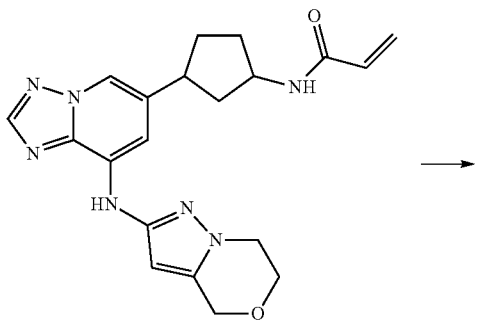

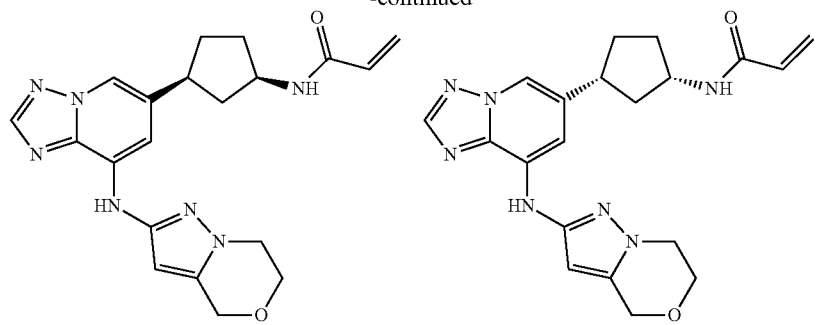

The N-(3-(8-(((6,7-dihydro-4H-pyrazolo[5,1-c][1,4]oxazin-2-yl)amino)-[1,2,4]triazolo[1,5-a]pyridin-6-yl)cyclopentyl)acrylamide (0.53 g, 1.4 mmol) was separated by chiral preparative HPLC (Table 2, Method 13) to give N-((1S,3R)-3-(8-((6,7-dihydro-4H-pyrazolo[5,1-c][1,4]oxazin-2-yl)amino)-[1,2,4]triazolo[1,5-a]pyridin-6-yl)cyclopentyl)acrylamide (0.036 g, 7%, OR=negative). BTK enzyme $IC_{50}$=A The remaining mixture was repurified by chiral preparative HPLC (Table 2, Method 14) to give N-((1R,3S)-3-(8-((6,7-dihydro-4H-pyrazolo[5,1-c][1,4]oxazin-2-yl)amino)-[1,2,4]triazolo[1,5-a]pyridin-6-yl)cyclopentyl)acrylamide (0.033 g, 17%, OR=positive): LC/MS (Table 1, Method m) $R_t$=1.42 min; MS m/z 394 (M+H)$^+$. BTK enzyme $IC_{50}$=A Example #9: N-((1S,3R)-3-(8-((5-morpholinopyridin-2-yl)amino)-[1,2,4]triazolo[1,5-a]pyridin-6-yl)cyclopentyl)acrylamide and N-((1R,3S)-3-(8-((5-morpholinopyridin-2-yl)amino)-[1,2,4]triazolo[1,5-a]pyridin-6-yl)cyclopentyl)acrylamide

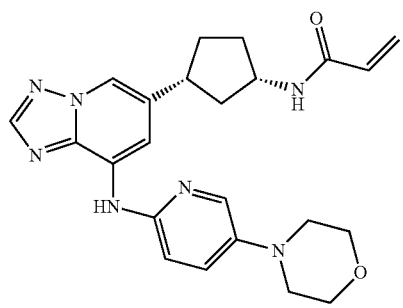

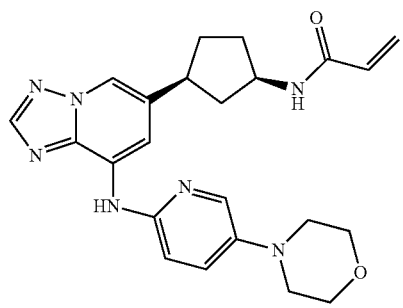

Step A: 6-chloro-N-(5-morpholinopyridin-2-yl)-[1,2,4]triazolo[1,5-a]pyridin-8-amine

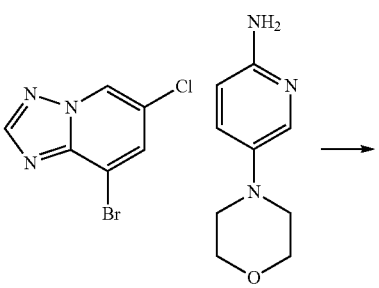

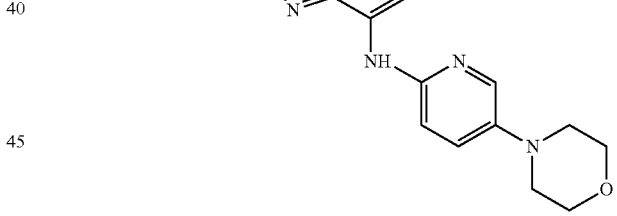

A reaction vial was charged with 8-bromo-6-chloro-[1,2,4]triazolo[1,5-a]pyridine (0.500 g, 2.15 mmol, Example #1, Step A), 5-morpholinopyridin-2-amine (0.385 g, 2.15 mmol, ArkPharm), 1,4-dioxane (10 mL), $Cs_2CO_3$ (1.40 g, 4.30 mmol), Xantphos (0.0622 g, 0.108 mmol) and $Pd_2(dba)_3$ (0.098 g, 0.11 mmol), The reaction vial was flushed with nitrogen, capped, stirred and heated to about 120° C. overnight. The reaction was cooled to rt and then diluted with DCM (100 mL) and water (80 mL). The organic layer was separated, washed with water (80 mL), brine (100 mL), and dried over $Na_2SO_4$. After concentrating the extract to dryness, the product was purified via silica chromatography eluting with a gradient of 20-50% EtOAc in petroleum ether to afford 6-chloro-N-(5-morpholinopyridin-2-yl)-[1,2,4]triazolo[1,5-a]pyridin-8-amine (0.50 g, 70.3%): LC/MS (Table 1, Method r) $R_t$=1.75 min; MS m/z 331 (M+H)$^+$.

Step B: 4-((tert-butoxycarbonyl)amino)cyclopent-1-en-1-yl trifluoromethanesulfonate

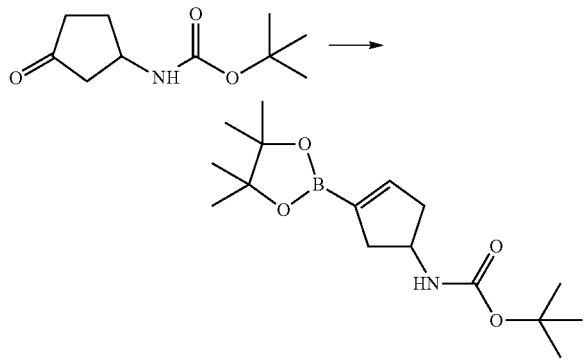

LDA (37.6 mL, 75 mmol, 2 M) was added to a solution of tert-butyl (3-oxocyclopentyl)carbamate (6 g, 30.1 mmol, ArkPharm) in THF (2 mL) at about −78° C. After about 20 min, 1,1,1-trifluoro-N-phenyl-N-((trifluoromethyl)sulfonyl)methanesulfonamide (11.83 g, 33.1 mmol) in THF (50 mL) was added and stirring was continued for about a further 10 min before the cooling bath was removed and the mixture allowed to reach rt. After about 2.5 h the mixture was diluted with Et$_2$O and washed sequentially with 1 N aqueous sodium hydroxide and 1 N aqueous hydrochloric acid. The solution was dried over MgSO$_4$, concentrated under reduced pressure and purified by flash chromatography to give the intermediate 4-((tert-butoxycarbonyl)amino)cyclopent-1-en-1-yl trifluoromethanesulfonate (1.4 g, 14%) and carried forward immediately. A round bottom flask was charged with 4-((tert-butoxycarbonyl)amino)cyclopent-1-en-1-yl trifluoromethanesulfonate (0.6 g, 1.811 mmol), DPPF (0.050 g, 0.091 mmol), and PdCl$_2$(dppf)-CH$_2$Cl$_2$ Adduct (0.074 g, 0.091 mmol) in 1,4-dioxane (10 mL) to give a brown suspension. Potassium acetate (0.53 g, 5.4 mmol) and bis(pinacolato)diboron (0.460 g, 1.81 mmol) were added. The resulting mixture was heated at about 100° C. overnight. The desired product was separated by column to give tert-butyl (3-(4,4,5,5-tetramethyl-1,3,2-dioxaborolan-2-yl)cyclopent-3-en-1-yl)carbamate (0.36 g, 64%): LC/MS (Table 1, Method s) R$_t$=1.85 min; MS m/z 310 (M+H)$^+$.

Step C: tert-butyl (3-(8-((5-morpholinopyridin-2-yl)amino)-[1,2,4]triazolo[1,5-a]pyridin-6-yl)cyclopent-3-en-1-yl)carbamate

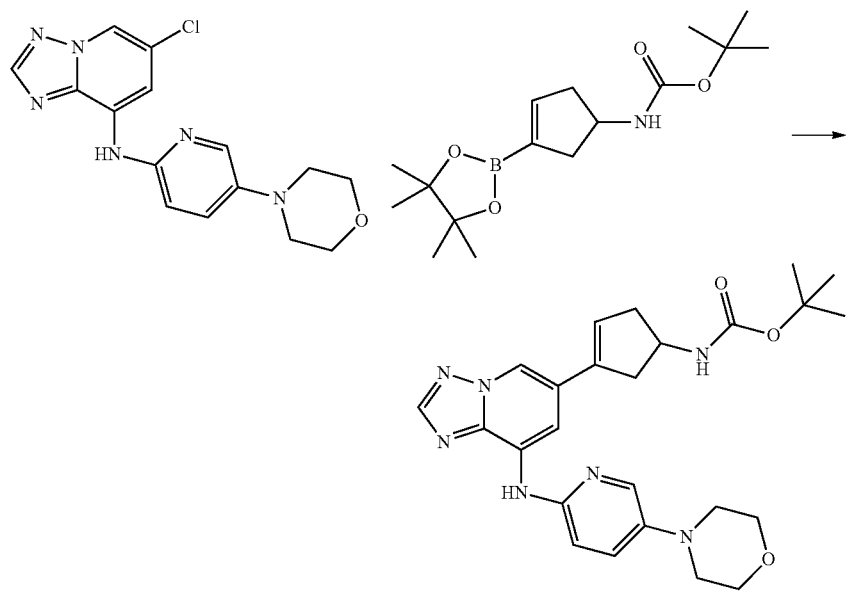

A mixture of 6-chloro-N-(5-morpholinopyridin-2-yl)-[1,2,4]triazolo[1,5-a]pyridin-8-amine (0.30 g, 0.91 mmol), tert-butyl (3-(4,4,5,5-tetramethyl-1,3,2-dioxaborolan-2-yl)cyclopent-3-en-1-yl)carbamate (0.393 g, 1.27 mmol), PdCl$_2$(dppf) (0.066 g, 0.091 mmol) and K$_2$CO$_3$ (0.91 mL, 2.72 mmol) in 1,4-dioxane (4 mL) was heated to about 130° C. for about 3 h in a 10 mL microwave reaction vial. The mixture was cooled to rt and DCM (150 mL) was added to the solution. The organic layer was washed with saturated NaCl (3×50 mL). The organic layer was dried over Na$_2$SO$_4$, filtered and concentrated. The crude product was purified by Prep-TLC to give tert-butyl (3-(8-((5-morpholinopyridin-2-yl)amino)-[1,2,4]triazolo[1,5-a]pyridin-6-yl)cyclopent-3-en-1-yl)carbamate (0.35 g, 66.3%) as a pale brown solid: LC/MS (Table 1, Method m) R$_t$=1.77 min; MS m/z 478 (M+H)$^+$.

Step D: tert-butyl (3-(8-((5-morpholinopyridin-2-yl)amino)-[1,2,4]triazolo[1,5-a]pyridin-6-yl)cyclopentyl)carbamate

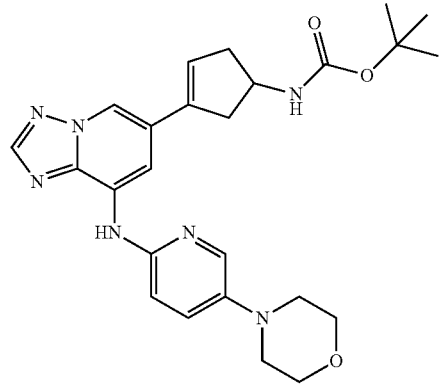

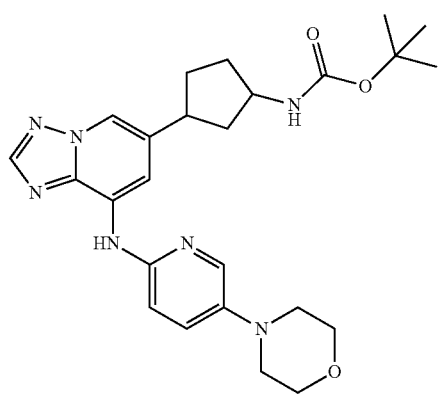

A round bottom flask was charged with a solution of tert-butyl (3-(8-((5-morpholinopyridin-2-yl)amino)-[1,2,4]triazolo[1,5-a]pyridin-6-yl)cyclopent-3-en-1-yl)carbamate (0.350 g, 0.733 mmol) in MeOH, (100 mL) followed by the addition of 10% Pd/C (0.050 g, 0.47 mmol). The suspension was stirred under an atmosphere of hydrogen at rt for about 1 day. The suspension was filtered, and the filtrate was concentrated under reduced pressure to give tert-butyl (3-(8-((5-morpholinopyridin-2-yl)amino)-[1,2,4]triazolo[1,5-a]pyridin-6-yl)cyclopentyl)carbamate (0.310 g, 88%): LC/MS (Table 1, Method m) $R_t$=1.76 min; MS m/z 480 (M+H)$^+$.

Step E: 6-(3-aminocyclopentyl)-N-(5-morpholinopyridin-2-yl)-[1,2,4]triazolo[1,5-a]pyridin-8-amine hydrochloride

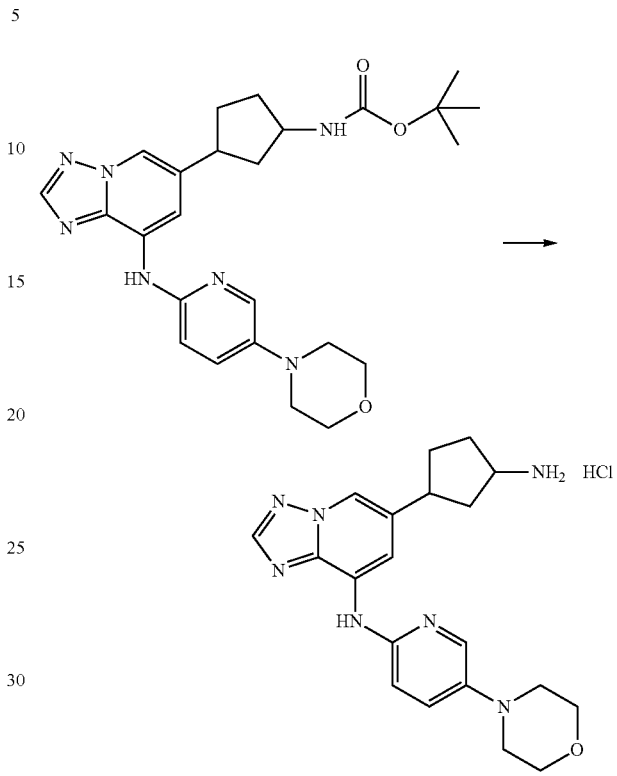

A solution of 4 M HCl (7 mL, 28.0 mmol) in 1,4-dioxane was added dropwise to a solution of tert-butyl (3-(8-((5-morpholinopyridin-2-yl)amino)-[1,2,4]triazolo[1,5-a]pyridin-6-yl)cyclopentyl)carbamate (0.310 g, 0.646 mmol) in THF (14 mL). The mixture was stirred at rt for about 3 h. The solvent was removed under reduced pressure to give 6-(3-aminocyclopentyl)-N-(5-morpholinopyridin-2-yl)-[1,2,4]triazolo[1,5-a]pyridin-8-amine hydrochloride (0.22 g, 81%): LC/MS (Table 1, Method n) $R_t$=1.38 min; MS m/z 380 (M+H)$^+$.

Step F: N-(3-(8-((5-morpholinopyridin-2-yl)amino)-[1,2,4]triazolo[1,5-I]pyridin-6-yl)cyclopentyl)acrylamide

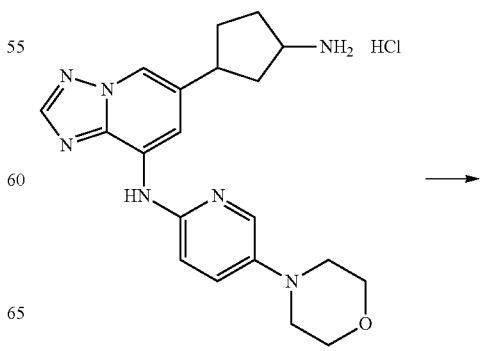

-continued

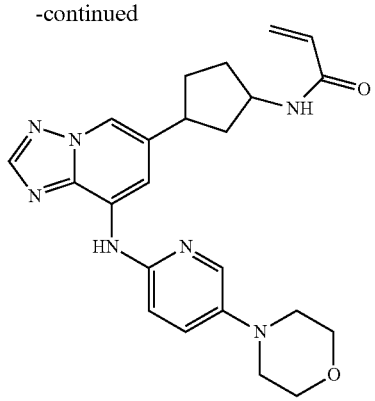

TEA (0.073 mL, 0.53 mmol) was added dropwise into a suspension of 6-(3-aminocyclopentyl)-N-(5-morpholinopyridin-2-yl)-[1,2,4]triazolo[1,5-a]pyridin-8-amine hydrochloride (0.219 g, 0.527 mmol) in DCM (8 mL) at about 0° C. The solution was stirred for about 10 min. Then a solution of acryloyl chloride (0.062 g, 0.68 mmol) in DCM (1 mL) was added dropwise. The mixture was stirred for about 20 min and the solvents were removed under reduced pressure. The crude product was purified by prep-HPLC to get N-(3-(8-((5-morpholinopyridin-2-yl)amino)-[1,2,4]triazolo[1,5-a]pyridin-6-yl)cyclopentyl)acrylamide (0.17 g, 74%): LC/MS (Table 1, Method n) $R_t$=1.56 min; MS m/z 434 (M+H)$^+$.

Step G: N-((1S,3R)-3-(8-((5-morpholinopyridin-2-yl)amino)-[1,2,4]triazolo[1,5-a]pyridin-6-yl)cyclopentyl)acrylamide and N-((1R,3S)-3-(8-((5-morpholinopyridin-2-yl)amino)-[1,2,4]triazolo[1,5-a]pyridin-6-yl)cyclopentyl)acrylamide

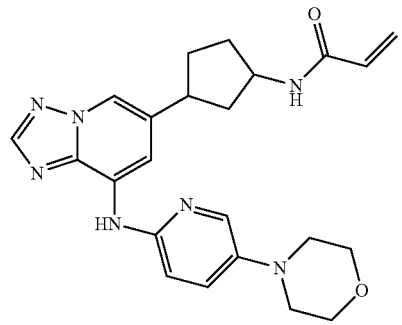 

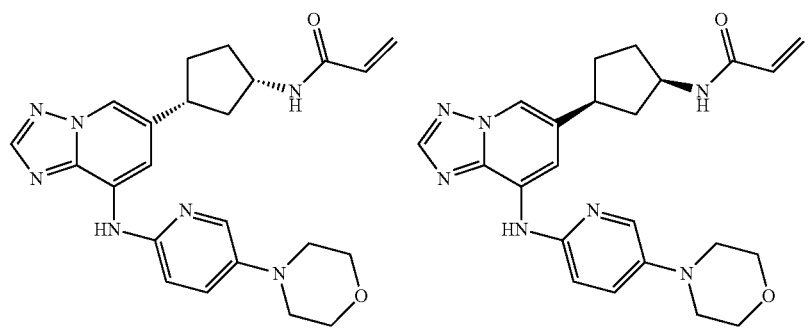

N-(3-(8-((5-Morpholinopyridin-2-yl)amino)-[1,2,4]triazolo[1,5-a]pyridin-6-yl)cyclopentyl)acrylamide (0.160 g, 0.369 mmol) was purified by chiral preparative HPLC (Table 2, Method 15) to give N-((1S,3R)-3-(8-((5-morpholinopyridin-2-yl)amino)-[1,2,4]triazolo[1,5-a]pyridin-6-yl)cyclopentyl)acrylamide (0.027 g, 17%, OR=negative). BTK enzyme IC$_{50}$=B The remaining mixture (0.035 g, 0.081 mmol) was repurified by chiral preparative HPLC (Table 2, Method 15) to give N-((1R,3S)-3-(8-((5-morpholinopyridin-2-yl)amino)-[1,2,4]triazolo[1,5-a]pyridin-6-yl)cyclopentyl)acrylamide (0.024 g, 69%, OR=positive): LC/MS (Table 1, Method m) $R_t$=1.49 min; MS m/z 434 (M+H)$^+$. BTK enzyme IC$_{50}$=A Example #10: (1R,3R)-3-(8-((1-methyl-1H-pyrazol-4-yl)amino)-[1,2,4]triazolo[1,5-a]pyrazin-6-yl)cyclohexanol

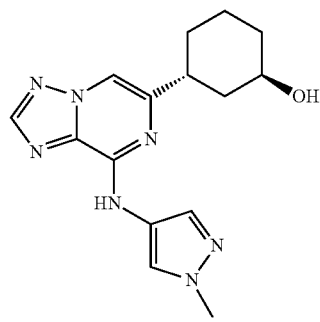 [SMILES: Cn1cc(Nc2nc([C@@H]3CCC[C@@H](O)C3)cn3ncnc23)cn1]

Step A: 6-bromo-N-(1-methyl-1H-pyrazol-4-yl)-[1,2,4]triazolo[1,5-a]pyrazin-8-amine

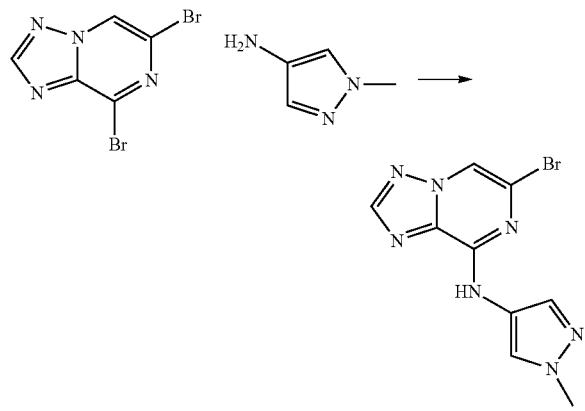

A reaction vial was charged with 6,8-dibromo-[1,2,4]triazolo[1,5-a]pyrazine (10.38 g, 37.3 mmol, ArkPharm), 1-methyl-1H-pyrazol-4-amine (3.989 g, 41.1 mmol, Astatech), DMF (100 mL), and N-ethyl-N-isopropylpropan-2-amine (12.92 ml, 74.7 mmol). The reaction vial was flushed with nitrogen, and heated to about 100° C. for about 90 minutes. The reaction was cooled to rt and then added dropwise to stirring water (200 mL) via an addition funnel. The resulting suspension was filtered, washed with THF, then 1:1 EtOAc/Heptanes to afford 6-bromo-N-(1-methyl-1H-pyrazol-4-yl)-[1,2,4]triazolo[1,5-a]pyrazin-8-amine (9.8 g, 87%): LC/MS (Table 1, Method b) $R_t$=1.66 min; MS m/z 295 (M+H)$^+$.

Step B: 3-(8-((1-methyl-1H-pyrazol-4-yl)amino)-[1,2,4]triazolo[1,5-a]pyrazin-6-yl)cyclohex-2-enone

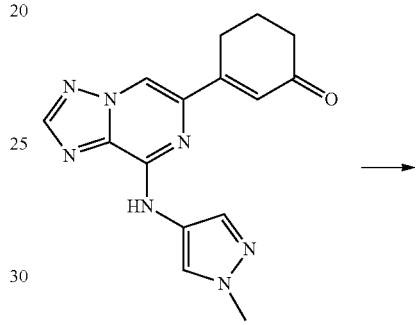

A mixture of 6-bromo-N-(1-methyl-1H-pyrazol-4-yl)-[1,2,4]triazolo[1,5-a]pyrazin-8-amine (1 g, 3.40 mmol), tert-butyl 3-(4,4,5,5-tetramethyl-1,3,2-dioxaborolan-2-yl)cyclohex-2-enone (0.755 g, 3.40 mmol), PdCl$_2$(dppf) (0.239 g, 0.340 mmol) and cesium carbonate (3.32 g, 10.20 mmol) was dissolved in 1,4-dioxane (12 mL) and water (4 mL) and was heated to about 90° C. for about 16 h. The mixture was cooled to rt and water (5 mL) was added to the solution. The suspension was filtered and washed with water (10 mL), heptanes (9 mL), and ether (6 mL). The remaining solid was purified via silica gel chromatography eluting with 0-10% MeOH/DCM to afford 3-(8-((1-methyl-1H-pyrazol-4-yl)amino)-[1,2,4]triazolo[1,5-a]pyrazin-6-yl)cyclohex-2-enone (0.9 g, 2.91 mmol, 86% yield) as a pale yellow solid: LC/MS (Table 1, Method h) $R_t$=1.47 min; MS m/z 310 (M+H)$^+$.

Step C: 3-(8-((1-methyl-1H-pyrazol-4-yl)amino)-[1,2,4]triazolo[1,5-a]pyrazin-6-yl)cyclohexanone

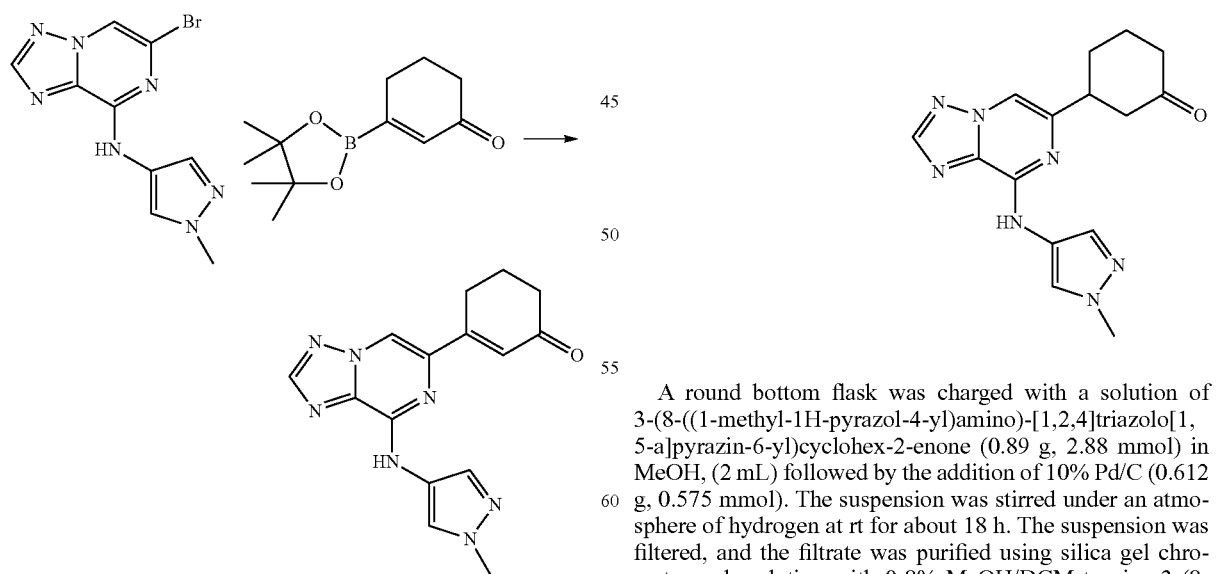

A round bottom flask was charged with a solution of 3-(8-((1-methyl-1H-pyrazol-4-yl)amino)-[1,2,4]triazolo[1,5-a]pyrazin-6-yl)cyclohex-2-enone (0.89 g, 2.88 mmol) in MeOH, (2 mL) followed by the addition of 10% Pd/C (0.612 g, 0.575 mmol). The suspension was stirred under an atmosphere of hydrogen at rt for about 18 h. The suspension was filtered, and the filtrate was purified using silica gel chromatography eluting with 0-8% MeOH/DCM to give 3-(8-((1-methyl-1H-pyrazol-4-yl)amino)-[1,2,4]triazolo[1,5-a]pyrazin-6-yl)cyclohexanone (0.32 g, 1.02 mmol, 35% yield): LC/MS (Table 1, Method h) $R_t$=1.54 min; MS m/z 312 (M+H)$^+$.

Step D: 3-(8-((1-methyl-1H-pyrazol-4-yl)amino)-[1,2,4]triazolo[1,5-a]pyrazin-6-yl)cyclohexanone

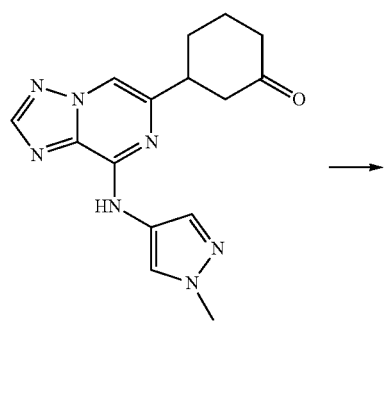

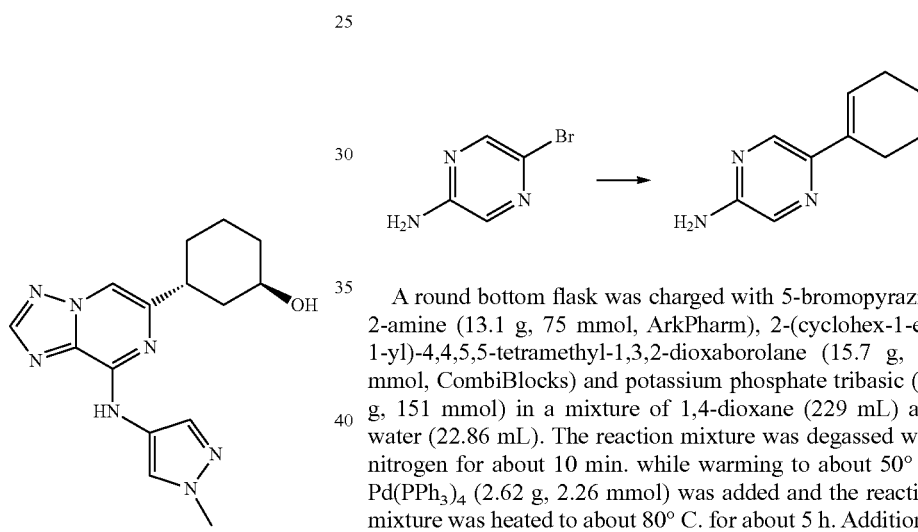

A round bottom flask was charged with a solution of 3-(8-((1-methyl-1H-pyrazol-4-yl)amino)-[1,2,4]triazolo[1,5-a]pyrazin-6-yl)cyclohexanone (0.32 g, 1.028 mmol)) in THF (10.28 mL) and was cooled to about −78° C. L-Selctride (2.056 ml, 2.056 mmol) was added dropwise to the reaction mixture and stirred at about −78° C. for 1 h then allowed to warm to rt over 4 h. The reaction was quenched with the addition of aq. saturated ammonium chloride (5 mL), then extracted with DCM (3×5 mL). The combined organic layers were concentrated under reduced pressure. The crude material was purified via silica gel chromatography eluting with 0-10% MeOH/DCM to give 3-(8-((1-methyl-1H-pyrazol-4-yl)amino)-[1,2,4]triazolo[1,5-a]pyrazin-6-yl)cyclohexanol (0.27 g, 84% yield) as an off-white solid: LC/MS (Table 1, Method h) $R_f$=1.45 min; MS m/z 314 (M+H)$^+$. 3-(8-((1-methyl-1H-pyrazol-4-yl)amino)-[1,2,4]triazolo[1,5-a]pyrazin-6-yl)cyclohexanol (0.260 g, 0.369 mmol) was purified by chiral preparative HPLC (Table 2, Method 16) to give (1R,3R)-3-(8-((1-methyl-1H-pyrazol-4-yl)amino)-[1,2,4]triazolo[1,5-a]pyrazin-6-yl)cyclohexanol (0.08 g, 24%, OR=negative). CSF-1R Enzyme IC$_{50}$=A.

Example #11: (1R,3R)-3-(8-((1-methyl-1H-pyrazol-4-yl)amino)-[1,2,4]triazolo[1,5-a]pyrazin-6-yl)cyclohexanol

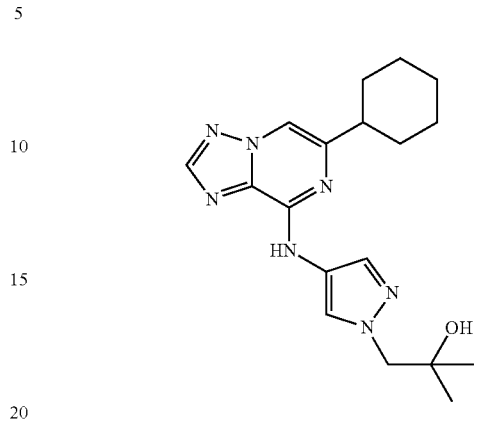

Step A: 5-(cyclohex-1-en-1-yl)pyrazin-2-amine

A round bottom flask was charged with 5-bromopyrazin-2-amine (13.1 g, 75 mmol, ArkPharm), 2-(cyclohex-1-en-1-yl)-4,4,5,5-tetramethyl-1,3,2-dioxaborolane (15.7 g, 75 mmol, CombiBlocks) and potassium phosphate tribasic (32 g, 151 mmol) in a mixture of 1,4-dioxane (229 mL) and water (22.86 mL). The reaction mixture was degassed with nitrogen for about 10 min. while warming to about 50° C. Pd(PPh$_3$)$_4$ (2.62 g, 2.26 mmol) was added and the reaction mixture was heated to about 80° C. for about 5 h. Additional Pd(PPh$_3$)$_4$ (0.7 mg) was added to the reaction mixture and stirred at about 80° C. overnight. The reaction was cooled to ambient temperature and partitioned between EtOAc and brine (2×50 mL). The combined organic portion was dried over anhydrous MgSO$_4$, and filtered through a plug of silica gel. The solvent was concentrated in vacuo. The residue was taken up in about 100 mL of EtOAc and 50 mL of Heptanes. The solid that precipitated was collected to give 5-(cyclohex-1-en-1-yl)pyrazin-2-amine (8.6 g, 96% yield): LC/MS (Table 1, Method h) $R_f$=1.78 min; MS m/z 176 (M+H)$^+$.

Step B: 5-cyclohexylpyrazin-2-amine

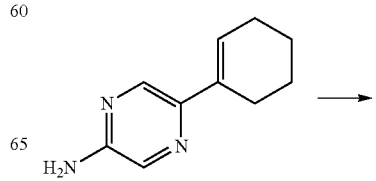

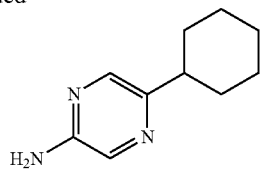

A round bottom flask was charged with 10% Pd/C carbon (3 g, 39.9 mmol) and wet EtOAc (5 mL). A solution of 5-(cyclohex-1-en-1-yl)pyrazin-2-amine (7 g, 39.9 mmol) in EtOH (256 mL) and acetic acid (10.24 mL) was added to the flask affixed with a hydrogen balloon. The reaction was purged with hydrogen and stirred for about 4 h at rt. The reaction mixture was filtered through a pad of Celite® and the solvents were removed under reduced pressure. The resulting solid was partitioned between EtOAc and saturated aq. NaHCO₃. The combined organic portion was dried over anhydrous MgSO₄, filtered, and concentrated in vacuo. The residue was purified via silica gel chromatography eluting with 0-80% EtOAc/Heptanes to give 5-cyclohexylpyrazin-2-amine (1.4 g, 19% yield): LC/MS (Table 1, Method h) $R_t$=1.78 min; MS m/z 178 (M+H)⁺.

Step C: 3-bromo-5-cyclohexylpyrazin-2-amine

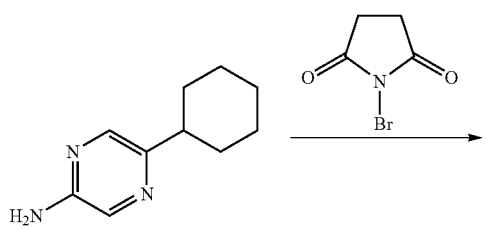

In a round bottom flask, N-bromosuccinimide (1.6 g, 9.08 mmol) was added portionwise to a solution of 5-cyclohexylpyrazin-2-amine (1.4 g, 7.90 mmol) in DMF (15 mL). The reaction stirred for about 2 h at rt. The reaction was quenched with the addition of ice-cold water (30 mL). The reaction was partitioned between EtOAc and saturated aq. NaHCO₃, dried over anhydrous MgSO4, filtered through a pad of silica gel, and concentrated under reduced pressure to give 3-bromo-5-cyclohexylpyrazin-2-amine (1.42 g, 49% yield): LC/MS (Table 1, Method h) $R_t$=2.35 min; MS m/z 256, 258 (M+H)⁺.

Step D: (E)-N'-(3-bromo-5-cyclohexylpyrazin-2-yl)-N-hydroxyformimidamide

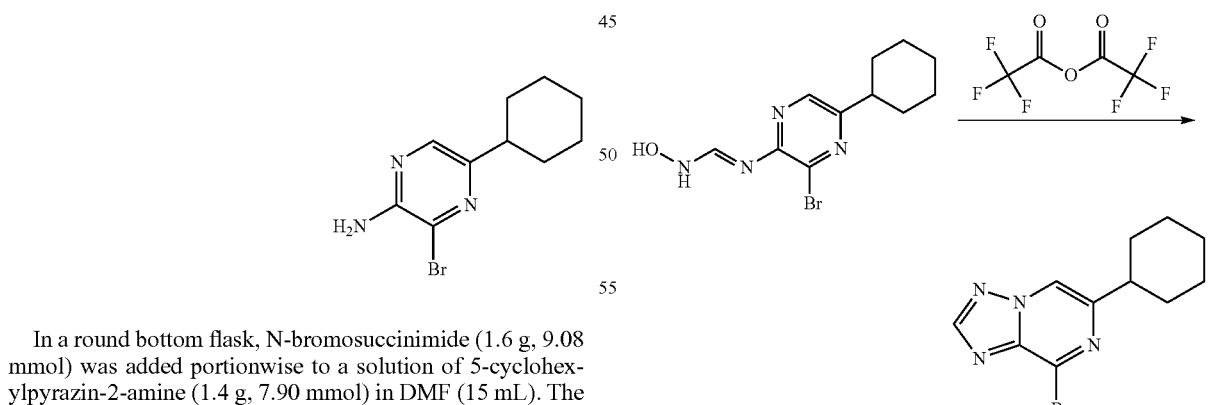

In a round bottom flask, 3-bromo-5-cyclohexylpyrazin-2-amine (1.2 g, 4.6 mmol) was dissolved in N,N-dimtheylformamide dimethyl acetal (1.9 mL, 13.82 mmol). The mixture was heated to about 100° C. for about 1 h. The solvent was concentrated in vacuo to afford a crude residue. The crude, (E)-N'-(3-bromo-5-cyclohexylpyrazin-2-yl)-N,N-dimethylformimidamide (1.4 g, 4.61 mmol) was dissolved in MeOH (12 mL) and treated with hydroxylamine hydrochloride (0.45 g, 6.45 mmol). The reaction stirred for about 4 h at rt. The solvent was concentrated under reduced pressure. 100 mL of water was added to the remaining residue and the pH was adjusted to 9 with the addition of 1M aq. NaOH. The solid that formed was filtered and collected to afford (E)-N'-(3-bromo-5-cyclohexylpyrazin-2-yl)-N-hydroxyformimidamide (1.2 g, 78% yield): LC/MS (Table 1, Method h) $R_t$=2.42 min; MS m/z=299, 301 (M+H)+.

Step E: 8-bromo-6-cyclohexyl-[1,2,4]triazolo[1,5-a]pyrazine

To a solution of (E)-N'-(3-bromo-5-cyclohexylpyrazin-2-yl)-N-hydroxyformimidamide (1.2 g, 4.03 mmol) in MeCN (20 mL) was added trifluoroacetic anhydride (0.85 mL, 6.05 mmol) and the mixture was stirred at rt for about 3 h. The reaction mixture was partitioned between 1M NaOH and EtOAc. The combined organic portion was dried over anhydrous Na$_2$SO$_4$, filtered, and concentrated under reduced pressure. The crude material was purified via silica gel chromatography eluting with 0-100% EtOAc/Heptanes to afford 8-bromo-6-cyclohexyl-[1,2,4]triazolo[1,5-a]pyrazine (0.75 g, 61% yield): LC/MS (Table 1, Method h) R$_t$=2.31 min; MS m/z=281, 283 (M+H)$^+$.

Step F: 1-(4-((6-cyclohexyl-[1,2,4]triazolo[1,5-a]pyrazin-8-yl)amino)-1H-pyrazol-1-yl)-2-methylpropan-2-ol

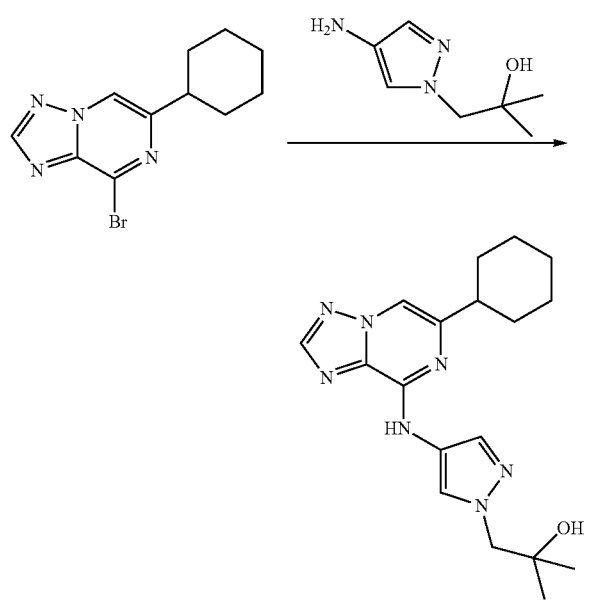

A flask was charged with 8-bromo-6-cyclohexyl-[1,2,4]triazolo[1,5-a]pyrazine (0.05 g, 0.178 mmol), 1-(4-amino-1H-pyrazol-1-yl)-2-methylpropan-2-ol (33.1 mg, 0.213 mmol, Preparation #3) and N-ethyl-N-isopropylpropan-2-amine (0.046 g, 0.356 mmol) in DMF (2 mL). The reaction was stirred at 100° C. for 12 hrs. The reaction was cooled to ambient temperature and purified via prep-HPLC (Table 1, Method u) to give 1-(4-((6-cyclohexyl-[1,2,4]triazolo[1,5-a]pyrazin-8-yl)amino)-1H-pyrazol-1-yl)-2-methylpropan-2-ol (0.03 g, 48% yield) as white solid.: LC/MS (Table 1, Method v) R$_t$=3.12 min; MS m/z=356 (M+H)$^+$. CSF-1R Enzyme IC$_{50}$=A Example #12: N-(6-cyclopentyl-[1,2,4]triazolo[1,5-a]pyridin-8-yl)-6,7-dihydro-4H-pyrazolo[5,1-c][1,4]oxazin-2-amine

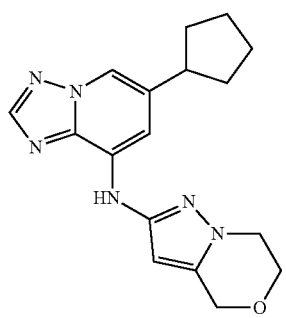 [SMILES: c1nc2c(Nc3cc4n(n3)CCOC4)cc(C3CCCC3)cn2n1]

Step A: 1-(4-((6-cyclohexyl-[1,2,4]triazolo[1,5-a]pyrazin-8-yl)amino)-1H-pyrazol-1-yl)-2-methylpropan-2-ol

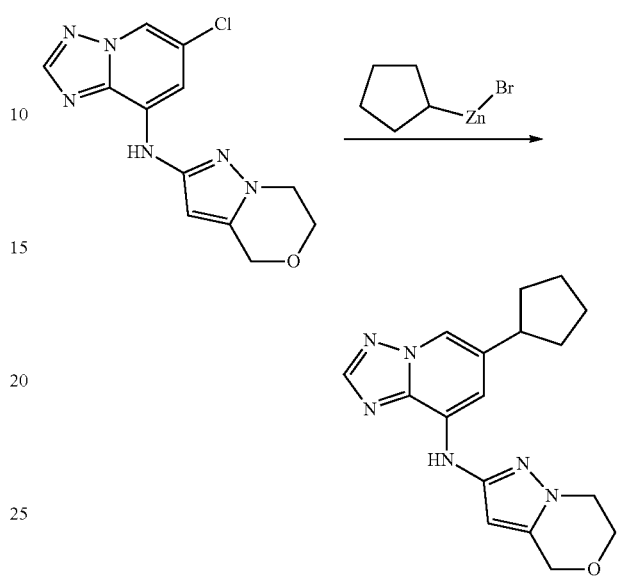

To a solution of N-(6-chloro-[1,2,4]triazolo[1,5-a]pyridin-8-yl)-6,7-dihydro-4H-pyrazolo[5,1-c][1,4]oxazin-2-amine (0.07 g, 0.241 mmol, Example 4, Step A) in 1,4-dioxane (2.4 mL) was added a 0.5 M THF solution of cyclopentyl zinc bromide (2.9 mL, 1.45 mmol, Alfa Aesar) dropwise via syringe. The reaction stirred under nitrogen for about 5 min. before the addition of Pd(dppf)Cl$_2$ (0.019 g, 0.024 mmol). The reaction was heated to 85° C. for 4 h. The reaction was cooled to ambient temperature and was partitioned between saturated aq. NaHCO$_3$ and EtOAc (2×20 mL). The combined organic portion was dried over anhydrous MgSO$_4$, filtered and concentrated in vacuo. The crude material was purified via silica gel chromatography, eluting with 0-100% EtOAc/Heptanes to give N-(6-cyclopentyl-[1,2,4]triazolo[1,5-a]pyridin-8-yl)-6,7-dihydro-4H-pyrazolo[5,1-c][1,4]oxazin-2-amine (0.036 g, 41% yield). LC/MS (Table 1, Method h) R$_t$=2.88 min; MS m/z=325 (M+H)$^+$. CSF-1R Enzyme IC$_{50}$=A Example #13: 1-(6-((6-cyclohexyl-[1,2,4]triazolo[1,5-a]pyridin-8-yl)amino)pyridin-3-yl)piperidin-4-ol

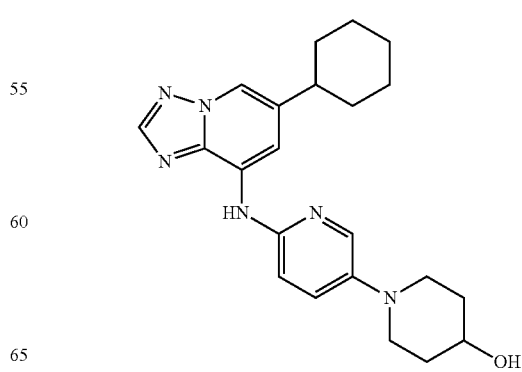

Step A: 1-(6-nitropyridin-3-yl)piperidin-4-ol

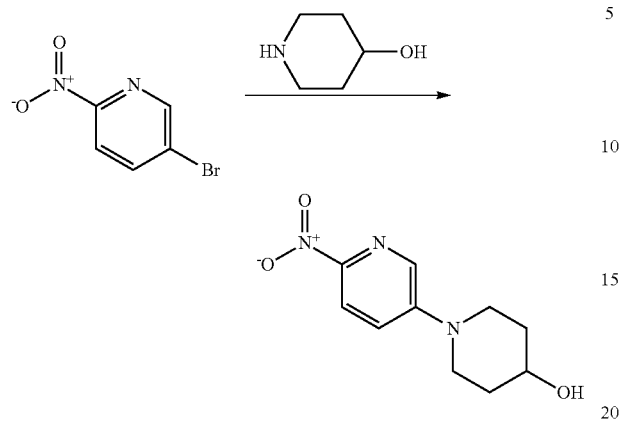

A round bottom flask was charged with 5-bromo-2-nitropyridine (4.0 g, 19.7 mmol), 4-hydroxypiperidine (2.4 g, 23.6 mmol), and potassium carbonate (5.5 g, 39.4 mmol) in DMSO (5 mL). The reaction stirred at rt for about 20 h. The solid that formed was filtered off, and the remaining filtrate was concentrated under reduced pressure. The remaining residue was triturated with DCM to afford 1-(6-nitropyridin-3-yl)piperidin-4-ol (1.89 g, 43% yield). LC/MS (Table 1, Method h) $R_f$=1.24 min; MS m/z=224 (M+H)$^+$.

Step B: 1-(6-aminopyridin-3-yl)piperidin-4-ol

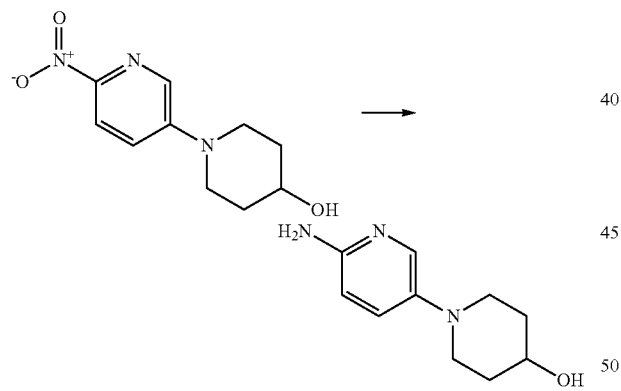

A stainless steel hydrogenation vessel was charged with 1-(6-nitropyridin-3-yl)piperidin-4-ol (1.89 g, 8.48 mmol) and 10% palladium on carbon (0.541 g, 0.509 mmol) in MeOH (200 mL). The mixture was shaken in a Parr hydrogenator pressurized with hydrogen (about 30 psi) at ambient temperature. After about 1 h, the reaction mixture was filtered through a pad of Celite®, washing with excess MeOH. The solvent was removed in vacuo to afford 1-(6-aminopyridin-3-yl)piperidin-4-ol (1.55 g, 95% yield). $^1$H NMR (400 MHz, DMSO-d6) δ 7.59 (dd, J=3.0, 0.7 Hz, 1H), 7.14 (dd, J=8.8, 3.0 Hz, 1H), 6.37 (dd, J=8.9, 0.7 Hz, 1H), 5.33 (bs, 2H), 4.62 (d, J=3.9 Hz, 1H), 3.54 (tq, J=8.3, 3.9 Hz, 1H), 3.24-3.13 (m, 2H), 2.62 (ddd, J=12.5, 10.0, 2.9 Hz, 2H), 1.85-1.74 (m, 2H), 1.54-1.42 (m, 2H).

Step C: 1-(6-((6-chloro-[1,2,4]triazolo[1,5-a]pyridin-8-yl)amino)pyridin-3-yl)piperidin-4-ol

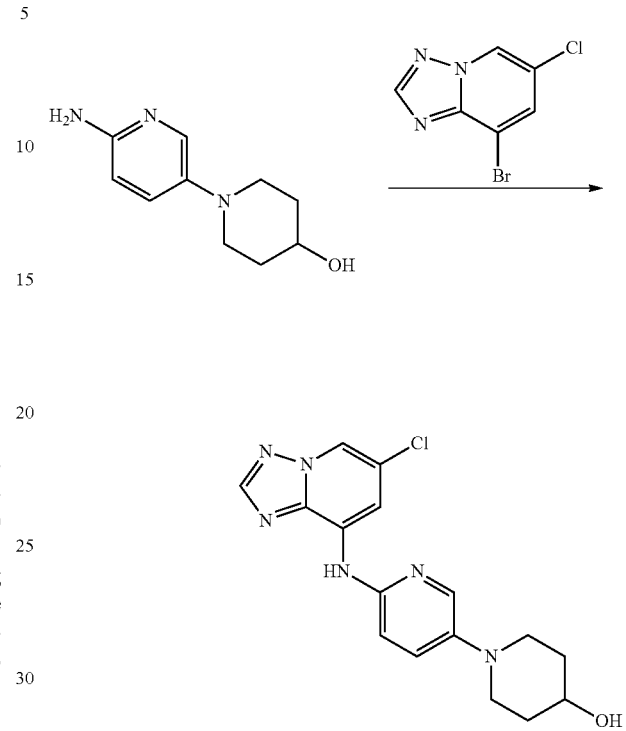

A round bottom flask was charged with 8-bromo-6-chloro-[1,2,4]triazolo[1,5-a]pyridine (1.1 g, 4.70 mmol, Example 1, Step A), 1-(6-aminopyridin-3-yl)piperidin-4-ol (1.0 g, 5.17 mmol), cesium carbonate (3.1 g, 9.41 mmol), and Xantphos (0.16 g, 0.282 mmol, Strem) in 1,4-dioxane (50 mL). The reaction mixture was sparged with nitrogen for 15 minutes, before the addition of Pd(OAc)$_2$ (0.03 g, 0.14 mmol). The reaction was heated to about 80° C. for about 16 h. The reaction was cooled to ambient temperature and the solvent was removed in vacuo. The crude material was purified via silica gel chromatography eluting with 10-100% EtOAc/MeOH to afford 1-(6-((6-chloro-[1,2,4]triazolo[1,5-a]pyridin-8-yl)amino)pyridin-3-yl)piperidin-4-ol (1.1 g, 64% yield). LC/MS (Table 1, Method h) $R_f$=1.75 min; MS m/z=345 (M+H)$^+$.

Step D: 1-(6-((6-cyclohexyl-[1,2,4]triazolo[1,5-a]pyridin-8-yl)amino)pyridin-3-yl)piperidin-4-ol

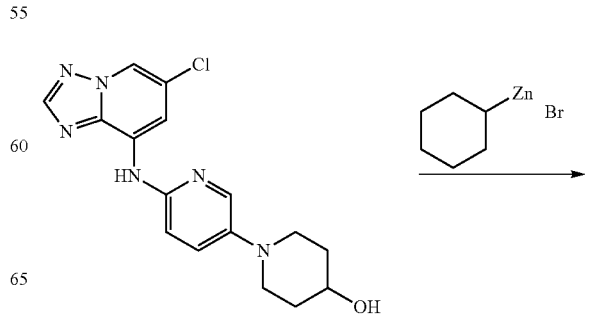

-continued

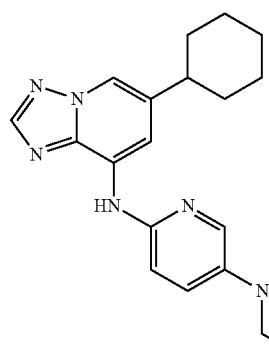

A reaction vial was charged with 1-(6-((6-chloro-[1,2,4]triazolo[1,5-a]pyridin-8-yl)amino)pyridin-3-yl)piperidin-4-ol (0.25 g, 0.73 mmol) in 1,4-dioxane (7.2 mL). The vial was sparged with nitrogen before the addition of 0.5 M solution of cyclohexyl zinc bromide in THF (11.6 mL, 5.80 mmol) and Pd(dppf)Cl$_2$ (0.05 g, 0.07 mmol). The reaction was heated to about 85° C. for about 1 h. The reaction was cooled to ambient temperature and partitioned between EtOAc and water. The combined organic portion was washed with 1N aq. NaOH, dried over MgSO$_4$, filtered, and concentrated under reduced pressure. The crude material was purified via Preparative HPLC (Table 1, Method y) to give 1-(6-((6-cyclohexyl-[1,2,4]triazolo[1,5-a]pyridin-8-yl)amino)pyridin-3-yl)piperidin-4-ol (0.01 g, 11% yield). LC/MS (Table 1, Method h) R$_t$=2.21 min; MS m/z=393 (M+H)$^+$. CSF-1R Enzyme IC$_{50}$=A Example #14: 6-cyclohexyl-N-(1-(1-methylpiperidin-4-yl)-1H-pyrazol-4-yl)-[1,2,4]triazolo[1,5-a]pyrazin-8-amine

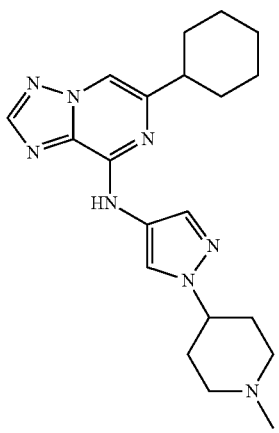 [SMILES: CN1CCC(n2cc(Nc3nc(C4CCCCC4)cn4ncnc34)cn2)CC1]

Step A: 6-cyclohexyl-N-(1-(1-methylpiperidin-4-yl)-1H-pyrazol-4-yl)-[1,2,4]triazolo[1,5-a]pyrazin-8-amine

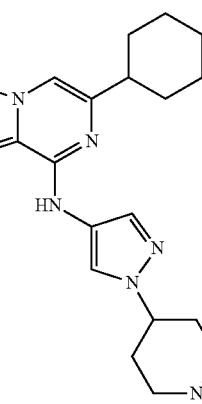

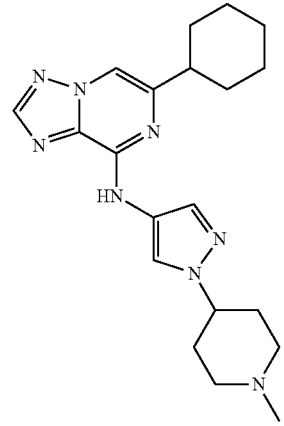

A round bottom flask was charged with 6-cyclohexyl-N-(1-(piperidin-4-yl)-1H-pyrazol-4-yl)-[1,2,4]triazolo[1,5-a]pyrazin-8-amine, hydrochloric acid (0.40 g, 0.99 mmol, Table D1.1), paraformaldehyde (0.06 g, 1.98 mmol), acetic acid (0.17 mL, 2.98 mmol), and sodium triacetoxyhydroborate (0.21 g, 0.99 mmol) in MeOH (9.93 mL). The reaction was heated to about 50° C. for about 18 h. The reaction was cooled to ambient temperature and the solvent was removed in vacuo. The residue was partitioned between saturated aq. NaHCO$_3$ (20 mL) and DCM (2×20 mL). The combined organic portion was dried over MgSO4, filtered, and concentrated under reduced pressure. The crude material was purified via preparative HPLC (Table 2, Method 20) to give 6-cyclohexyl-N-(1-(1-methylpiperidin-4-yl)-1H-pyrazol-4-yl)-[1,2,4]triazolo[1,5-a]pyrazin-8-amine (0.032 g, 9% yield). LC/MS (Table 1, Method h) R$_t$=1.65 min; MS m/z=381 (M+H)$^+$. CSF-1R Enzyme IC$_{50}$=A Example #15: 3-(4-((6-cyclohexyl-[1,2,4]triazolo[1,5-a]pyrazin-8-yl)amino)-1H-pyrazol-1-yl)propan-1-ol

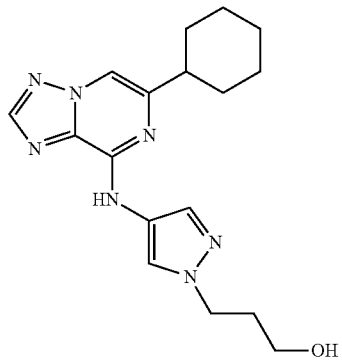 [SMILES: OCCCn1cc(Nc2nc(C3CCCCC3)cn3ncnc23)cn1]

Step A: 6-bromo-N-(1H-pyrazol-4-yl)-[1,2,4]triazolo[1,5-a]pyrazin-8-amine

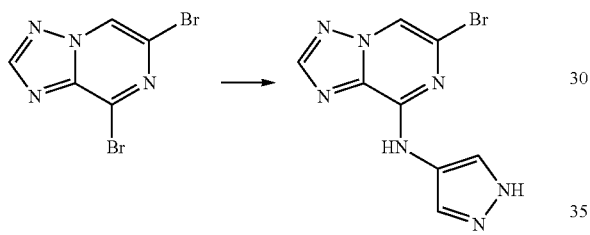

To a solution of 6,8-dibromo-[1,2,4]triazolo[1,5-a]pyrazine (0.989 g, 3.56 mmol, ArkPharm) in DMF (18 mL) was added DIEA (1.9 ml, 10.6 mmol) and 1H-pyrazol-4-amine (0.44 g, 5.34 mmol, Combi Blocks). The reaction was heated to about 95° C. for about 3 h. The reaction was cooled to ambient temperature and the solvent was removed in vacuo. The remaining residue was suspended in H₂O (20 mL) and stirred overnight at rt. The resulting solid was filtered, resuspended in EtOAc (20 mL), and filtered to afford 6-bromo-N-(1H-pyrazol-4-yl)-[1,2,4]triazolo[1,5-a]pyrazin-8-amine (0.9 g, 90% yield) as a grey solid. LC/MS (Table 1, Method h) $R_t$=1.52 min; MS m/z=280 (M+H)⁺.

Step B: tert-butyl 4-((6-bromo-[1,2,4]triazolo[1,5-a]pyrazin-8-yl)amino)-1H-pyrazole-1-carboxylate

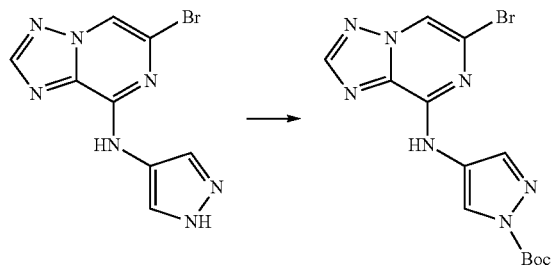 [SMILES: Brc1cn2ncnc2c(Nc2cn[nH]c2)n1 ; CC(C)(C)OC(=O)n1cc(Nc2nc(Br)cn3ncnc23)cn1]

To a solution of 6-bromo-N-(1H-pyrazol-4-yl)-[1,2,4]triazolo[1,5-a]pyrazin-8-amine (0.79 g, 2.8 mmol), N,N-dimethylpyridin-4-amine (0.03 g, 0.28 mmol), and TEA (0.59 mL, 4.26 mmol) in DCM (19 mL) was added Boc₂O (0.62 g, 2.84 mmol). The mixture was stirred at rt for about 4 h. The solvent was removed in vacuo. The remaining residue was purified via silica gel chromatography eluting with MeOH/DCM (0-3%) to afford tert-butyl 4-((6-bromo-[1,2,4]triazolo[1,5-a]pyrazin-8-yl)amino)-1H-pyrazole-1-carboxylate (0.72 g, 66% yield) as a white solid. LC/MS (Table 1, Method h) $R_t$=2.23 min; MS m/z=378 (M−H)⁻.

Step C: 6-cyclohexyl-N-(1H-pyrazol-4-yl)-[1,2,4]triazolo[1,5-a]pyrazin-8-amine

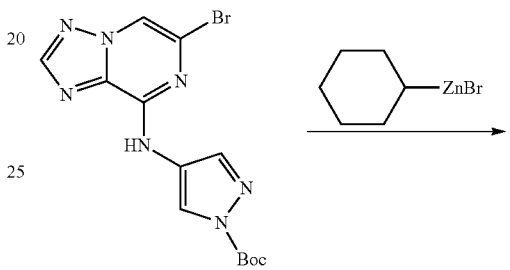

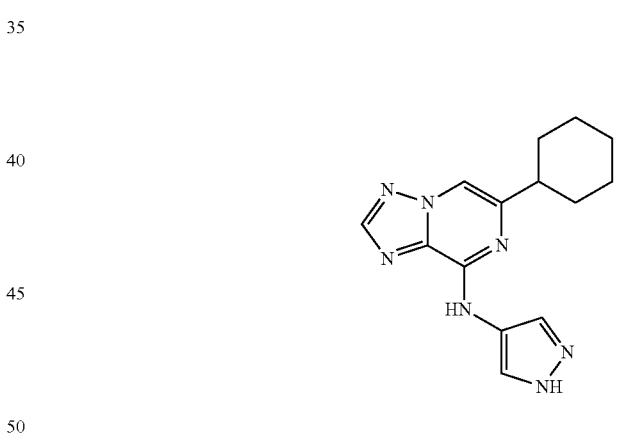

A reaction vial was charged with tert-butyl 4-((6-bromo-[1,2,4]triazolo[1,5-a]pyrazin-8-yl)amino)-1H-pyrazole-1-carboxylate (0.72 g, 1.88 mmol) in 1,4-dioxane (7.5 mL). The vial was sparged with nitrogen for about 5 min. before the addition of 0.5 M solution of cyclohexyl zinc bromide in THF (22 mL, 11.33 mmol), and Pd(dppf)Cl₂ (0.14 g, 0.19 mmol). The reaction was heated to about 75° C. for about 30 minutes. The reaction was cooled to ambient temperature and was partitioned between DCM (3×40 mL) and saturated aq. NaHCO₃ (40 mL). The combined organic portion was dried over MgSO₄, filtered, and concentrated under reduced pressure. The crude material was purified via silica gel chromatography eluting with MeOH/DCM (0-10%) to give 6-cyclohexyl-N-(1H-pyrazol-4-yl)-[1.2.4]triazolo[1,5-a]pyrazin-8-amine (0.41 g, 77% yield). LC/MS (Table 1, Method h) $R_t$=2.01 min; MS m/z=284 (M+H)⁺.

Step D: 3-(4-((6-cyclohexyl-[1,2,4]triazolo[1,5-a]pyrazin-8-yl)amino)-1H-pyrazol-1-yl)propan-1-ol

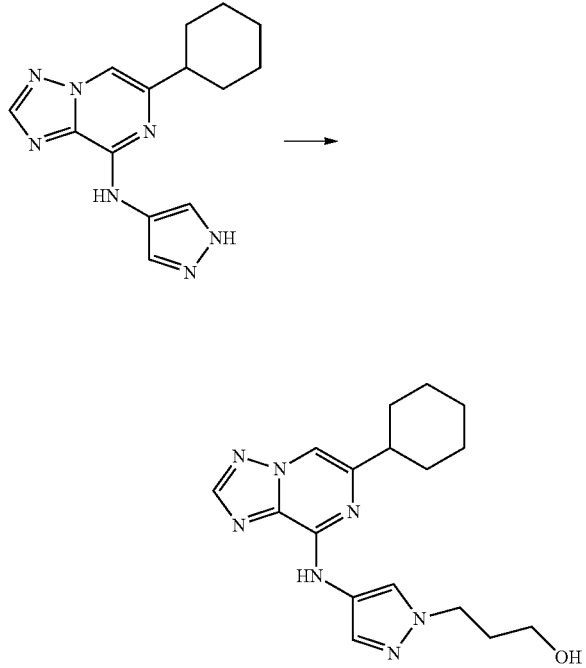

A reaction vial was charged with 6-cyclohexyl-N-(1H-pyrazol-4-yl)-[1,2,4]triazolo[1,5-a]pyrazin-8-amine (0.12 g, 0.43 mmol), $K_2CO_3$ (0.08 g, 0.64 mmol), and 3-iodopropan-1-ol (1 mL, 0.86 mmol) in DMF (4.5 mL). The reaction was heated to about 90° C. for about 16 h. An additional 2 equivalents of 3-iodopropan-1-ol (2 mL, 0.86 mmol) was then added to the reaction and continued to stir at about 90° C. for about 4 h. The reaction was cooled to ambient temperature and was purified via preparative HPLC (Table 1, Method aa) to give 3-(4-((6-cyclohexyl-[1,2,4]triazolo[1,5-a]pyrazin-8-yl)amino)-1H-pyrazol-1-yl)propan-1-ol (0.04 g, 25% yield) as an off-white solid. LC/MS (Table 1, Method h) $R_t$=1.97 min; MS m/z=342 (M+H)+. CSF-1R Enzyme $IC_{50}$=A Example #16: cis-4-(4-((6-cyclohexyl-[1,2,4]triazolo[1,5-a]pyrazin-8-yl)amino)-1H-pyrazol-1-yl)cyclohexanecarboxylic acid

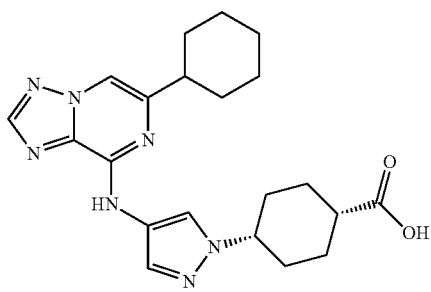

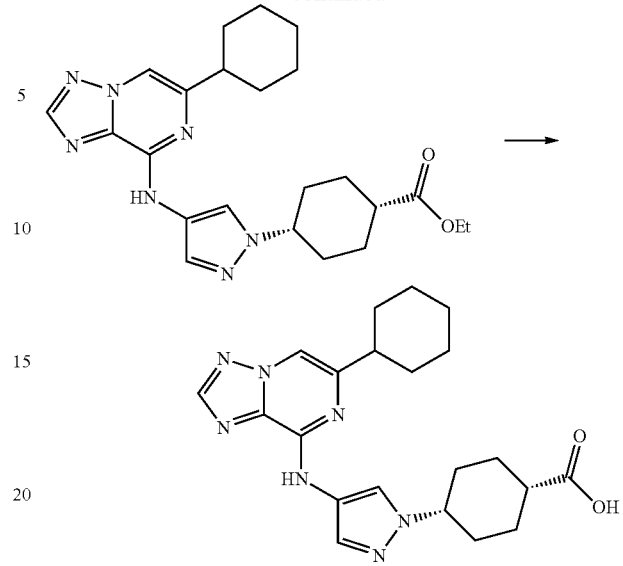

To a solution of cis-ethyl 4-(4-((6-cyclohexyl-[1,2,4]triazolo[1,5-a]pyrazin-8-yl)amino)-1H-pyrazol-1-yl)cyclohexanecarboxylate (0.05 g, 0.12 mmol, Table A.1.8) in MeOH (0.6 mL) was added 1N aq. NaOH (0.25 mL, 0.25 mmol). The reaction as stirred at rt for about 16 h. The solvent was concentrated under reduced pressure, and the remaining residue was purified via preparative HPLC (Table 1, Method ab) to afford cis-4-(4-((6-cyclohexyl-[1,2,4]triazolo[1,5-a]pyrazin-8-yl)amino)-1H-pyrazol-1-yl)cyclohexanecarboxylic acid (0.018 g, 35% yield) as an off-white solid. LC/MS (Table 1, Method h) $R_t$=2.27 min; MS m/z=410 (M+H)+. CSF-1R Enzyme $IC_{50}$=A Example #17: 6-cyclohexyl-N-(1-((2R,4S,6S)-2,6-dimethylpiperidin-4-yl)-1H-pyrazol-4-yl)-[1,2,4]triazolo[1,5-a]pyrazin-8-amine

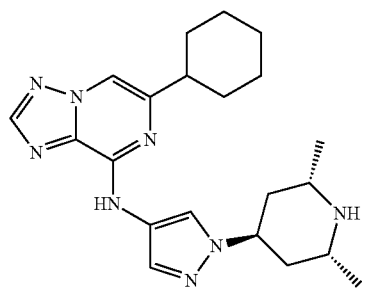 [SMILES: C[C@@H]1C[C@@H](n2cc(Nc3nc(C4CCCCC4)cn4ncnc34)cn2)C[C@H](C)N1]

Step A: tert-butyl 4-(4-((6-bromo-[1,2,4]triazolo[1,5-a]pyrazin-8-yl)amino)-1H-pyrazol-1-yl)-2,6-dimethylpiperidine-1-carboxylate

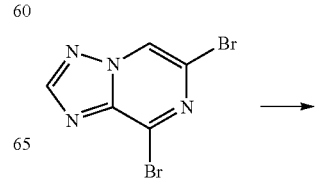

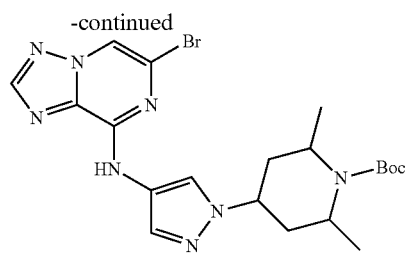

To a solution of 6,8-dibromo-[1,2,4]triazolo[1,5-a]pyrazine (1.54 g, 5.54 mmol, ArkPharm) in DMF (20 mL) was added tert-butyl 4-(4-amino-1H-pyrazol-1-yl)-2,6-dimethylpiperidine-1-carboxylate (1.79 g, 6.10 mmol, Preparation #10), and DIEA (1.16 ml, 6.65 mmol). The reaction mixture was heated to about 100° C. for about 14 h. The reaction cooled to ambient temperature and was partitioned between water (40 mL) and EtOAc (3×40 mL). The combined organic portion was dried over Na$_2$SO$_4$, filtered, and concentrated under reduced pressure. The residue was purified via silica gel chromatography eluting with EtOAc/Petroleum ether (0-10%) to afford tert-butyl 4-(4-((6-bromo-[1,2,4]triazolo[1,5-a]pyrazin-8-yl)amino)-1H-pyrazol-1-yl)-2,6-dimethylpiperidine-1-carboxylate (2.5 g, 92% yield) as a yellow solid. LC/MS (Table 1, Method w) R$_t$=1.50 min; MS m/z=492 (M+H)$^+$.

Step B: (2R,4S,6S)-tert-butyl 4-(4-((6-(cyclohex-1-en-1-yl)-[1,2,4]triazolo[1,5-a]pyrazin-8-yl)amino)-1H-pyrazol-1-yl)-2,6-dimethylpiperidine-1-carboxylate

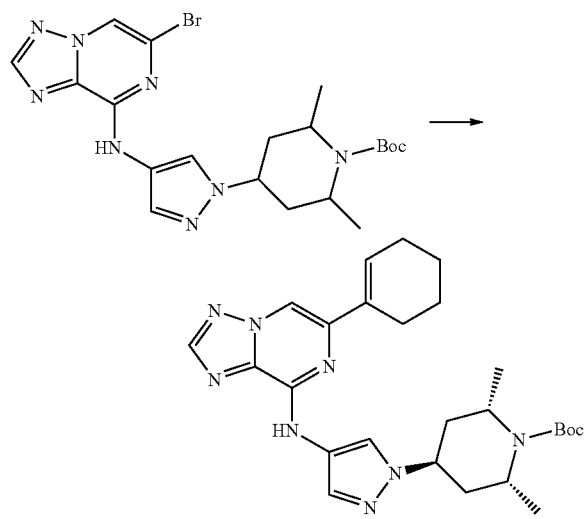

A round bottom flask was charged with tert-butyl 4-(4-((6-bromo-[1,2,4]triazolo[1,5-a]pyrazin-8-yl)amino)-1H-pyrazol-1-yl)-2,6-dimethylpiperidine-1-carboxylate (2.4 g, 4.88 mmol), 2-(cyclohex-1-en-1-yl)-4,4,5,5-tetramethyl-1,3,2-dioxaborolane (1.220 g, 5.86 mmol, ArkPharm), Na$_2$CO$_3$ (1.5 g, 14.6 mmol), and Pd(Ph$_3$P)$_4$ (0.56 g, 0.488 mmol) in DMF (12 mL) and Water (9 mL). The reaction was heated to about 80° C. for about 14 h. The reaction cooled to ambient temperature and was partitioned between water (40 mL) and EtOAc (3×50 mL). The combined organic portion was dried over Na$_2$SO$_4$, filtered, and concentrated under reduced pressure. The residue was purified via silica gel chromatography eluting with EtOAc/Petroleum ether (0-10%) to afford racemic product. The racemate was subjected to preparative chiral SFC (Table 2, Method 19) to give (2R,4S,6S)-tert-butyl 4-(4-((6-(cyclohex-1-en-1-yl)-[1,2,4]triazolo[1,5-a]pyrazin-8-yl)amino)-1H-pyrazol-yl)-2,6-dimethylpiperidine-1-carboxylate (0.71 g, 29% yield) as a white solid. LC/MS (Table 2, Method 19) R$_t$=3.12 min; MS m/z=493 (M+H)$^+$.

Step C: (2R,4r,6S)-tert-butyl 4-(4-((6-cyclohexyl-[1,2,4]triazolo[1,5-a]pyrazin-8-yl)amino)-1H-pyrazol-1-yl)-2,6-dimethylpiperidine-1-carboxylate

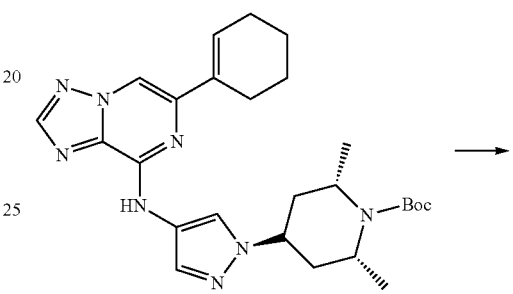

To a solution of (2R,6S)-tert-butyl 4-(4-((6-(cyclohex-1-en-1-yl)-[1,2,4]triazolo[1,5-a]pyrazin-8-yl)amino)-1H-pyrazol-1-yl)-2,6-dimethylpiperidine-1-carboxylate (200 mg, 0.41 mmol) in a mixture of MeOH (5 mL), THF (5 mL), and AcOH (0.25 mL) was added 10% Pd/C (216 mg, 2.03 mmol). The reaction was stirred at rt under an atmosphere of hydrogen for about 16 hrs. The reaction mixture was filtered through a pad of Celite® and concentrated under reduced pressure to afford (2R,6S)-tert-butyl 4-(4-((6-cyclohexyl-[1,2,4]triazolo[1,5-a]pyrazin-8-yl)amino)-1H-pyrazol-1-yl)-2,6-dimethylpiperidine-1-carboxylate (170 mg, 85% yield) as a white solid.

$^1$H NMR (400 MHz, CDCl$_3$) δ 8.61 (s, 1H), 8.25 (s, 1H), 8.13 (s, 1H), 7.93 (s, 1H), 7.77 (s, 1H), 4.77-4.72 (m, 1H), 4.61-4.56 (m, 2H), 2.67-2.61 (m, 1H), 2.17-2.04 (m, 8H), 1.91-1.95 (m, 4H), 1.51 (s, 9H), 1.47 (s, 3H), 1.44 (s, 3H), 1.37-1.29 (m, 2H).

Step D: 6-cyclohexyl-N-(1-((2R,4s,6S)-2,6-dimethylpiperidin-4-yl)-1H-pyrazol-4-yl)-[1,2,4]triazolo[1,5-a]pyrazin-8-amine

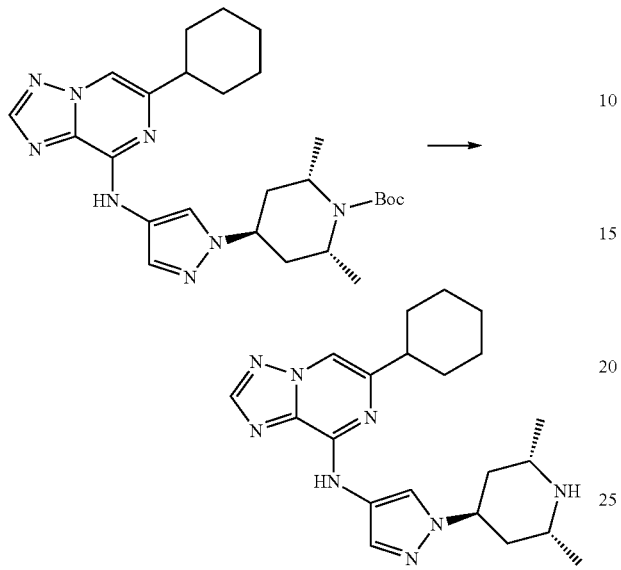

To a solution of (2R,4S,6S)-tert-butyl 4-(4-((6-cyclohexyl-[1,2,4]triazolo[1,5-a]pyrazin-8-yl)amino)-1H-pyrazol-1-yl)-2,6-dimethylpiperidine-1-carboxylate (170 mg, 0.344 mmol) in DCM (15 mL) was added TFA (5 mL, 64.9 mmol). The reaction mixture was stirred at rt for about 2 h. The reaction was stirred at rt for about 16 h. The solvent was concentrated under reduced pressure, and the remaining residue was partitioned between DCM and saturated aq. NaHCO$_3$. The organic portion was dried over anhydrous Na2SO4, filtered, and concentrated under reduced pressure. The resulting solid was recrystallized from EtOAc (2 mL) to afford 6-cyclohexyl-N-(1-((2R,4S,6S)-2,6-dimethylpiperidin-4-yl)-1H-pyrazol-4-yl)-[1,2,4]triazolo[1,5-a]pyrazin-8-amine (52 mg, 39% yield) as a white solid. LC/MS (Table 1, Method w) R$_f$=2.69 min; MS m/z=395 (M+H)$^+$. CSF-1R Enzyme IC$_{50}$=A

What is claimed:
1. A compound of Formula (I)

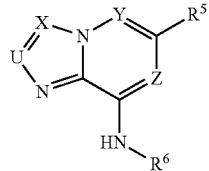

Formula (I)

or a pharmaceutically acceptable salt thereof, wherein
U is CR$^1$;
X is N;
Y is CR$^3$;
Z is CR$^4$;
R$^1$ is independently H or deuterium;
R$^3$ is H, deuterium or optionally substituted (C$_1$-C$_3$)alkyl;
R$^4$ is H or deuterium;
R$^5$ is —R$^{501}$-L-R$^{502}$, wherein R$^{501}$ is a bond, —O—, —OCH$_2$—, or optionally substituted (C$_1$-C$_3$)alkylene,
L is —C(=O)—, —CH$_2$N(H)C(=O)—, —N(H)C(=O)—, or —N(H)S(O)$_2$—; or
L is a bond and R$^{502}$ is —CN; or
L is -L$^1$-L$^2$, wherein L$^1$ is attached to R$^{501}$, wherein
L$^1$ is optionally substituted phenyl, optionally substituted heteroaryl, optionally substituted saturated or partially saturated heterocyclyl, or optionally substituted saturated or partially saturated (C$_3$-C$_7$)cycloalkyl and L$^2$ is a bond, —CH$_2$N(R$^a$)—, —CH$_2$N(R$^a$)C(O)—, —N(R$^a$)C(O)—, —N(R$^a$)S(O)$_2$— or —N(R$^a$)—; or
L$^1$ is a saturated or partially saturated heterocyclyl containing one or more heteroatoms wherein at least one heteroatom is nitrogen and L$^2$ is a bond, —C(=O)—, or —S(O)$_2$—;
R$^{502}$ is optionally substituted alkenyl, optionally substituted alkynyl, CN, or optionally substituted (C$_3$-C$_6$)cycloalkenyl;
R$^6$ is optionally substituted (C$_1$-C$_6$)alkyl, optionally substituted (C$_3$-C$_{12}$)cycloalkyl, optionally substituted phenyl, optionally substituted heteroaryl, or optionally substituted heterocyclyl; or
R$^6$ is —R$^{601}$-R$^{602}$, wherein R$^{601}$ is attached to the —N(H)— and
R$^{601}$ is optionally substituted heteroaryl;
R$^{602}$ is —N(R$^a$)$_2$, optionally substituted (C$_1$-C$_6$)alkyl, optionally substituted (C$_3$-C$_6$)cycloalkyl, or optionally substituted heterocyclyl; and
R$^a$ is independently H or optionally substituted (C$_1$-C$_6$)alkyl.

2. The compound according to claim 1, wherein
U is CR$^1$;
X is N;
Y is CR$^3$;
Z is CR$^4$;
R$^1$ is independently H or deuterium;
R$^3$ is H, deuterium or optionally substituted (C$_1$-C$_3$)alkyl;
R$^4$ is H or deuterium;
R$^5$ is —R$^{501}$-L-R$^{502}$, wherein
R$^{501}$ is a bond, —O—, —OCH$_2$—, or optionally substituted (C$_1$-C$_3$)alkylene,
L is —C(=O)—, —CH$_2$N(H)C(=O)—, —N(H)C(=O)—, or —N(H)S(O)$_2$—; or
L is a bond and R$^{502}$ is —CN; or
L is -L$^1$-L$^2$, wherein L$^1$ is attached to R$^{501}$, wherein
L$^1$ is optionally substituted phenyl, optionally substituted heteroaryl, optionally substituted saturated or partially saturated heterocyclyl, or optionally substituted saturated or partially saturated (C$_3$-C$_6$)cycloalkyl and L$^2$ is —CH$_2$N(R$^a$)—, —CH$_2$N(R$^a$)C(O)—, —N(R$^a$)C(O)—, —N(R$^a$)S(O)$_2$— or —N(R$^a$)—; or
L$^1$ is a saturated or partially saturated heterocyclyl containing one or more heteroatoms wherein at least one heteroatom is nitrogen and L$^2$ is a bond, —C(=O)—, or —S(O)$_2$—;
R$^{502}$ is optionally substituted alkenyl, optionally substituted alkynyl, CN, or optionally substituted (C$_3$-C$_6$)cycloalkenyl;
R$^6$ is optionally substituted (C$_1$-C$_6$)alkyl, optionally substituted (C$_3$-C$_{12}$)cycloalkyl, optionally substituted phenyl, optionally substituted heteroaryl, or optionally substituted heterocyclyl; and
R$^a$ is independently H or optionally substituted (C$_1$-C$_6$) alkyl.

3. The compound of claim 2, wherein
L is —C(=O)—, —CH$_2$N(H)C(=O)—, or —N(H)C(=O)—; and R$^{502}$ is —CH=CH$_2$ or —C≡CH; or
L is a bond and R$^{502}$ is —CN; or
L is -L$^1$-L$^2$, wherein L$^1$ is attached to R$^{501}$, wherein
L$^1$ is optionally substituted phenyl, optionally substituted heteroaryl or optionally substituted saturated or partially saturated (C$_3$-C$_6$)cycloalkyl and L$^2$ is —CH$_2$N(R$^a$)—, —CH$_2$N(R$^a$)C(O)—, —N(R$^a$)C(O)—, —N(R$^a$)S(O)$_2$— or —N(R$^a$)—; or
L$^1$ is azepanyl, azetidinyl, morpholinyl, oxazepanyl, piperidinyl, or pyrrolidinyl, and L$^2$ is a bond, —C(=O)—, or —S(O)$_2$—.

4. The compound of claim 3, wherein R$^6$ is optionally substituted (C$_1$-C$_6$)alkyl, optionally substituted phenyl, optionally substituted bicyclo[1.1.1]pentanyl, optionally substituted 1,2,4 oxadiazolyl, optionally substituted pyrazolyl, optionally substituted pyridazinyl, optionally substituted pyridinyl, 4,5-dihydro-1H-benzo[b]azepin-2(3H)-one, 3,4-dihydroquinolin-2(1H)-one, 2H-benzo[b][1,4]oxazin-3(4H)-one, or 6,7-dihydro-4H-pyrazolo[5,1-c][1,4]oxazinyl.

5. The compound of claim 4, wherein R$^6$ is optionally substituted with one or more substituents independently selected from (C$_1$-C$_3$)alkyl, (C$_1$-C$_3$)alkoxy, optionally substituted imidazolidinone, and morpholinyl.

6. The compound of claim 5, wherein -L-R$^{502}$ forms —CN, —CH$_2$N(H)C(=O)CH=CH$_2$, —C(=O)CH=CH$_2$, or —N(H)C(=O)CH=CH$_2$.

7. The compound according to claim 1, wherein the compound is
1-(3-(8-((1-methyl-1H-pyrazol-3-yl)amino)-[1,2,4]triazolo[1,5-a]pyridin-6-yl)pyrrolidin-1-yl)prop-2-en-1-one;
8-((6-(1-acryloylpyrrolidin-3-yl)-[1,2,4]triazolo[15-a]pyridin-8-yl)amino)-4,5-dihydro-1H-benzo[b]azepin-2(3H)-one;
1-(3-(8-((6,7-dihydro-4H-pyrazolo[5,1-c][1,4]oxazin-2-yl)amino)-[1,2,4]triazolo[1,5-a]pyridin-6-yl)pyrrolidin-1-yl)prop-2-en-1-one;
1-(3-(8-((1-methyl-1H-pyrazol-3-yl)amino)-[1,2,4]triazolo[1,5-a]pyridin-6-yl)piperidin-1-yl)prop-2-en-1-one;
1-(3-(8-((6-morpholinopyridazin-3-yl)amino)-[1,2,4]triazolo[1,5-a]pyridin-6-yl)piperidin-1-yl)prop-2-en-1-one;
1-(3-(8-((5-morpholinopyridin-2-yl)amino)-[1,2,4]triazolo[1,5-a]pyridin-6-yl)piperidin-1-yl)prop-2-en-1-one;
1-(3-(8-((6-morpholinopyridin-2-yl)amino)-[1,2,4]triazolo[1,5-a]pyridin-6-yl)piperidin-1-yl)prop-2-en-1-one;
1-(3-(8-((6,7-dihydro-4H-pyrazolo[5,1-c][1,4]oxazin-2-yl)amino)-[1,2,4]triazolo[1,5-a]pyridin-6-yl)piperidin-1-yl)prop-2-en-1-one;
(S)-1-(3-(8-((1-methyl-1H-pyrazol-3-yl)amino)-[1,2,4]triazolo[1,5-a]pyridin-6-yl)pyrrolidin-1-yl)prop-2-en-1-one;
(R)-1-(3-(8-((1-methyl-1H-pyrazol-3-yl)amino)-[1,2,4]triazolo[1,5-a]pyridin-6-yl)pyrrolidin-1-yl)prop-2-en-1-one;
1-(3-(8-((3-isopropyl-1,2,4-oxadiazol-5-yl)amino)-[1,2,4]triazolo[1,5-a]pyridin-6-yl)piperidin-1-yl)prop-2-en-1-one;
N-((1R,3S)-3-(8-((1-methyl-1H-pyrazol-3-yl)amino)-[1,2,4]triazolo[1,5-a]pyridin-6-yl)cyclohexyl)acrylamide;
1-(3-(8-((3-methyl-1,2,4-oxadiazol-5-yl)amino)-[1,2,4]triazolo[1,5-a]pyridin-6-yl)piperidin-1-yl)prop-2-en-1-one;
N-((1S,3S)-3-(8-((1-methyl-1H-pyrazol-3-yl)amino)-[1,2,4]triazolo[1,5-a]pyridin-6-yl)cyclohexyl)cyanamide;
3-(8-((1-methyl-1H-pyrazol-3-yl)amino)-[1,2,4]triazolo[1,5-a]pyridin-6-yl)piperidine-1-carbonitrile;
3-(8-((1-methyl-1H-pyrazol-3-yl)amino)-[1,2,4]triazolo[1,5-a]pyridin-6-yl)pyrrolidine-1-carbonitrile;
N-((1R,3S)-3-(8-((1-methyl-1H-pyrazol-3-yl)amino)-[1,2,4]triazol[1,5-a]pyridin-6-yl)cyclopentyl) acrylamide;
N-((1S)-3-(8-((1-methyl-1H-pyrazol-3-yl)amino)-[1,2,4]triazolo[1,5-a]pyridin-6-yl)cyclopentyl) acrylamide;
3-(8-((6,7-dihydro-4H-pyrazolo[5,1-c][1,4]oxazin-2-yl)amino)-[1,2,4]triazolo[1,5-a]pyridin-6-yl)piperidine-1-carbonitrile;
(S)-1-(3-(8-((6,7-dihydro-4H-pyrazolo[5,1-c][1,4]oxazin-2-yl)amino)-[1,2,4]triazolo[1,5-a]pyridin-6-yl)pyrrolidin-1-yl)prop-2-en-1-one;
(R)-1-(3-(8-((6,7-dihydro-4H-pyrazolo[5,1-c][1,4]oxazin-2-yl)amino)-[1,2,4]triazolo[1,5-a]pyridin-6-yl)pyrrolidin-1-yl)prop-2-en-1-one;
(S)-1-(3-(8-((6,7-dihydro-4H-pyrazolo[5,1-c][1,4]oxazin-2-yl)amino)-[1,2,4]triazolo[1,5-a]pyridin-6-yl)piperidin-1-yl)prop-2-en-1-one; or
(R)-1-(3-(8-((6,7-dihydro-4H-pyrazolo[5,1-c][1,4]oxazin-2-yl)amino)-[1,2,4]triazolo[1,5-a]pyridin-6-yl)piperidin-1-yl)prop-2-en-1-one.

8. The compound according to claim 1, wherein
R$^5$ is —R$^{501}$-L-R$^{502}$, wherein
R$^{501}$ is a bond;
L is -L$^1$-L$^2$, wherein L$^1$ is attached to R$^{501}$, wherein
L$^1$ is optionally substituted saturated or partially saturated (C$_3$-C$_7$)cycloalkyl and L$^2$ is a bond, —CH$_2$N(R$^a$)C(O)—, or —N(R$^a$)C(O)—; and
R$^{502}$ is optionally substituted alkenyl, optionally substituted alkynyl, CN, or optionally substituted (C$_3$-C$_6$)cycloalkenyl.

9. A compound according to claim 8, wherein
R$^6$ is optionally substituted (C$_1$-C$_6$)alkyl, optionally substituted (C$_3$-C$_{12}$)cycloalkyl, optionally substituted phenyl, optionally substituted pyrazolyl, optionally substituted 6,7-dihydro-4H-pyrazolo[5,1-c][1,4]oxazinyl, optionally substituted 4,5,6,7-tetrahydropyrazolo[1,5-a]pyrazinyl; or
R$^6$ is —R$^{601}$-R$^{602}$ wherein R$^{601}$ is attached to the —N(H)— and
R$^{601}$ is optionally substituted pyrazolyl, or optionally substituted pyridinyl;
R$^{602}$ is —N(R$^a$)$_2$, optionally substituted (C$_1$-C$_6$)alkyl, optionally substituted (C$_3$-C$_6$)cycloalkyl, optionally substituted azetidinyl, optionally substituted morpholinyl, optionally substituted piperidinyl, or optionally substituted tetrahydropyranyl.

10. The compound according to claim 9, wherein R$^1$ is H.

11. The compound according to claim 5, wherein R$^{502}$ is optionally substituted alkenyl.

12. The compound according to claim 11, wherein R$^1$ is H, R$^3$ is H, and R$^4$ is H.

* * * * *